US012343489B2

(12) United States Patent
Irving et al.

(10) Patent No.: US 12,343,489 B2
(45) Date of Patent: Jul. 1, 2025

(54) INTRANASAL AND OLFACTORY DELIVERY DEVICES AND METHODS OF USE

(71) Applicant: Rocket Science Health Corp., Victoria (CA)

(72) Inventors: Kenneth Irving, Victoria (CA); James Jackson, Victoria (CA); Kenza Enright, Victoria (CA); Robert Magyar, Victoria (CA); Alec Lillis, Victoria (CA); Manu Sharma, Victoria (CA); Nicholas Allan, Victoria (CA)

(73) Assignee: Rocket Science Health Corp., Victoria (CA)

( * ) Notice: Subject to any disclaimer, the term of this patent is extended or adjusted under 35 U.S.C. 154(b) by 0 days.

(21) Appl. No.: 19/038,367

(22) Filed: Jan. 27, 2025

(65) Prior Publication Data
US 2025/0170377 A1    May 29, 2025

Related U.S. Application Data

(63) Continuation of application No. PCT/IB2024/054107, filed on Apr. 27, 2024.
(Continued)

(51) Int. Cl.
*A61M 31/00* (2006.01)

(52) U.S. Cl.
CPC ..... *A61M 31/00* (2013.01); *A61M 2202/0007* (2013.01); *A61M 2205/3379* (2013.01); *A61M 2206/11* (2013.01); *A61M 2210/0618* (2013.01)

(58) Field of Classification Search
CPC .......... A61M 31/00; A61M 2210/0618; A61M 2202/0007; A61M 11/006; A61M 11/007;
(Continued)

(56) References Cited

U.S. PATENT DOCUMENTS

| 5,961,489 A | * | 10/1999 | Hirota | A61M 11/007 |
| | | | | 604/94.01 |
| 2007/0119451 A1 | * | 5/2007 | Wang | A61M 15/08 |
| | | | | 128/207.18 |
| 2010/0160897 A1 | * | 6/2010 | Ducharme | A61M 5/1409 |
| | | | | 604/82 |

FOREIGN PATENT DOCUMENTS

| CA | 3227029 A1 | 2/2023 |
| WO | 2024224372 A1 | 10/2024 |

OTHER PUBLICATIONS

International Search Report and Written Opinion Issued in PCT Application No. PCT/IB2024/054107, Mailed Date: Aug. 12, 2024, 11 Pages.

* cited by examiner

*Primary Examiner* — Nilay J Shah
(74) *Attorney, Agent, or Firm* — Mintz, Levin, Cohn, Ferris, Glovsky and Popeo, P.C.

(57) ABSTRACT

The present disclosure describes devices for intranasal delivery. The devices may have a housing with a dispensing element, and a positioning or trigger element coupled to the housing that engages a columella region of the subject to position the dispensing element within the nasal channel and limit its depth of insertion. The devices can also include two insertable portions, each for insertion into a nasal channel of the subject, and an actuator that delivers the composition from either or both of the insertable portions. The devices can be transitioned from a first configuration to a second configuration. Devices of the present disclosure may provide a convenient and effective way to deliver compositions intranasally and to accomplish lateralized delivery to targeted regions of the brain.

3 Claims, 80 Drawing Sheets

Related U.S. Application Data

(60) Provisional application No. 63/618,104, filed on Jan. 5, 2024, provisional application No. 63/516,036, filed on Jul. 27, 2023, provisional application No. 63/499,204, filed on Apr. 28, 2023.

(58) Field of Classification Search
CPC .. A61M 11/06; A61M 15/0003; A61M 15/08; A61M 15/009; A61M 2206/11
See application file for complete search history.

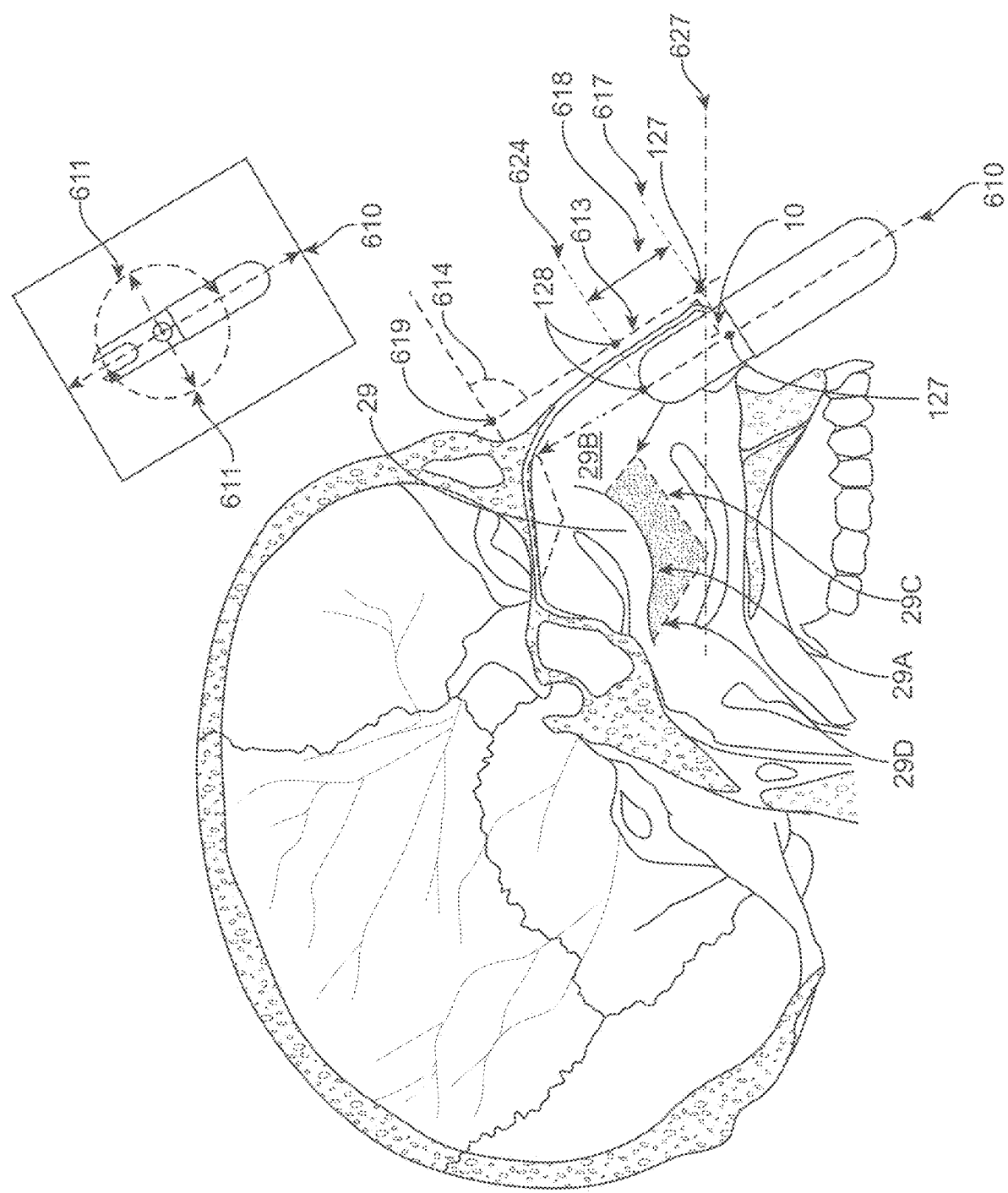

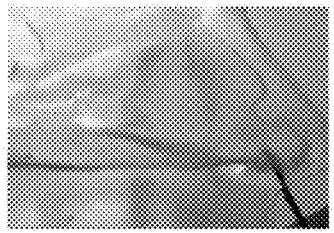
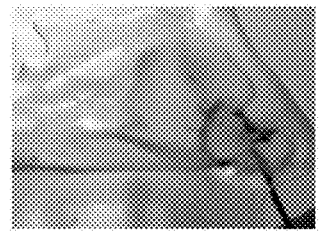
FIG. 14A             FIG. 14B             FIG. 14C
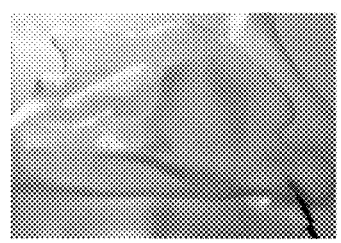
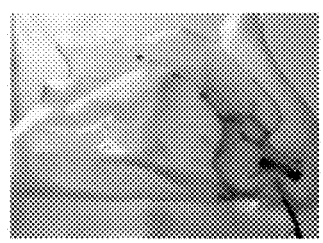
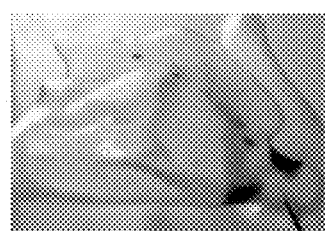
FIG. 14D             FIG. 14E             FIG. 14F
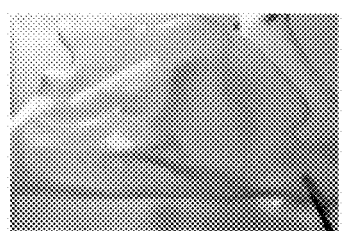
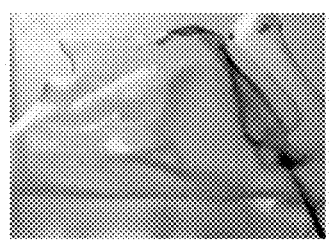
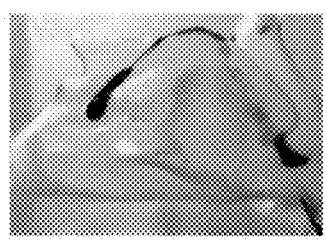
FIG. 14G             FIG. 14H             FIG. 14I
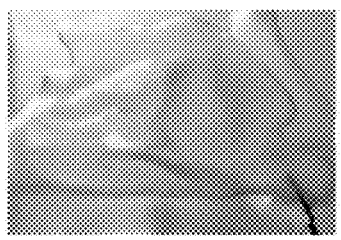
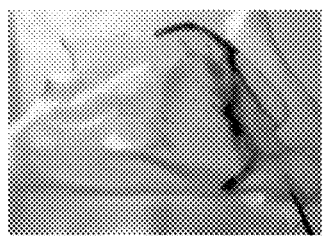
FIG. 14J             FIG. 14K             FIG. 14L

INTRANASAL AND OLFACTORY DELIVERY DEVICES AND METHODS OF USE

CROSS REFERENCE

This application is a continuation of International Patent Application No. PCT/IB2024/054107 filed on Apr. 27, 2024, which claims the benefit to priority to U.S. Provisional Application No. 63/499,204, filed Apr. 28, 2023, U.S. Provisional Application No. 63/516,036, filed on Jul. 27, 2023, and U.S. Provisional Application No. 63/618,104, filed Jan. 4, 2024, the contents of which are incorporated herein by reference in its entirety, including any drawings.

BACKGROUND

Intranasal drug delivery is an effective route for the administration of certain medications, for example, those that act locally in the nasal channel, or those that are rapidly absorbed into the bloodstream through the nasal mucosa. Among the challenges associated with delivering compositions to the nasal channel of a subject includes difficulty in accommodating for variations in nasal channel, targeting deposition of the therapeutic compound at the correct location in the nasal channel, and providing a device which can reliably and repeatably deliver a composition to locations within the nasal channel with a high degree of precision across a population of subjects.

SUMMARY

It is appreciated by the inventors that difficulties in nasal delivery include anatomical, cognitive, and dexterity related challenges are presented in providing a reliable and effective nasal delivery device. For example, the internal nasal valve is a flow-limiting segment of the nasal channel bounded medially by the dorsal septum, laterally by the caudal portion of the upper lateral cartilage and inferiorly by the head of the inferior turbinate that together present a physical barrier between the nasal vestibule and the rest of the nasal channel, including the respiratory region and the olfactory cleft. The internal nasal valve is bounded by nasal tissue that can swell or block the path to the nasal channel, which varies based on time of day, environmental factors, and genetically among individuals. Devices may need to be inserted at particular angles or depths in order to target a specific area, and users may struggle with correct placement and actuation of a device. Users with motor skill impairment (e.g., persons with Parkinson's disease, arthritis) or cognitive impairments (e.g., Alzheimer's disease) may especially struggle to correctly articulate, position, and actuate an intranasal delivery device.

To counter such difficulties, this disclosure provides a novel introducer device for targeted delivery of a composition to a target region of a nasal cavity of a subject, which can readily actuated and positioned by users of various patient populations, and reliability deliver the composition to the target region of the nasal cavity. Exemplary devices utilize a dual nostril inserter with a columella engaging portion positioned therebetween in order to quickly and reliable seat the insertable portions of the device within a ejection zone of a subject's nasal cavity. The exemplary devices disclosed herein can permit for quick, easy, and reliable positioning of a dispensing element within the nasal channel so as to permit for accurate and targeted deposition of compositions to target regions of the nasal cavity. Further, exemplary devices disclosed herein can enable quick, easy, and reliable positioning and targeted deposition across diverse patient populations (e.g., users that are elderly, cognitively impaired, dexterity impaired, or have variations in nasal anatomy), by users of varying skill (e.g., untrained bystanders), under high stress circumstances (e.g., a medical emergency medical), which may otherwise prevent proper use of intranasal delivery devices.

The devices of the present disclosure may comprise housing comprising one or a combination of the following: a subject engaging portion, one or more insertable portions, one or more dispensing elements, and a trigger.

In one aspect, the disclosure provides a device for intranasal delivery to a subject, the device comprising: a housing comprising an insertable portion comprising a distal end, and a proximal end; a subject engaging portion which engages a columella region of the subject to seat the distal end of the insertable portion within an ejection zone of a nasal channel of the subject. In some embodiments, the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule. As used herein, the term "distal" generally refers to the direction towards the end of the device configured to dispense fluid and the term "proximal" generally refers to the direction towards the end of the device furthest from a fluid dispensing tip. As a non-limiting example, a device may have one or more insertable portions at the distal end and a handle portion at the proximal end. However, these designations are only for description of relative positioning of features, and opposite use of the terms may also be appropriate.

In some embodiments, the ejection zone is further 0 mm to 40 mm inferior to a horizontal line that is parallel to the inferior aspect of the olfactory cleft, 0 mm to 20 mm posterior to the internal nasal dorsum, 10 mm and 50 mm superior to a horizontal line that intersects the inferior aspect of the columella, 0 mm to 30 mm superior to a horizontal line that intersects the superior aspect of the inferior turbinate, 0 mm to 3 mm from the septum, or any combination thereof.

In some embodiments, the insertable portion, upon insertion into a nasal channel of the subject, opens or expands the internal nasal valve by pushing the upper lateral cartilage and surrounding tissue up and away from the septum. In some embodiments, the insertable portion, upon insertion into a nasal channel of the subject, is proximal to the septum. In some embodiments, the subject engaging portion prevents movement of the distal end within or away from the ejection zone when the subject engaging portion is seated on the columella region. As used herein, the term "seated" refers to positioning in contact, such as when the subject engaging portion is positioned in contact with the columella region. The term "seated" due not necessarily require that the seated component be totally locked in place with no freedom of movement. For example, a device may have some rotational freedom while the subject engaging portion is seated on the columella region. However, the shape of the intransal portion and the way this shape interacts with the intranasal geometry may significantly limit freedom of movement of the device while the subject engaging portion is seated on the columella region, such that a desired orientation is easily maintained. In some embodiments, the ejection zone is in line with the olfactory cleft as defined by a linear vector between an olfactory cleft and the distal end of the insertable portion. In some embodiments, dispensing a composition from the ejection zone increases on target deposition of the composition to an olfactory cleft. In some embodiments, dispensing a composition from the ejection zone increases on target deposition of the composition to an aspect of a respiratory region such as a middle turbinate. In some embodiments, dispensing a composition from the ejection zone increases on target deposition of the composition to two or more regions or sub-regions of a nasal channel. In some embodiments, the subject engaging portion is seated on the columella region when the subject engaging portion simultaneously contacts a downward facing lateral face of the columella, a leftward facing lateral face of the columella, and a rightward facing lateral face of the columella. In some embodiments, the subject engaging portion limits a depth of insertion of the insertable portion into the nasal channel. In some embodiments, the insertable portion incorporates one or more dispensing channels leading to one or more dispensing ports configured for delivery of a composition to one or more regions or sub-regions of the nasal channel of the subject. In some embodiments, the insertable portion comprises a dispensing element for delivery of a composition to a region or sub-region of the nasal channel of the subject. In some embodiments, the housing comprises a trigger, wherein upon application of pressure to the trigger, the trigger actuates the device to dispense a composition to the subject from the insertable portion or the dispensing element. In some embodiments, the subject engaging portion comprises a trigger coupled to the housing and the subject engaging portion, wherein upon application of pressure of the subject engaging portion to the columella region, the trigger actuates the device to dispense a composition to the subject from the insertable portion or the dispensing element. In some embodiments, the subject engaging portion comprises a trigger release coupled to the housing and the subject engaging portion, wherein upon application of pressure of the subject engaging portion to the columella region, the trigger release permits actuation of the device to deliver a composition to the subject from the insertable portion or the dispensing element. In some embodiments, the device further comprises a trigger which is actuatable upon engagement of the trigger release. In some embodiments, the housing defines two insertable portions, each for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the insertable portions for delivery of a composition to the subject, the device further comprising an actuator which delivers a composition from the either or both of the insertable portions when the device is actuated. In some embodiments, the housing defines two insertable portions, each for delivery of a composition into a nasal channel of the subject, the device further comprising an actuator which delivers the composition from either or both of the insertable portions when the device is actuated. In some embodiments, the device is transitionable from a first configuration to a second configuration, the device further comprising one or two dispensing elements coupled to the insertable portion, the at least one dispensing element revealing from the at least one insertable portion upon transition of the device from the first configuration to the second configuration. In some embodiments, the device is transitionable from the first configuration to the second configuration upon application of pressure about a longitudinal axis of the device, wherein the at least one dispensing element reveals in a linear vector relative to a longitudinal axis of the at least one insertable portion, or wherein the device is configured to be transitioned from the first configuration to the second configuration with only one hand. In some embodiments, the device is simultaneously actuated upon being transitioned from the first configuration to the second configuration. In some embodiments, the distal aspect of the at least one dispensing element is positioned in the ejection zone when the device is in the second configuration.

In one aspect, the disclosure provides a device for intranasal delivery to a subject, the device comprising: a housing comprising an insertable portion configured for insertion into a nasal channel of the subject; and a subject engaging portion which engages a columella region of the subject coupled to the housing, wherein application of pressure by the subject engaging portion to the columella region of the subject enables and/or causes delivery of a composition to the subject from the insertable portion. In some embodiments, the insertable portion incorporates one or more dispensing channels leading to one or more dispensing ports configured for intranasal delivery of a composition to one or more regions or sub-regions of the nasal channel of the subject. In some embodiments, the insertable portion comprises a dispensing element for delivery of a composition to a region or sub-region of the nasal channel of the subject. In some embodiments, the housing comprises a trigger, wherein the trigger actuates the device to deliver a composition to the subject from the insertable portion or the dispensing element. In some embodiments, the subject engaging portion comprises a trigger coupled to the housing and the subject engaging portion, wherein upon application of pressure of the subject engaging portion to the columella region, the trigger actuates the device to dispense a composition to the subject from the insertable portion or the dispensing element. In some embodiments, the subject engaging portion comprises a trigger release coupled to the housing and the subject engaging portion, wherein upon application of pressure of the subject engaging portion to the columella region, the trigger release permits actuation of the device to deliver a composition to the subject from the insertable portion or the dispensing element. In some embodiments, the device further comprising a trigger which is actuatable upon engagement of the trigger release. In some embodiments, the subject engaging portion positions the insertable portion within a nasal channel of the subject and limits the depth of insertion of the insertable portion into the nasal channel. In some embodiments, the housing defines two insertable portions, each for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the insertable portions for delivery of the composition to the subject, the device further comprising an actuator which delivers the composition from the either or both of the insertable portions when the device is actuated. In some embodiments, the housing defines two insertable portions, each for delivery of the composition into a nasal channel of the subject, the device further comprising an actuator which delivers the composition from either or both of the insertable portions when the device is actuated. In some embodiments, the device is transitionable from a first configuration to a second configuration, the device further comprising a dispensing element coupled to the housing, the dispensing element revealing from the first insertable portion upon transition of the device from the first configuration to the second configuration. In some embodiments, the device is simultaneously actuated upon being transitioned from the first configuration to the second configuration. In some embodiments, the device is transitionable from the first configuration to the second configuration upon application of pressure about a longitudinal axis of the device, wherein the dispensing element reveals in a linear vector relative to a longitudinal axis of the first insertable portion, or wherein the device is configured to be transitioned from the first configuration to the second configuration with only one hand. In some embodiments, the subject engaging portion engages a columella region of the subject to seat a distal end of the insertable portion within an ejection zone of a nasal cavity of the subject ejection zone. In some embodiments, the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule, and one or more of the following: 0 mm to 40 mm inferior to a horizontal line that is parallel to the inferior aspect of the olfactory cleft, 0 mm to 20 mm posterior to the internal nasal dorsum, 10 mm and 50 mm superior to a horizontal line that intersects the inferior aspect of the columella, 0 mm to 30 mm superior to a horizontal line that intersects the superior aspect of the inferior turbinate, 0 mm to 3 mm from the septum, or any combination thereof. In some embodiments, the subject engaging portion prevents movement of the distal end within or away from the ejection zone when the subject engaging portion is seated on the columella region. In some embodiments, the ejection zone is in line with the olfactory cleft as defined by a linear vector between the olfactory cleft and the distal end of the insertable portion. In some embodiments, dispensing a composition from the ejection zone increases on target deposition of the composition to the olfactory cleft. In some embodiments, the subject engaging portion is seated on the columella region when the subject engaging portion simultaneously contacts a downward facing lateral face of the columella, a leftward facing lateral face of the columella, and a rightward facing lateral face of the columella. In some embodiments, dispensing a composition from the ejection zone increases on target deposition of the composition to an aspect of a respiratory region such as the middle turbinate.

In one aspect, the disclosure provides a device for intranasal delivery to a subject, the device comprising: a housing defining first and second insertable portions, each for insertion into a nasal channel of the subject, wherein, upon insertion of the first insertable portion into the nasal channel of the subject, the at least one insertable portion engages tissue within the nasal channel to open or expand an internal nasal valve of the subject thereby positioning at least one of the insertable portions for delivery of a composition to the subject; and an actuator which delivers the composition from the either or both of the insertable portions when the device is actuated. In some embodiments, the at least one insertable portion to open or expand an internal nasal valve does so by moving a superior lateral cartilage defining the internal nasal valve away from a septum of the subject. In some embodiments, the at least one insertable portion to open or expand an internal nasal valve does so by moving superior lateral cartilage defining the internal nasal valve towards an internal nasal dorsum of the subject. In some embodiments, the insertable portion incorporates one or more dispensing channels leading to one or more dispensing ports configured for intranasal delivery of a composition to one or more regions or sub-regions of the nasal channel of the subject. In some embodiments, the insertable portion comprises a dispensing element for delivery of a composition to a region or sub-region of the nasal channel of the subject. In some embodiments, the device further comprises a trigger coupled to the housing, wherein upon application of pressure to the trigger, the trigger actuates the device to dispense a composition to the subject from the insertable portion or the dispensing element. In some embodiments, the device further comprises a trigger coupled to the housing and the subject engaging portion, wherein upon application of pressure of the subject engaging portion to the columella region, the trigger actuates the device to dispense a composition to the subject from the insertable portion or the dispensing element. In some embodiments, the device further comprises a subject engaging portion, wherein the subject engaging portion comprises a trigger release coupled to the housing, wherein upon application of pressure of the subject engaging portion to the columella region, the trigger release permits actuation of the device to deliver a composition to the subject from the insertable portion or the dispensing element. In some embodiments, the device further comprises a trigger which is actuatable upon engagement of the trigger release. In some embodiments, the device further comprises a subject engaging portion coupled to the housing, which engages a columella region, wherein the subject engaging portion positions the insertable portion within the nasal channel of the subject and limits a depth of insertion of the delivery element into the nasal channel. In some embodiments, the housing defines two insertable portions, each for delivery of a composition into a nasal channel of the subject, the device further comprising an actuator which delivers the composition from either or both of the dispensing elements when the device is actuated. In some embodiments, the device is transitionable from a first configuration to a second configuration, the housing defining a first insertable portion, the device further comprising a dispensing element coupled to the housing, the dispensing element revealing from the first insertable portion upon transition of the device from the first configuration to the second configuration. In some embodiments, the device is simultaneously actuated upon being transitioned from the first configuration to the second configuration. In some embodiments, the device is transitionable from the first configuration to the second configuration upon application of pressure about a longitudinal axis of the device, wherein the dispensing element reveals in a linear vector relative to a longitudinal axis of the first insertable portion, or wherein the device is configured to be transitioned from the first configuration to the second configuration with only one hand. In some embodiments, the subject engaging portion engages a columella region of the subject to seat a distal end of the insertable portion within an ejection zone of a nasal cavity of the subject, wherein the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule, and one or more of the following: 0 mm to 40 mm inferior to a horizontal line that is parallel to the inferior aspect of the olfactory cleft, 0 mm to 20 mm posterior to the internal nasal dorsum, 10 mm and 50 mm superior to a horizontal line that intersects the inferior aspect of the columella, 0 mm to 30 mm superior to a horizontal line that intersects the superior aspect of the inferior turbinate, 0 mm to 3 mm from the septum, or any combination thereof. In some embodiments, the subject engaging portion prevents movement of the distal end within or away from the ejection zone when the subject engaging portion is seated on the columella region. In some embodiments, the ejection zone is in line with the olfactory cleft as defined by a linear vector between the olfactory cleft and the distal end of the insertable portion. In some embodiments, dispensing a composition from the ejection zone increases on target deposition of the composition to the olfactory cleft. In some embodiments, the subject engaging portion is seated on the columella region when the subject engaging portion simultaneously contacts a downward facing lateral face of the columella, a leftward facing lateral face of the columella, and a rightward facing lateral face of the columella. In some embodiments, dispensing a composition from the ejection zone increases on target deposition of the composition to an aspect of a respiratory region such as the middle turbinate.

In one aspect, the disclosure provides a device for intranasal delivery to a subject, the device transitionable from a first configuration to a second configuration, the device comprising: a housing defining a first insertable portion configured to be inserted into a nasal channel of the subject; and a dispensing element coupled to the housing, the dispensing element revealing from the first insertable portion upon transition of the device from the first configuration to the second configuration, wherein the device is transitioned from the first configuration to the second configuration by application of pressure about a longitudinal axis of the device, and wherein the device is simultaneously actuated upon being transitioned from the first configuration to the second configuration. In some embodiments, the dispensing element the simultaneous actuation refers to transition for the first configuration to the second configuration and actuation occurring in a single motion upon application of pressure about a longitudinal axis of the device. In some embodiments, the dispensing element reveals in a linear vector parallel to the internal nasal dorsum from the first insertable portion at a location above an inferior turbinate of the subject. In some embodiments, the device avoids contaminating the dispensing element with bacteria from the lower nasal cavity by enclosing it in the insertable portion prior to revealing the dispensing element upon transition from the first configuration to the second configuration. In some embodiments, the device avoids contaminating the dispensing element by concealing it within the insertable portion prior to actuation. In some embodiments, the insertable portion incorporates one or more dispensing channels leading to one or more dispensing ports configured for intranasal delivery of a composition to one or more regions or sub-regions of the nasal channel of the subject. In some embodiments, the dispensing element reveals in a linear vector relative to a longitudinal axis of the first insertable portion. In some embodiments, the device is configured to be transitioned from the first configuration to the second configuration with only one hand. In some embodiments, the dispensing element reveals from the insertable portion upon transition of the device from the first configuration to the second configuration. In some embodiments, the dispensing element reveals from the insertable portion upon transition of the device from the first configuration to the second configuration, upon application of pressure of a portion of the housing to a columella region of a subject. In some embodiments, the second configuration moves a first portion of the housing towards a second portion of the housing about a longitudinal axis of the device. In some embodiments, the device further comprises a subject engaging portion coupled to the housing which engages a columella region, wherein the subject engaging portion positions the insertable portion within a nasal channel of the subject and limits the depth of insertion of the dispensing element into the nasal channel. In some embodiments, the subject engaging portion which engages a columella region of the subject seats the distal end of the dispensing element within an ejection zone of a nasal cavity of the subject, wherein the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule, and one or more of the following: 0 mm to 40 mm inferior to a horizontal line that is parallel to the inferior aspect of the olfactory cleft, 0 mm to 20 mm posterior to the internal nasal dorsum, 10 mm and 50 mm superior to a horizontal line that intersects the inferior aspect of the columella, 0 mm to 30 mm superior to a horizontal line that intersects the superior aspect of the inferior turbinate, 0 mm to 3 mm from the septum, or any combination thereof. In some embodiments, the subject engaging portion prevents movement of the distal end of the dispensing element within or away from the ejection zone when the subject engaging portion is seated on the columella region. In some embodiments, the ejection zone is in line with the olfactory cleft as defined by a linear vector between the olfactory cleft and the distal end of the insertable portion. In some embodiments, the dispensing a composition from the ejection zone increases on target deposition of the composition to the olfactory cleft. In some embodiments, the dispensing a composition from the ejection zone increases on target deposition of the composition to an aspect of a respiratory region such as the middle turbinate. In some embodiments, the subject engaging portion is seated on the columella region when the subject engaging portion simultaneously contacts a downward facing lateral face of the columella, a leftward facing lateral face of the columella, and a rightward facing lateral face of the columella. In some embodiments, the further comprising a trigger coupled to the housing and the subject engaging portion, the subject engaging portion engaging a columella region of the subject, wherein upon application of pressure of the subject engaging portion to the columella region, the trigger actuates the device to deliver a composition to the subject from the dispensing element. In some embodiments, the housing defines two insertable portions, each for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the insertable portions for delivery of a composition to the subject, the device further comprising an actuator which delivers a composition from the either or both of the insertable portions when the device is actuated. In some embodiments, the housing defines two dispensing elements, each for delivery of a composition into a nasal channel of the subject, the device further comprising an actuator which delivers the composition from either or both of the dispensing elements when the device is actuated. In some embodiments, the further comprising a trigger release coupled to the housing and the subject engaging portion, wherein upon application of pressure of the subject engaging portion to the columella region, the trigger release permits actuation of the device to deliver a composition to the subject from the insertable portion. In some embodiments, the further comprising a trigger which is actuatable upon engagement of the trigger release. In some embodiments, the device avoids contaminating the dispensing element by concealing it within the insertable portion prior to actuation. In some embodiments, the composition is dispensed from a distal end of the insertable portion. In some embodiments, the dispensing element is in the ejection zone when the device is in the second configuration. In some embodiments, the dispensing element is at a distal end of the ejection zone when the device is in the second configuration. In some embodiments, the device is simultaneously actuated upon being transitioned from the first configuration to the second configuration. In some embodiments, the dispensing element reveals in a linear vector parallel to the internal nasal dorsum from the first insertable portion at a location above an inferior turbinate of the subject. In some embodiments, the device avoids contaminating the dispensing element with bacteria from the lower nasal cavity by enclosing it in the insertable portion prior to revealing the dispensing element upon transition from the first configuration to the second configuration. In some embodiments, the at least one insertable portion to open or expand an internal nasal valve does so by moving upper lateral cartilage away from a septum of the subject. In some embodiments, the at least one insertable portion to open or expand an internal nasal valve does so by moving upper lateral cartilage defining the internal nasal valve towards an internal nasal dorsum of the subject. In some embodiments, the subject engaging portion prevents movement of the distal end of an insertable portion or a dispensing element within or away from the ejection zone when the subject engaging portion is seated on the columella region. In some embodiments, the ejection zone is in line with the olfactory cleft as defined by a linear vector between the olfactory cleft and the distal end of the insertable portion. In some embodiments, the dispensing a composition from the ejection zone increases on target deposition of the composition to the olfactory cleft. In some embodiments, the dispensing a composition from the ejection zone increases on target deposition of the composition to an aspect of a respiratory region such as the middle turbinate. In some embodiments, the subject engaging portion is seated on the columella region when the subject engaging portion simultaneously contacts a downward facing lateral face of the columella, a leftward facing lateral face of the columella, and a rightward facing lateral face of the columella. In some embodiments, the subject engaging portion limits a depth of insertion of the insertable portion into the nasal channel. In some embodiments, the subject engaging portion limits a depth of insertion of the dispensing element into the nasal channel. In some embodiments, the first and second insertable portion are configured to dispense a composition from the first and second insertable portion simultaneously. In some embodiments, the first and second insertable portion are configured to dispense a composition from the first and second insertable portion sequentially. In some embodiments, the first and second dispensing elements are configured to dispense a composition from the first and second dispensing elements simultaneously. In some embodiments, the first and second dispensing elements are configured to dispense a composition from the first and second dispensing elements sequentially. In some embodiments, the first insertable portion moves along a septum and moves a superior lateral cartilage away from the septum. In some embodiments, the first and second dispensing elements move along a septum. In some embodiments, the two insertable portions each contact opposite sides of a septum. In some embodiments, the two dispensing elements each contact opposite sides of a septum. In some embodiments, the two insertable portions each contact opposite sides of a septum and apply force to a superior lateral cartilage in a direction away from the septum. In some embodiments, the two insertable portions each contact opposite sides of a septum and apply force to a superior lateral cartilage in a direction orthogonal to a lateral axis of the septum. In some embodiments, the at least one insertable portion to open or expand an internal nasal valve does so by moving a superior lateral cartilage defining the internal nasal valve away from a septum of the subject. In some embodiments, the at least one insertable portion to open or expand an internal nasal valve does so by moving superior cartilage defining the internal nasal valve towards an internal nasal dorsum of the subject. In some embodiments, the insertable portion is configured to fit into a wedge shape of a nasal valve where a septum contacts a superior lateral cartilage. In some embodiments, the anterior aspect of the insertable portion is configured to fit into the narrow anterior aspect of the internal nasal valve. In some embodiments, the anterior aspect of the insertable portion is configured to fit into an opening comprising a 9 to 15 degree angle. In some embodiments, the insertable portion is configured to fit into the narrow anterior aspect of the internal nasal valve when seated about the columella region. In some embodiments, the insertable portion is configured to fit into an opening comprising a 9 to 15 degree angle when seated about the columella region. In some embodiments, the insertable portion is configured to be inserted into a wedge shaped internal nasal valve of a subject. In some embodiments, the insertable portion is tapered about a distal end of the insertable portion and is configured to be inserted into a wedge shaped internal nasal valve of a subject. In some embodiments, the insertable portion is tapered about a distal end of the insertable portion with rounded edges and is configured to be inserted into a wedge shaped internal nasal valve of a subject. In some embodiments, the insertable portion comprises a tip portion having a width which corresponds to the diameter of a circle approximating the average cross sectional area of an internal nasal valve. In some embodiments, the insertable portion comprises a flat surface on a lateral face of the insertable portion which contacts the septum. In some embodiments, the insertable portion comprises a rounded surface on a lateral face of the insertable portion which is opposite the septum. In some embodiments, the insertable portion comprises a width up to 3 mm. In some embodiments, the one or both insertable portions comprises a proximal end and a distal end, wherein a dispensing element reveals from the distal end of the insertable portion. In some embodiments, the distal end of an insertable portion is configured for insertion into the nasal channel of the subject. In some embodiments, the revealing of the dispensing element from the first insertable portion upon transition of the device from the first configuration to the second configuration comprises extending of the dispensing element from the first insertable portion.

In some embodiments, the subject engaging portion engages both a right side and a left side of the columella region. In some embodiments, the subject engaging portion comprises a concave shape. In some embodiments, the subject engaging portion comprises a U shape. In some embodiments, the subject engaging portion comprises a saddle shape. In some embodiments, the subject engaging portion comprises a concave ellipsoidal shape. In some embodiments, the subject engaging portion comprises a trench with a rounded bottom or rounded edges. In some embodiments, the subject engaging portion centers the two insertable portions about the subject's columella. In some embodiments, the subject engaging portion is a positioning element which aligns at least one of the insertable portion, the dispensing element, or the housing relative to the user's nasal channel. In some embodiments, the device targets an olfactory cleft or a portion thereof, wherein the subject engaging portion aligns a dispensing element with an olfactory cleft of the subject. In some embodiments, the insertable portion comprises a single dispensing channel leading to a dispensing port positioned at the distal aspect of the insertable portion. In some embodiments, the insertable portion comprises a single dispensing channel leading to a dispensing port positioned along the length of the insertable portion. In some embodiments, the insertable portion comprises two or more dispensing channels leading to two or more dispensing ports positioned at various aspects of the insertable portion. In some embodiments, the insertable portion comprises a single dispensing channel leading to a dispensing port positioned to deliver a composition to an olfactory cleft. In some embodiments, the insertable portion comprises a single dispensing channel leading to a dispensing port positioned to deliver a composition to an aspect of the respiratory region, such as a middle turbinate. In some embodiments, the insertable portion comprises two or more dispensing channels leading to two or more dispensing ports positioned to deliver a composition to one or more regions or sub-regions of a nasal channel such as an olfactory cleft and/or a middle turbinate. In some embodiments, a first insertable portion comprises a single dispensing channel leading to a dispensing port positioned at the distal aspect of the insertable portion and a second insertable portion comprises a single dispensing channel leading to a dispensing port positioned along the length of the insertable portion. In some embodiments, the first insertable portion comprises a single dispensing channel leading to a dispensing port positioned at the distal aspect of the insertable portion and a second insertable portion comprises two or more dispensing channels leading to two or more dispensing ports positioned at various aspects of the insertable portion. In some embodiments, a composition is dispensed from two insertable portions simultaneously. In some embodiments, the composition is dispensed from two insertable portions sequentially. In some embodiments, a composition is dispensed from two dispensing elements simultaneously. In some embodiments, a composition is dispensed from two dispensing elements sequentially. In some embodiments, the trigger and/or the subject engaging portion actuates the device and dispenses the composition from one cannula when pressed against the subject's columella. In some embodiments, the dispensing element comprises a cannula contained therein through which the fluid flows. In some embodiments, the cannula is entirely contained within the dispensing element. In some embodiments, an end of the dispensing element is coextensive with the end of the insertable portion. In some embodiments, the dispensing element is entirely contained within the insertable portion. In some embodiments, the end of the dispensing element is coextensive with the end of the insertable portion when the device is actuated. In some embodiments, an end of the dispensing element is coextensive with the end of the insertable portion when the device is transitioned from the first position to the second position, or the first configuration to the second configuration. In some embodiments, the dispensing element does not extend or reveal from the insertable portion when the device is actuated. In some embodiments, the trigger is positioned on the subject engaging portion or the columella saddle, and is configured to actuate the device when pressure is applied to the trigger by a subject's columella. In some embodiments, the dispensing element comprises a cannula. In some embodiments, the trigger and/or the subject engaging portion comprises an actuator which dispenses the composition from the reservoir when the housing is moved from the first position to the second position. In some embodiments, the subject engaging portion engages the columella of the subject to limit depth of insertion of the first insertable portion and the second insertable portion into the subject's nasal channel. In some embodiments, the subject engaging portion engages the columella of the subject to limit depth of insertion of the first dispensing element and the second dispensing element into the subject's nasal channel. In some embodiments, the subject engaging portion engages the columella of the subject about multiple sides of the columella in a concave shape. In some embodiments, the trigger comprises a saddle shaped portion for receiving the columella of the subject. In some embodiments, the saddle shaped portion positions the first insertable portion and the second insertable portion as to align the one or more dispensing elements with the olfactory cleft when the device is actuated. In some embodiments, the saddle portion, subject engaging portion, or positioning trigger comprises a shape which matches the anatomy of the subject's columella and aligns the one or more dispensing elements with the subject's olfactory cleft. In some embodiments, the one or more dispensing elements are positioned in line with an unobstructed path to the olfactory cleft of the subject when the subject engaging portion is engaging the columella of the subject. In some embodiments, the dispensing element is positioned 0 mm to about 40 mm from the inferior aspect of an olfactory cleft of the subject when the subject engaging portion is engaging the columella of the subject. In some embodiments, the saddle comprises an impression of the subject's columella. In some embodiments, the subject engaging portion comprises dimension of about 20 mm by about 17 mm. In some embodiments, the saddle shaped portion engages the columella of the subject about multiple sides of the columella. In some embodiments, the subject engaging portion depresses a trigger coupled to the subject engaging portion to actuate the device. In some embodiments, the first and/or second insertable portion limits a sagittal angle or an anterior-posterior angle of the device. In some embodiments, the first and/or second insertable portion limits a coronal angle or a medial-lateral angle of the device. In some embodiments, the first and/or second insertable portion limits a sagittal angle or an anterior-posterior angle of the device. In some embodiments, the first and/or second insertable portion and subject engaging portion limits a sagittal angle, an anterior-posterior angle of the device, a coronal angle or a medial-lateral angle of the device, a sagittal angle or an anterior-posterior angle of the device, or any combination thereof. In some embodiments, the internal nasal valve of the subject is bounded medially by the septum, laterally by the caudal portion of the upper lateral cartilage and inferiorly by the head of the inferior turbinate. In some embodiments, the first and/or second insertable portion displaces the upper lateral cartilage thereby opening or enlarging at least a portion of internal nasal valve of the subject. In some embodiments, the first and/or second insertable portion is torsionally flexible. In some embodiments, the first and/or second insertable portion is tortional flexible so as to adjust to the angle of an anterior aspect or wedge of the internal nasal valve. In some embodiments, the first and/or second insertable portion(s) runs proximal to a septum of the user. In some embodiments, the one or more dispensing elements extend outwards or are revealed from the insertable portion when the device is actuated. In some embodiments, the two dispensing elements reveal outwards from the insertable portion when the device is actuated. In some embodiments, the device dispenses a composition from one or more dispensing elements when the device is actuated. In some embodiments, the housing further comprises a second insertable portion for insertion into a second nasal channel of the user. In some embodiments, the first and/or second insertable portion moves tissue within the nasal channel to define a path between the one or more dispensing elements and a delivery site. In some embodiments, the first and/or second insertable portion moves tissue within the nasal channel to open or enlarge an internal nasal valve of a subject. In some embodiments, the dispensing element is contained within the insertable portion. In some embodiments, the device further comprises a second dispensing element, wherein the first dispensing elements is contained within the first insertable portion, wherein the second dispensing element is contained within the second insertable portion. In some embodiments, the first and/or second insertable portion comprises dimension of about 20 mm by about 3.5 mm. In some embodiments, the first and/or second insertable portion are wedge-shaped, paddle-shaped, cylindrical, bulbous, cone-shaped, spherical, hemispherical, or any combination thereof. In some embodiments, the transition of the device from the first configuration to the second configuration is actuated by the subject engaging portion which reveals the dispensing element from the first insertable portion. In some embodiments, the transition of the device from the first configuration to the second configuration is actuated by an actuator which reveals the dispensing element from the first insertable portion. In some embodiments, the first or second insertable portion displaces cartilage and/or tissue within the nasal channel when the device is inserted in the first configuration. In some embodiments, the first or second insertable portion fits proximal to a septal-lateral cartilage junction of the subject when the device is in the second configuration. In some embodiments, the housing is movable from a first position to the second position. In some embodiments, the housing comprises a proximal portion and a distal portion, wherein the distal portion is pushed relative to the proximal portion to actuate the device when the housing is transitioned from the first configuration to the second configuration. In some embodiments, the distal portion is inserted into the proximal portion when the housing is transitioned from the first configuration to the second configuration. In some embodiments, upon transition from the first configuration to the second configuration, the distal portion moves relative to the subject, while the proximal portion remains stationary relative to the subject, wherein the proximal portion or the distal portion is coupled to the dispensing element. In some embodiments, upon transition from the first configuration to the second configuration, the dispensing element reveals outward from the distal portion. In some embodiments, the columella region comprises: the subnasale, the subnasion, the anterior nasal spine, or any combination thereof. In some embodiments, the insertable portion has the following flexibility characteristics: a medial-lateral flexibility along a width orthogonal to a length of the insertable portion; a lack anterior-posterior flexibility about a length of the insertable portion; or an inferior-superior flexibility about a rotational axis orthogonal to a length of the insertable portion.

In some embodiments, the dispensing element is configured to dispense the composition into a single nasal channel of a subject. In some embodiments, the dispensing element fits proximal to a septal-lateral cartilage junction of the subject. In some embodiments, the dispensing element fits proximal to a septum of the subject. In some embodiments, the dispensing element comprises a dispensing port. In some embodiments, a dispensing element comprises a cannula or a catheter. In some embodiments, the dispensing element comprises a cannula contained therein through which the fluid flows. In some embodiments, an end of the dispensing element is coextensive with the end of the insertable portion. In some embodiments, the dispensing element is entirely contained within the insertable portion. In some embodiments, the end of the dispensing element is coextensive with the end of the insertable portion when the device is actuated. In some embodiments, an end of the dispensing element is coextensive with the end of the insertable portion when the device is transitioned from the first position to the second position, or the first configuration to the second configuration. In some embodiments, the dispensing element does not extend or reveal from the insertable portion when the device is actuated. In some embodiments, the trigger is positioned on the subject engaging portion or the columella saddle, and is configured to actuate the device when pressure is applied to the trigger by a subject's columella. In some embodiments, the dispensing element comprises a cannula. In some embodiments, the one or more insertable portions comprise a plurality of dispensing ports. In some embodiments, an end of the dispensing element is coextensive with the end of the insertable portion. In some embodiments, the dispensing element is entirely contained within the insertable portion. In some embodiments, the end of the dispensing element is coextensive with the end of the insertable portion when the device is actuated. In some embodiments, an end of the dispensing element is coextensive with the end of the insertable portion when the device is transitioned from the first position to the second position, or the first configuration to the second configuration. In some embodiments, the dispensing element does not extend or reveal from the insertable portion when the device is actuated. In some embodiments, the trigger is positioned on the subject engaging portion or the columella saddle, and is configured to actuate the device when pressure is applied to the trigger by a subject's columella. In some embodiments, the dispensing element comprises a cannula.

In some embodiments, the one or more dispensing elements comprise a dispensing port. In some embodiments, the dispensing port has one dispensing port at its distal end, one or more dispensing ports along its length, or a combination of both. In some embodiments, the dispensing port is directed at different target areas within the nasal channel. In some embodiments, the dispensing port comprises an atomizer. In some embodiments, the dispensing element comprises an atomizer. In some embodiments, the dispensing port is configured to dispense a laminar flow. In some embodiments, the dispensing port is configured to dispense a fluid jet. In some embodiments, the one or more dispensing elements are 20 mm to 50 mm in length. In some embodiments, the one or more dispensing elements reveal 0 mm to 40 mm from the insertable portion. In some embodiments, the one or more dispensing elements comprise multiple dispensing ports. In some embodiments, the one or more dispensing elements comprise multiple fluid channels. In some embodiments, the one or more dispensing elements comprise a dispensing port. In some embodiments, the one of the multiple fluid channels is configured to dispense a gas. In some embodiments, the one of the multiple fluid channels is configured to dispense a gas following dispensing a composition by another fluid channel. In some embodiments, the device is configured to target the olfactory cleft or a portion thereof. In some embodiments, the one or more dispensing elements comprise a first tubular section which surrounds the dispensing element. In some embodiments, the first tubular section remains within a first insertable portion when the device is actuated to the second position. In some embodiments, the insertable portion is flexible. In some embodiments, the one or more dispensing elements are flexible. In some embodiments, further comprising a reservoir fluidically connected to the one or more insertable portions. In some embodiments, further comprising a reservoir fluidically connected to the one or more dispensing elements. In some embodiments, the compound comprises a therapeutic agent. In some embodiments, the compound comprises a sampling agent. In some embodiments, the compound comprises a liquid, powder or gas, or a combination thereof. In some embodiments, the target region is one or both olfactory clefts, or a sub-area thereof. In some embodiments, the target area is one or both respiratory areas, or a sub-area thereof. In some embodiments, the actuator is spring loaded. In some embodiments, the actuator dispenses approximately equal amounts of fluid form each insertable portion. In some embodiments, the actuator dispenses approximately equal amounts of fluid form each dispensing element. In some embodiments, the actuator dispenses fluid from only one insertable portion. In some embodiments, the actuator dispenses fluid from only one dispensing element. In some embodiments, the one or more dispensing are contained with a secondary tubular member. In some embodiments, the reservoir is removable. In some embodiments, the reservoir is comprised within a removable cartridge. In some embodiments, the positioned trigger depresses a switch underneath the positioning trigger to actuate the device. In some embodiments, further comprising a central tube fluidically connected to the one or more insertable portions, wherein the central tube is inserted into the reservoir when the device is actuated. In some embodiments, further comprising a central tube fluidically connected to the one or more dispensing elements, wherein the central tube is inserted into the reservoir when the device is actuated. In some embodiments, the device comprises a central tube fluidically connected to two insertable portions, wherein the central tube is inserted into the reservoir when the device is actuated. In some embodiments, further comprising a central tube fluidically connected to two dispensing elements, wherein the central tube is inserted into the reservoir when the device is actuated. In some embodiments, the device further comprises one or more bases connected to the bottom of the one or more dispensing elements which move the one or more dispensing elements upon actuation of the device. In some embodiments, the dispensing channels comprise a diameter of about 0.3 mm to about 3 mm. In some embodiments, the dispensing element comprises an inner diameter of about 0.3 mm to about 3 mm. In some embodiments, the dispensing element is configured to prevent the introduction of bacteria or microbes from the lower nasal cavity or external environment into different another region of the nasal cavity.

In one aspect, the disclosure provides a device for intranasal delivery to a subject, the device transitionable from a first configuration to a second configuration, the device comprising: a housing defining two insertable portions comprising at least one dispensing element, each insertable portion for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the dispensing elements for delivery of a composition to the subject; a subject engaging portion coupled to the housing comprising a trigger, the trigger comprising a subject engaging portion which engages a columella region, wherein upon application of pressure to the subject engaging portion, the trigger permits actuation of the device to deliver a composition to the subject from the dispensing element; and the dispensing element revealing from the first insertable portion upon transition of the device from the first configuration to the second configuration.

In one aspect, the disclosure provides a method for intranasal delivery to a subject with a device, the method comprising: positioning an insertable portion of the device within an ejection zone of a nasal cavity of the subject by engaging a columella region of the subject with a subject engaging portion of the device, seating the insertable portion within the ejection zone of the subject's nasal cavity, wherein the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule, and one or more of the following: 0 mm to 40 mm inferior to a horizontal line that is parallel to the inferior aspect of the olfactory cleft, 0 mm to 20 mm posterior to the internal nasal dorsum 10 mm and 50 mm superior to a horizontal line that intersects the inferior aspect of the columella, 0 mm to 30 mm superior to a horizontal line that intersects the superior aspect of the inferior turbinate, 0 mm to 3 mm from the septum, or any combination thereof. In some embodiments, the method further comprises actuating the device by applying pressure to the columella region of the subject with the subject engaging portion of the device. In some embodiments, the method further comprises the positioning the insertable portion of the device comprises positioning two insertable portions into two nasal channels of the subject, thereby opening or expanding an opening of an internal nasal valve of the subject. In some embodiments, the method further comprises positioning the dispensing element of the device comprises positioning two dispensing elements of the device into a nasal channel of the subject, wherein the two dispensing elements reveal from the insertable portion. In some embodiments, the method further comprises transitioning the device from a first configuration to a second configuration, wherein the dispensing element reveals from the insertable portion upon transition of the device from the first configuration to the second configuration.

In one aspect, the disclosure provides a method for intranasal delivery to a subject with a device, the method comprising: inserting two insertable portions into nasal channels of the subject, wherein upon the inserting at least one of the insertable portion engages tissue within the nasal channel thereby opening or expanding an opening of an internal nasal valve of the subject, thereby positioning at least one of the insertable portions for delivery of a composition to the subject. In some embodiments, the method further comprises positioning the insertable portions into nasal channels of the subject by engaging a columella region of the subject with a subject engaging portion of the device, thereby limiting a depth of insertion of the device into the subject's nasal channel and aligning the insertable portions within the nasal channel of the subject. In some embodiments, the method further comprises actuating the device by applying pressure to the subject engaging portion of the device with the columella region of the subject. In some embodiments, the method further comprises the two insertable portions comprise at least one dispensing element. In some embodiments, the method further comprises the at least one dispensing element reveals outwards from at least one of the two insertable portions. In some embodiments, the method further comprises transitioning the device from a first configuration to a second configuration, wherein the dispensing element reveals from the insertable portion upon transition of the device from the first configuration to the second configuration. In some embodiments, the method further comprises the inserting two insertable portions of a. advances the two insertable portions along the inner dorsum and/or on along either side of the septum until a columella engaging region of the device contacts a columella of the subject, preventing further insertion, and establishing a depth datum. In some embodiments, the method further comprises a dispensing port is positioned at a targeted region or subregion in the nasal cavity. In some embodiments, the method further comprises the inserting two insertable portions of a. uses the nasofrontal angle as an angular reference to position the insertable portions within the nasal channels.

In some embodiments, the method further comprises a dispensing port is positioned at a targeted region or subregion in the nasal cavity. In some embodiments, the method further comprises the inserting two insertable portions of a. advances the two insertable portions along the inner dorsum until a columella engaging region of the device contacts a columella of the subject, preventing further insertion, and establishing a depth datum, and wherein the inserting two insertable portions of a. uses the nasofrontal angle as an angular reference to position the insertable portions within the nasal channels, thereby positioning the two insertable portions within the nasal cavity at known position. In some embodiments, the method further comprises the inserting two insertable portions of a. comprises inserting the two insertable portions past a nasal vestibule. In some embodiments, the method further comprises the inserting two insertable portions of a. comprises inserting the two insertable portions along soft tissues of a superior cleft in an orientation parallel to the soft tissues. In some embodiments, the method further comprises the inserting two insertable portions of a. prevents rotation of the device about an axis parallel to the subject's height. In some embodiments, the method further comprises the inserting two insertable portions of a. creates a reference yaw angle a coronal plane relative to a y-axis of the device. In some embodiments, the method further comprises the inserting two insertable portions of a. creates a substantially unimpeded flow channel to an olfactory cleft. In some embodiments, the method further comprises the inserting two insertable portions of a. creates a substantially unimpeded flow to a nasal turbinate.

In one aspect, the disclosure provides a method for intranasal delivery to a subject with a device, the method comprising: positioning an insertable portion of the device within a nasal channel of the subject; and transitioning the device from a first configuration to a second configuration by applying pressure about a longitudinal axis of the device, thereby revealing a dispensing element from the first insertable portion and simultaneously actuating the device to deliver the composition to the subject. In some embodiments, the simultaneous actuation refers to transition for the first configuration to the second configuration and actuation occurring in a single motion upon application of pressure about a longitudinal axis of the device. In some embodiments, positioning the insertable portion of the device within the nasal channel of the subject occurs by engaging a columella region of the subject with a subject engaging portion of the device. In some embodiments, the method further comprises actuating the device by applying pressure to the subject engaging portion of the device with the columella region of the subject. In some embodiments, the method further comprises the positioning the insertable portion of the device within the nasal channel of the subject engages tissue within the nasal channel to open or expand an internal nasal valve of the subject, thereby positioning the insertable portion for delivery of a composition to the subject. In some embodiments, the insertable portion of the device comprises two insertable portions, each for insertion into a nasal channel of the subject, wherein a. comprises inserting two insertable portions into nasal channels of the subject. In some embodiments, the inserting two insertable portions of a. advances the two insertable portions along the inner dorsum and/or on along either side of the septum until a columella engaging region of the device contacts a columella of the subject, preventing further insertion, and establishing a depth datum. In some embodiments, the method further comprises the inserting two insertable portions of a. uses the nasofrontal angle as an angular reference to position the insertable portions within the nasal channels. In some embodiments, the method further comprises a dispensing port is positioned at a targeted region or subregion in the nasal cavity. In some embodiments, the method further comprises the inserting two insertable portions of a. advances the two insertable portions along the inner dorsum and/or on along either side of the septum until a columella engaging region of the device contacts a columella of the subject, preventing further insertion, and establishing a depth datum, and wherein the inserting two insertable portions of a. uses the nasofrontal angle as an angular reference to position the insertable portions within the nasal channels, thereby positioning the two insertable portions within the nasal cavity at known position. In some embodiments, the method further comprises the inserting two insertable portions of a. comprises inserting the two insertable portions past a nasal vestibule. In some embodiments, the method further comprises the inserting two insertable portions of a. comprises inserting the two insertable portions along soft tissues of a superior cleft in an orientation parallel to the soft tissues. In some embodiments, the method further comprises the inserting two insertable portions of a. prevents rotation of the device about an axis parallel to the subject's height. In some embodiments, the method further comprises the inserting two insertable portions of a. creates a reference yaw angle a coronal plane relative to a y-axis of the device. In some embodiments, the method further comprises the inserting two insertable portions of a. creates a substantially unimpeded flow channel to an olfactory cleft.

In one aspect, the disclosure provides a method for intranasal delivery of a composition to a target region of the nasal cavity of a subject, the method comprising: inserting a dispensing element into an ejection zone of a nasal cavity, wherein the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule, and one or more of the following: 0 mm to 40 mm inferior to a horizontal line that is parallel to the inferior aspect of the olfactory cleft, 0 mm to 20 mm posterior to the internal nasal dorsum, 10 mm and 50 mm superior to a horizontal line that intersects the inferior aspect of the columella, 0 mm to 30 mm superior to a horizontal line that intersects the superior aspect of the inferior turbinate, 0 mm to 3 mm from the septum, or any combination thereof, and dispensing the composition from the dispensing element to contact the target region with the composition, wherein dispensing the composition from the ejection zone: a) increases on target delivery of the composition to the target region, b) decreases off target delivery of the composition to the nasal cavity, or c) both. In some embodiments, the ejection zone is a trapezium or irregular quadrilateral comprising (i) an inferior side being a 10-25 mm line extending posteriorly and horizontally from the anterior aspect of the internal nasal valve, (ii) an anterior side being a 10-35 mm line extending superiorly and parallel to the internal nasal dorsum from the anterior aspect of the internal nasal valve, (iii) a superior side being a 10-25 mm line extending posteriorly and horizontally from a point on the internal nasal dorsum that is 0-10 mm inferior to the inferior aspect of the olfactory cleft, and (iv) a posterior line being a 10-35 mm line extending vertically along a plane that intersects the anterior aspect of the middle turbinate. In some embodiments, the target region is one or both olfactory clefts, or a sub-area thereof, and wherein dispensing the composition from an anterior end of the dispensing element increases on target delivery of the composition to the target region. In some embodiments, the target region is the middle meatus, and wherein dispensing the composition from a posterior end of the dispensing element increases on target delivery of the composition to the target region. In some embodiments, the ejection zone is further: parallel with a middle turbinate of the subject, and not within the middle meatus. In some embodiments, the ejection zone is in line with the olfactory cleft as defined by a linear vector between the olfactory cleft and the distal end of the insertable portion. In some embodiments, the target region is one or both olfactory clefts, or a sub-area thereof.

The devices and methods of the present disclosure provide several advantages over existing intranasal drug delivery devices. For example, the device is easy to use and provides precise, consistent, and effective drug delivery. Additionally, the device is capable of accurately delivering drugs to the target site within the nasal channel, resulting in several therapeutic benefits, for example, reduced drug loss, improved comfort, greater compliance, improved subject experience, and improved therapeutic outcomes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings.

FIG. 6H depicts an exemplary embodiment of an Exemplary Device along a side view of the sagittal plane aiming from the respiratory region in the subject, according to some embodiments.

FIGS. 14A-14C, show images of an exemplary nasal cavity of a subject during pre-ejection (left), during ejection (middle) and post-ejection (right) of a composition with the exemplary device from varying front angles from a position of a −10 degree angle towards the center of the nasal cavity, and illustrates that dispensing a composition from outside the ejection zone in this position prevents deposition of the composition to a target region.

FIGS. 14D-14F, show images of an exemplary nasal cavity of a subject during pre-ejection (left), during ejection (middle) and post-ejection (right) of a composition with the exemplary device from varying front angles from a position where the angle is 0 degrees from the center of the nasal cavity, and illustrates that dispensing a composition from outside the ejection zone in this position prevents deposition of the composition to a target region.

FIGS. 14G-14I, show images of an exemplary nasal cavity of a subject during pre-ejection (left), during ejection (middle) and post-ejection (right) of a composition with the exemplary device from varying front angles from a position where the angle is increased 15 degrees from the center of the nasal cavity, and illustrates that dispensing a composition from this position prevents proper deposition of the composition to a target region, and shows a partial deposition failure with most of the composition missing the target region.

FIGS. 14J-14L, show images of an exemplary nasal cavity of a subject during pre-ejection (left), during ejection (middle) and post-ejection (right) of a composition with the exemplary device from varying front angles from a position where the angle is increased 30 degrees from the center of the nasal cavity, and illustrates that dispensing a composition from this position prevents proper deposition of the composition to a target region, and shows a partial deposition failure with most of the composition missing the target region.

DETAILED DESCRIPTION

Figure 1A:
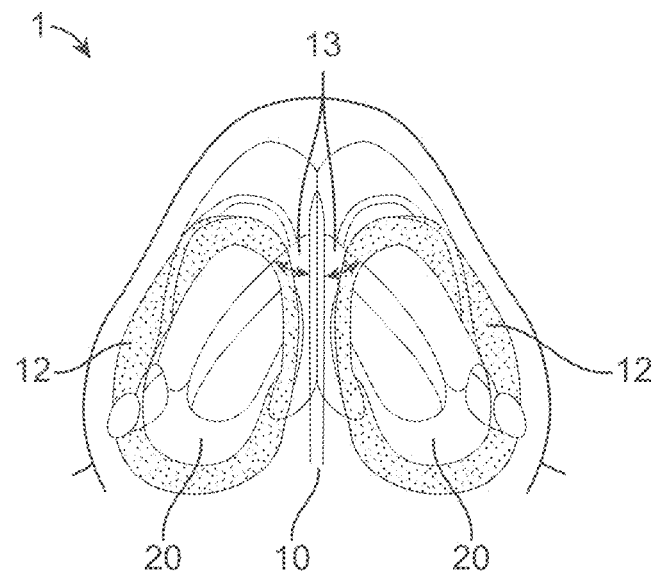
FIG. 1A depicts a bottom view of an exemplary embodiment of a subject's nose.

The nasal cavity is comprised of a nasopharyngeal region and two nasal channels, separated by the septum, each comprising a vestibule, a respiratory region, and an olfactory cleft. It is appreciated by the inventors that there are a number of difficulties in facilitating intranasal delivery of therapeutic compositions including anatomical, cognitive, and dexterity related challenges depending on the subject population. For example, the internal nasal valve is a flow-limiting segment of the nasal channel bounded medially by the dorsal septum, laterally by the caudal portion of the upper lateral cartilage and inferiorly by the head of the inferior turbinate that together present a physical barrier between the nasal vestibule and the rest of the nasal channel, including the respiratory region and the olfactory cleft. The internal nasal valve is bounded by nasal tissue that can swell or block the path to the nasal channel, which varies based on time of day, environmental factors, and genetically among individuals. Devices may need to be inserted at particular angles or depths in order to target a specific area, and users may struggle with correct placement and actuation of a device. Users with motor skill impairment (e.g., persons with Parkinson's disease, arthritis) or cognitive impairments (e.g., Alzheimer's disease) may especially struggle to correctly articulate, position, and actuate an intranasal delivery device.

To counter such difficulties, this disclosure provides a novel introducer device for targeted delivery of a composition to a target region of a nasal cavity of a subject, which can readily actuated and positioned by users of various patient populations, and reliability deliver the composition to the target region of the nasal cavity. Exemplary devices utilize a dual nostril inserter with a columella engaging portion positioned therebetween in order to quickly and reliable seat the insertable portions of the device with a ejection zone of a subject's nasal cavity. The exemplary devices disclosed herein can permit for quick, easy, and reliable positioning of a dispensing element within the nasal channel so as to permit for accurate and targeted deposition of compositions to target regions of the nasal cavity. Further, exemplary devices disclosed herein can enable quick, easy, and reliable positioning and targeted deposition across diverse patient populations (e.g., users that are elderly, cognitively impaired, dexterity impaired, or have variations in nasal anatomy), by users of varying skill (e.g., untrained bystanders), under high stress circumstances (e.g., a medical emergency medical), which may otherwise prevent proper use of intranasal delivery devices The devices of the present disclosure may comprise a subject engaging portion that engages a columella region of a subject and one or more insertable portions that open or expand one or both internal nasal valves of a subject, with the subject engaging portion thereby properly positioning either one or more insertable portions, or one or more dispensing elements of the device, within an ejection zone for targeted delivery of a composition to one or more specific areas of the nasal cavity, such as one or both olfactory clefts, one or both middle meatuses, or one or both middle turbinates. The subject engaging portion can engage the columella region about one or both sides of the columella region, may comprise a saddle or concave shape, and may slide onto the columella region such that the device uses the columella region as a depth datum and the nasal dorsum line as an angular reference for positioning the insertable portions and/or dispensing elements at a desired depth and orientation within the ejection zone. Such a subject engaging portion utilizing the columella region as a depth datum and the nasal dorsum line as an angular reference, can permit for the placement of the device, and dispensing of a composition there from, to a targeted area of one or both nasal cavities in a reproduceable manner across a population of subjects. For example, subjects of differing anatomy, backgrounds, cognitive abilities, and motor skills may be able to position the device in approximately the same position within one or both nasal channels. The columella region and the nasal dorsum line can position the introducer device to achieve precise and consistent positioning of either one or both insertable portions and/or one or both dispensing elements within one or both nasal channels. By relying on the columella region and the nasal dorsum line, a reliable reference point is established that can be used across different populations and anthropometric variances. This eliminates the need for subject-specific tuning or measurements, making the process more efficient, accurate, cost-effective, and user friendly. The subject engaging portion may comprise or be coupled to an actuator, trigger, or both which actuates or permits the device to be actuated and dispense a composition when pressure is applied to the user's columella region by the subject engaging portion or when pressure is applied to the subject engaging portion by the user's columella. The devices of the present disclosure may further comprise one or more insertable portions which are inserted into one or both nasal channels of a subject and open or expand one or both internal nasal valves by pushing the upper lateral cartilage and surrounding tissue up and away from the septum and define a path through which the composition can be delivered to one or more target areas of one or both of the subject's nasal channels such as one or both olfactory clefts, the meatuses, e.g., the middle meatus, or one or both middle turbinates.

The one or more insertable portions may travel along the nasal channel advancing along the inner nasal dorsum and the septum until the subject engaging portion contacts the columella region. The one or more insertable portions may use the columella region as a depth datum and the nasal dorsum line as an angular reference. The one or more insertable portions may align with the nasal dorsum line. The one or more insertable portions may be configured to follow the shape of inner nasal dorsum, and lateral aspects of the septum, allowing them to maintain a consistent and repeatable angle on a sagittal plane. The form of the one or more insertable portions may be configured to hold them to, and guide them along, the soft tissues of the inner nasal dorsum, ensuring that they remain parallel to these tissues. The device may further comprise one or more dispensing elements that emerge from or are revealed by the one or more insertable portions when the device is transitioned from a first position to a second position (e.g., from a first configuration to a second configuration).

Such features may serve to permit for the design of a universal intranasal delivery device that is usable across a wide variety of subject populations and anthropometric variances. For example, using the columella region and the nasal dorsum as a datum to position the one or more insertable portions within the subject's nasal channels achieves precise and consistent positioning of the insertable portions and the dispensing elements within the nasal cavity. Further, in some cases, when the device comprises, a trigger coupled to the subject engaging portion which is actuated by applying pressure to the columella region with the subject engaging portion, it permits for an easy administration of a composition to one or more nasal channels without the user having to use a digit to actuate the device or the user having to be concerned with the proper alignment or insertion depth of the device within the nasal channels. Such easy administration permitted by the devices of the present disclosure may enable subjects with limited cognitive abilities (e.g., dementia subjects), subjects with limited motor skills (e.g., arthritis subjects), or users in high stress situations (e.g., paramedics, medical personnel, or untrained bystanders treating an overdose victim) to reliably, conveniently, and quickly make use of the targeted intranasal delivery devices disclosed herein to accurately and reliably deliver a composition to a target region of a nasal cavity. Similarly, the one or more insertable portions can align closely with the septum preventing the one or more dispensing elements that extend therefrom or are revealed thereby from snagging or catching on tissue within the nasal channels, while also pushing away hair in the nasal channels and minimizing the likelihood of a sneeze reflex that may negatively impact administration. In some cases, the one or more insertable portions that enable comfortable and accurate insertion into and past the internal nasal valve by moving the upper lateral cartilage up and away from the septum—as needed depending on user anatomy and conditions, can permit for highly targeted delivery to the olfactory clefts, the meatuses, e.g., the middle meatus, the turbinates, or other regions of the nasal anatomy, with one or more dispensing elements that extend from or are revealed by one or more insertable portions in the direction of the olfactory clefts, the meatuses, e.g., the middle meatus, the turbinates, or other regions of the nasal anatomy, thereby enabling accurate delivery of a composition to the olfactory clefts, the meatuses, e.g., the middle meatus, the turbinates, or other regions of the nasal anatomy, and from there access to the CNS through various pathways.

Embodiments of the present disclosure include an intranasal drug delivery device with a housing comprising one or a combination of the following: a subject engaging portion, one or more insertable portions, one or more dispensing elements, and a trigger. The subject engaging portion engages the columella region of a subject with a columella saddle to seat the distal end of the insertable portion within an ejection zone of a nasal channel of the subject, allowing for accurate positioning of the device in one or both nasal channels, wherein the ejection zone 29 is: 0 mm to 30 mm superior to a horizontal line 624 that intersects the anterior aspect of the internal nasal valve, and 0 mm to 20 mm anterior to an inclined line that intersects the anterior aspect of the middle turbinate and the posterior aspect of the vestibule. The one or more insertable portions move the upper lateral cartilage up and away from the septum of a subject's nasal channels, allowing a composition, upon actuation of the device, to be accurately delivered from the one or more insertable portions to one or more targeted areas in the nasal channels such as the olfactory clefts, the meatuses, e.g., the middle meatus, or the middle turbinates. The one or more dispensing elements, either independently or upon being extended from or revealed by one or more insertable portions, deliver a composition, upon actuation of the device, accurately to one or more areas of the nasal channels such as the olfactory clefts, the meatuses, e.g., the middle meatus, or the middle turbinates. The trigger actuates the device, either by the subject applying pressure on the subject engaging portion against the columella region, or by the subject directly applying pressure to a trigger release.

As used herein composition may include therapeutic compounds (small and large molecules), medicaments in liquid, powder, or gas form, or a combination thereof, or sampling fluids. The columella region comprises the columella, a subnasale, or an anterior nasal spine, or a combination thereof. A dispensing element comprises a cannula or a catheter, an insertable portion, a syringe, a fluid chamber, or a combination thereof, or anything that acts upon the cannula or the catheter, the syringe, or the fluid chamber. In some embodiments, the end of the dispensing element is coextensive with the end of the insertable portion when the device is fully actuated.

Figure 1B:
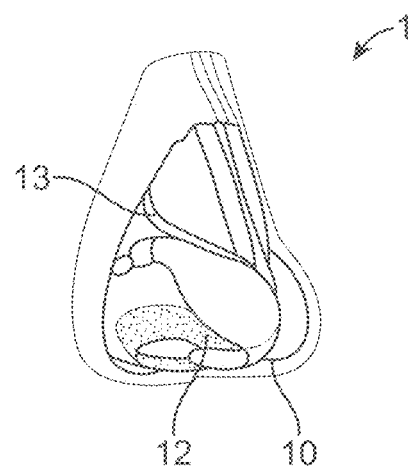
FIG. 1B depicts a side view of an exemplary embodiment of a subject's nose.

FIG. 1A depicts a bottom view of an exemplary embodiment of a subject's nose. FIG. 1B depicts a side view of an exemplary embodiment of a subject's nose. In some embodiment's the nose 1 has a columella region 10 between the entrance to two nasal channels 20. In some embodiments, the nose 1 has an external nasal valve 12 coupled to the nasal channel 20. In some embodiments, the nose 1 has an internal nasal valve 13 (INV) coupled to the nasal channel 20.

Figure 1C:
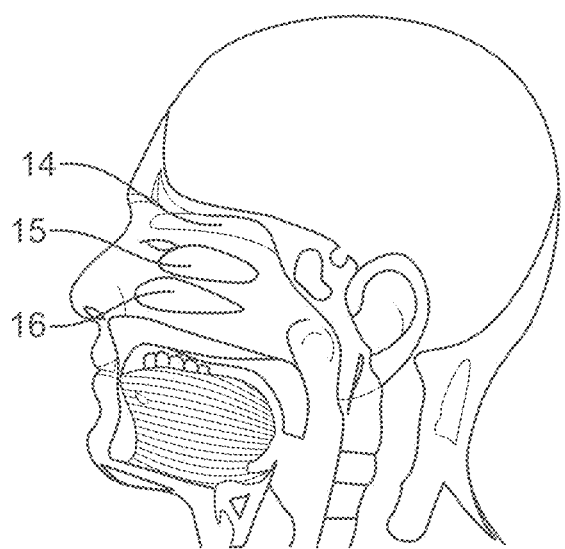
FIG. 1C depicts a side view of a side view of a representation subject's nasal channel.
Figure 1D:
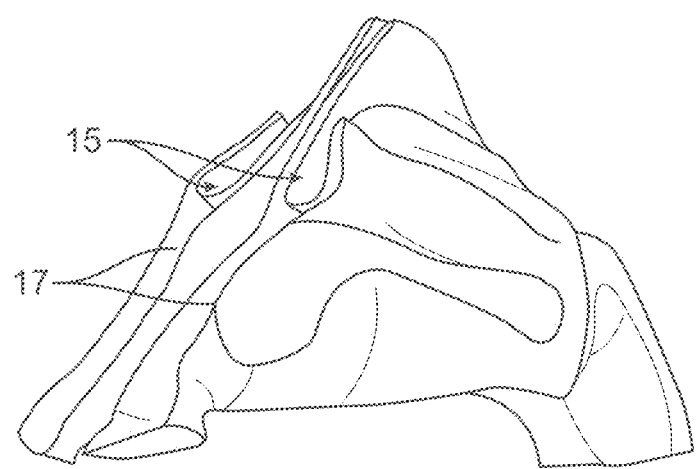
FIG. 1D depicts a side view of an exemplary embodiment of a representation subject's nasal channels from the vestibule to the olfactory cleft based on a posteriorly oriented plane.
Figure 1E:
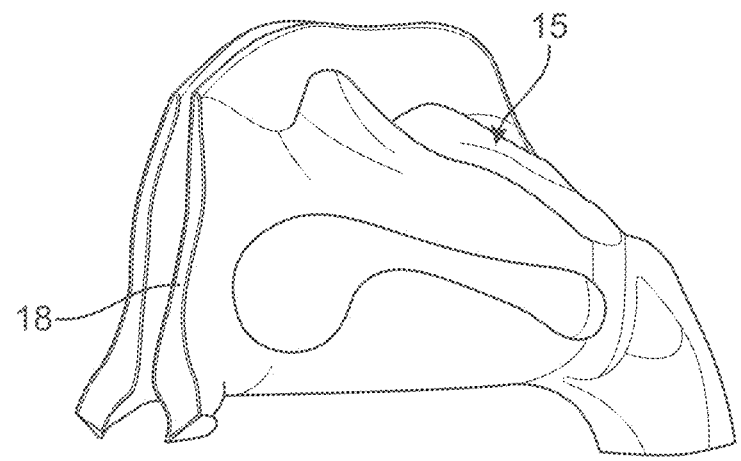
FIG. 1E depicts a side view of an exemplary embodiment of a representation subject's nasal channels from the vestibule to the olfactory cleft based on an anteriorly oriented plane.
Figure 1F:
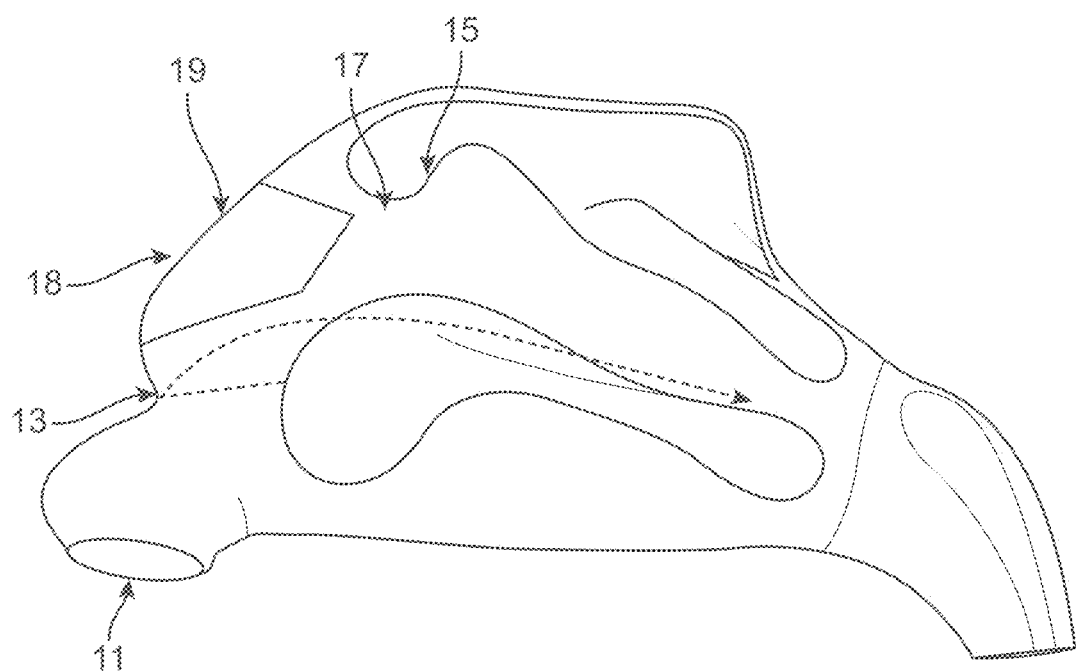
FIG. 1F depicts a side view of an exemplary embodiment of a representation a ejection zone, according to some embodiments.
Figure 1G:
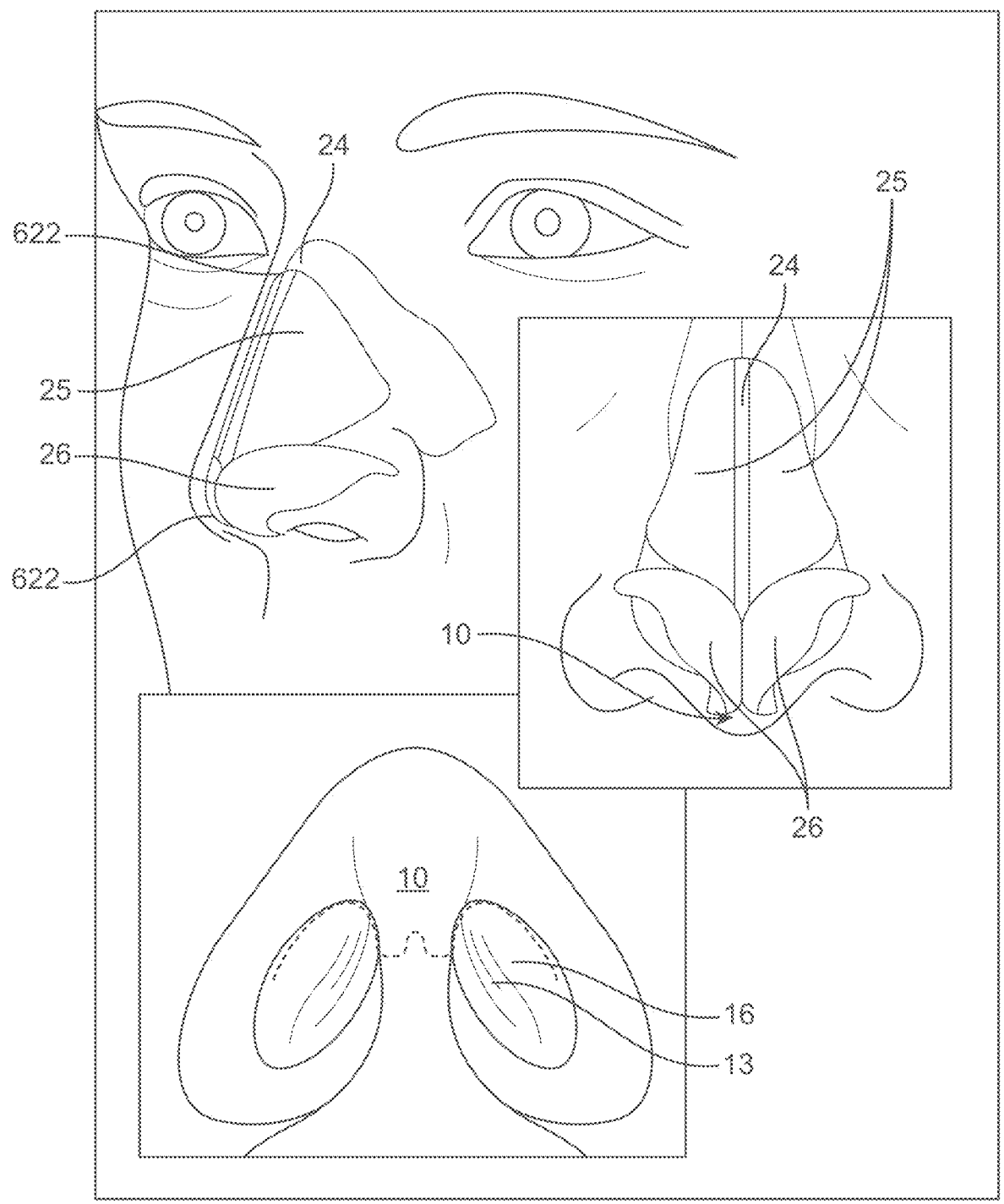
FIG. 1G depicts a front, base and perspective view of an exemplary embodiment of a subject's nose and the columella region.

FIG. 1C depicts a side view of an exemplary embodiment of a subject's nasal cavity showing an inferior turbinate 16, a middle turbinate 15, and a superior turbinate 14. FIG. 1D depicts an angled side view of an exemplary embodiment of a representation subject's nasal channels 20 from the vestibules 21 to the olfactory clefts 23 based on a first plane intersecting at least one posterior pathway 17 showing the middle turbinates 15. FIG. 1E depicts an angled side view of an exemplary embodiment of a representation subject's nasal channels 20 from the vestibules to the olfactory clefts based on a second plane intersecting at least one anterior pathway 18. FIG. 1F depicts a side view of an exemplary embodiment of a representation subject's target ejection area 19. FIG. 1G depicts a front, base and perspective view of an exemplary embodiment of a representation subject's nose exposing the columella region 10. The respiratory regions comprise turbinates that present physical obstacles to delivery to the upper reaches of a nasal channels 20, e.g., the olfactory clefts 23. Each respiratory region comprises at least one superior turbinate 14. Each respiratory region comprises at least one middle turbinate 15. Each respiratory region comprises at least one inferior turbinate 16. Each respiratory region comprises at least one posterior pathway 17 that involves at least one middle turbinate 15. Each respiratory region comprises at least one anterior pathway 18 that does not involve at least one middle turbinate 15.

In some cases, the middle turbinate 15 comprises a physical obstruction for composition delivery to an olfactory cleft. In some cases, the middle turbinate 15 comprises a most anterior aspect about aligned with the cheek bone. In some embodiments, the middle turbinate 15 comprises a most anterior aspect not aligned with the cheek bone. In some cases, the nasal channels 20 simplify anteriorly, and comprise angled pathways without one or more turbinates presenting physical obstacles to delivering a composition 111 to the upper nasal channels, including the olfactory clefts 23, or directing compositions 111 down one or more meatuses, e.g., the middle meatus 30, to the nasopharynx. In some cases, the nasal channel 20 comprises one pathway from the vestibule 21 to the olfactory cleft 23 based on a second plane 18 with a target region 19. In some embodiments, the nose comprises the nasal septum 24, upper lateral cartilage 25, and lower lateral cartilage 26.

Figure 1H:
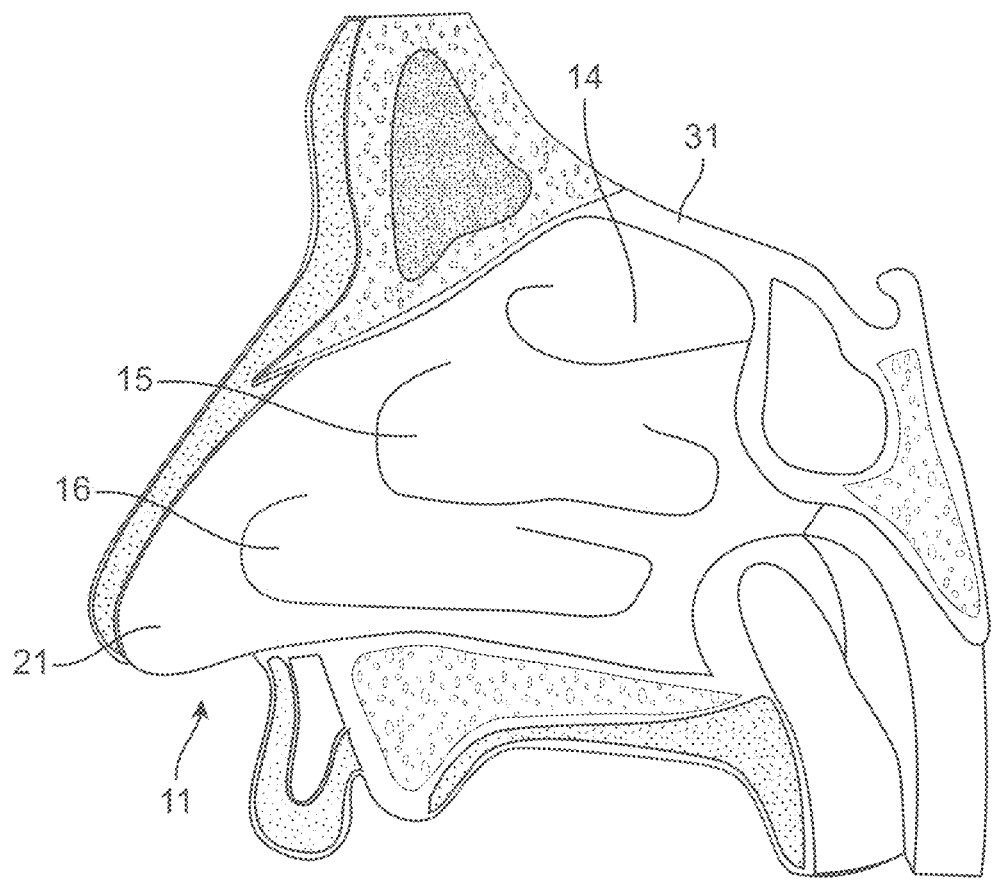
FIG. 1H depicts a side view of an exemplary embodiment of a representation subject's nasal cavity, including internal anatomical features.

FIG. 1H depicts a side view of an exemplary embodiment of a representation subject's nasal cavity. In some cases, the subject's nasal cavity 11 comprises the nasal vestibule 21, inferior turbinate 16, middle turbinate 15, superior turbinate 14, cribriform plate 31 or a combination thereof.

Figure 1I:
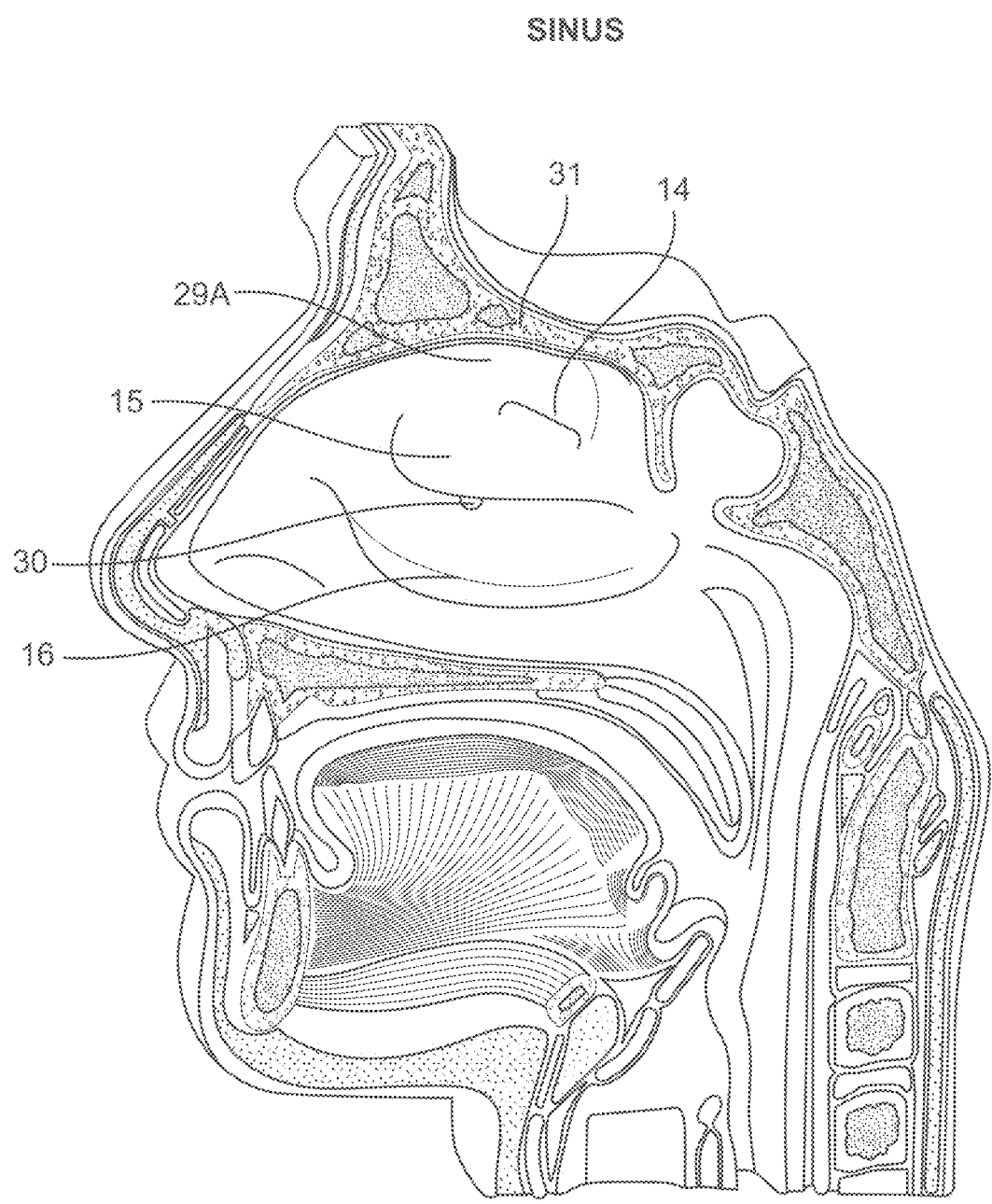
FIG. 1I depicts a side view of an exemplary embodiment of a representation subject's sinus, according to some embodiments.
Figure 1J:
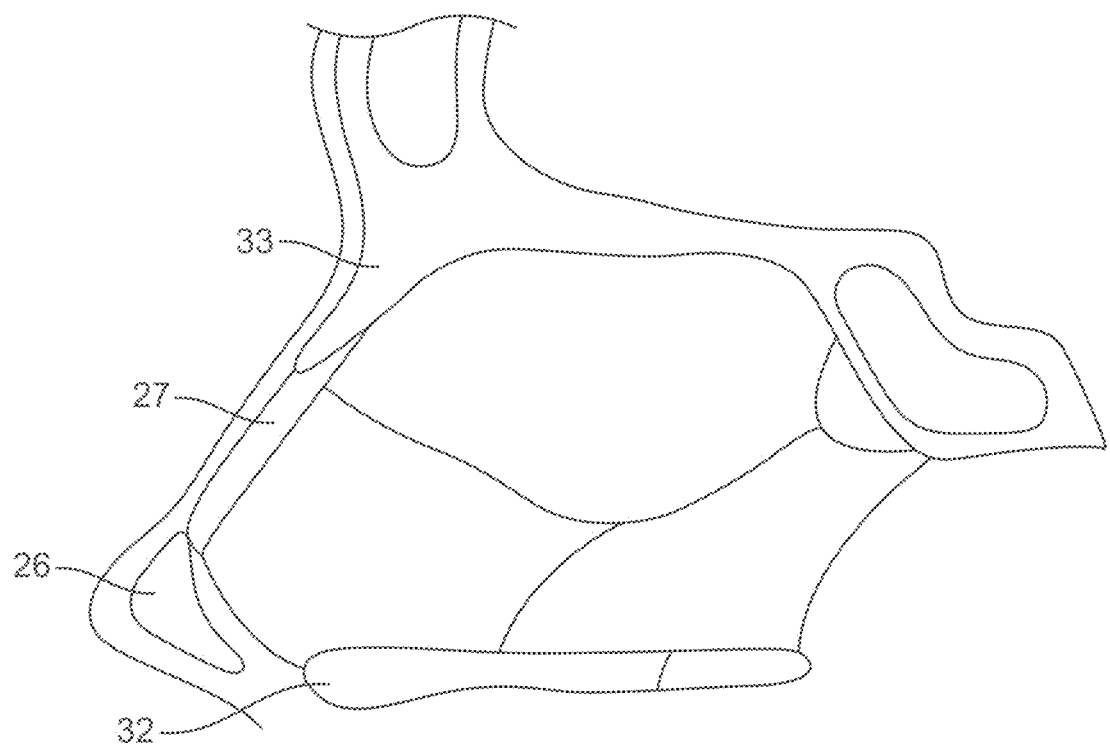
FIG. 1J depicts a side view of a subject's nasal cavity.

FIG. 1I depicts a side view of an exemplary embodiment of a representation subject's sinus. In some cases, the subject's sinus comprises the inferior turbinate 16, middle turbinate 15, superior turbinate 14, cribriform plate 31, middle meatus 30, or a combination thereof FIG. 1J depicts a side view of an exemplary embodiment of a representation subject's nasal cavity. In some embodiments, the nasal cavity 11 comprises the nasal bone 33, septal-lateral cartilage junction 27, lower lateral cartilage 26, anterior nasal spine 32, or a combination thereof.

Figure 2A:
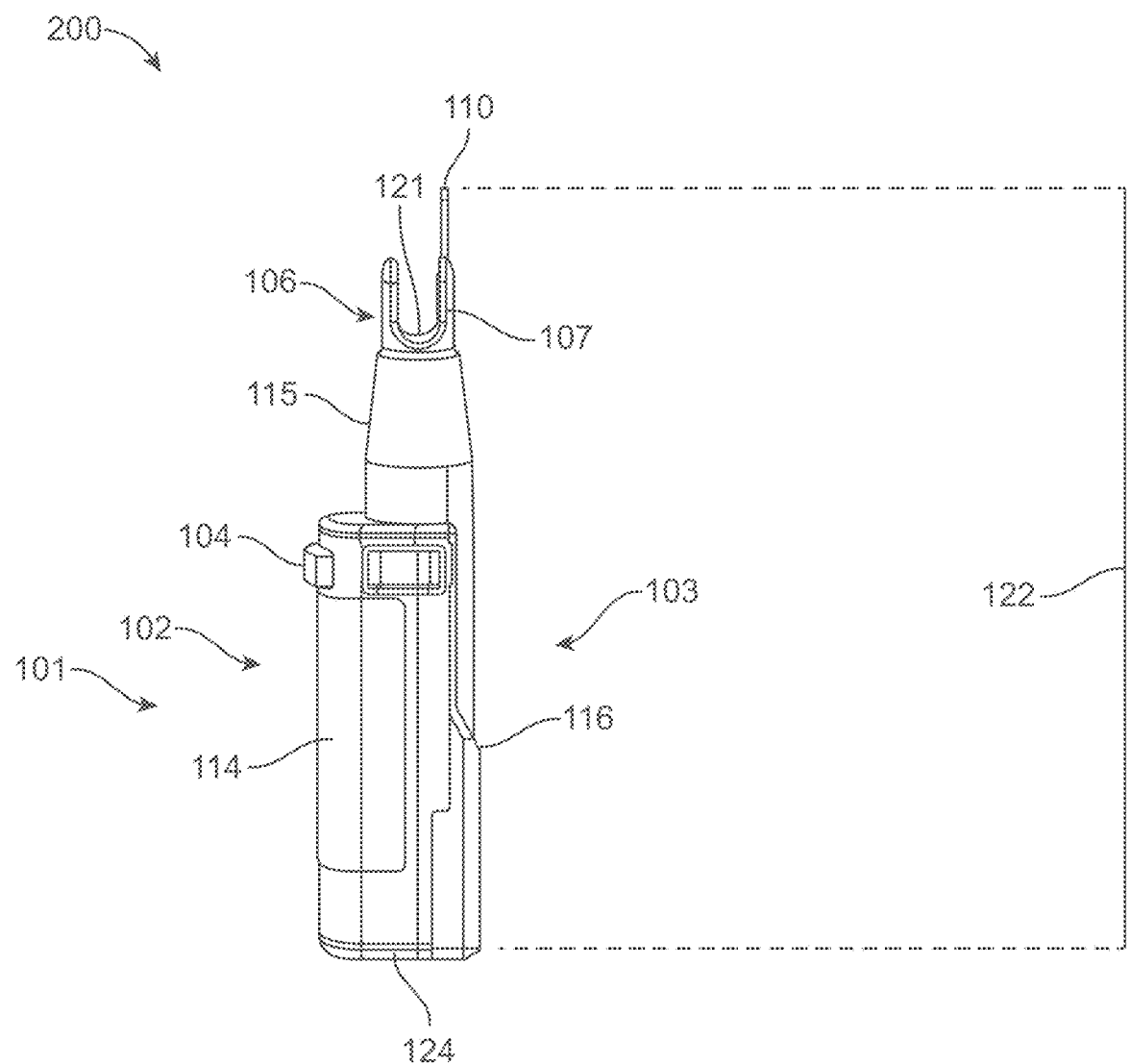
FIG. 2A depicts an exemplary embodiment of an Exemplary Device in a second configuration, according to some embodiments.
Figure 2B:
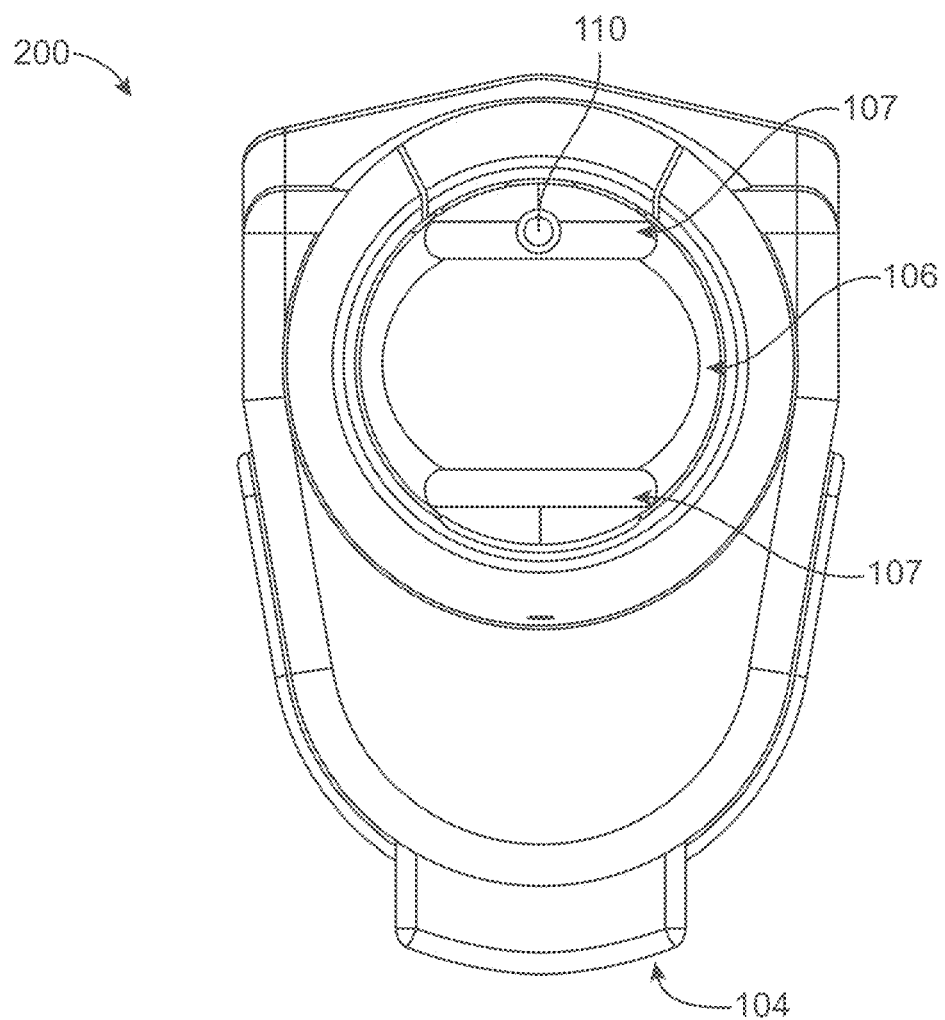
FIG. 2B depicts an exemplary embodiment top view of an Exemplary Device in the second configuration, according to some embodiments.
Figure 2C:
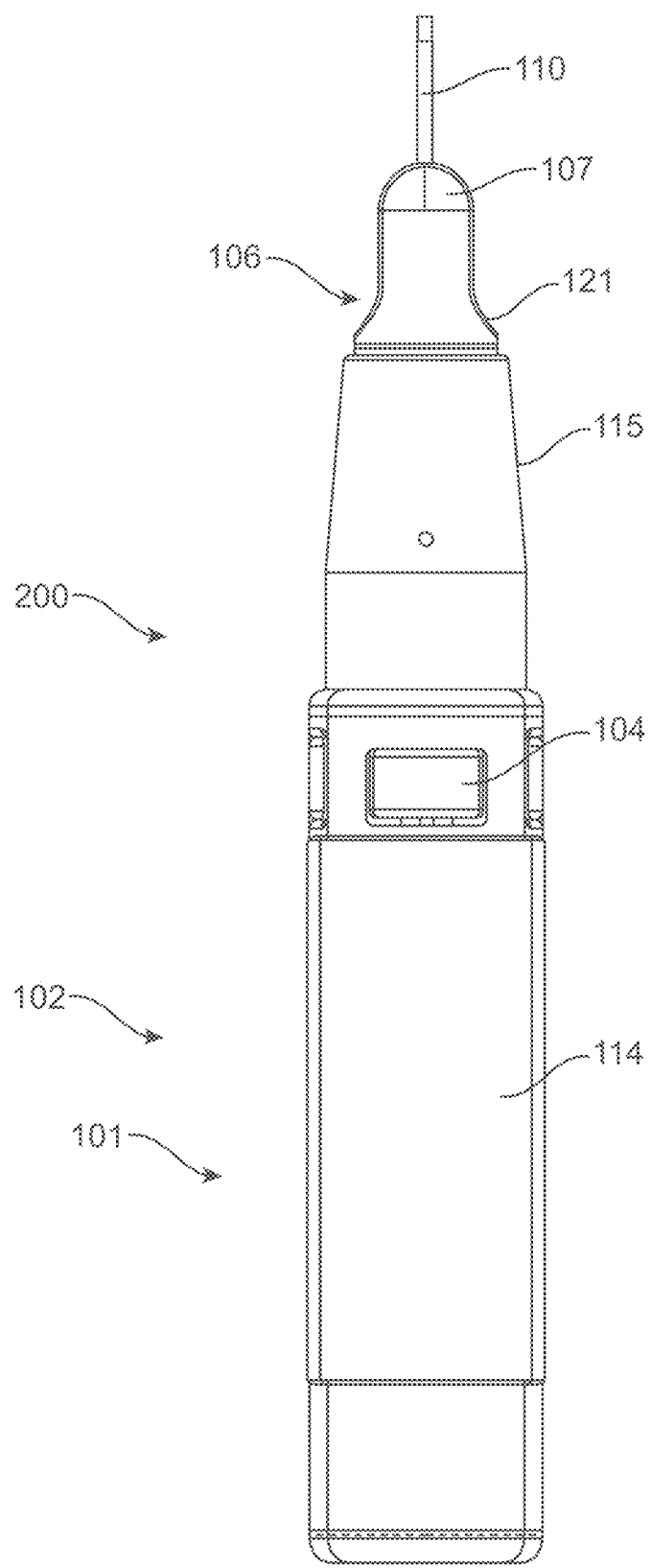
FIG. 2C depicts an exemplary embodiment trigger release side view of an Exemplary Device in the second configuration, according to some embodiments.
Figure 2D:
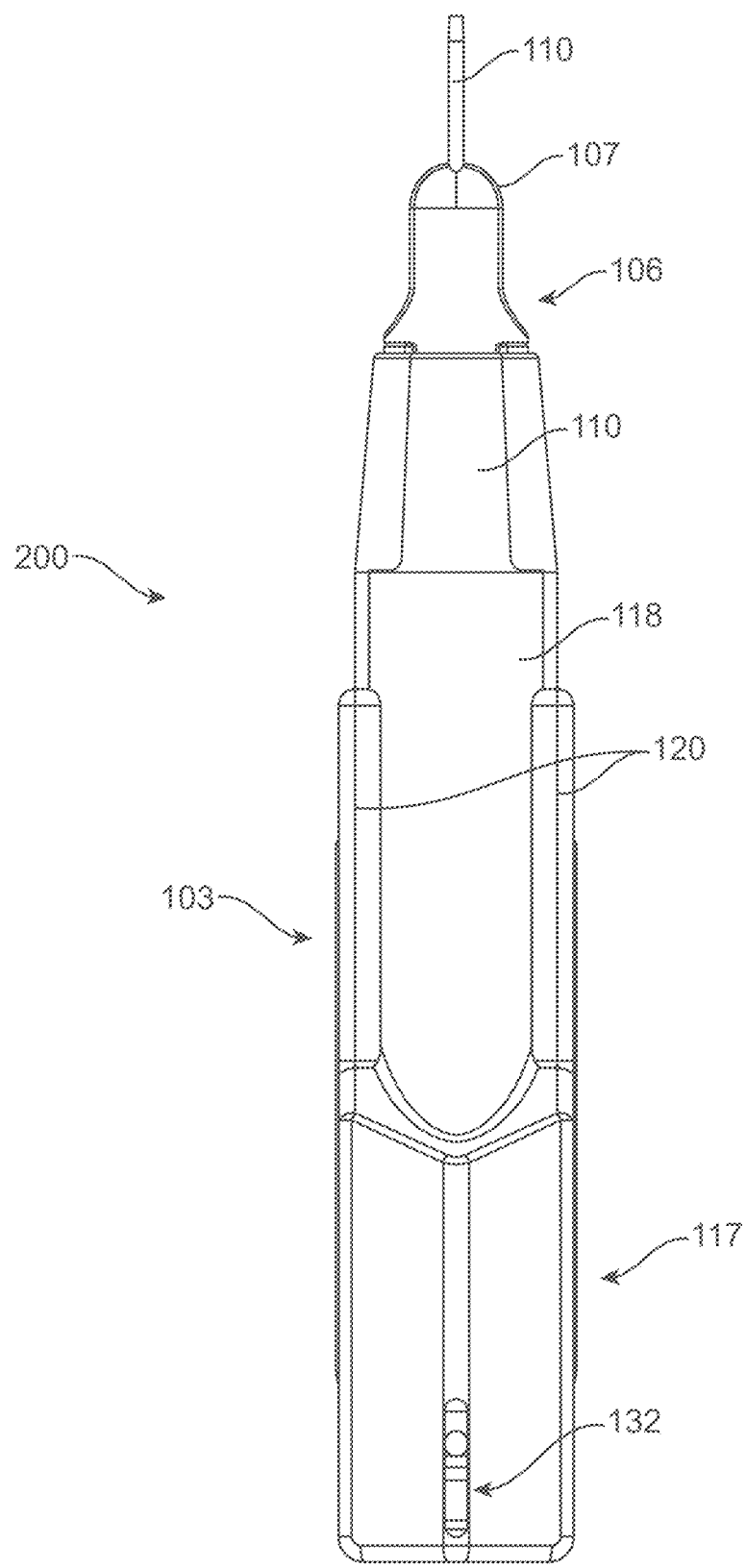
FIG. 2D depicts an exemplary embodiment chassis side view of an Exemplary Device in the second configuration, according to some embodiments.
Figure 2E:
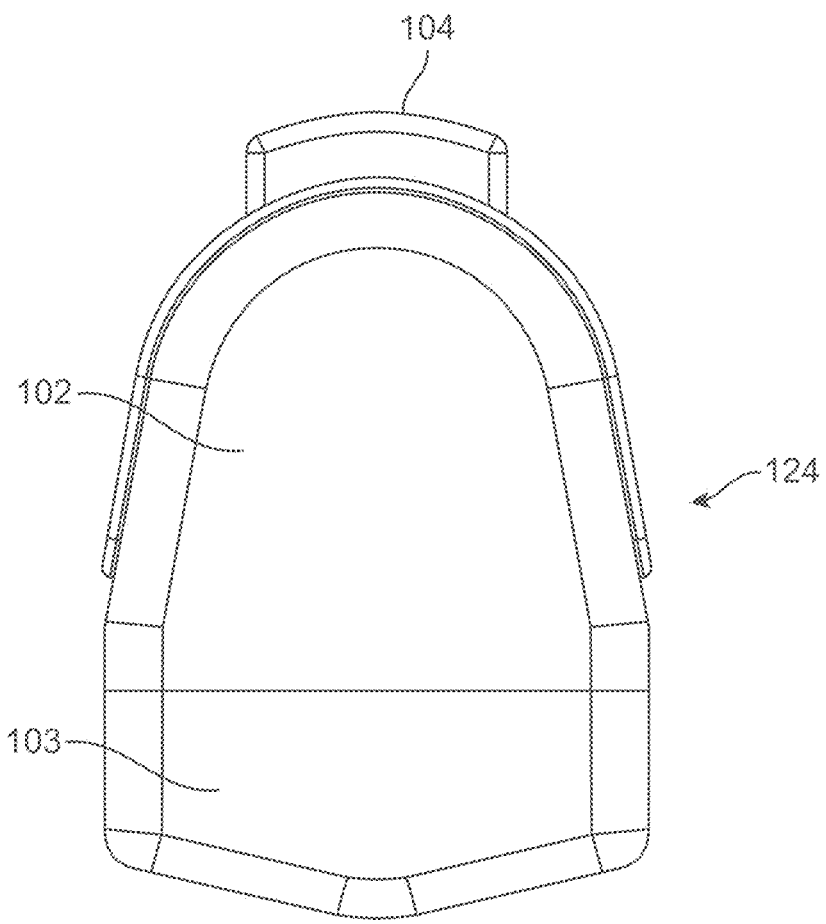
FIG. 2E depicts an exemplary embodiment bottom view of an Exemplary Device in the second configuration, according to some embodiments.
Figure 2F:
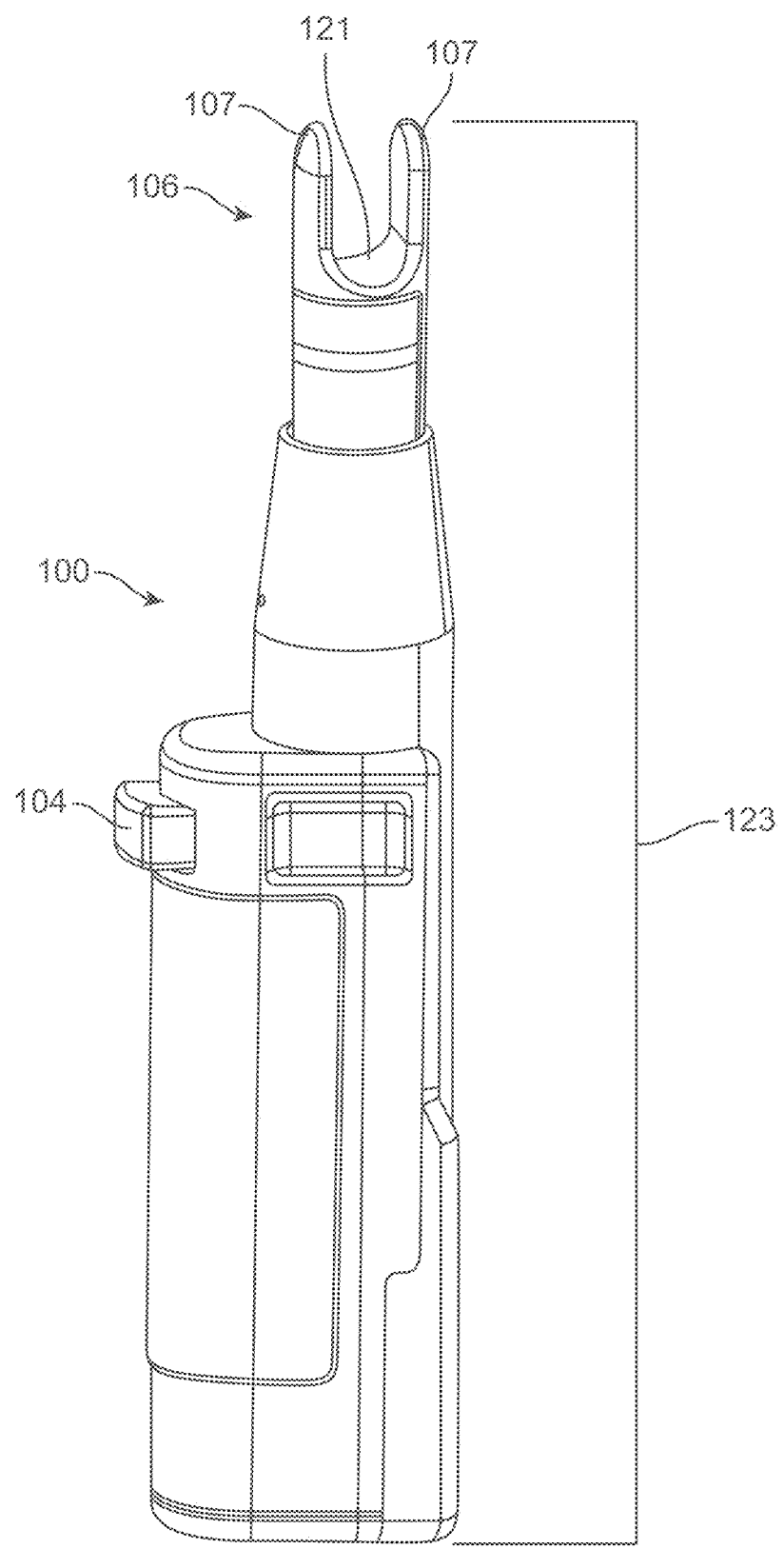
FIG. 2F depicts an exemplary embodiment perspective view of an Exemplary Device in the first configuration, according to some embodiments.

FIG. 2A depicts an exemplary embodiment of the Exemplary Device in a second configuration. FIG. 2B depicts a top view of the Exemplary Device in the second configuration. FIG. 2C depicts a trigger release side view of the Exemplary Device in the second configuration. FIG. 2D depicts a chassis side view of the Exemplary Device in the second configuration. FIG. 2E depicts a bottom view of the Exemplary Device in the second configuration. FIG. 2F depicts an exemplary embodiment of the Exemplary Device in a first configuration.

Referring to FIGS. 7A-7E, in some embodiments, the subject engaging portion 106 limits a depth of insertion of the insertable portion 107 into the nasal channel 20. In some embodiments, the insertable portion 107 incorporates one or more dispensing channels 125 leading to one or more dispensing ports 126 configured for delivery of a composition 111 to one or more regions or sub-regions of the nasal channel 20 of the subject. In some embodiments, the insertable portion 107 comprises a dispensing element 110 for delivery of a composition 111 to a region or sub-region of the nasal channel 20 of the subject. In some embodiments, wherein the housing 101 comprises a trigger, upon application of pressure to the trigger, the trigger actuates the device to dispense a composition 111 to the subject from the insertable portion 107 or the dispensing element 110. In some embodiments, the subject engaging portion 106 comprises a trigger coupled to the housing 101 and the subject engaging portion 106, and upon application of pressure of the subject engaging portion 106 to the columella region 10, the trigger actuates the device to dispense a composition 111 to the subject from the insertable portion 107 or the dispensing element 110. In some embodiments, the subject engaging portion 106 comprises a trigger release 104 coupled to the housing 101 and the subject engaging portion 106, and upon application of pressure of the subject engaging portion 106 to the columella region 10, the trigger release 104 permits actuation of the device to deliver a composition 111 to the subject from the insertable portion 107 or the dispensing element 110. In some embodiments, the device further comprises a trigger which is actuatable upon engagement of the trigger release 104. In some embodiments, wherein the housing 101 defines two insertable portions 107, each for insertion into a nasal channel 20 of the subject, wherein, upon insertion of the first insertable portion 107 into a nasal channel 20 of the subject, the first insertable portion 107 engages tissue within the nasal channel 20 to open or expand an internal nasal valve 13 of the subject thereby positioning at least one of the insertable portions 107 for delivery of a composition 111 to the subject within the ejection zone. The device can further include an actuator which delivers a composition 111 from the either or both of the insertable portions 107 when the device is actuated. In some embodiments, wherein the housing 101 defines two insertable portions 107, each for delivery of a composition 111 into a nasal channel 20 of the subject, the device further comprising an actuator which delivers the composition 111 from either or both of the insertable portions 107 when the device is actuated. In some embodiments, wherein the device is transitionable from a first configuration 100 to a second configuration 200, the device further comprising one or two dispensing elements 110 coupled to the insertable portion 107, the at least one dispensing element 110 revealing from the at least one insertable portion 107 upon transition of the device from the first configuration 100 to the second configuration 200.

In some embodiments, the device is transitionable from the first configuration 100 to the second configuration 200 upon application of pressure about a longitudinal axis 610 of the device, wherein the at least one dispensing element 110 reveals in a linear vector relative to a longitudinal axis 610 of the at least one insertable portion 107, or wherein the device is configured to be transitioned from the first configuration 100 to the second configuration 200 with only one hand. In some embodiments, the device is simultaneously actuated upon being transitioned from the first configuration 100 to the second configuration 200. In some embodiments, the distal aspect 131 of the at least one dispensing element 110 is positioned in the ejection zone 29 when the device is in the second configuration 200.

In one aspect, the disclosure provides a device for intranasal delivery to a subject, the device comprising: a housing 101 comprising a dispensing element 110; a subject engaging portion 106 coupled to the housing 101, wherein the subject engaging portion 106 engages a columella region 10, wherein the subject engaging portion 106 positions a dispensing element 110 within a nasal channel 20 of the subject and limits a depth of insertion of a delivery element 111 into the nasal channel 20. In some embodiments, the subject engaging portion 106 comprises a columella saddle 121, wherein the columella saddle 121 comprises a "U" or "saddle" shape adapted for engaging the columella region 10 of a subject. In some embodiments, the device comprises at least one insertable portion 107. In some embodiments, the device comprises two insertable portions 107, each for insertion into a nasal channel 20 of the subject. In some embodiments, the subject engaging portion 106 engages the columella region 10 of the subject about multiple sides of the columella region 10 in a concave shape. In some embodiments, the at least one dispensing element 110 emerges from or is revealed by the at least one insertable portion 107 upon transition of the device from the first configuration 100 to the second configuration 200. In some embodiments, the housing 101 defines an external shell of the device. In some embodiments the housing comprises a first portion 102, wherein the first portion 102 defines part of the outer shell of the device. In some embodiments, the device comprises a trigger release 104. In some embodiments, the trigger release 104 actuates the ejection mechanism, which in turn delivers a composition 111 from the device. In some embodiments, the trigger release 104 engages an actuation mechanism, which in turn actuates the composition 111 ejection mechanism. In some embodiments, the trigger release 104 may comprise safety or locking mechanisms. In some embodiments, the device is actuated by the user application of force onto the trigger release 104. In some embodiments, the user may use any digit to actuate the device.

Figure 2G:
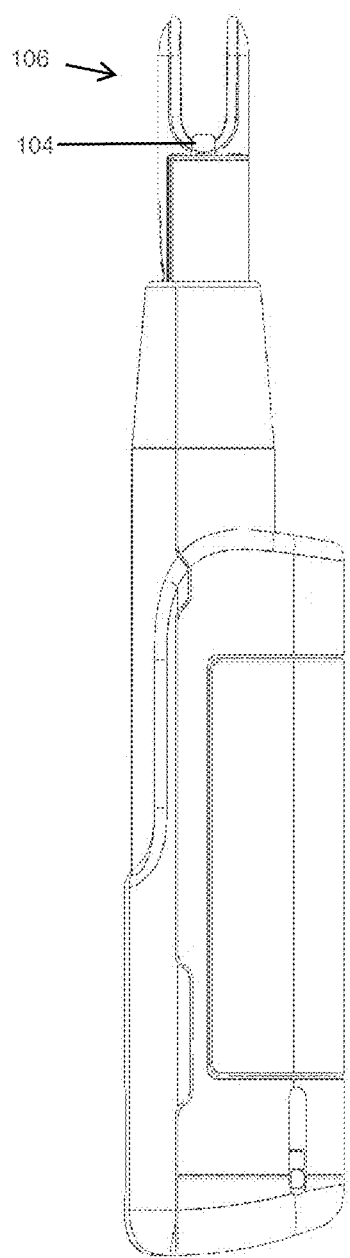
FIG. 2G depicts an exemplary embodiment front view of another Exemplary Device in the first configuration, according to some embodiments.
Figure 2H:
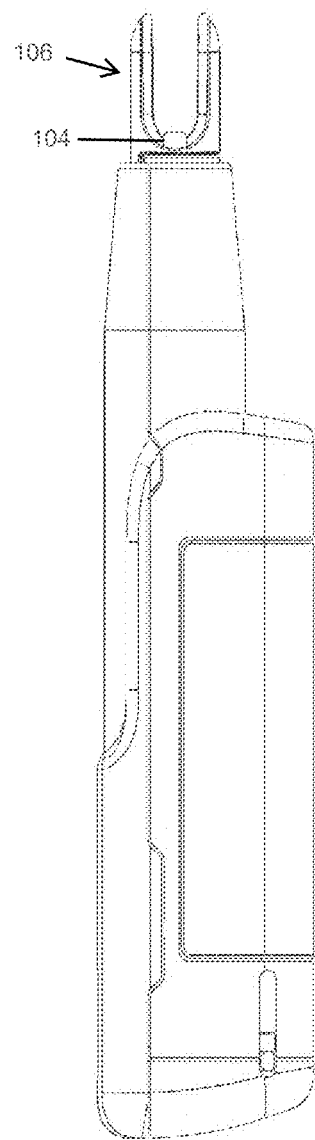
FIG. 2H depicts an exemplary embodiment front view of an Exemplary Device in the second configuration, according to some embodiment.
Figure 2I:
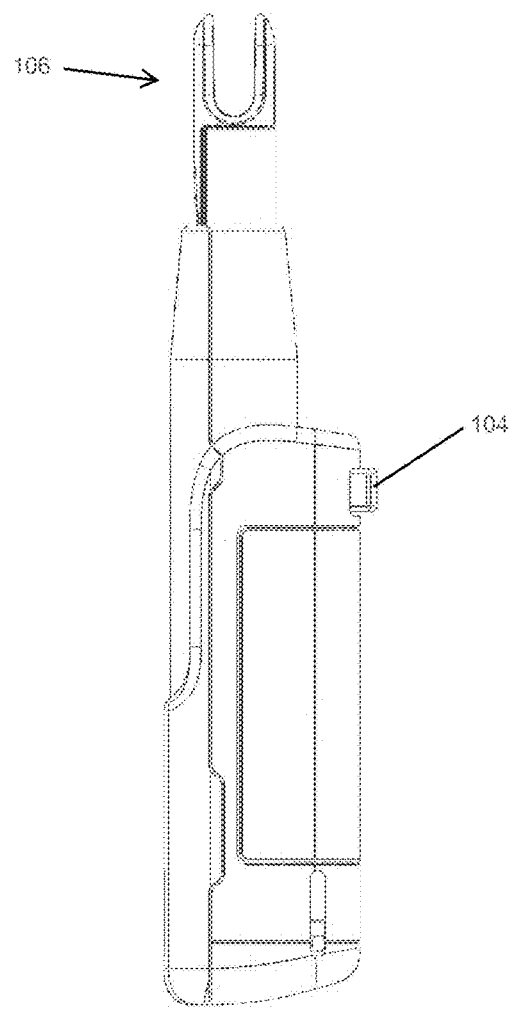
FIG. 2I depicts an exemplary embodiment front view of another Exemplary Device in the first configuration, according to some embodiments.
Figure 2J:
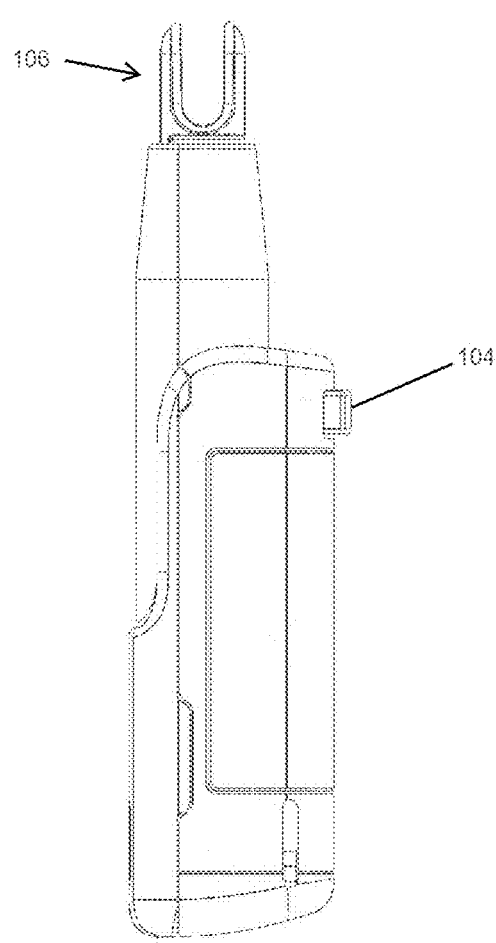
FIG. 2J depicts an exemplary embodiment front view of an Exemplary Device in the second configuration, according to some embodiment.

In some embodiments, the device comprises at least one dispensing element 110. In some embodiments, the device comprises at least one insertable portion 107. In some embodiments the at least one dispensing element 110 extends from or is revealed by the at least one insertable portion 107 In some embodiments, at least one insertable portion 107 comprises the at least one dispensing element 110. In some embodiments, a cannula is within an insertable portion 107, or the at least one dispensing element 110 comprises an internal diameter defining a channel. In some embodiments, the cannula is entirely contained within the dispensing element. In some embodiments, an end of the dispensing element is coextensive with the end of the insertable portion. In some embodiments, a dispensing element is entirely contained within the insertable portion when the device is actuated, or when the housing is moved from the first position to the second position (see FIGS. 2G-2J). In some embodiments, an end of the dispensing element is coextensive with an end of the insertable portion when the device is actuated, or when the housing is moved from the first position to the second position (see FIGS. 2G-2J). In some embodiments, the dispensing element does not extend or reveal from the insertable portion when the device is actuated, or when the housing is moved from the first position to the second position (see FIGS. 2G-2J). In some embodiments, the device may further include a trigger or trigger release 104 coupled to the subject engaging portion 106 on the columella saddle, and may actuate the device when pressure is applied to the trigger release 104 by a subject's columella (see FIGS. 2G-2H).). In some embodiments, dispensing element comprises a cannula.

In some embodiments, the at least one channel 125 within an insertable portion 107, or the at least one dispensing element 110 has an inner diameter 129 of 0.3 to 3.0 mm. In some embodiments, the at least one composition channel 125 within an insertable portion 107, or the at least one dispensing element 110 has an inner diameter 129 of 0.3 to 0.7 mm. In some embodiments, the at least one composition channel 125 within an insertable portion 107, or the at least one dispensing element 110 has an inner diameter 129 of 0.5 to 1.0 mm. In some embodiments, the at least one dispensing element 110, e.g., cannula, may be adapted to deliver the composition 111 having a low, intermediate, or high viscosity along the passageway to the subject's olfactory cleft 23, middle meatus 30, or other areas of nasal anatomy to enter the CNS. In some embodiments, the at least one dispensing element 110, e.g., cannula, may be adapted to deliver the composition 111 having a moderate (e.g., greater than 1 cP) or high viscosity (e.g., greater than or equal to 50 cP) to the passageway to the subject's olfactory cleft 23.

In some embodiments the first portion 102 comprises a semi-ellipse outer shell 114. In some embodiments, the semi-ellipse outer shell 114 comprises the outermost portion of the first portion 102. In some embodiments, the first portion 102 comprises an at least one tiered semi-conical outer shell 115 located horizontally adjacent to the semi-ellipse outer shell 114. In some embodiments, the at least one tiered semi-conical outer shell 115 comprises two tiers of semi-conical outer shell, wherein each tier of semi-conical outer shell is vertically adjacent to the other tier or tiers of semi-conical outer shell. In some embodiments, the at least one tiered semi-conical outer shell 115 comprises a top tier of semi-conical outer shell which partially encloses a bottom tier of semi-conical outer shell. In some embodiments, the first portion 102 comprises a trigger release 104. In some embodiments, the first portion 102 comprises a rectangular cut-out opening, wherein the rectangular cut-out opening has approximately the same length and width dimensions as the trigger release 104. In some embodiments, the trigger release 104 is inserted into the housing 101 through the rectangular cut-out opening, wherein the rectangular cut-out opening has approximately a same length and width dimensions as the trigger release 104. In some embodiments, the housing comprises a second portion 103. In some embodiments, the second portion 103 comprises a chassis 116. In some embodiments, the chassis 116 comprises a chassis rectangular region 117, a chassis semi-conical region 118, and a chassis finial region 119. In some embodiments, the chassis rectangular region 117 comprises an oval shaped hole 132 revealing vertically along a horizontal center of the rectangular region 117. In some embodiments, the semi-conical region 118 is vertically adjacent to the rectangular region 117. In some embodiments, the rectangular region 117 reveals along the length of the semi-conical region 118 such that two adjacent rectangular regions are formed 120. In some embodiments, the finial region 119 is located vertically adjacent to the semi-conical region 118. In some embodiments, the finial region 119 comprises a horizontal width shorter than a horizontal width of the semi-conical region 118. In some embodiments, the chassis 116 comprises a shape for insertion into the first portion 102. In some embodiments, the chassis rectangular region 117 aligns with the at least one tiered semi-conical outer shell 115, wherein such alignment creates a bottom 124 of the housing 101. In some embodiments, the chassis finial region 119 aligns with the at least one tiered semi-conical outer shell 115, wherein such alignment creates an outer shell of the insertable portion 107 of the housing 101.

In some embodiments, the device is transitionable from a first configuration 100 to a second configuration 200. In some embodiments, the subject engaging portion 106 is engaged with the user's columella region 10 when inserting the device into the subject's nasal channel 20, where the subject engaging portion 106 recesses the columella saddle 121 into the first portion 102 of the housing 101 or the at least one tiered semi-conical outer shell 115. In some embodiments, the at least one dispensing element 110 reveals from the at least one insertable portion 107 upon transition of the device from the first configuration 100 to the second configuration 200. In some embodiments, the vertical length in the second configuration 122 is longer than the vertical length in the first configuration 123. In some embodiments, when the device is transitionable from the first configuration 100 to the second configuration 200, the housing 101 defines the first insertable portion 107, and the device further comprises the dispensing element 110 coupled to the housing 101, the dispensing element 110 revealing from the first insertable portion 107 upon transition of the device from the first configuration 100 to the second configuration 200. In some embodiments, the device comprises a bottom 124 wherein the first portion 102 and the second portion 103 interface or connect.

In some embodiments, the device comprises a housing 101 with a subject engaging portion 106 and one or insertable portions 107 that are coupled to the housing 101. In some embodiments, the subject engaging portion 106 includes a subject engaging portion 106 that engages the columella region 10 to position the one or insertable portions 107 within one or both nasal channels 20 of the subject and limit the depth of insertion of one or both one or insertable portions 107. In some embodiments, the device may further include a trigger release 104 coupled to the housing 101 and the subject engaging portion 106, which actuates one or both one or dispensing elements, either simultaneously or sequentially, to deliver a composition 111 to one or both nasal channels 20 of the subject upon application of pressure by the subject engaging portion 106 to the columella region 10. In some embodiments, the trigger release 104 can be positioned on the subject engaging portion 106 on the columella saddle (see FIG. 2G). In some embodiments, the device can be actuated by upon application of pressure to the trigger release 104 by the columella.

In some embodiments, the housing 101 may define a subject engaging portion 106 and one or two insertable portions 107 for insertion into one or both nasal channels 20 of the subject. In some embodiments, upon insertion of one or both insertable portions 107 into one or both nasal channels 20 of the subject, the one or both insertable portions 107 engage tissue within the nasal channel 20 to open or expand one or both internal nasal valves 13, thereby positioning the one or both insertable portions 107 for delivery of a composition 111 to the subject, either simultaneously or sequentially, from one or more dispensing ports 126. In some embodiments, the device may further include a trigger or trigger release 104 coupled to the housing 101 and the subject engaging portion 106, which actuates one or both insertable portions 107, either simultaneously or sequentially, to deliver a composition 111 to one or both nasal channels 20 of the subject upon application of pressure by the subject engaging portion to the columella region 10. In some embodiments, the housing 101 may define a subject engaging portion 106, one or two insertable portions 107 for insertion into one or both nasal channels 20 of the subject, and one or two dispensing elements 110 that extend from, or are revealed by, the one or two insertable portions 107. In some embodiments, the device is in the first configuration, wherein upon insertion of one or both insertable portions 107 into one or both nasal channels 20 of the subject, the one or both insertable portions 107 engage tissue within the nasal channel 20 to open or expand one or both internal nasal valves 13. In some embodiments, the device is in the second configuration 200, wherein one or both dispensing elements 110 extend from, or are revealed by, one or both insertable portions 107, and are positioned to deliver a composition 111 to the subject, either simultaneously or sequentially, from one or more dispensing ports 126. In some embodiments, the device may further include a trigger or trigger release 104 coupled to the housing 101 and the subject engaging portion 106, which actuates one or both dispensing elements 110, either simultaneously or sequentially, to deliver a composition 111 to one or both nasal channels 20 of the subject upon application of pressure by the subject engaging portion 106 to the columella region 10. In some embodiments, an end of the dispensing element is coextensive with the end of the insertable portion. In some embodiments, a dispensing element is entirely contained within the insertable portion when the device is actuated, or when the housing is moved from the first position to the second position (see FIGS. 2G-2J). In some embodiments, an end of the dispensing element is coextensive with an end of the insertable portion when the device is actuated, or when the housing is moved from the first position to the second position (see FIGS. 2G-2J). In some embodiments, the dispensing element does not extend or reveal from the insertable portion when the device is actuated, or when the housing is moved from the first position to the second position (see FIGS. 2G-2J). In some embodiments, the device may further include a trigger or trigger release 104 coupled to the subject engaging portion 106 on the columella saddle, and may actuate the device when pressure is applied to the trigger release 104 by a subject's columella (see FIGS. 2G-2H).). In some embodiments, dispensing element comprises a cannula.

In some embodiments, the housing 101 comprises a dispensing element in the first configuration 100. In some embodiments, the at least one dispensing element 110 comprises a cylindrical shape. In some embodiments, the at least one composition channel 125 within an insertable portion 107, or the at least one dispensing element 110 comprises an internal diameter. In some embodiments, the at least one composition channel 125 within an insertable portion 107, or the at least one dispensing element 110 has an inner diameter 129 of 0.3 to 3.0 mm. In some embodiments, the at least one composition channel within an insertable portion 107, or the at least one dispensing element 110 has an inner diameter 129 of 0.3 to 0.7 mm. In some embodiments, the at least one composition channel 125 within an insertable portion 107, or the at least one dispensing element 110 has an inner diameter 129 of 0.5 to 1.0 mm. In some embodiments, the dispensing element 110 is configured to dispense the composition 111 having a low, intermediate, or high viscosity into a single nasal channel 20 of a subject. In some embodiments, the dispensing element 110 is configured to dispense the composition 111 having a low, intermediate, or high viscosity into both nasal channels 20 of a subject.

In some embodiments, the insertable portion 107 may limit contamination of biome from different sub-regions of a nasal channel 20 and/or stabilize the dispensing element 110. The insertable portion 107 may allow for a shorter dispensing element 110 which is more stable and less prone to bending and deflection.

The device may comprise insertable portions 107 designed to fit snuggly with the anterior tight angle of the internal nasal valve 13 where the septum 24 meets the upper lateral cartilage 25. The device may comprise insertable portions 107 comprising a shape 130, wherein the shape comprises a wing, a foil, a wedge, an oval or oblong, or even a round form. The device may comprise one insertable portion 107, wherein the insertable portion 107 comprises one or more channels 125 leading to one or more dispensing ports 126.

The device may further comprise one insertable portion 107, wherein one or more dispensing elements 110 are fixed relative to the insertable portion 107 leading to one or more dispensing ports 126. The device may further comprise one insertable portion 107, wherein one or more dispensing elements 110 that are movable relative to the insertable portion 107 with one or more dispensing ports 126. The device may further comprise one insertable portion 107, wherein a composition 111 can be delivered to any subregion of a nasal channel 20, e.g., an olfactory cleft or a turbinate. The device may further comprise one insertable portion 107 and a subject engaging portion 106 that engages the columella region 10. The device may further comprise one insertable portion 107, a subject engaging portion 106 that engages the columella region 10, and a trigger or trigger release 104, wherein the trigger or trigger release 104 actuates the device upon pressure being applied by the subject engaging portion 106 against the columella 10.

Figure 3A:
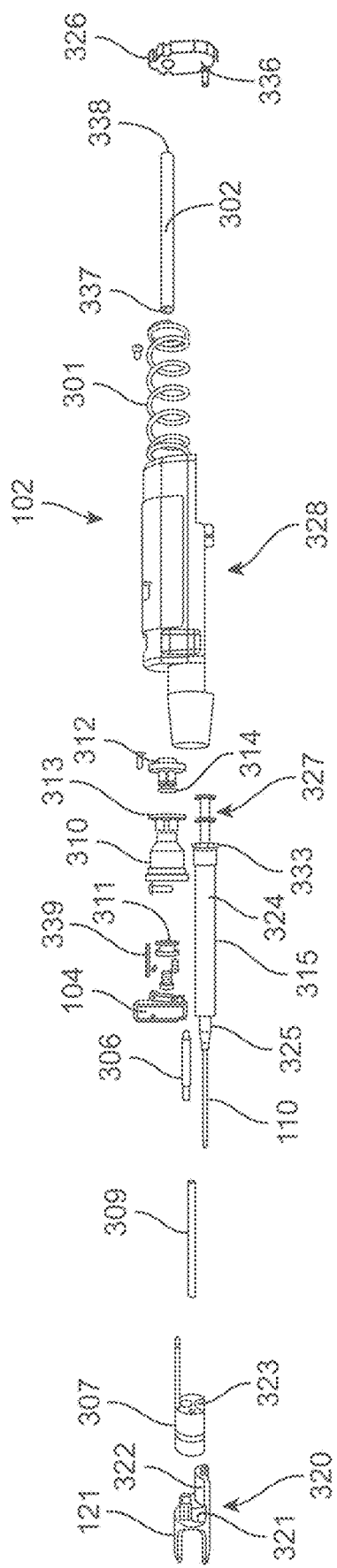
FIG. 3A depicts an exploded view of an Exemplary Device without a chassis, according to some embodiments.
Figure 3B:
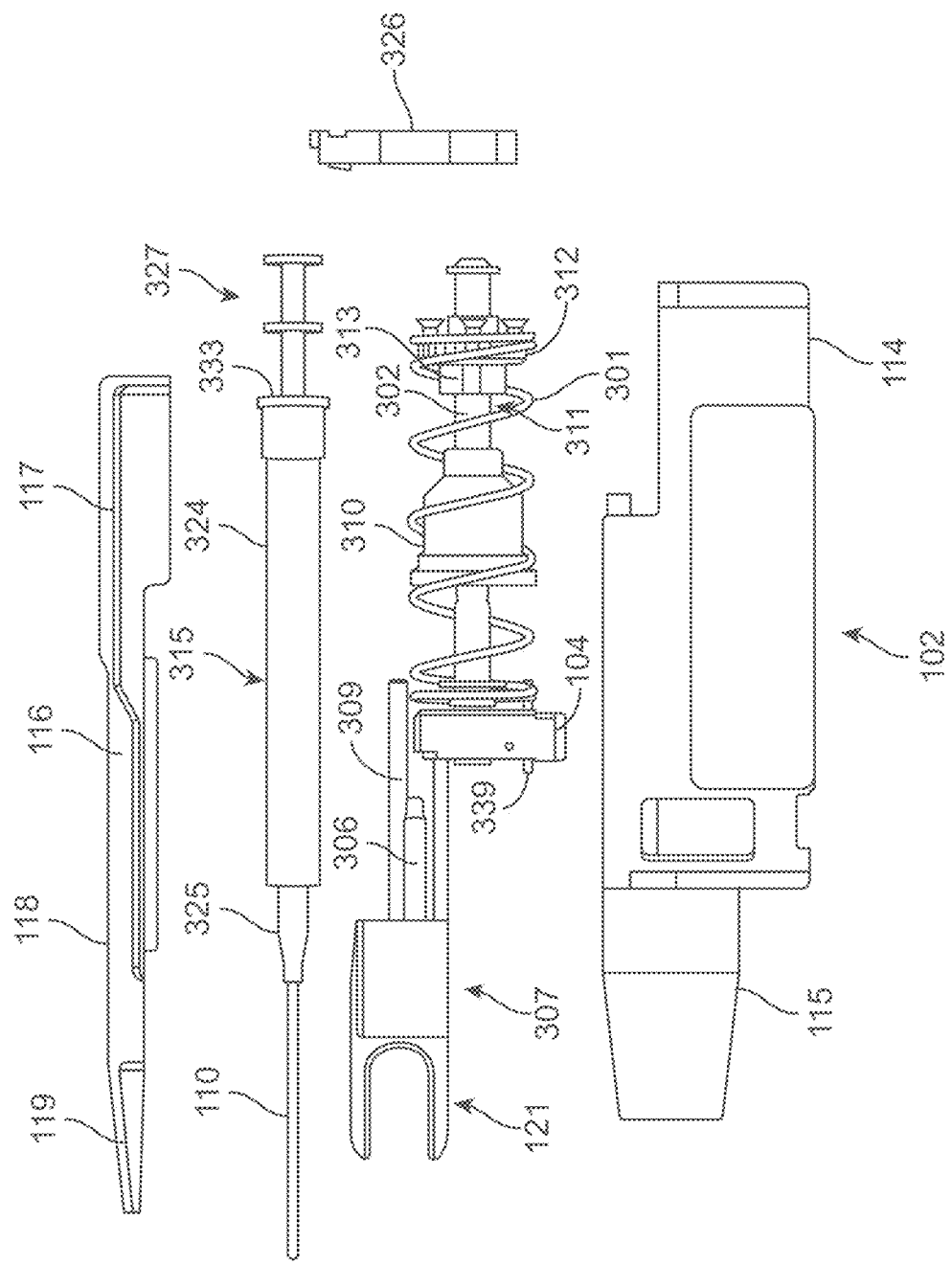
FIG. 3B depicts an exemplary exploded view of an Exemplary Device, according to some embodiments.
Figure 3C:
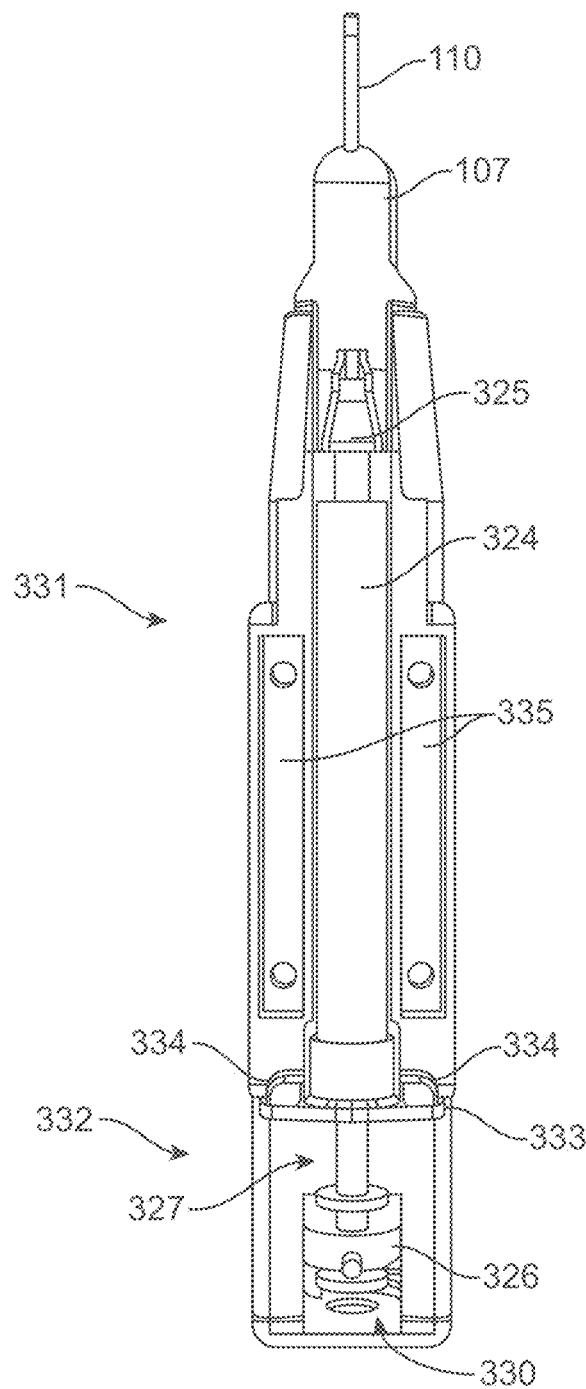
FIG. 3C depicts a view of an Exemplary Device without a chassis, according to some embodiments. The back cover is removed in this view, allowing for insertion of a syringe or cannula.

FIG. 3A depicts an exemplary exploded internal component view of the Exemplary Device without a chassis. FIG. 3B depicts an exemplary partially exploded internal component view of the Exemplary Device. FIG. 3C depicts an assembled internal component view of the Exemplary Device without a chassis.

In some embodiments, the device comprises an adjustable or re-configurable spring 301. In some embodiments, the device comprises a lay shaft 302. In some embodiments, the device comprises a spring core guide 306. In some embodiments, the device comprises a columella slider 307. In some embodiments, the device comprises a columella saddle 121. In some embodiments, the device comprises a guide dowel 309. In some embodiments, the device comprises a spring support 310. In some embodiments, the device comprises a travel limit 311. In some embodiments, the device comprises a trigger release 104. In some embodiments, the device comprises a turcite damper 312. In some embodiments, the device comprises a bushing support 314. In some embodiments, the device comprises a turcite preload ring 313. In some embodiments, the device comprises a syringe 315 comprising a therapeutic composition. In some embodiments, the syringe 315 comprises a syringe volume. In some embodiments the syringe volume is between 1 cc and 5 cc. In some embodiments the syringe volume is at most 10 cc. In some embodiments the syringe volume is at least 1 cc. In some embodiments the syringe volume is at least 1 cc, 2 cc, 3 cc, 4 cc, 5 cc, 6 cc, 7 cc, 8 cc, 9 cc or 10 cc. In some embodiments the syringe volume is up to 1 cc, 2 cc, 3 cc, 4 cc, 5 cc, 6 cc, 7 cc, 8 cc, 9 cc or 10 cc In some embodiments, the columella saddle 121 comprises a "U-shaped" saddle perpendicular to a columella slider insert 320. In some embodiments, the columella slider insert 320 comprises a columella saddle recessed region 321 and columella saddle semi-conical region 322. In some embodiments, the columella slider insert 320 is designed for insertion into a columella slider 307. In some embodiments, the columella slider 307 is designed for insertion into the columella slider insert 320. In some embodiments, the columella slider 307 comprises a cylinder comprising a cut-out columella slider semi-conical region 323, wherein the cut-out columella slider semi-conical region 323 comprises a larger radius than a radius of the columella saddle semi-conical region 322. In some embodiments, the columella slider 307 comprises a recessed cut-out region, wherein the recessed rectangular cut-out is about the same dimensions as the columella saddle recessed region 321. In some embodiments, the syringe 315 comprises the dispensing element 110, a syringe cylindrical barrel 324, a syringe funnel region 325, a syringe arm region 333 and a syringe actuation region 327. In some embodiments, the syringe actuation region 327 comprises two circular stoppers, wherein at least one circular stopper is configured for applying pressure to the syringe cylindrical barrel 324. In some embodiments, the syringe actuation region 327 comprises two circular stoppers, wherein at least one circular stopper is configured for stopping the movement of the syringe 315. In some embodiments, the syringe 315 is inserted into the cut-out columella slider 323 and into columella saddle semi-conical region 322. In some embodiments, a syringe push arm 326 comprises a circular cut-out for insertion of the syringe actuation region 327 region. In some embodiments the first portion 102 comprises a first portion backside 328, wherein the chassis 116 is inserted. In some embodiments, the backside 328 comprises a semi-cylindrical cut-out region for insertion of the syringe cylindrical barrel 324. In some embodiments, the first portion backside 328 comprises a first portion backside cut-out recessed rectangular region 330. In some embodiments, the cut-out recessed rectangular region 330 comprises a storage region, wherein the syringe actuation region 327 region and the syringe push arm 326 regions are stored. In some embodiments, the first portion backside 328 comprises a first portion backside rectangular region 331 and a first portion backside recessed rectangular region 332. In some embodiments, the first portion backside rectangular region 331 comprises a rectangular region to recessed rectangular region interface with at least one arm stopper 334. In some embodiments, the at least one arm stopper 334 is flush with a syringe arm 333. In some embodiments, the rectangular region 331 comprises two first portion backside recessed cut-out rectangular regions 335. In some embodiments, the chassis 116 comprises two chassis rectangular regions 345, wherein the two recessed cut-out rectangular regions 335 are inserted into the two rectangular regions 345. In some embodiments, the syringe push arm 326 comprises at least one syringe push arm cylindrical cutout region 336 for insertion of the lay shaft 302. In some embodiments, the lay shaft 302 comprises at least one screw hole extending across the horizontal length of the lay shaft 302, wherein the screw hole is located at a lay shaft second end 338 of the lay shaft 302. In some embodiments, the second end 338 is connected to at least one cylindrical cutout region 336 via a screw. In some embodiments, the lay shaft 302 extends from the bottom 124 of the device to the trigger release 104. In some embodiments, turcite preload ring 313 has a greater circumference than the turcite bushing 312. In some embodiments, turcite preload ring 313 is wrapped around the lay shaft 302 such that turcite preload ring 313 extends along a portion of the vertical length the lay shaft 302. In some embodiments, turcite preload ring 313 comprises an inner surface such that the inner surface of turcite preload ring 313 contacts an outer surface of the lay shaft 302. In some embodiments, turcite bushing 312 is wrapped around turcite preload ring 313 such that turcite bushing 312 extends along approximately the same portion of the vertical length of the lay shaft 302 as turcite preload ring 313. In some embodiments, a spring support 310 is located along the vertical length of the shaft 302. In some embodiments, the lay shaft 302 comprises at least one screw hole, wherein at least one screw is inserted to affix the spring support 310 to the lay shaft 302. In some embodiments, the lay shaft 302 comprises at least one screw hole extending across the horizontal length of the lay shaft 302, wherein the screw hole is located at a lay shaft first end 337 of the lay shaft 302. In some embodiments, the first end 337 is connected to the trigger release 104 via a screw. In some embodiments, the trigger release 104 comprises a pin hole for insertion of a stainless steel dowel pin 339. In some embodiments, the spring 301 extends vertically along 302. In some embodiments, the spring 301 has a spring first end 340 and a spring second end 341. In some embodiments, the first end 340 is wrapped around the circumference of turcite bushing 312. In some embodiments, the second end 341 is wrapped around stainless steel dowel pin 339. In some embodiments, columella slider 307 comprises a guide dowel hole 342. In some embodiments, the guide dowel 309 comprises a guide dowel first end 343 and a guide dowel second end 344. In some embodiments, guide dowel first end 343 contacts the columella saddle recessed region 321. In some embodiments, the guide dowel extends along a vertical length of the device such that the guide dowel see end 344 is located parallel to the spring 301. In some embodiments, the trigger release 104 has a recessed semi-cylindrical region, wherein actuation of the trigger release 104 presses the trigger release 104 against the guide dowel 309. In some embodiments, the device is actuated application of force onto the trigger release 104 by the user. In some embodiments, the device is actuated by the user application of force onto the trigger release 104 following unlocking of the trigger by application of pressure to the subject engaging portion 106 with the user's columella region 10. In some embodiments, the user may use any digit to actuate the device.

Figure 3D:
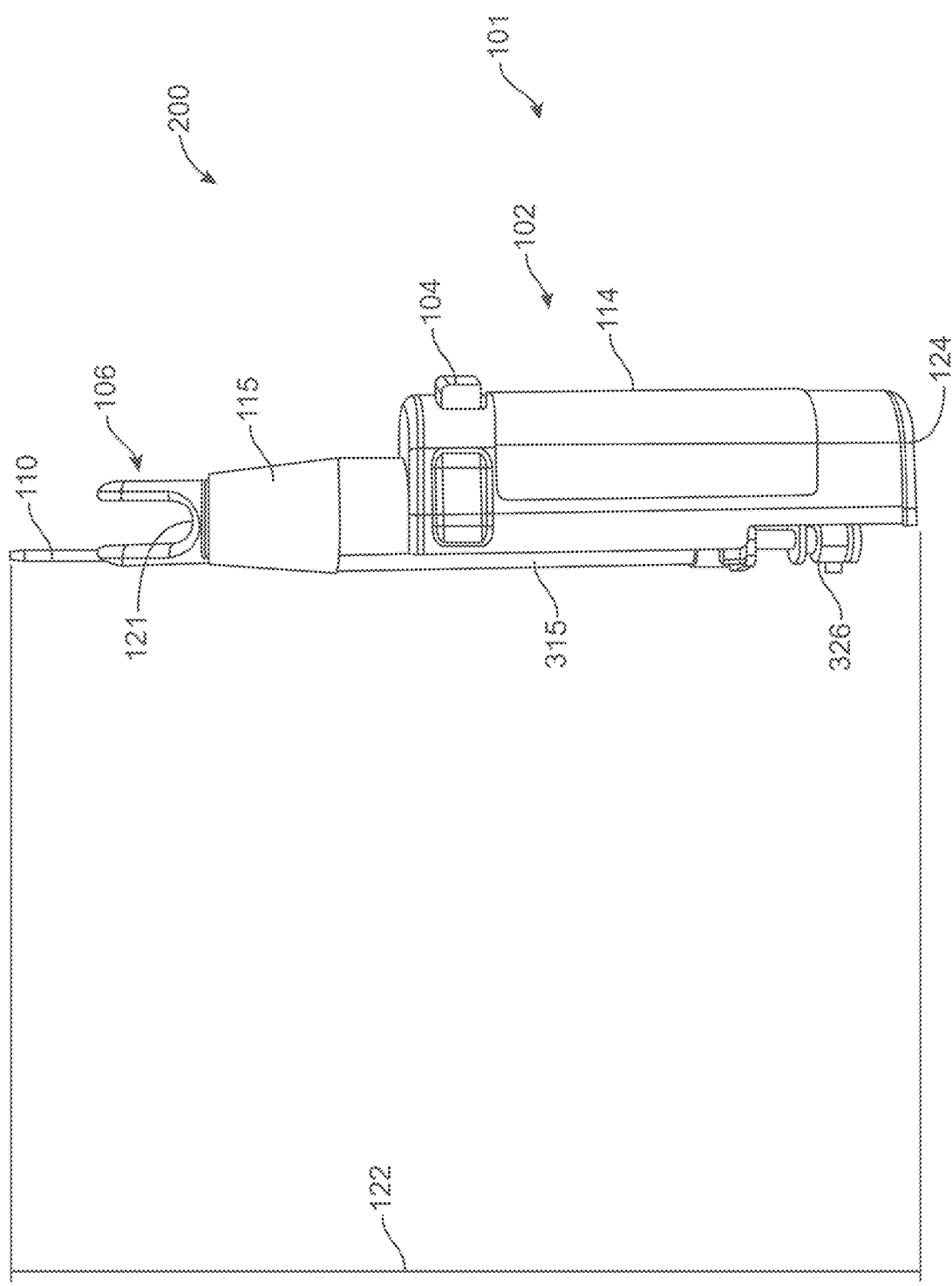
FIG. 3D depicts a side view with internal components displayed of an Exemplary Device in a second configuration with one dispensing element revealed, according to some embodiments. A back cover of the device is removed for better visibility of internal components.

FIG. 3D depicts a forward view with internal components displayed of the Exemplary Device in a second configuration with one dispensing element revealed. In some embodiments, the device is transitionable from the first configuration 100 to the second configuration 200. In some embodiments, engaging the subject engaging portion 106 recesses the columella saddle 121 into the first portion 102. In some embodiments, the at least one dispensing element 110 reveals from the at least one insertable portion 107 upon transition of the device from the first configuration 100 to the second configuration 200. In some embodiments, the vertical length in the second configuration 122 is longer than the vertical length in the first configuration 123. In some embodiments, wherein the device is transitionable from the first configuration 100 to the second configuration 200, the housing 101 defining the first insertable portion 107, the device further comprising the dispensing element 110 coupled to the housing, the dispensing element 110 reveals from the first insertable portion 107 upon transition of the device from the first configuration 100 to the second configuration 200.

Figure 4A:
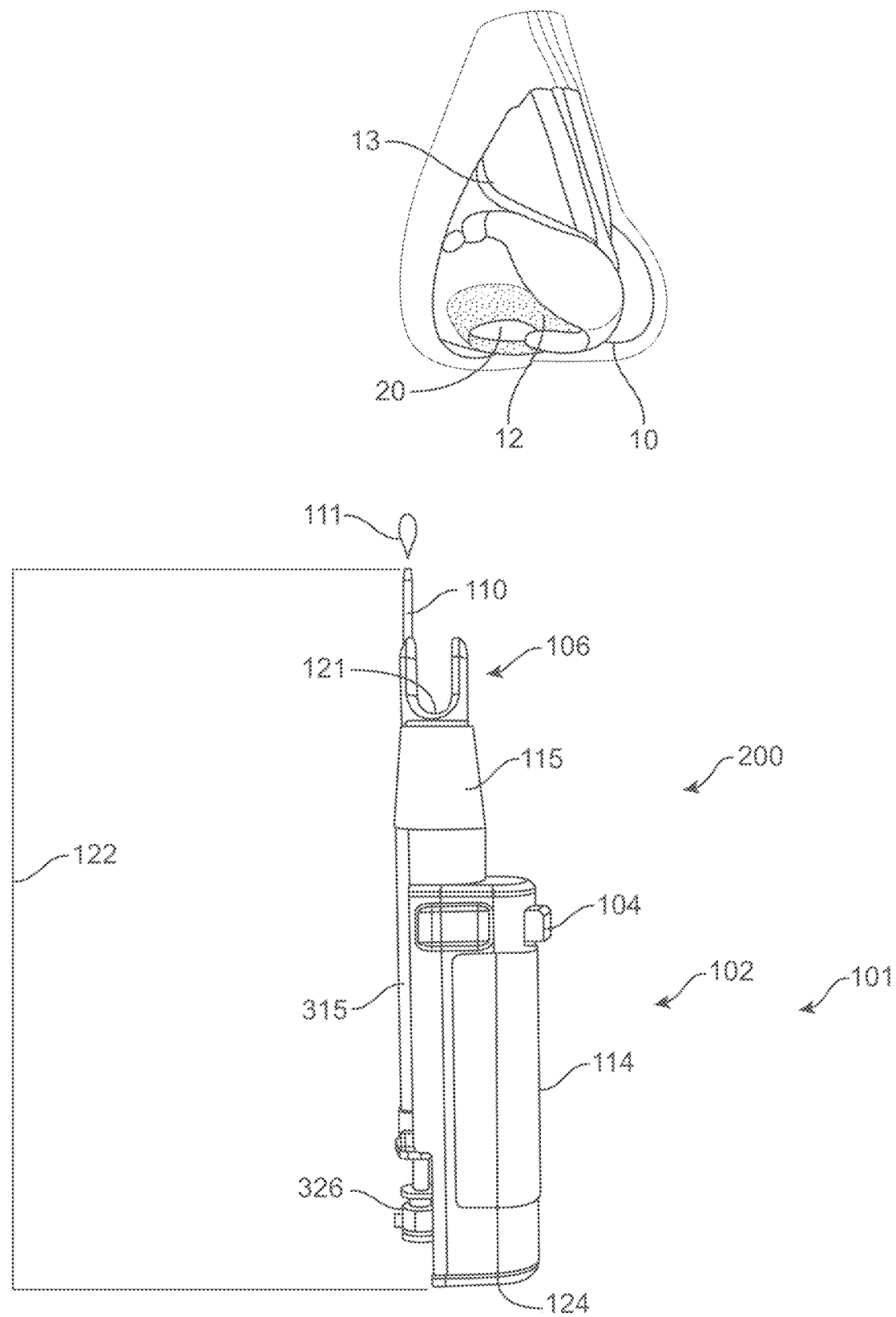
FIG. 4A depicts an exemplary embodiment of an Exemplary Device in the second configuration with one dispensing element revealed and a side view of an exemplary embodiment of a subject's nose, according to some embodiments. A back cover of the device is removed for better visibility of internal components.
Figure 4B:
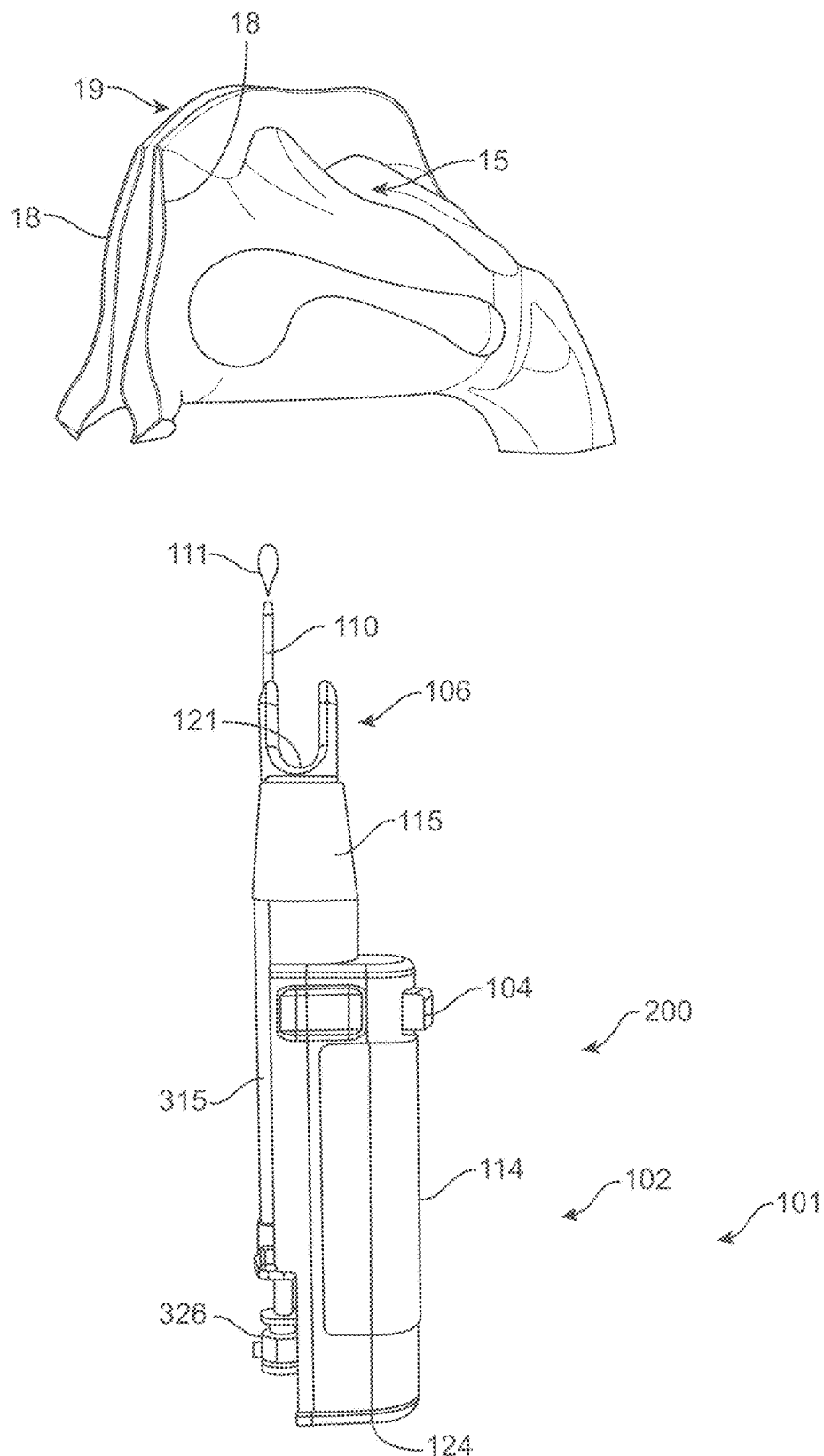
FIG. 4B depicts an exemplary embodiment of an Exemplary Device in the second configuration with one dispensing element revealing along the passageway and a side view of an exemplary embodiment of a representation subject's nasal channels from the vestibule to the olfactory cleft based on an anteriorly oriented plane, according to some embodiments. A back cover of the device is removed for better visibility of internal components.

FIG. 4A depicts an exemplary embodiment of the Exemplary Device in the second configuration with the insertable portion in the nasal channel with one dispensing element revealed. FIG. 4B depicts an exemplary embodiment of the Exemplary Device in the second configuration with one dispensing element revealed In one aspect, the disclosure provides a device for intranasal delivery to a subject, the device comprising: a housing 101 comprising an insertable portion 107 configured for insertion into a nasal channel 20 of the subject; and a subject engaging portion 106 which engages a columella region 10 of the subject coupled to the housing 101, wherein application of pressure by the subject engaging portion 106 to the columella region 10 of the subject enables and/or causes delivery of a composition 111 to the subject from the insertable portion 107. In some embodiments, the insertable portion 107 incorporates one or more dispensing channels 125 leading to one or more dispensing ports 126 configured for intranasal delivery of a composition 111 to one or more regions or sub-regions of the nasal channel 20 of the subject.

In some embodiments, the insertable portion 107 comprises a dispensing element 110 for delivery of a composition 111 to a region or sub-region of the nasal channel 20 of the subject. In some embodiments, the housing 101 comprises a trigger, wherein the trigger actuates the device to deliver a composition 111 to the subject from the insertable portion 107 or the dispensing element 110. In some embodiments, the subject engaging portion 106 comprises a trigger coupled to the housing 101 and the subject engaging portion 106, wherein upon application of pressure of the subject engaging portion 106 to the columella region 10, the trigger actuates the device to dispense a composition 111 to the subject from the insertable portion 107 or the dispensing element 110.

In some embodiments, the subject engaging portion 106 comprises a trigger release 104 coupled to the housing 101 and the subject engaging portion 106, wherein upon application of pressure of the subject engaging portion 106 to the columella region 10, the trigger release 104 permits actuation of the device to deliver a composition 111 to the subject from the insertable portion 107 or the dispensing element 110. In some embodiments, the device further comprises a trigger which is actuatable upon engagement of the trigger release 104.

In some embodiments, the subject engaging portion 106 positions the insertable portions 107 and/or the dispensing elements 110 within the nasal channel 20 of the subject and limits the depth of insertion of the insertable portions 107 and/or the dispensing elements 110 into the nasal channel 20. In some embodiments, upon insertion of the first insertable portion 107 into a nasal channel 20 of the subject, the first insertable portion 107 opens or expands the internal nasal valve 13 by pushing the upper lateral cartilage 25 and surrounding tissue up and away 625 from the septum 24 of the subject thereby positioning at least one of the insertable portions 107 for delivery of the composition 111 to the subject. In some embodiments, the internal nasal valve 13 is located approximately 1.3 cm from the entrance to the nasal vestibule 21. In some embodiments, the internal nasal valve 13 comprises a narrowest portion of the nasal channel 20. The internal nasal valve 13 comprises an average angle in a Caucasian ranging from 9° to 15°. In some embodiments, the device is actuated by the user application of force onto the trigger release 104. In some embodiments, the user may use any digit to actuate the device.

In some embodiments, the columella saddle shaped subject engaging portion 106 comprises a trigger, wherein the columella saddle shaped subject engaging portion 106 centers at least one dispensing element 110 about the subject's columella 10. In some embodiments, the columella saddle shaped subject engaging portion 106 comprises a positioning trigger, wherein the positioning trigger actuates the device and dispenses the composition 111 from at least two insertable portions 107 and/or the dispensing elements 110 in parallel when pressed against the subject's columella 10. In some embodiments, the device comprises the positioning trigger actuates the device and dispenses the composition 111 from at least two insertable portions 107 and/or the dispensing elements 110 in series when pressed against the subject's columella 10. In some embodiments, the positioning trigger unlocks the trigger release 104 such that pressing the button dispenses the composition 111 from at least one insertable portion 107 and/or dispensing element 110 when pressed against the subject's columella 10. In some embodiments, the positioning trigger actuates the device and dispenses the composition 111 from at least one insertable portion and/or dispensing element 110 when pressed against the subject's columella 10. In some embodiments, the positioning trigger comprises an actuator which dispenses the composition 111 from the syringe 315 when the housing 101 is moved from the first position to the second position. In some embodiments, the syringe 315 comprises a cylindrical barrel 324. In some embodiments, the device further comprises the syringe 315 fluidically connected to the at least one insertable portion and/or dispensing element 110. In some embodiments, the columella saddle 121 comprises a trigger for receiving the columella 10 of the subject. In some embodiments, the positioned trigger depresses a switch underneath the positioning trigger to actuate the device, or to permit actuation of the device by releasing a safety or lock on the trigger mechanism. In some embodiments, the switch comprises the columella saddle 121, the columella saddle slider 307 and the syringe 315. In some embodiments, the subject engaging portion 106, which includes the columella saddle 121, can comprise a trigger, such that when the subject engaging portion 106 is pressed against the columella 10, the trigger actuates the device mechanism.

In some embodiments, the columella saddle 121 positions the first insertable portion 107 and the second insertable portion 107 as to align the at least one insertable portion 107 and/or dispensing element 110 with the olfactory cleft 23 when the device is actuated. In some embodiments, the columella saddle n 121 positions the first insertable portion 107 and the second insertable portion 107 as to align the at least one insertable portion 107 and/or dispensing element 110 along the passageway to the olfactory cleft 23 the device is actuated. In some embodiments, the columella saddle 121 comprises a shape 130 which matches an anatomy of the subject's columella 10 and aligns the one or more insertable portion 107 and/or dispensing element 110 with the subject's olfactory cleft 23. In some embodiments, the device comprises the insertable portion 107 and/or dispensing element 110 positioned proximal to the olfactory cleft 23 of the subject when the columella saddle 121 is engaging the columella 10 of the subject. In some embodiments, the columella saddle 121 comprises an impression of the subject's columella 10.

In some embodiments, the columella saddle 121 positions the first insertable portion 107 and the second insertable portion 107 as to align the at least one insertable portion 107 and/or dispensing element 110 with the middle meatus 30 when the device is actuated. In some embodiments, the columella saddle 121 positions the first insertable portion 107 and the second insertable portion 107 as to align the at least one insertable portion 107 and/or dispensing element 110 along the passageway to the middle meatus 30 when the device is actuated. In some embodiments, the columella saddle 121 comprises a shape 130 which matches an anatomy of the subject's columella 10 and aligns the one or more insertable portion 107 and/or dispensing element 110 with the subject's middle meatus 30. In some embodiments, the device comprises the insertable portion 107 and/or dispensing element 110 positioned proximal to the middle meatus 30 of the subject when the columella saddle 121 is engaging the columella 10 of the subject.

In some embodiments, the first and/or second insertable portion 107 opens or expands the internal nasal valve 13 by pushing the upper lateral cartilage 25 and surrounding tissue up and away 625 from the septum 24 and clearing a pathway for dispensing of the compound 111. In some embodiments, the pressure is applied to the subject engaging portion 106 by the columella region 10. In some embodiments, the at least one insertable portion 107 and/or dispensing element 110 reveals from the insertable portions 107 toward the target region, e.g., to the olfactory cleft 23, middle meatus 30, or other nasal anatomy, based on an anteriorly oriented plane 18 to dispense the composition 111.

In some embodiments, the subject engaging portion 106 may be configured for delivering a sampling fluid, guiding an endoscope, or a combination thereof. In some embodiments, the device is configured to target the olfactory cleft 23 or a portion thereof. In some embodiments, the target region 19 is one or both olfactory clefts, or a sub-area thereof. In some embodiments, the target area is one or both respiratory areas, or a sub-area thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end 128 of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition 111 is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition 111 is dispensed to all regions simultaneously.

The device may comprise two insertable portions 107, wherein one insertable portion 107, has one or more channels 125 leading to one or more dispensing ports 126. The device may comprise two insertable portions 107, wherein both insertable portions 107 have one or more channels 125 leading to one or more dispensing ports 126. The device may comprise two insertable portions 107, wherein both insertable portions 107 have one or more channels 125 leading to one or more dispensing ports 126, wherein a composition 111 can be delivered at the same time or sequentially from each insertable portion 107 or the dispensing element 110. The device may comprise two insertable portions 107, wherein one insertable portion 107 includes one or more dispensing elements 110 that are fixed relative to the insertable portion 107 leading to one or more dispensing ports 126. The device may comprise two insertable portions 107, wherein both insertable portions 107 include one or more dispensing elements 110 that are fixed relative to the insertable portions 107 leading to one or more dispensing ports 126. The device may comprise two insertable portions 107, wherein both insertable portions 107 include one or more dispensing elements 110 that are fixed relative to the insertable portions 107 leading to one or more dispensing ports 126, wherein a compound 111 can be delivered at the same time or sequentially from each insertable portion 107 or the dispensing element 110. The device may comprise two insertable portions, 107 wherein one insertable portion 107 includes one or more dispensing elements 110 that are moveable relative to the insertable portion 107 with one or more dispensing ports 126. The device may comprise two insertable portions 107, wherein both insertable portions 107 include one or more dispensing elements 110 that are moveable relative to the insertable portion 107 with one or more dispensing ports 126. The device may comprise two insertable portions 107, wherein both insertable portions 107 include one or more dispensing elements that are moveable relative to the insertable portion 107 with one or more dispensing ports 126, wherein a composition 111 can be delivered at the same time or sequentially from each insertable portion 107 or the dispensing element 110. The device may further comprise two insertable portions 107, wherein the composition 111 can be delivered to any subregion of a nasal channel 20, e.g., an olfactory cleft 23 or a turbinate.

The device may further comprise two insertable portions 107 and a subject engaging portion 106 that engages the columella 10. The device may further comprise two insertable portions 107, a user engaging element that engages the columella 10, and a trigger, wherein the trigger actuates the device upon pressure being applied by the subject engaging portion 106 against the columella 10.

In some embodiments, the one or more dispensing elements 110 are contained within a secondary tubular member. In some embodiments, the trigger release 104 comprises a button, wherein the button is pushed to actuate the device. In some embodiments, the device cannot be actuated until the device is in the second configuration 200. In some embodiments, the device cannot be actuated until the device is not in the first configuration 100. In some embodiments, the device is in the first configuration 100, wherein the trigger release 104 cannot actuate the device. In some embodiments, the device is in the second configuration 200, wherein the trigger release 104 can actuate the device. In some embodiments, the trigger release 104 can be thumb actuated. In some embodiments, the trigger release 104 can be actuated by index and middle fingers.

Figure 5:
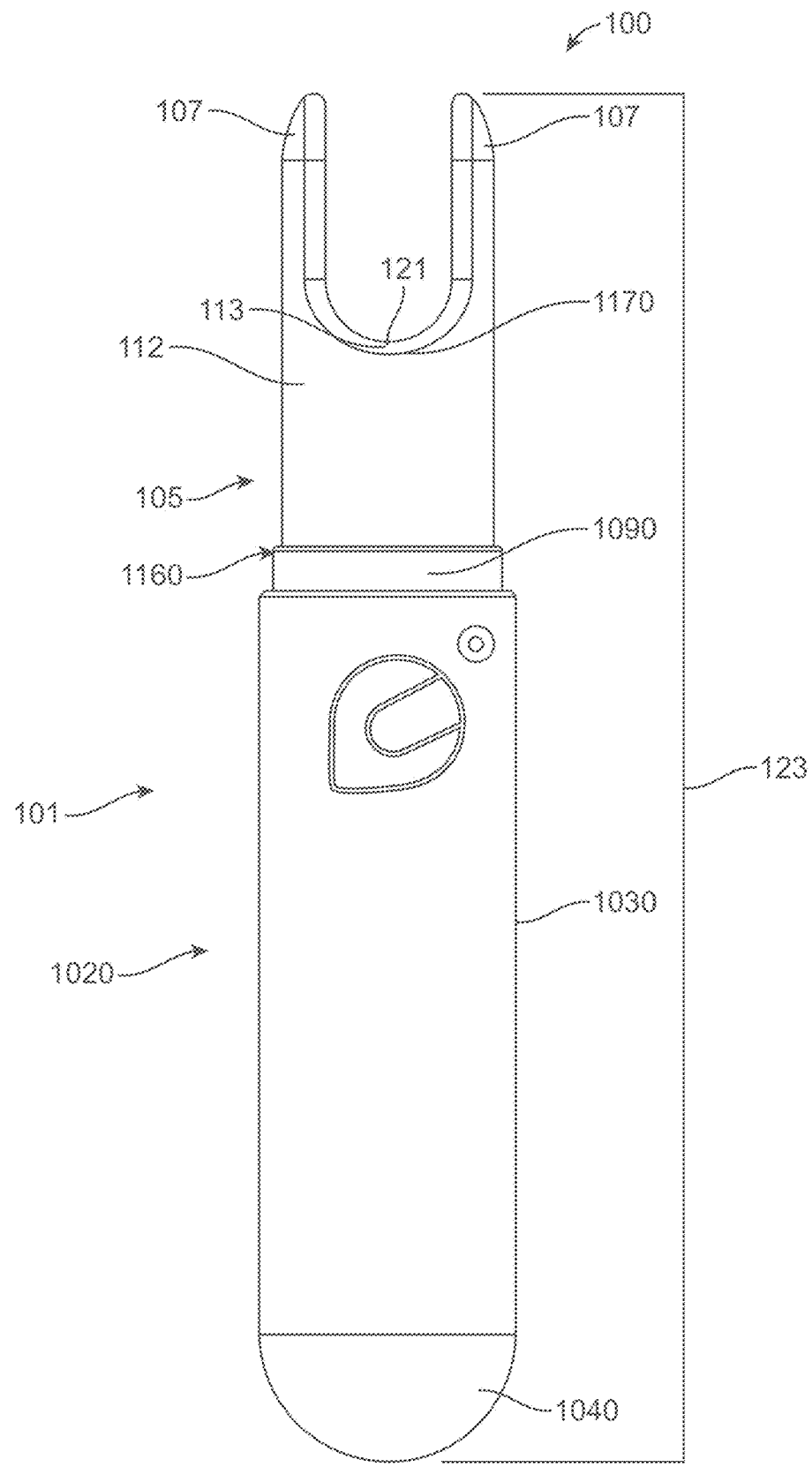
FIG. 5 depicts an exemplary embodiment of an Exemplary Device in a first configuration, according to some embodiments.

FIG. 5 depicts an exemplary embodiment of an exemplary device in a first configuration. In one aspect, this disclosure provides for a device comprising the at least one insertable portion 107. In one aspect, this disclosure provides for a device with at least one dispensing element 110 in a first configuration 100. In one aspect, the disclosure provides a device for intranasal delivery to a subject, the device comprising: a housing 101 comprising a dispensing element 110; a subject engaging portion 106 coupled to the housing, the subject engaging portion 106 comprising a subject engaging portion 106 which engages a columella region 10, wherein the subject engaging portion 106 positions the dispensing element 110 within a nasal channel 20 of the subject and limits the depth of insertion of the insertable portion into the nasal channel 20. In some embodiments, the subject engaging portion 106 engages the columella 10 of the subject about multiple sides of the columella 10 in a concave shape. In some embodiments, the housing 101 defines the entire external shell of the device. In some embodiments, the housing 101 comprises a first portion 1020 which defines a cylindrical portion 1030 and a rounded bottom 1040. In some embodiments, the housing 101 comprises a second portion 105 which is located vertically adjacent to the first portion 1020, wherein the first portion 1020 may have a larger diameter than the second portion 105 to accommodate insertion of the second portion 105 into the first portion 1020. In some embodiments, the second portion 105 comprises the subject engaging portion 106, wherein the subject engaging portion 106 comprising a "U" or "saddle" shaped element 121. In some embodiments, the subject engaging portion 106 engages the columella region of a subject 10. In some embodiments, the second portion 105 comprises at least one insertable portion 107. In some embodiments, the second portion 105 comprises two insertable portions 107, each for insertion into a nasal channel 20 of the subject.

In some embodiments, the second portion 105 of the housing 101 comprises the subject engaging portion 106. In some embodiments, the subject engaging portion 106 comprises a recessed top portion. In some embodiments, the recessed top portion comprises the "U" or "saddle" shape element 121. In some embodiments, the "U" or "saddle" shape element 121 comprises the center of the recessed top portion. In some embodiments, the cylindrical middle portion 112 is located vertically adjacent to the "U" or "saddle" shape element 121 such that the center of the recessed top portion 106 is coplanar with a top surface of the cylindrical middle portion 112 such that they form a unilateral plane 1170. In some embodiments, the device comprises the first configuration 100 wherein the first fiducial marker 1080 is completely visible. In some embodiments, the device in the first configuration 100 comprises a vertical length in the first configuration 123. In some embodiments, the device comprises a second cylindrical fiducial marker 1090, wherein the second cylindrical fiducial marker is partially revealed from the cylindrical portion 1030 of the first portion 1020 of the housing 101. In some embodiments, the cylindrical middle portion 112 has a bottom surface substantially coplanar with a top surface of the second fiducial marker 1090 such that they form a unilateral plane 1160. In some embodiments, the housing 101 comprises a dispensing element 110 in the first configuration 100. In some embodiments, the at least one cannula comprises a cylindrical shape. In some embodiments, the dispensing element 110 is configured to dispense the composition 111 into a single nasal channel 20 of a subject.

In some embodiments, the columella trigger release 104 design is configured to enable triggering only upon proper insertion and limit movement upon triggering.

In some embodiments, the columella saddle 121 comprises an anchor or datum 617 from which to establish insertion depth as a free-standing attribute.

In some embodiments, the columella trigger release 104 comprises a hand grip for the hand to simply grip the device without concerning any digit with the task of actuating. In some embodiments, the device comprises a grasping configuration, wherein the subject can grasp the device with the intent (i.e., grasp intention) of lifting the device to their face and not have to readjust grasp to actuate. In some embodiments, the device comprises the columella trigger release 104, wherein the columella trigger release 104 facilitates low/no cognition actuation as no judgement is required for when to actuate so the subject can focus singularly on insertion.

In some embodiments, the insertable portions 107 comprise an insertion angle configured to open the passageway between the septum 24 and nasal valve 13 and reduce cannula insertion depth appearance. In some embodiments, the columella saddle 121 reduces the insertion angle concern. In some embodiments, full insertions require proper insertion. In some embodiments, the width 1103 of the insertable portions 107 fills the lower aspect of the nasal channel 20, pushing hair aside minimizing the chance of a sneeze reflex as compared to the smaller diameter catheter being pushed up through the insertable portoin 107. In some embodiments, the insertable portion 107 is comparable to an "ear", optionally a flat "ear". In some embodiments, the device comprises two flat ears, wherein the two flat ears help each other hug the septum 24 side of each nasal channel 20, minimizing the potential for fetching up on the nasal valve 13. In some embodiments, the device comprises at least one flat insertable portion 107, wherein the at least one flat insertable portion 107 makes it uncomfortable or awkward to twist sideways so proper insertion is not negatively impacted while the subject is holding the device when it is partially or fully inserted. In some embodiments, the device comprises the 'wedge' shape 130 at the leading edge, wherein the 'wedge' shape 130 pushes the compressible and malleable cartilage of the nasal valve 13 up and away 625 from the septum 24, giving the forward aspect of the insertable portion 107 a more direct line-of-sight to the olfactory clefts 23 or portions thereof, middle meatus 30 or back to the turbinates of the nasal channel 20. In some embodiments, the device comprises the flat shape of the insertable portion 107, wherein the flat shape of the insertable portion 107 provides preferential bending to accommodate irregular surfaces along the septum 24. In some embodiments, the device comprises the flat shape of the insertable portion 107, 'wherein the flat shape of the insertable portion 107 provides preferential stiffness to minimize deflection back into the nasal channel 20 should there be irregular intrusions of, for example, the inferior nasal cartilage. In some embodiments, the device comprises the insertable portion 107, wherein the insertable portion 107 are configured to accommodate various degrees of columella flaring. In some embodiments, the various degrees of columella flaring comprise wider, closer to the face, or further from the tip of nose. In some embodiments, the device comprises the lower aspect of the insertable portion 107 joining the columella saddle 121 in a manner which allows the fully inserted insertable portion 107 to comfortable bend to the subject's columella shape 10 without affecting the overall positioning of the inserted insertable portion 107. In some embodiments, the two insertable portions 107 can hug the septum 24 and rest comfortably without handholding when fully inserted. In some embodiments, facilitating a stationary insertion of a cannula could enable the deposition and retrieval of a liquid bolus, e.g., a liquid swab, for retrieving a biological sample from the subject's nasal cavity. In some embodiments, the dual insertable portion can hug the septum 24 and rest comfortably without handholding which could enable passive involvement of the subject for an independently timed actuation. In some embodiments, a sleeping or sedated subject may have drug or liquid swab released simultaneously timed to slow brain wave sleep. In some embodiments, dosing both nasal channels 20 at the same time removes the concern of nasal cycling, for example, in lower nasal 35 delivery (in some embodiments, reference number 35 corresponds to an ejection site, for example an ejection site within an ejection zone). In some embodiments, averaging both nasal cavities 11 should minimize dosing fluctuations related to dosing to one nasal channel 20 which may open or congested depending on what stage that nasal channel 20 is in its cycle.

In some embodiments, the at least one cannula is configured for administration of large volumes of drug at once, minimizing time and complexity in rescue situation e.g., reducing multi-administrations for opioid reversal. In some embodiments, the cannula tip comprises a bulbous to facilitate insertion without risk of fetching (e.g., snagging on tissue in the nasal channel). In some embodiments, the cannula anterior lumen can be made of drug compatible materials sheathed in a different material that is biocompatible with the mucus membrane, but not necessarily drug comparable. In some embodiments, the cannula anterior lumen can be made of drug compatible materials sheathed in a different material that is biocompatible with the mucus membrane, but not necessarily drug comparable enables for lower manufacturing expense and complexity. In some embodiments, the inner lumen can be extruded for consistent inner diameter. In some embodiments, the manufacturing of outer aspects of the cannula can be molded, printed, etc. without concern for the tighter tolerances of the inner diameter. In some embodiments, the inner lumen can be made of stock material for example a cannula for drug delivery of a different route of administration e.g., hand iv cannula. In some embodiments, the inner lumen of a sheathed nasal cannula can provide structural strength to the outer sheath allowing the outer sheath to be made of more compliant material that is more comfortable and safer to the mucus membrane. In some embodiments, the device comprises the inner lumen, wherein the inner lumen is configured to accommodate different drugs and formulations, e.g., inner diameter, while still using the same outer sheath. In some embodiments, the device comprises minimizing SKUs and simplifying, e.g., converting filling line from one formulation to another. In some embodiments, the cannula comprises a sheath, wherein the sheath allows for gas (air) or liquid to be simultaneously ejected along deliberate channels in the annulus between the inner lumen and the sheath. In some embodiments, the cannula comprises a cannula annulus facilitates, e.g., an ejection of gas at the tip of the cannula to assist in liquid jet or spray patterns, or combining with a reactive component of a drug formulation at the time it is ejected an in the body of a subject. In some embodiments, the device comprises a smaller diameter cannula, wherein the cannula is configured to be introduced beyond the nasal channel 20 hairs (avoid a sneeze reflect), the outer nasal channels (avoiding cross contamination of bacteria known to occupy the biome of this aspect of the anatomy), and will not snag on the nasal valve 13 or be diverted back into lower nasal channel 35. In some embodiments, the device comprises a smaller diameter cannula, wherein the small diameter cannula enables access the tighter space behind the nasal bone, a vantage point 34 which provides a more direct line of sight to the olfactory cleft 23, middle meatus 30, or other turbinates. In some embodiments, the device comprises not revealing the smaller diameter cannula until after device is inserted and out-of-sight can reduce fear associated with perception of 'poking a pointy and narrow object' deep into a nasal channel, e.g., fainting.

In some embodiments, the dispensing element 110 is positioned from about 0.1 mm to about 30 mm from the olfactory region 23 or an anterior entry to the olfactory region 23, the middle meatus 30, or other nasal anatomy. In some embodiments, the distal aspect 131 is positioned from about 0.1 mm to about 25 mm from the olfactory region 23 or an anterior entry to the olfactory region 23, the middle meatus 30, or other nasal anatomy. In some embodiments, the distal aspect 131 is positioned from about 0.1 mm to about 3 mm, about 0.1 mm to about 5 mm, about 0.1 mm to about 9 mm, about 0.1 mm to about 12 mm, about 0.1 mm to about 18 mm, about 0.1 mm to about 20 mm, about 0.1 mm to about 25 mm, about 3 mm to about 5 mm, about 3 mm to about 9 mm, about 3 mm to about 12 mm, about 3 mm to about 18 mm, about 3 mm to about 20 mm, about 3 mm to about 25 mm, about 5 mm to about 9 mm, about 5 mm to about 12 mm, about 5 mm to about 18 mm, about 5 mm to about 20 mm, about 5 mm to about 25 mm, about 9 mm to about 12 mm, about 9 mm to about 18 mm, about 9 mm to about 20 mm, about 9 mm to about 25 mm, about 12 mm to about 18 mm, about 12 mm to about 20 mm, about 12 mm to about 25 mm, about 18 mm to about 20 mm, about 18 mm to about 25 mm, or about 20 mm to about 25 mm, including increments therein. In some embodiments, the tip is positioned from about 0.1 mm, about 3 mm, about 5 mm, about 9 mm, about 12 mm, about 18 mm, about 20 mm, or about 25 mm from the olfactory region 23 or an anterior entry to the olfactory region 23, the middle meatus 30, or other nasal anatomy. In some embodiments, the tip is positioned from at least about 0.1 mm, about 3 mm, about 5 mm, about 9 mm, about 12 mm, about 18 mm, or about 20 mm from the olfactory region 23 or an anterior entry to the olfactory region 23, the middle meatus 30, or other nasal anatomy. In some embodiments, the dispensing element is positioned from at most about 3 mm, about 5 mm, about 9 mm, about 12 mm, about 18 mm, about 20 mm, or about 25 mm from the olfactory region 23 or an anterior entry to the olfactory region 23, the middle meatus 30, or other nasal anatomy.

Figure 7A:
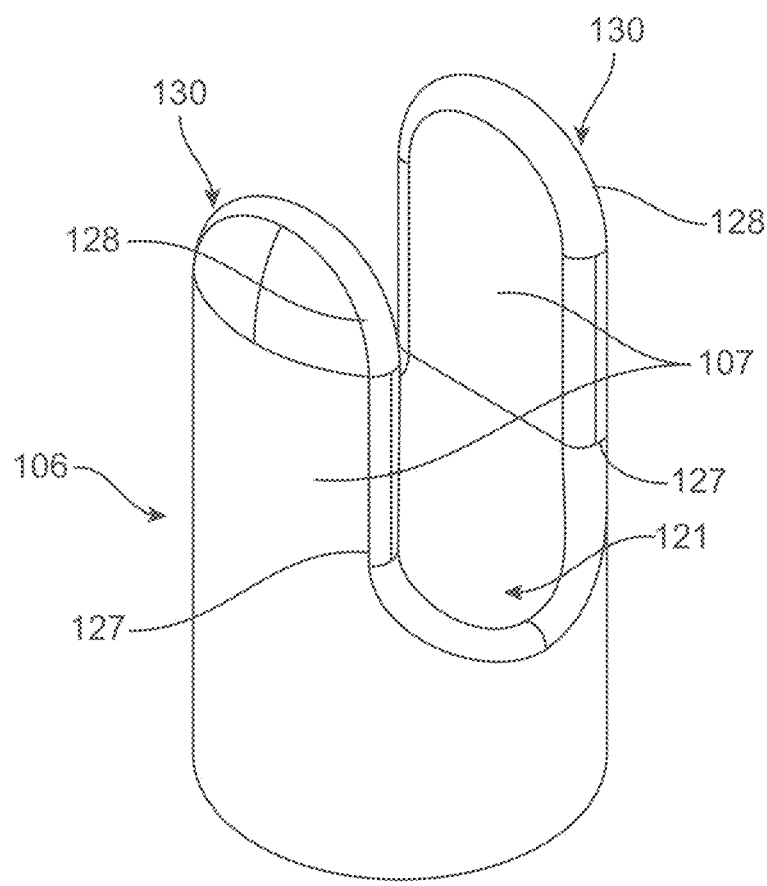
FIG. 7A depicts an exemplary embodiment perspective view of an exemplary insertable portion and a columella subject engaging portion in the first configuration, according to some embodiments.

FIG. 7A depicts an exemplary embodiment perspective view of an Exemplary Columella Saddle in the first configuration. In some embodiments, the device comprises a subject engaging portion 106, a columella saddle 121, and two insertable portions 107.

In some embodiments, the device comprises at least one insertable portion 107. In some embodiments, the device comprises two insertable portions 107. In some embodiments, the at least one insertable portion 107 comprises a shape 130, wherein the shape comprises a wing, a foil, a wedge, an oval or oblong, or even a round form. In some embodiments, the distalend 128 of the insertable portion 107 comprise a rounded shape 130. In some embodiments, the at least one insertable portion 107 comprises a shape 130 whereby an aspect of the at least one insertable portion 107 fits snuggly into the narrow "slit-like" anterior aspect of the internal nasal valve 13 where the septum 24 meets the upper lateral cartilage 25. In some embodiments, the at least one insertable portion 107 has a height of about 10 mm to about 30 mm, a depth of about 3 mm to about 15 mm, and a width of about 1 mm to 5 mm.

In some embodiments, the columella saddle 121 comprises a "U" or "saddle" shape adapted for engaging the columella region 10 of a subject. In some embodiments, the subject engaging portion 106 engages the columella region 10 of the subject about multiple sides of the columella region 10 in a concave shape.

Figure 7B:
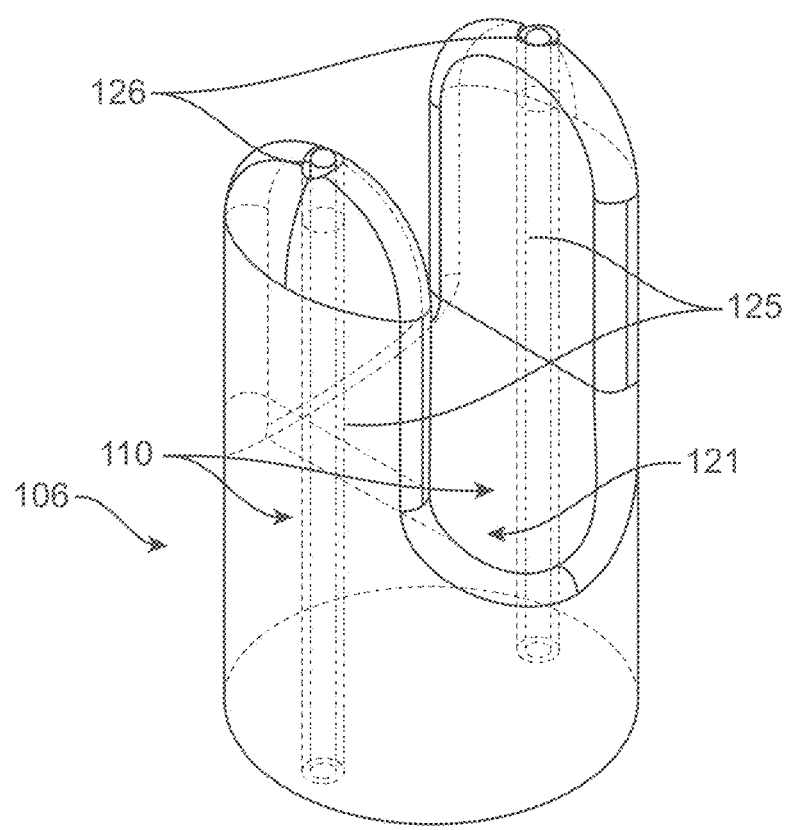
FIG. 7B depicts an exemplary embodiment perspective internal component view of an exemplary insertable portion and a columella subject engaging portion in the first configuration, according to some embodiments.

FIG. 7B depicts an exemplary embodiment perspective internal component view of an exemplary columella saddle in the first configuration. In some embodiments, the device comprises a subject engaging portion 106, the subject engaging portion 106 may function as a positioning element and may include a columella saddle 121, two insertable portions 107, and two dispensing elements or dispensing channels 125 with dispensing ports 126 positioned at the at the distal aspect 131 of the dispensing elements 125 for delivering a composition 111 to a targeted area of the nasal channels 20, such as the olfactory clefts 23, middle meatus 30, or turbinates. In some embodiments, the composition 111 is delivered from both dispensing ports 126 simultaneously. In some embodiments, the composition 111 is delivered from both dispensing ports 126 sequentially. In some embodiments, the dispensing channels 125 may be dispensing elements 110. In some embodiments, the dispensing elements 110 may be cannulas.

Figure 19A:
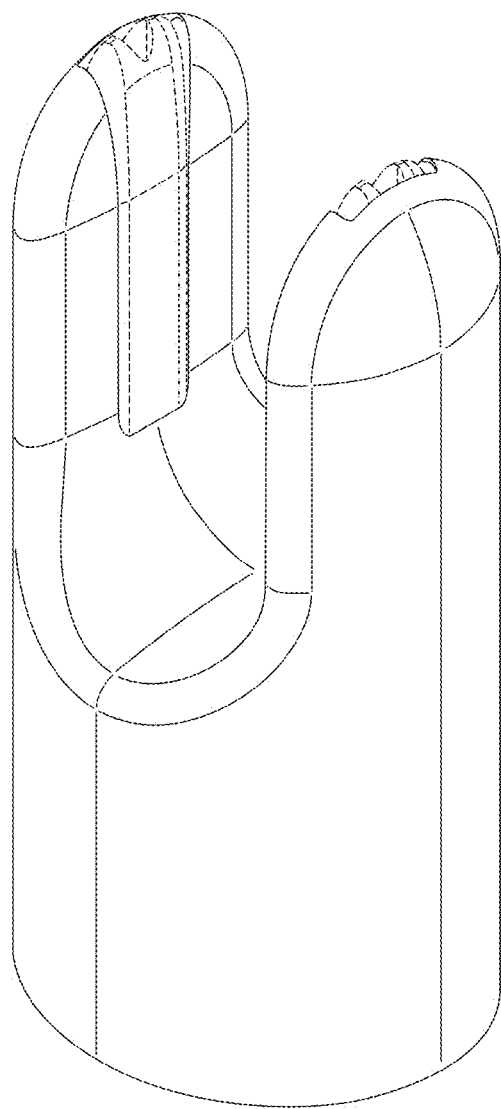
FIG. 19A shows a front, right, top perspective view of an exemplary insertable portion and a columella subject engaging portion in the first configuration, according to some embodiments.
Figure 19B:
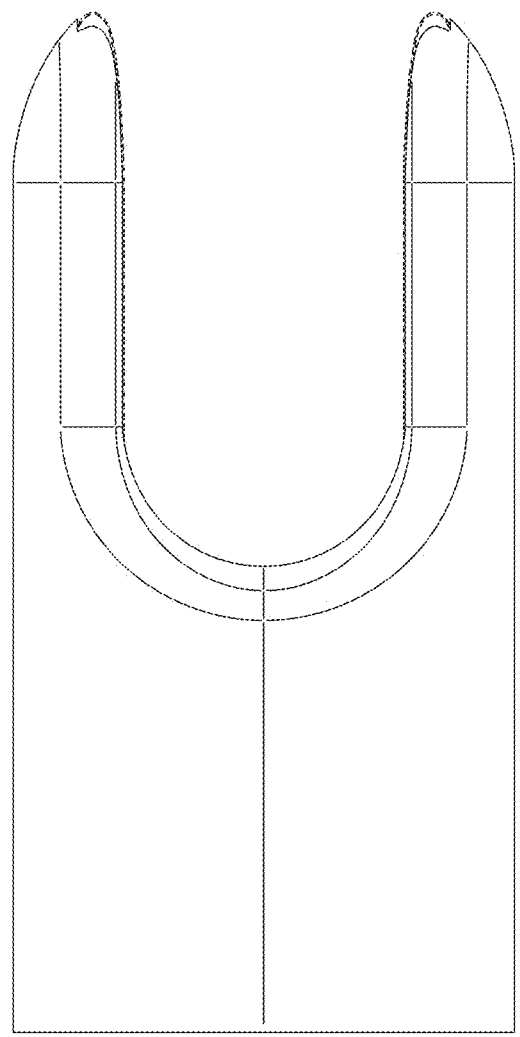
FIG. 19B shows a front view of an exemplary insertable portion and a columella subject engaging portion in the first configuration, according to some embodiments.
Figure 19C:
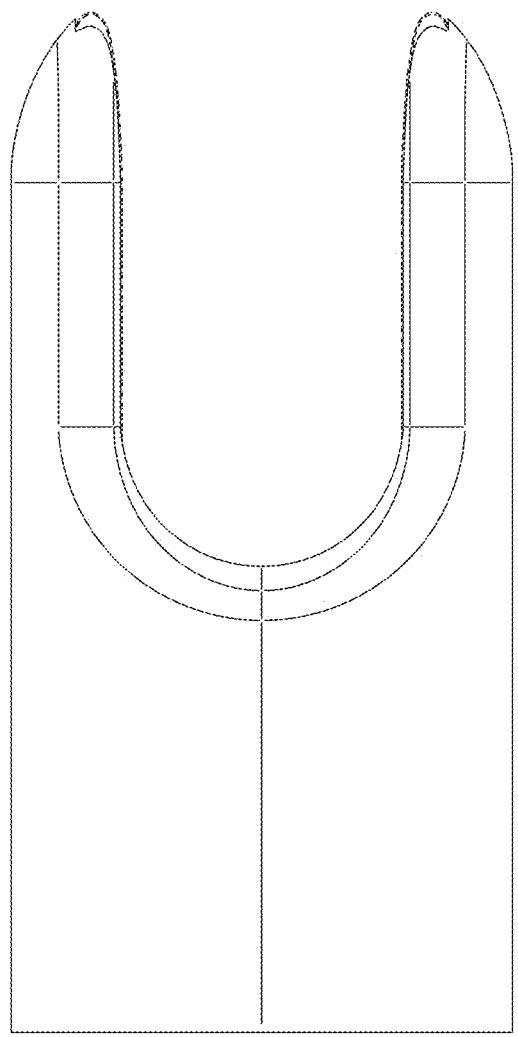
FIG. 19C shows a back view of an exemplary insertable portion and a columella subject engaging portion in the first configuration, according to some embodiments.
Figure 19D:
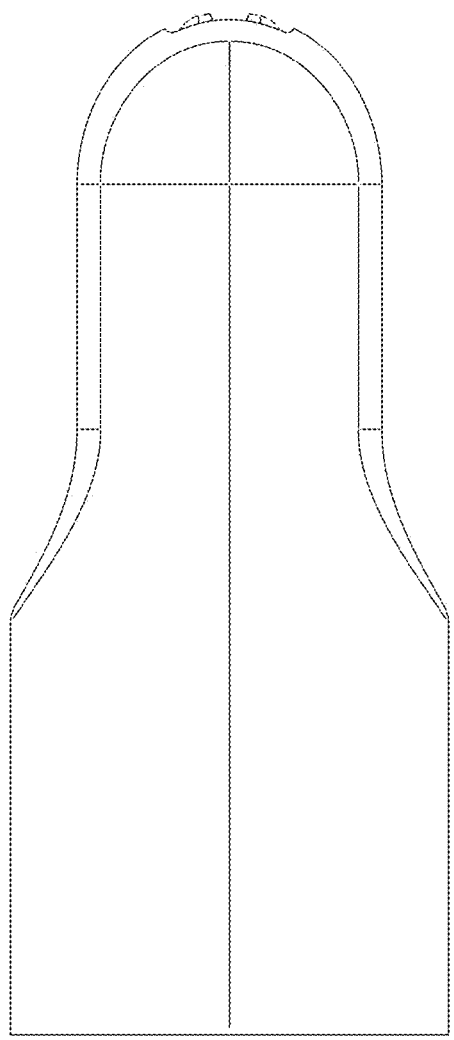
FIG. 19D shows a side view of an exemplary insertable portion and a columella subject engaging portion in the first configuration, according to some embodiments.
Figure 19E:
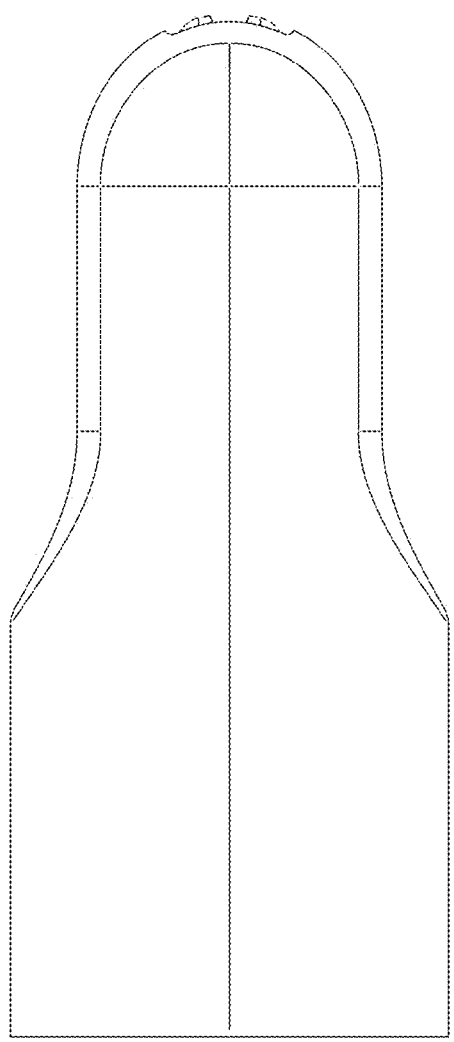
FIG. 19E shows an opposite side view of an exemplary insertable portion and a columella subject engaging portion in the first configuration, according to some embodiments.
Figure 19F:
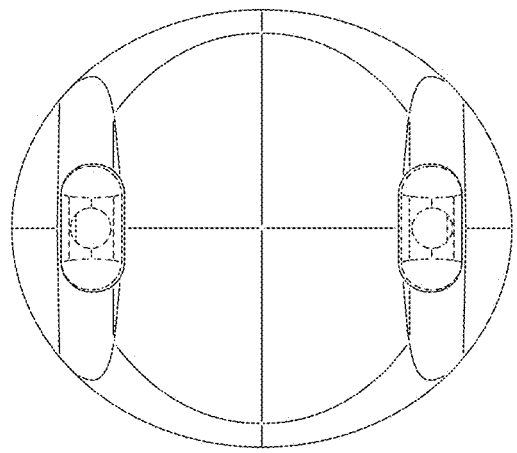
FIG. 19F shows a top view of an exemplary insertable portion and a columella subject engaging portion in the first configuration, according to some embodiments.
Figure 19G:
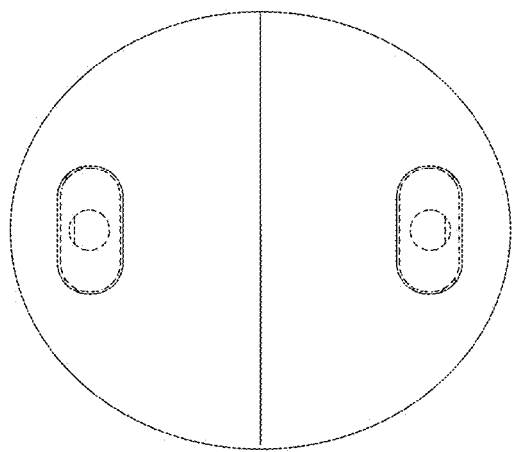
FIG. 19G shows a bottom view of an exemplary insertable portion and a columella subject engaging portion in the first configuration, according to some embodiments.
Figure 19H:
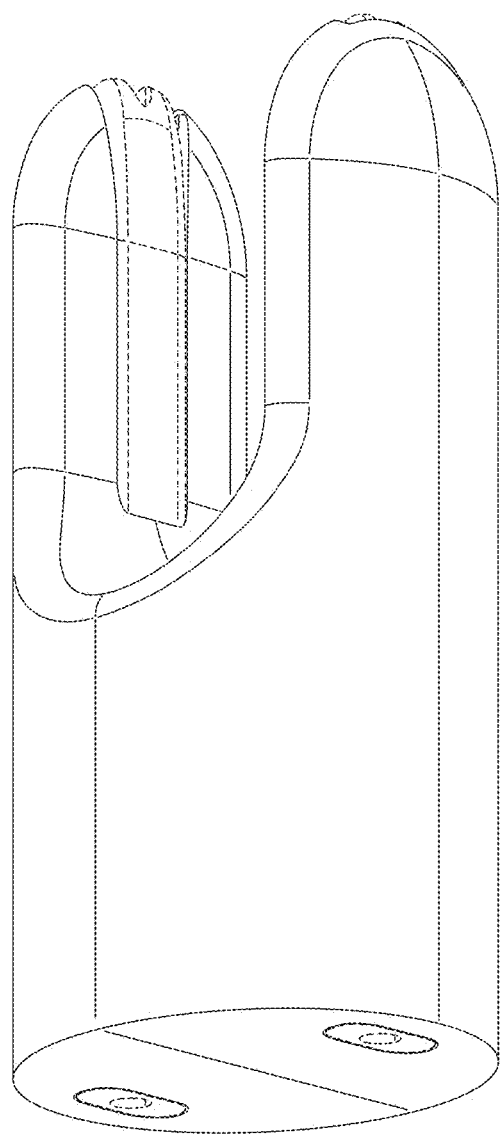
FIG. 19H shows a front, right, bottom view of an exemplary insertable portion and a columella subject engaging portion in the first configuration, according to some embodiments.
Figure 20A:
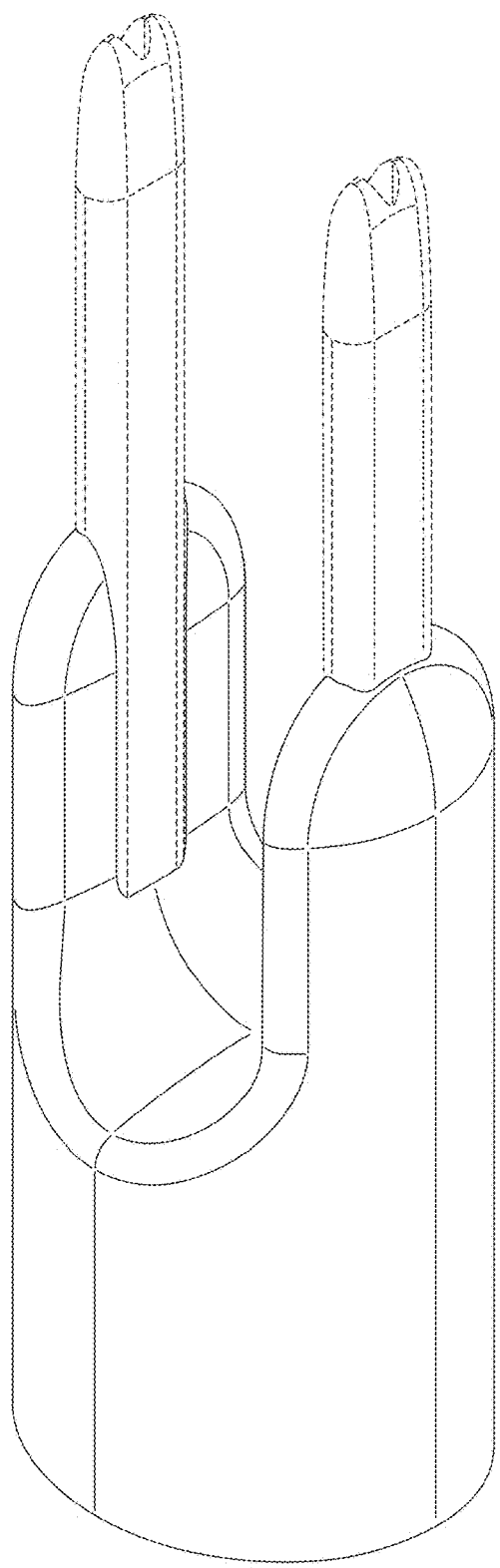
FIG. 20A shows a front, right, top perspective view of an exemplary insertable portion and a columella subject engaging portion in the second configuration, according to some embodiments.
Figure 20B:
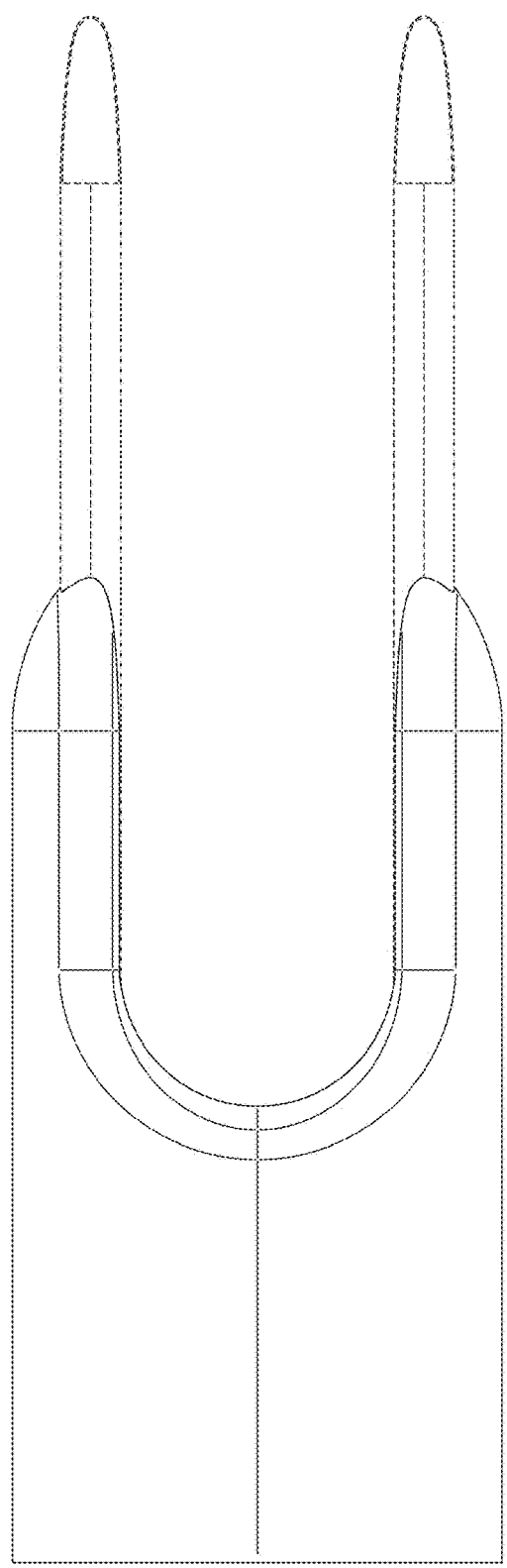
FIG. 20B shows a front view of an exemplary insertable portion and a columella subject engaging portion in the second configuration, according to some embodiments.
Figure 20C:
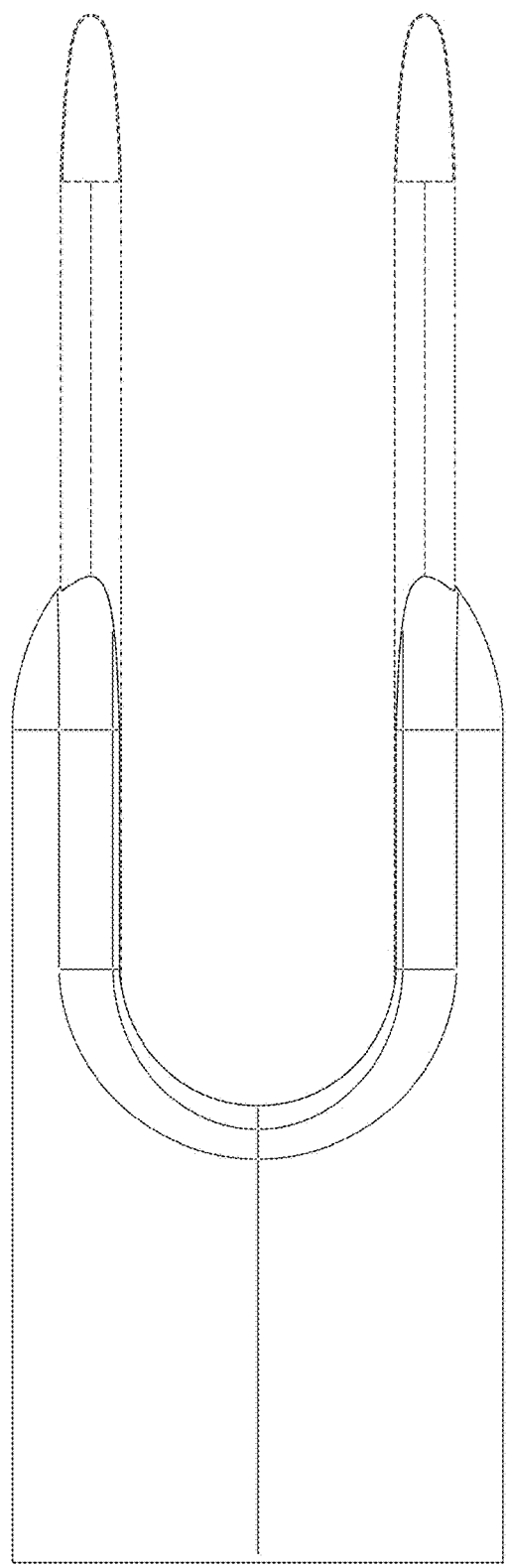
FIG. 20C shows a back view of an exemplary insertable portion and a columella subject engaging portion in the second configuration, according to some embodiments.
Figure 20D:
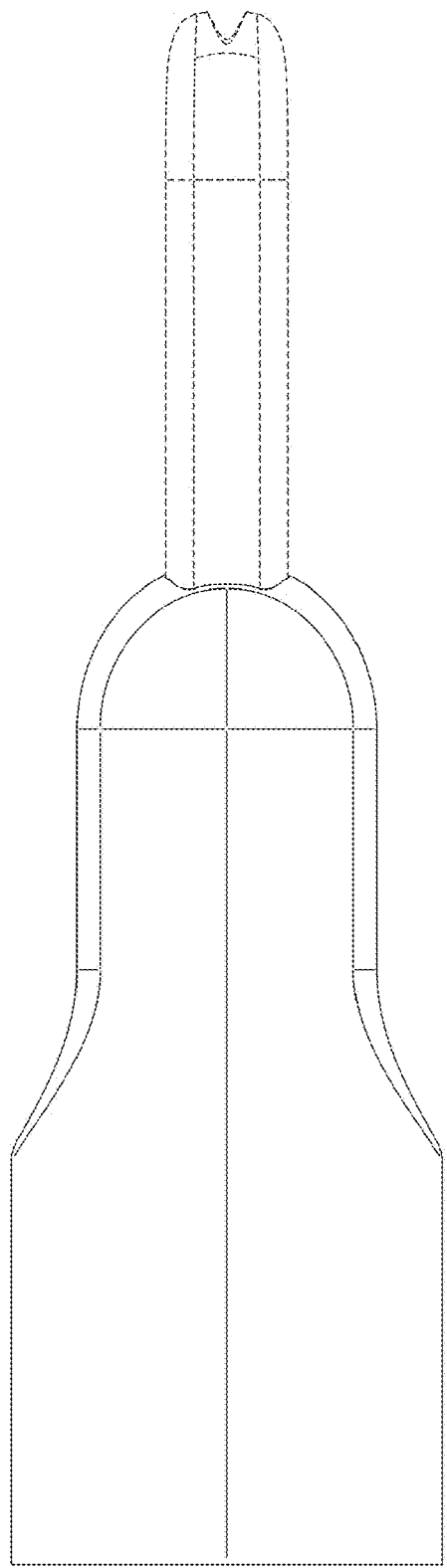
FIG. 20D shows a side view of an exemplary insertable portion and a columella subject engaging portion in the second configuration, according to some embodiments.
Figure 20E:
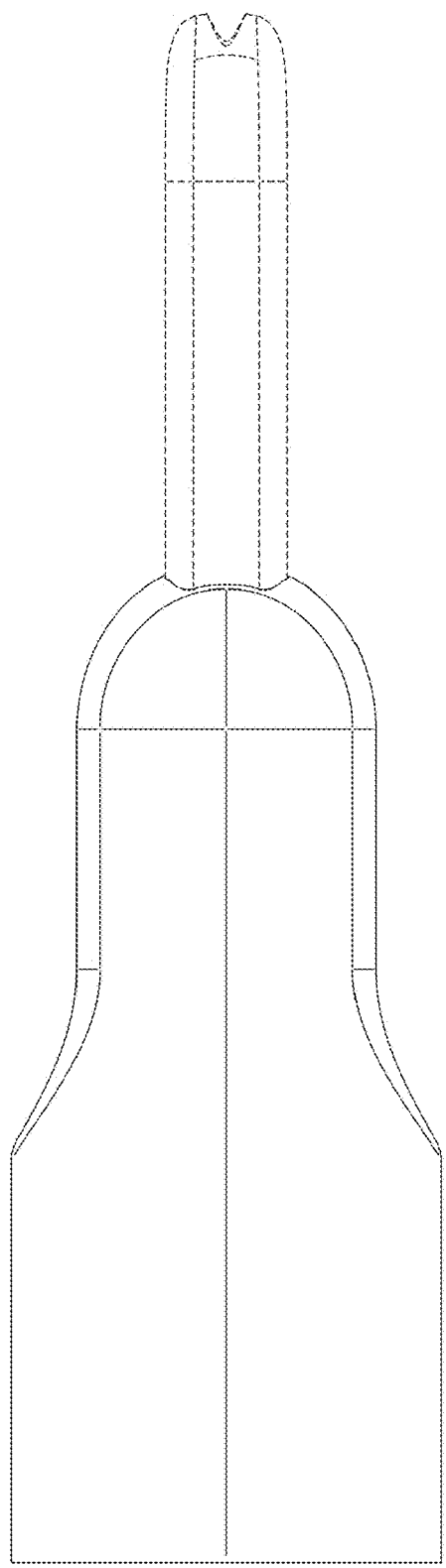
FIG. 20E shows an opposite side view of an exemplary insertable portion and a columella subject engaging portion in the second configuration, according to some embodiments.
Figure 20F:
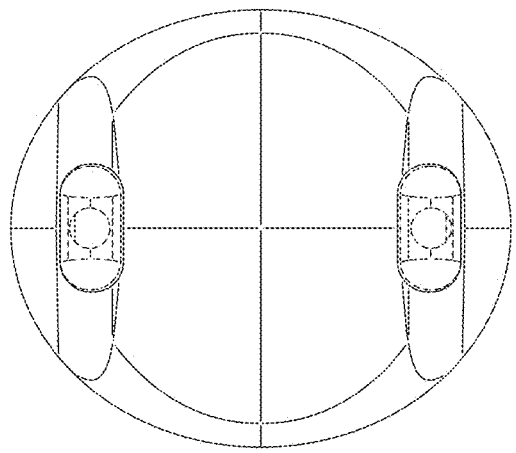
FIG. 20F shows a top view of an exemplary insertable portion and a columella subject engaging portion in the second configuration, according to some embodiments.
Figure 20G:
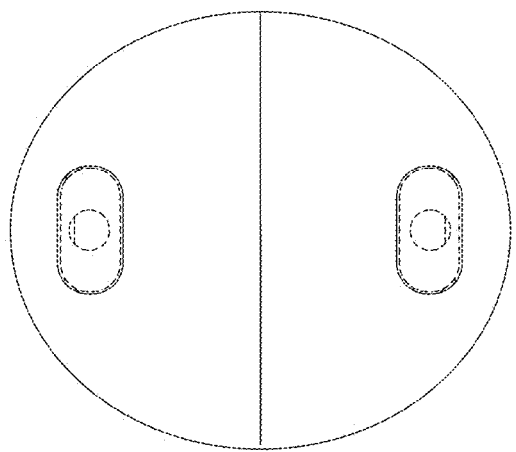
FIG. 20G shows a bottom view of an exemplary insertable portion and a columella subject engaging portion in the second configuration, according to some embodiments.
Figure 20H:
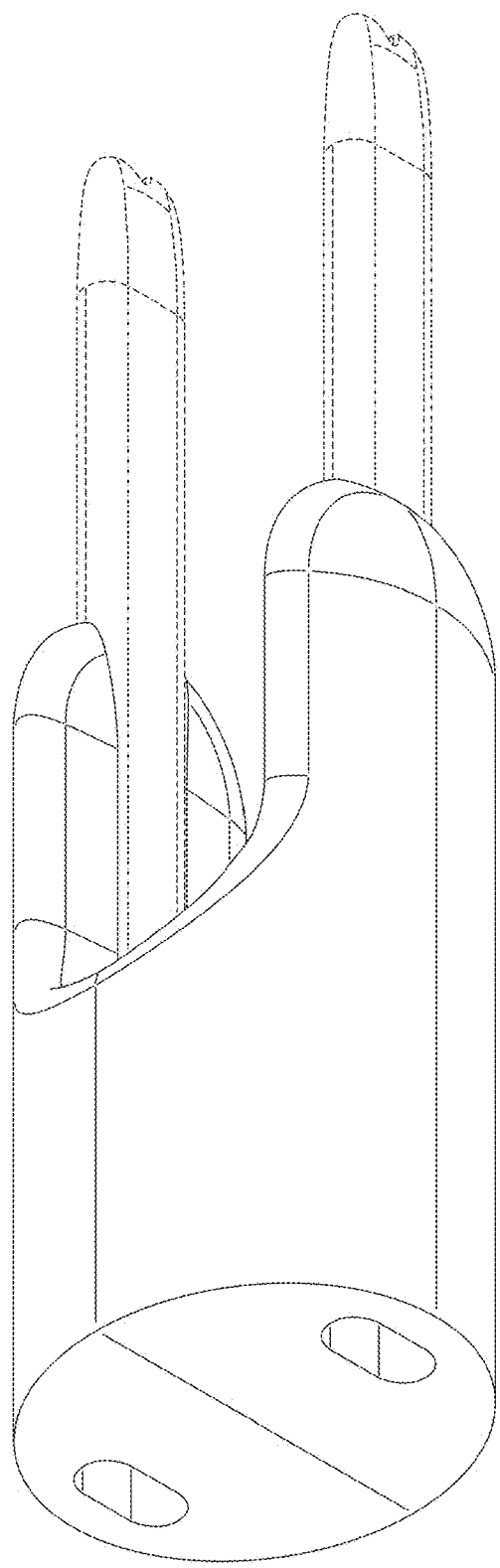
FIG. 20H shows a front, right, bottom view of an exemplary insertable portion and a columella subject engaging portion in the second configuration, according to some embodiments.
Figure 21C:
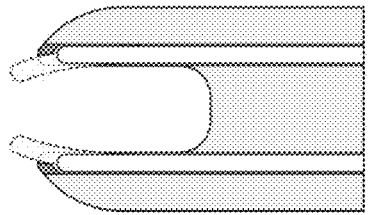
FIG. 21C shows a front view of an exemplary insertable portion and a columella subject engaging portion in the first configuration and in the second configuration, according to some embodiments. In this non-limiting example, the saddle width is 9 mm. The two cannulas extend inwardly towards each other such while the cannula width is 9 mm in the first configuration, it decreases to 6 mm in the second configuration.
Figure 21B:
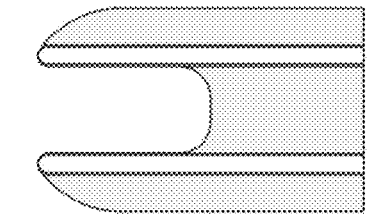
FIG. 21B shows a front view of an exemplary insertable portion and a columella subject engaging portion in the first configuration, according to some embodiments. In this non-limiting example, the saddle width is 9 mm and the two insertable portions are biased inwards such that the cannula width is only 6 mm.
Figure 21A:
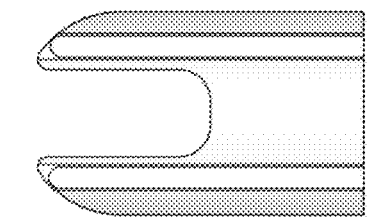
FIG. 21A shows a front view of an exemplary insertable portion and a columella subject engaging portion in the first configuration, according to some embodiments. In this non-limiting example, the two extendable cannulas are slightly inset within the insertable portion such that the width of the saddle is 9 mm and the width between the two cannula is 11 mm. The two insertable portions and the two cannulas are all essentially parallel.

In some embodiments, the device comprises at least one dispensing element/channel 125 (e.g., cannula) and at least one dispensing port 126. In some embodiments, the device comprises two dispensing channels 125 and two dispensing ports 126. In some embodiments, the at least one dispensing channel 125 is unlined. In some embodiments, the at least one dispensing channel 125 is lined with a material that is distinct from the material of the one or more insertable portions 107. In some embodiments, the at least one dispensing channel 125 comprises at least one dispensing element 110, e.g., cannula, that is immovable relative to the at least one insertable portion 107. In some embodiments, the at least one dispensing channel 125 has an inner diameter 129 of 0.5 mm to 3 mm. In some embodiments, the at least one dispensing channel 125 has a round cylindrical shape. In some embodiments, the at least one dispensing channel 125 has an elliptic cylindrical shape. In some embodiments, the first and/or second insertable portion has a cross sectional shape comprising an elongated oval with consistent width and symmetrical rounded ends. In some embodiments, the first and/or second insertable portion has a cross sectional shape comprising a long rounded rectangular shape with semi-circular ends. An example cross sectional shape for the insertable portions is shown in FIG. 19F.

In some embodiments, the at least one dispensing port 126 delivers a composition 111 to a targeted area of a nasal channel 20, such as an olfactory cleft 23, middle meatus 30, or turbinates. In some embodiments, the at least one dispensing port 126 comprises an atomizer. In some embodiments, the at least one dispensing port 126 doesn't comprise an atomizer.

Figure 7C:
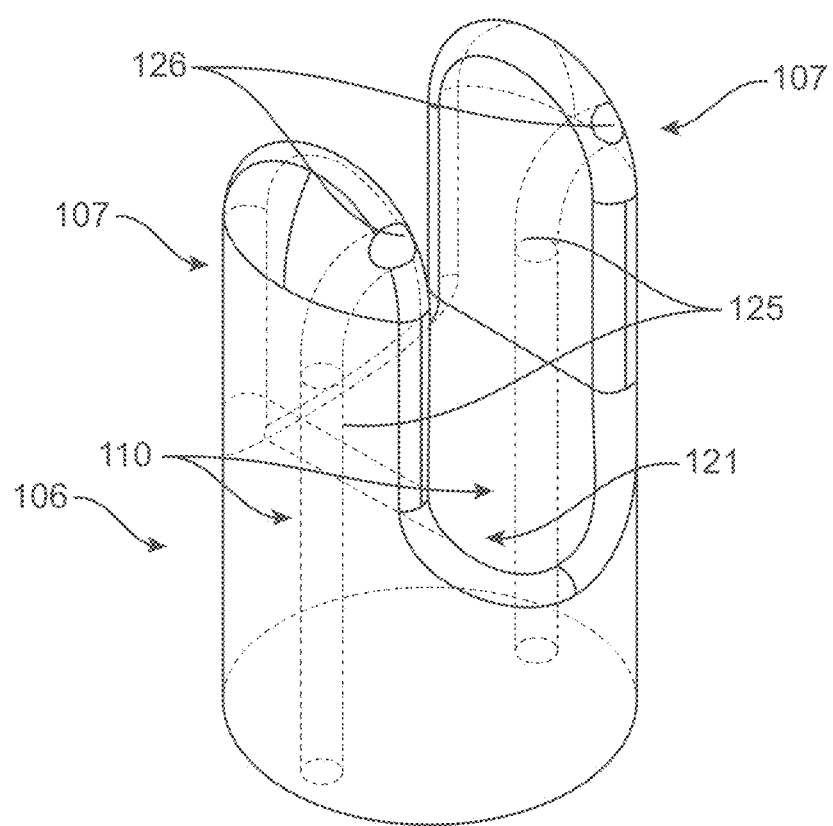
FIG. 7C depicts an exemplary embodiment perspective internal component view of an exemplary insertable portion and a columella subject engaging portion in the first configuration, according to some embodiments.

FIG. 7C depicts an exemplary embodiment perspective internal component view of an Exemplary Columella Saddle in the first configuration. In some embodiments, the device comprises a positioning element, the positioning element comprising a subject engaging portion 106, a columella saddle 121, two insertable portions 107, and two dispensing channels 125 with dispensing ports 126 positioned at a point along the edge of the insertable portions 107 for delivering a composition 111 from the device to a targeted area of the nasal channels 20, such as the middle turbinates 15, middle meatus 30, or olfactory clefts 23.

In some cases, the middle turbinate 15 comprises a physical obstruction for composition 111 delivery to an olfactory cleft 23, middle meatus 30, or turbinates. In some cases, the middle turbinate 15 comprises a most anterior aspect about aligned with the cheek bone. In some embodiments, the middle turbinate 15 comprises a most anterior aspect not aligned with the cheek bone. In some embodiments, the nasal channels 20 simplify anteriorly, and comprise angled pathways without one or more turbinates presenting physical obstacles to delivering a composition 111 to the upper nasal channels 20, including the olfactory clefts 23, or directing compositions down one or more meatuses to the nasopharynx.

In some embodiments, the nasal channel 20 comprises one pathway from the vestibule 21 to the olfactory cleft 23 based on a second plane 18 with a target region 19. In some embodiments, the device is adapted to target delivery of the composition 111 to an olfactory cleft 23 or a portion thereof, and the positioning element may align at least one insertable portion 107 or one dispensing element 110 with an olfactory cleft 23 of the subject. In some embodiments, the at least one composition channel 125 within an insertable portion 107, or the at least one dispensing element 110 has an inner diameter 129 of 0.3 to 3.0 mm. In some embodiments, the at least one composition channel 125 within an insertable portion 107, or the at least one dispensing element 110 has an inner diameter 129 of 0.3 to 0.7 mm. In some embodiments, the at least one composition channel 125 within an insertable portion 107, or the at least one dispensing element 110 has an inner diameter 129 of 0.5 to 1.0 mm. In some embodiments, a wider inner diameter 129 may be used to deliver high viscosity compositions. In some embodiments, the composition channel 125 within an insertable portion 107, or the dispensing element 110 may be adapted to deliver a composition 111 having a low, intermediate, or high viscosity.

In some embodiments, the at least dispensing channel 125 splits into multiple dispensing channels 125 leading to multiple dispensing ports 126 positioned at multiple locations on the at least one insertable portion 107 for delivering a composition to multiple targeted regions 19 of one or both nasal channels 20, such as the olfactory clefts 23, middle meatus 30, and the middle turbinates 15.

Figure 7D:
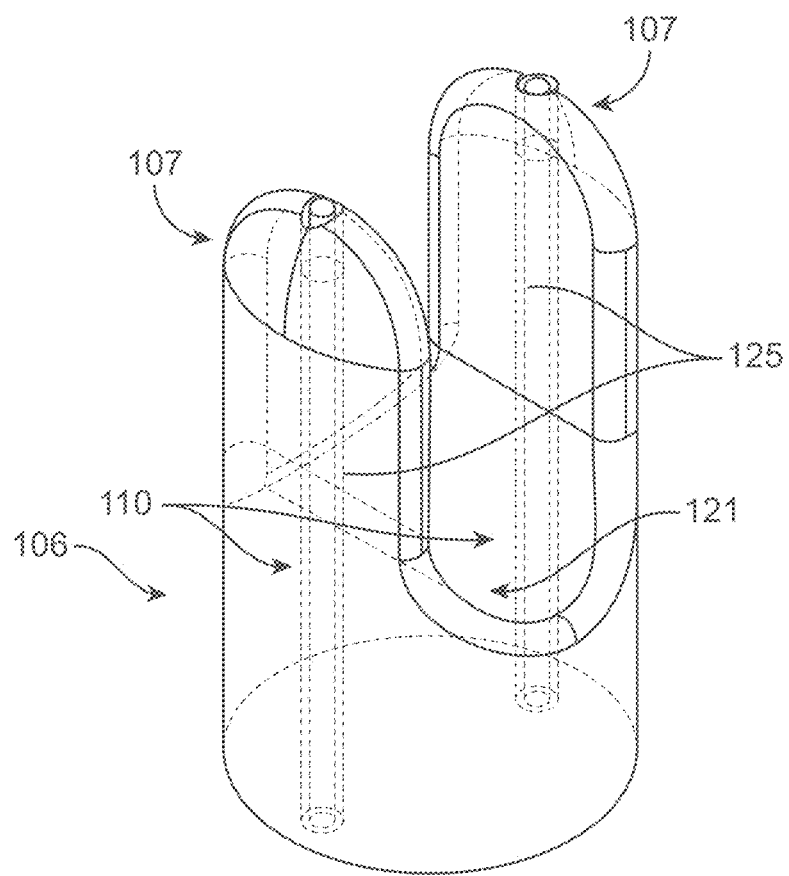
FIG. 7D depicts an exemplary embodiment perspective internal component view of an exemplary insertable portion and a columella subject engaging portion in the first configuration, according to some embodiments.

FIG. 7D depicts an exemplary embodiment perspective internal component view of an Exemplary Columella Saddle in the first configuration. In some embodiments, the device comprises a subject engaging portion 106, a columella saddle 121, two insertable portions 107, and two dispensing elements 110 in a first configuration 100.

In some embodiments, the device comprises at least one dispensing element 110. In some embodiments, the device comprises two dispensing elements 110. In some embodiments, the at least one dispensing element 110 comprises a cannula or a catheter. In some embodiments, the at least one dispensing element 110 has an inner diameter 129 of 0.5 mm to 3 mm. In some embodiments, the at least one dispensing element 110 has a round cylindrical shape. In some embodiments, the at least one dispensing element 110 has an elliptic cylindrical shape.

Figure 7E:
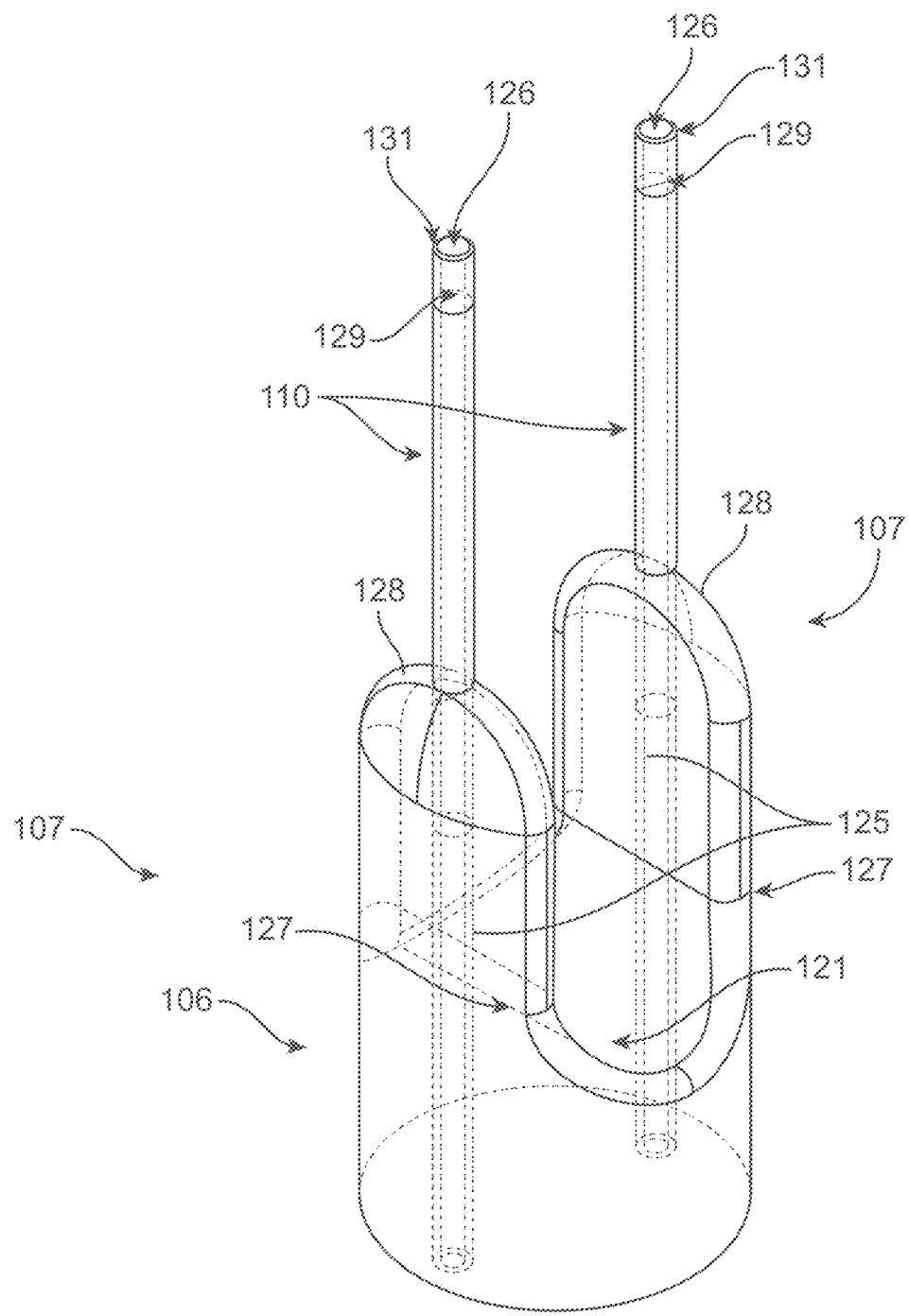
FIG. 7E depicts an exemplary embodiment perspective internal component view of an exemplary insertable portion and a columella subject engaging portion in the second configuration, according to some embodiments.

FIG. 7E depicts an exemplary embodiment perspective internal component view of an Exemplary Columella Saddle in the second configuration. In some embodiments, the device comprises a positioning element, the positioning element comprising a subject engaging portion 106, a columella saddle 121, two insertable portions 107, and two dispensing elements 110 in a second configuration 200.

In some embodiments, the device comprises at least one dispensing element 110. In some embodiments, the device comprises two dispensing elements 110. In some embodiments, the at least one dispensing element emerges from or is revealed by the at least one insertable portion 107 from the distal aspect 131 of the insertable portion 107 upon transition of the device from the first configuration 100 to the second configuration 200. In some embodiments, the at least one dispensing element 110 emerges from or is revealed by the at least one insertable portion 107 from another aspect of the insertable portion 107, such as along the edge of the at least one insertable portion 107. In some embodiments, the at least one dispensing element 110 is positioned to deliver a composition 111 to a target area in one or both nasal channels 20, such as one or both olfactory clefts 23, the middle meatus 30, or the turbinates. In some embodiments, the length of the portion of the at least one dispensing element 110 that extends from or is revealed by the at least one insertable portion 107 is about 5 mm to about 40 mm. In some embodiments, the distance from the distal aspect 131 of the at least one dispensing element 110 to the anterior aspect of the cribriform plate 31 is about 5 mm to about 40 mm. In some embodiments, the distance from the distal aspect 131 of the at least one dispensing element 110 to the anterosuperior aspect of one or both olfactory clefts 23 are about 5 mm to about 40 mm. In some embodiments, the composition 111 is delivered from both dispensing elements 110 simultaneously. In some embodiments, the composition 111 is delivered from both dispensing elements 110 sequentially.

In some embodiments, the device is adapted to target delivery of the composition 111 to an olfactory cleft 23 or a portion thereof, and the subject engaging portion 106 may align at least one insertable portion 107 or one dispensing element 110 with an olfactory cleft 23 of the subject. In some embodiments, the device is adapted to target delivery of the composition 111 to a middle meatus 30 or a portion thereof, and the subject engaging portion 106 may align at least one insertable portion 107 or one dispensing element 110 with a middle meatus 30 of the subject. In some embodiments, the at least one composition channel 125 within an insertable portion 107, or the at least one dispensing element 110 has an inner diameter 129 of 0.3 to 3.0 mm. In some embodiments, the at least one composition channel 125 within an insertable portion 107, or the at least one dispensing element 110 has an inner diameter 129 of 0.3 to 0.7 mm. In some embodiments, the at least one composition channel 125 within an insertable portion 107, or the at least one dispensing element 110 has an inner diameter 129 of 0.5 to 1.0 mm. In some embodiments, a wider inner diameter 129 may be used to deliver high viscosity compositions. In some embodiments, the composition channel 125 within an insertable portion 107, or the dispensing element 110 may be adapted to deliver a composition 111 having a low, intermediate, or high viscosity.

In some embodiments, the subject engaging portion 106 positions the insertable portion 107 within a nasal channel 20 of the subject and limits the depth of insertion of the insertable portion 107 into the nasal channel 20. In some embodiments, the housing 101 defines two insertable portions 107, each for insertion into a nasal channel 20 of the subject, wherein, upon insertion of the first insertable portion 107 into a nasal channel 20 of the subject, the first insertable portion 107 engages tissue within the nasal channel 20 to open or expand an internal nasal valve 13 of the subject thereby positioning at least one of the insertable portions 107 for delivery of the composition 111 to the subject, the device further comprising an actuator which delivers the composition 111 from the either or both of the insertable portions 107 when the device is actuated.

In some embodiments, the housing 101 defines two insertable portions 107, each for delivery of the composition 111 into a nasal channel 20 of the subject, the device further comprising an actuator which delivers the composition 111 from either or both of the insertable portions 107 when the device is actuated. In some embodiments, the device is transitionable from a first configuration 100 to a second configuration 200, the device further comprising a dispensing element 110 coupled to the housing 101, the dispensing element 110 revealing from the first insertable portion 107 upon transition of the device from the first configuration 100 to the second configuration 200. In some embodiments, the device is simultaneously actuated upon being transitioned from the first configuration 100 to the second configuration 200. In some embodiments, the device is transitionable from first configuration 100 to the second configuration 200 upon application of pressure about a longitudinal axis 610 of the device, wherein the dispensing element 110 reveals in a linear vector relative to a longitudinal axis 610 of the first insertable portion 107, or wherein the device is configured to be transitioned from the first configuration 100 to the second configuration 200 with only one hand. In some embodiments, the subject engaging portion 106 engages a columella region 10 of the subject to seat a distal end 128 of the insertable portion 107 within an ejection zone 29 of a nasal cavity 11 of the subject.

Figure 11:
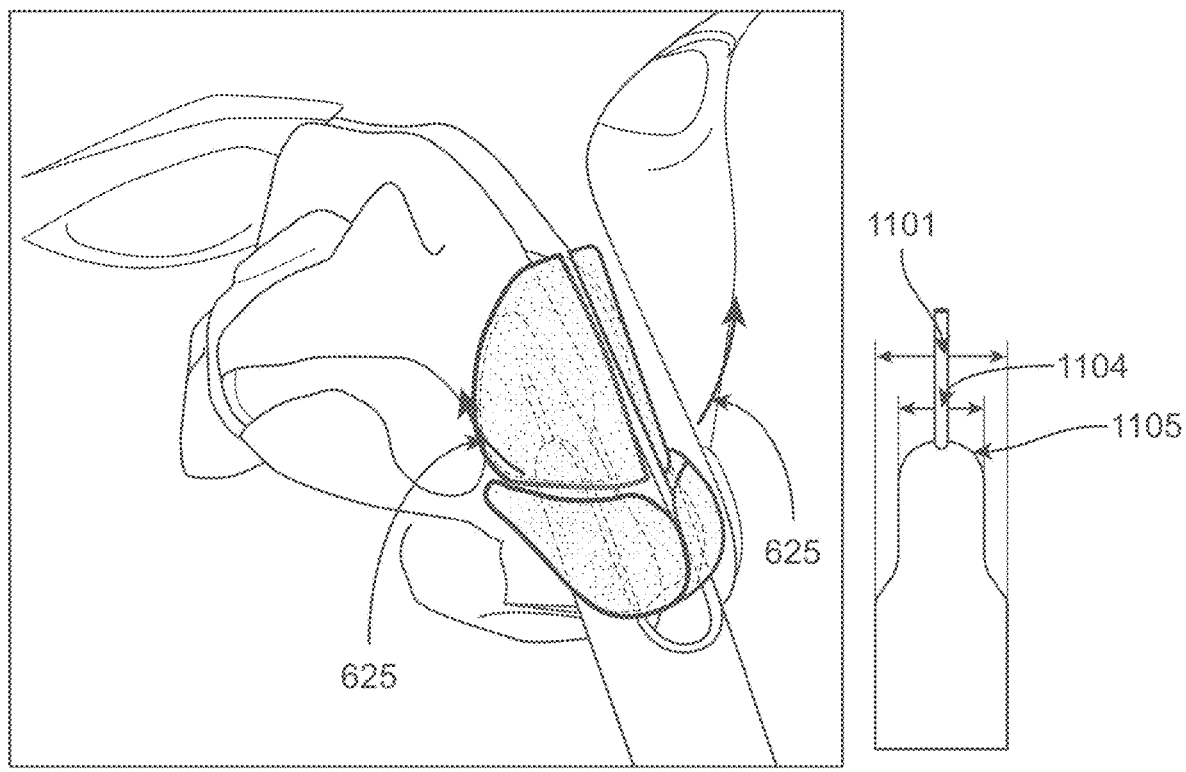
FIG. 11 depicts the anatomy of the nasal cavity in a subject and an exemplary device opening or expanding the internal nasal valve and an exemplary side view of an exemplary insertable portion and a columella subject engaging portion in the first configuration, according to some embodiments.

FIG. 11 depicts the anatomy of the nasal cavity and an exemplary device configuration opening or expanding an exemplary internal nasal valve and an exemplary embodiment side view perspective of an Exemplary Columella Saddle.

In one aspect, the disclosure provides a device for intranasal delivery to a subject, the device comprising: a housing 101 defining first and second insertable portions 107, each for insertion into a nasal channel 20 of the subject, wherein, upon insertion of the first insertable portion 107 into the nasal channel 20 of the subject, the at least one insertable portion 107 engages tissue within the nasal channel 20 to open or expand an internal nasal valve 13 of the subject thereby positioning at least one of the insertable portions 107 for delivery of a composition 111 to the subject; and an actuator which delivers the composition 111 from the either or both of the insertable portions 107 when the device is actuated.

In some embodiments, the at least one insertable portion 107 to open or expand an internal nasal valve 13 does so by moving a superior lateral cartilage 25 defining the internal nasal valve 13 away 625 from a septum 24 of the subject. In some embodiments, the at least one insertable portion 107 to open or expand an internal nasal valve 13 does so by moving superior lateral cartilage 25 defining the internal nasal valve 13 towards an internal nasal dorsum 622 of the subject. In some embodiments, the insertable portion 107 incorporates one or more dispensing channels 125 leading to one or more dispensing ports 126 configured for intranasal delivery of a composition 111 to one or more regions or sub-regions of the nasal channel 20 of the subject. In some embodiments, the insertable portion 107 comprises a dispensing element 110 for delivery of a composition 111 to a region or sub-region of the nasal channel 20 of the subject.

In some embodiments, the device further comprising a trigger coupled to the housing 101, wherein upon application of pressure to the trigger, the trigger actuates the device to dispense a composition 111 to the subject from the insertable portion 107 or the dispensing element 110. In some embodiments, the device further comprises a trigger coupled to the housing 101 and the subject engaging portion 106, wherein upon application of pressure of the subject engaging portion 106 to the columella region 10, the trigger actuates the device to dispense a composition 111 to the subject from the insertable portion 107 or the dispensing element 110. In some embodiments, the device further comprises a subject engaging portion 106, wherein the subject engaging portion 106 comprises a trigger release coupled to the housing 101, wherein upon application of pressure of the subject engaging portion 106 to the columella region 10, the trigger release permits actuation of the device to deliver a composition 111 to the subject from the insertable portion 107 or the dispensing element 110.

In some embodiments, the device further comprises a trigger which is actuatable upon engagement of the trigger release 104. In some embodiments, the device further comprises a subject engaging portion 106 coupled to the housing 101, which engages a columella region 10, wherein the subject engaging portion 106 positions the insertable portion 107 within the nasal channel 20 of the subject and limits a depth of insertion of the delivery element 111 into the nasal channel 20. In some embodiments, wherein the housing 101 defines two insertable portions 107, each for delivery of a composition 111 into a nasal channel 20 of the subject, the device further comprising an actuator which delivers the composition from either or both of the dispensing elements 110 when the device is actuated. In some embodiments, the device is transitionable from a first configuration 100 to a second configuration 200, the housing 101 defining a first insertable portion 107, the device further comprising a dispensing element 110 coupled to the housing 101, the dispensing element 110 revealing from the first insertable portion 107 upon transition of the device from the first configuration 100 to the second configuration 200. In some embodiments, the device is simultaneously actuated upon being transitioned from the first configuration 100 to the second configuration 200. In some embodiments, the device is transitionable from the first configuration 100 to the second configuration 200 upon application of pressure about a longitudinal axis 610 of the device, wherein the dispensing element 110 reveals in a linear vector relative to a longitudinal axis 610 of the first insertable portion 107, or wherein the device is configured to be transitioned from the first configuration 100 to the second configuration 200 with only one hand.

In some embodiments, the ejection zone 29 is: 0 mm to 30 mm superior to a horizontal line 627 that intersects the anterior aspect of the internal nasal valve 13, and 0 mm to 20 mm anterior to an inclined line 610 that intersects the anterior aspect of the middle turbinate 15 and the posterior aspect of the vestibule 21.

In some embodiments, the subject engaging portion 106 engages a columella region 10 of the subject to seat a distal end 128 of the insertable portion 107 within an ejection zone 29 of a nasal cavity 11 of the subject, wherein the ejection zone 29 is: 0 mm to 30 mm superior to a horizontal line 627 that intersects the anterior aspect of the internal nasal valve 13, and 0 mm to 20 mm anterior to an inclined line 610 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 23, 0 mm to 20 mm posterior to the internal nasal dorsum 622, 10 mm and 50 mm superior to a horizontal line 623 that intersects the inferior aspect of the columella 10, 0 mm to 30 mm superior to a horizontal line 624 that intersects the superior aspect of the inferior turbinate 16, 0 mm to 3 mm from the septum 24 or any combination thereof.

In some embodiments, the subject engaging portion 106 prevents movement of the distal end 128 within or away from the ejection zone 29 when the subject engaging portion 106 is seated on the columella region 10. In some embodiments, the ejection zone 29 is in line with the olfactory cleft 23 as defined by a linear vector between the olfactory cleft 23 and the distal end 128 of the insertable portion 107. In some embodiments, dispensing a composition 111 from the ejection zone 29 increases on target deposition of the composition 111 to the olfactory cleft 23. In some embodiments, the subject engaging portion 106 is seated on the columella region 10 when the subject engaging portion 106 simultaneously contacts a downward facing lateral face of the columella, a leftward facing lateral face of the columella, and a rightward facing lateral face of the columella. In some embodiments, dispensing a composition 111 from the ejection zone 29 increases on target deposition of the composition to an aspect of a respiratory region such as the middle turbinate 15. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

In one aspect, the disclosure provides a device for intranasal delivery to a subject, the device transitionable from a first configuration 100 to a second configuration 200, the device comprising: a housing 101 defining a first insertable portion 100 configured to be inserted into a nasal channel 20 of the subject; and a dispensing element 110 coupled to the housing 101, the dispensing element 110 revealing from the first insertable portion 107 upon transition of the device from the first configuration 100 to the second configuration 200, wherein the device is transitioned from the first configuration 100 to the second configuration 200 by application of pressure about a longitudinal axis 610 of the device, and wherein the device is simultaneously actuated upon being transitioned from the first configuration 100 to the second configuration 200. In some embodiments, the simultaneous actuation refers to transition for the first configuration 100 to the second configuration 200 and actuation occurring in a single motion upon application of pressure about a longitudinal axis 610 of the device.

In some embodiments, the dispensing element 110 reveals in a linear vector parallel to the internal nasal dorsum 622 from the first insertable portion 100 at a location above an inferior turbinate 16 of the subject. In some embodiments, the device avoids contaminating the dispensing element with bacteria from the lower nasal cavity by enclosing it in the insertable portion 107 prior to revealing the dispensing element 110 upon transition from the first configuration 100 to the second configuration 200. In some embodiments, the device avoids contaminating the dispensing element 110 by concealing it within the insertable portion 107 prior to actuation. In some embodiments, the insertable portion 107 incorporates one or more dispensing channels 125 leading to one or more dispensing ports 126 configured for intranasal delivery of a composition 111 to one or more regions or sub-regions of the nasal channel 20 of the subject. In some embodiments, the dispensing element reveals in a linear vector relative to a longitudinal axis 610 of the first insertable portion 107. In some embodiments, the device is configured to be transitioned from the first configuration 100 to the second configuration 200 with only one hand. In some embodiments, the dispensing element 110 reveals from the insertable portion 107 upon transition of the device from the first configuration 100 to the second configuration 200. In some embodiments, the dispensing element reveals from the insertable portion 107 upon transition of the device from the first configuration 100 to the second configuration 200, upon application of pressure of a portion of the housing 101 to a columella region 10 of a subject. In some embodiments, the second configuration 200 moves a first portion 1020 of the housing towards a second portion 105 of the housing about a longitudinal axis 610 of the device. In some embodiments, the device further comprising a subject engaging portion 106 coupled to the housing 101 which engages a columella region 10, wherein the subject engaging portion 106 positions the insertable portion 107 within a nasal channel 20 of the subject and limits the depth of insertion of the dispensing element 110 into the nasal channel 20. In some embodiments, the subject engaging portion which engages a columella region 10 of the subject seats the distal end of the dispensing element 110 within an ejection zone 29 of a nasal cavity 11 of the subject, wherein the ejection zone 29 is: 0 mm to 30 mm superior to a horizontal line 627 that intersects the anterior aspect of the internal nasal valve 13, and 0 mm to 20 mm anterior to an inclined line 610 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 21, 0 mm to 20 mm posterior to the internal nasal dorsum 622, 10 mm and 50 mm superior to a horizontal line 623 that intersects the inferior aspect of the columella, 0 mm to 30 mm superior to a horizontal line 624 that intersects the superior aspect of the inferior turbinate 16, 0 mm to 3 mm from the septum 24 or any combination thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

In some embodiments, the subject engaging 106 portion prevents movement of the distal end 128 of the dispensing element 110 within or away from the ejection zone 29 when the subject engaging portion 106 is seated on the columella region 10. In some embodiments, the ejection zone 29 is in line with the olfactory cleft 23 as defined by a linear vector between the olfactory cleft 23 and the distal end 126 of the insertable portion 107. In some embodiments, dispensing a composition 111 from the ejection zone 29 increases on target deposition of the composition 111 to the olfactory cleft 23. In some embodiments, dispensing a composition 111 from the ejection zone 29 increases on target deposition of the composition 111 to an aspect of a respiratory region such as the middle turbinate 15. In some embodiments, the subject engaging portion 106 is seated on the columella region 10 when the subject engaging portion simultaneously contacts a downward facing lateral face of the columella 10, a leftward facing lateral face of the columella 10, and a rightward facing lateral face of the columella 10. In some embodiments, the device further comprising a trigger coupled to the housing 101 and the subject engaging portion 106, the subject engaging portion 106 engaging a columella region 10 of the subject, wherein upon application of pressure of the subject engaging portion 106 to the columella region 10, the trigger actuates the device to deliver a composition 111 to the subject from the dispensing element 110.

In some embodiments, the housing 101 defines two insertable portions 107, each for insertion into a nasal channel 20 of the subject, wherein, upon insertion of the first insertable portion 107 into a nasal channel 20 of the subject, the first insertable portion 107 engages tissue within the nasal channel 20 to open or expand an internal nasal valve 13 of the subject thereby positioning at least one of the insertable portions 107 for delivery of a composition 111 to the subject, the device further comprising an actuator which delivers a composition 111 from the either or both of the insertable portions 107 when the device is actuated. In some embodiments, the housing 101 defines two dispensing elements 110, each for delivery of a composition 111 into a nasal channel 20 of the subject, the device further comprising an actuator which delivers the composition 111 from either or both of the dispensing elements 110 when the device is actuated. In some embodiments, the device further comprising a trigger release 104 coupled to the housing 101 and the subject engaging portion 106, wherein upon application of pressure of the subject engaging portion to the columella region 10, the trigger release 104 permits actuation of the device to deliver a composition 111 to the subject from the insertable portion 107. In some embodiments, the device further comprises a trigger which is actuatable upon engagement of the trigger release 104.

In some embodiments, the device avoids contaminating the dispensing element 110 by concealing it within the insertable portion 107 prior to actuation. In some embodiments, the composition 111 is dispensed from a distal end 126 of the insertable portion 107. In some embodiments, the dispensing element 110 is in the ejection zone 29 when the device is in the second configuration 200. In some embodiments, the dispensing element 110 is at a distal end 126 of the ejection zone 29 when the device is in the second configuration 200. In some embodiments, the device is simultaneously actuated upon being transitioned from the first configuration 100 to the second configuration 200. In some embodiments, the dispensing element 110 reveals in a linear vector parallel to the internal nasal dorsum 622 from the first insertable portion 107 at a location above an inferior turbinate 16 of the subject. In some embodiments, the device avoids contaminating the dispensing element 110 with bacteria from the lower nasal cavity by enclosing it in the insertable portion 107 prior to revealing the dispensing element 110 upon transition from the first configuration 100 to the second configuration 200.

In some embodiments, the at least one insertable portion 107 to open or expand an internal nasal valve 13 does so by moving upper lateral cartilage 25 away from a septum 24 of the subject. In some embodiments, the at least one insertable portion 107 to open or expand an internal nasal valve 13 does so by moving upper lateral cartilage 25 defining the internal nasal valve 13 towards an internal nasal dorsum 622 of the subject. In some embodiments, the subject engaging portion 106 prevents movement of the distal end 126 of an insertable portion 107 or a dispensing element 110 within or away from the ejection zone 29 when the subject engaging portion 106 is seated on the columella region 10. In some embodiments, the ejection zone 29 is in line with the olfactory cleft 23 as defined by a linear vector between the olfactory cleft 23 and the distal end 128 of the insertable portion 107. In some embodiments, dispensing a composition 111 from the ejection zone 29 increases on target deposition of the composition 111 to the olfactory cleft 23. In some embodiments, dispensing a composition 111 from the ejection zone 29 increases on target deposition of the composition 111 to an aspect of a respiratory region such as the middle turbinate 15. In some embodiments, the subject engaging portion 106 is seated on the columella region 10 when the subject engaging portion 106 simultaneously contacts a downward facing lateral face of the columella, a leftward facing lateral face of the columella, and a rightward facing lateral face of the columella.

In some embodiments, the subject engaging portion 106 limits a depth of insertion of the insertable portion 107 into the nasal channel 20. In some embodiments, the subject engaging portion 106 limits a depth of insertion of the dispensing element 110 into the nasal channel 20. In some embodiments, the first and second insertable portion 107 are configured to dispense a composition 111 from the first and second insertable portion 107 simultaneously. In some embodiments, the first and second insertable portion 107 are configured to dispense a composition 111 from the first and second insertable portion 107 sequentially. In some embodiments, the first and second dispensing elements 110 are configured to dispense a composition 111 from the first and second dispensing elements 110 simultaneously. In some embodiments, the first and second dispensing elements 110 are configured to dispense a composition 111 from the first and second dispensing elements 110 sequentially. In some embodiments, the first insertable portion 107 moves along a septum 24 and moves a superior lateral cartilage 25 away from the septum 24. In some embodiments, the first and second dispensing elements 110 move along a septum 24. In some embodiments, the two insertable portions 107 each contact opposite sides of a septum 24. In some embodiments, the two dispensing elements 110 each contact opposite sides of a septum 24. In some embodiments, the two insertable portions 107 each contact opposite sides of a septum 24 and apply force to a superior lateral cartilage 25 in a direction away from the septum 24. In some embodiments, the two insertable portions 107 each contact opposite sides of a septum 24 and apply force to a superior lateral cartilage 25 in a direction orthogonal to a lateral axis of the septum 24. In some embodiments, the at least one insertable portion 107 to open or expand an internal nasal valve 13 does so by moving a superior lateral cartilage 25 defining the internal nasal valve 13 away from a septum 24 of the subject. In some embodiments, the at least one insertable portion 107 to open or expand an internal nasal valve 13 does so by moving superior cartilage 25 defining the internal nasal valve 13 towards an internal nasal dorsum 622 of the subject.

Figure 6A:
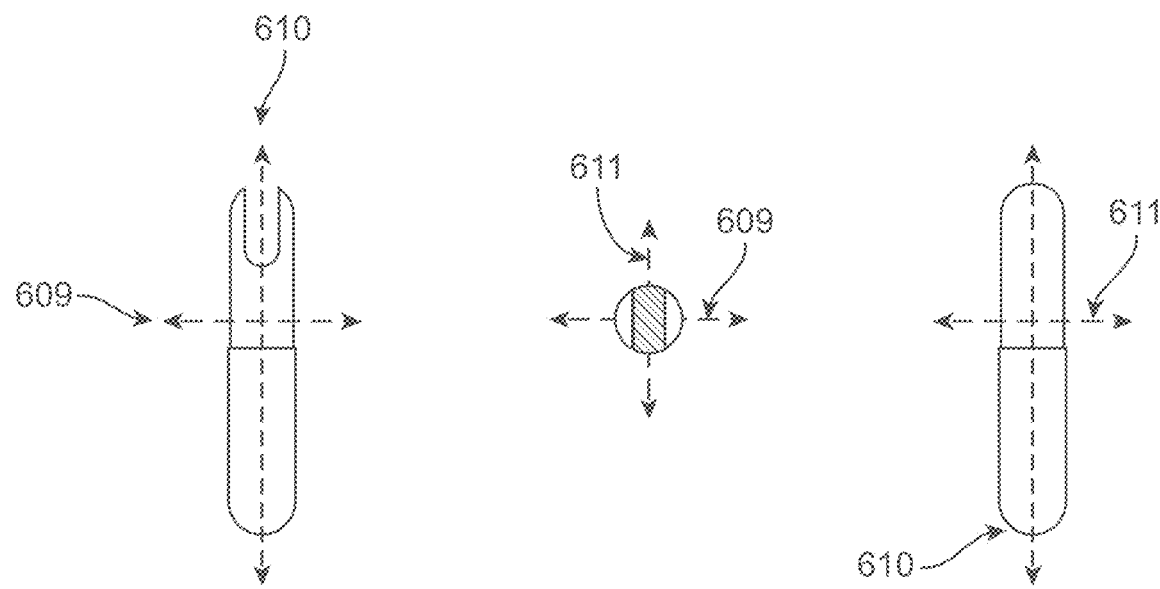
FIG. 6A depicts an exemplary embodiment of a cartesian reference plane of (left to right) a front, a top, and a side view of an Exemplary Device., according to some embodiments.
Figure 6B:
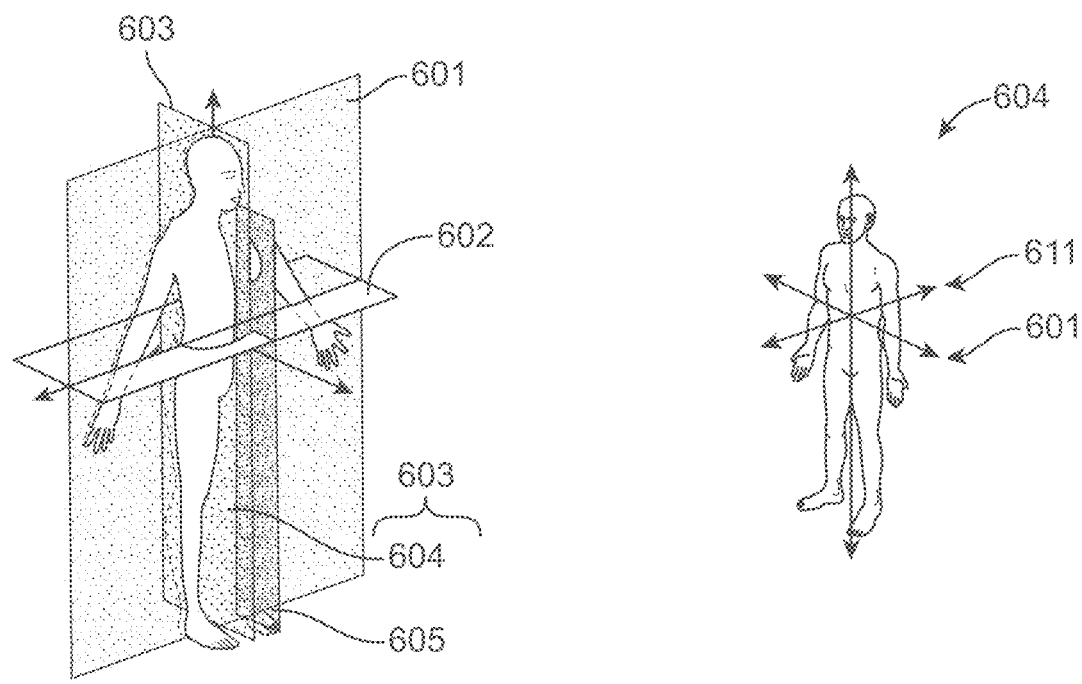
FIG. 6B depicts an exemplary embodiment of the subject plane, according to some embodiments.
Figure 6C:
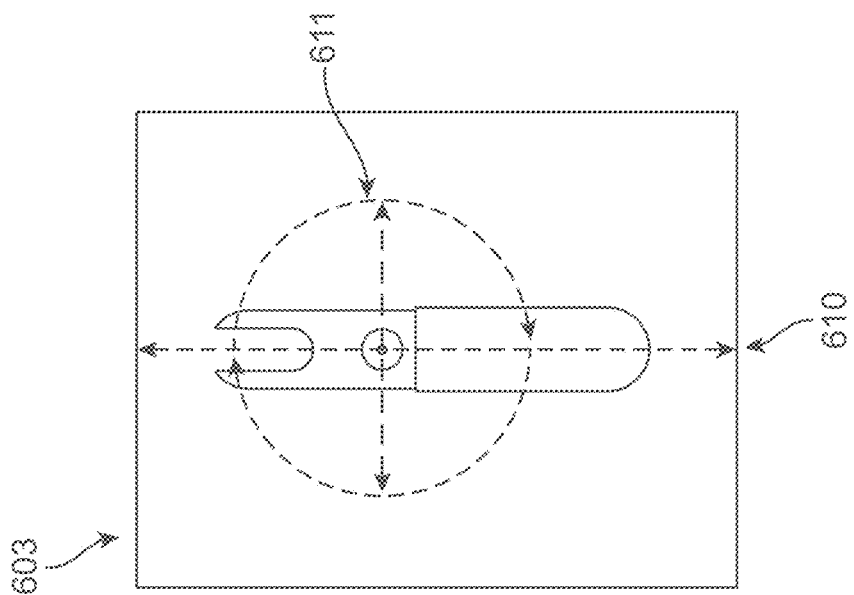
FIG. 6C depicts an exemplary embodiment of (left to right) a front Coronal Plane, a top Transverse Plane, and a back Sagittal Plane view, according to some embodiments.
Figure 6C:
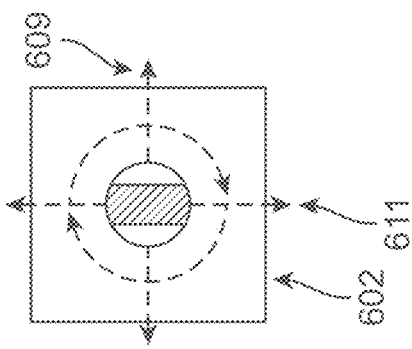
Figure 6C:
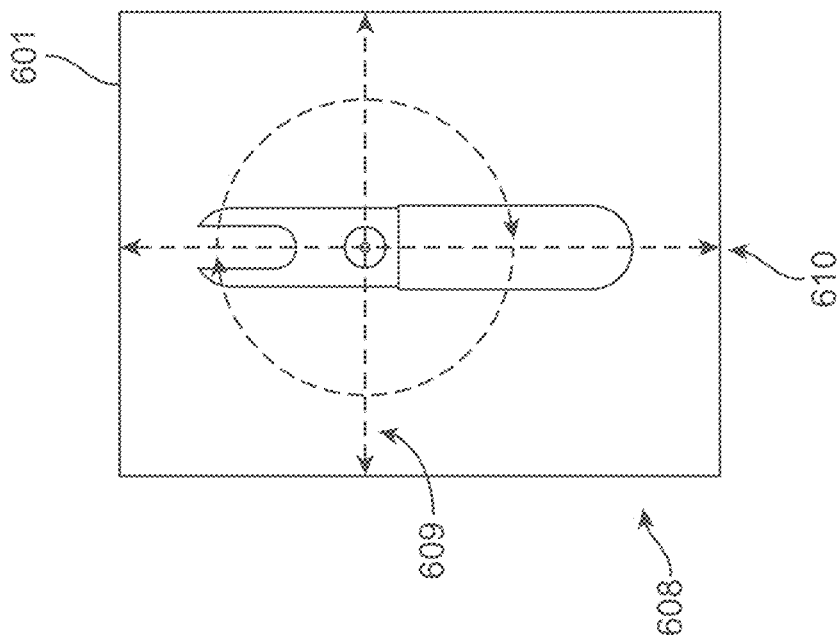

FIG. 6A depicts an exemplary embodiment of a cartesian reference plane of (left to right) a front, a top, and a side view of the Exemplary Device. FIG. 6B depicts an exemplary embodiment of the subject plane. FIG. 6C depicts an exemplary embodiment of (left to right) a front Coronal Plane, a top Transverse Plane, and a back Sagittal Plane view of angular reference plane of the Exemplary Device. In some embodiments, the device is configured for a subject having a coronal or frontal plane 601, horizontal or axial or transverse plane 602, sagittal or longitudinal plane 603, median plane 604, or parasagittal plane 605, or combination thereof. In some embodiments, the device comprises a relative angular coordinate system of roll on the Y-axis of the device 606, pitch on the subject sagittal plane 607, and yaw on the subject coronal plane 608. In some embodiments the device is configured for a subject having a subject linear coordinate system x relative to subject medial/lateral 609, y relative to subject superior/inferior 610, and z relative to subject anterior/posterior 611.

Figure 6D:
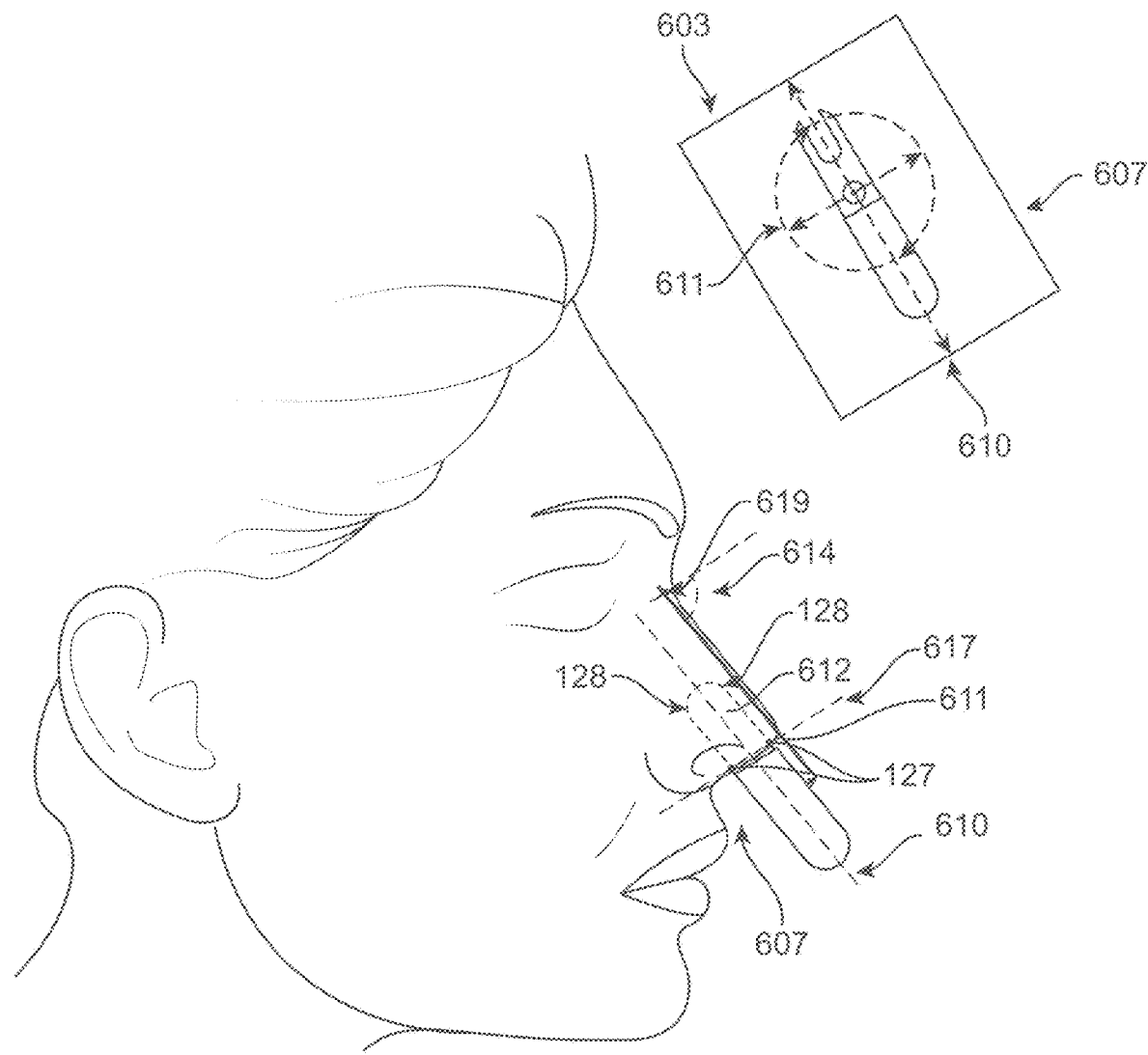
FIG. 6D depicts an exemplary embodiment of an Exemplary Device Sagittal Angle positioning in the subject, according to some embodiments.

FIG. 6D depicts an exemplary embodiment of the Exemplary Device Sagittal Angle positioning in the subject. In some embodiments, the insertable portions 107 are positioned along its y-axis in relation to other anatomy, creating a predictable/repeatable relationship with regards to the devices pitch angle 607 on the subject's sagittal plane 603. In some embodiments, from the devices predictable/repeatable relationship to other anatomy, the pitch angle 607 can be related to known anthropometric data. In some embodiments, the insertable portions 107 are configured to follow the shape of the interior dorsum cleft 612, and lateral aspects of the septum 24 in the nasal cavity 11, allowing it to maintain a consistent and repeatable angle on the sagittal plane 603, wherein this positioning is achieved when the insertable portions 107 are inserted past the nasal vestibule 21 and into the nasal cavity 11. In some embodiments, the insertable portions 107 are configured to hold it to, and guide it along, the soft tissues of the superior cleft, ensuring that it remains parallel to these tissues. In some embodiments, as the tissues of the superior cleft are parallel to known anthropometric axis 613 drawn from nasion 619 to tip, used in both the nasofacial and nasofrontal angle 614, a known angler anthropometric range can be determined for the position of the inserter Y axis 610 on the sagittal plane 603 relative to subject anatomy.

Figure 6E:
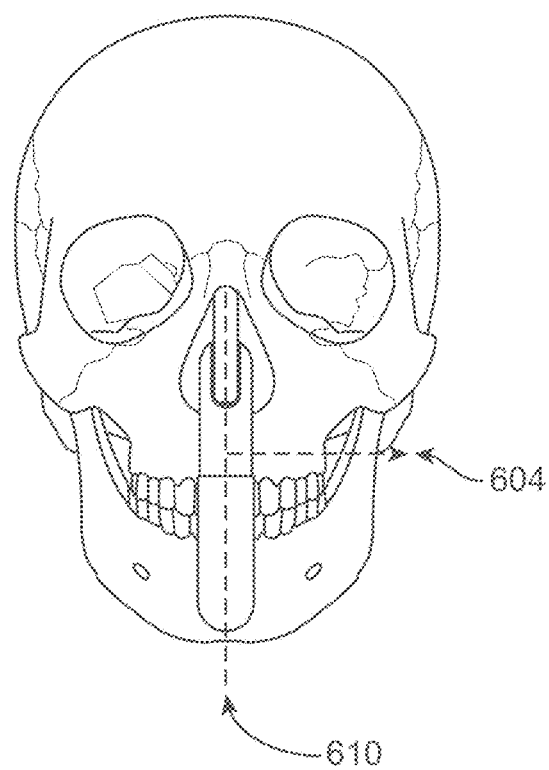
FIG. 6E depicts an exemplary embodiment of an Exemplary Device Coronal-Medial Angle positioning in the subject, along a front view of the Coronal Plane, and a top view along a transverse plane, according to some embodiments.
Figure 6E:
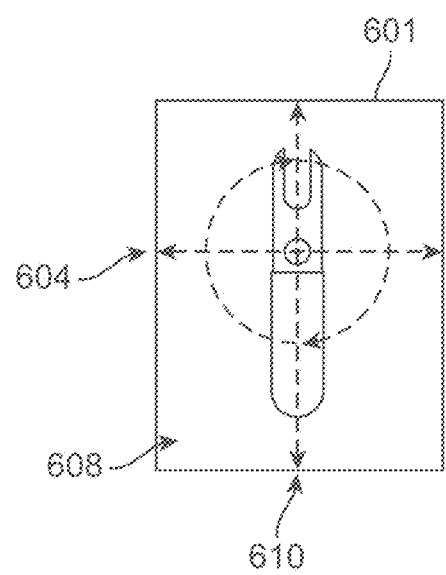
Figure 6E:
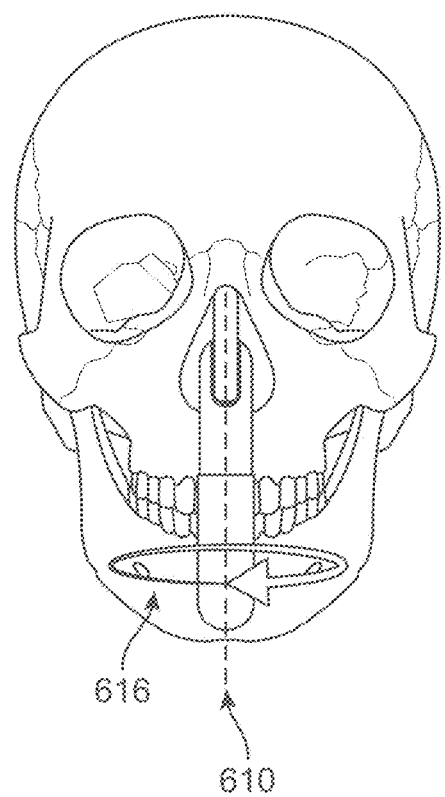
Figure 6E:
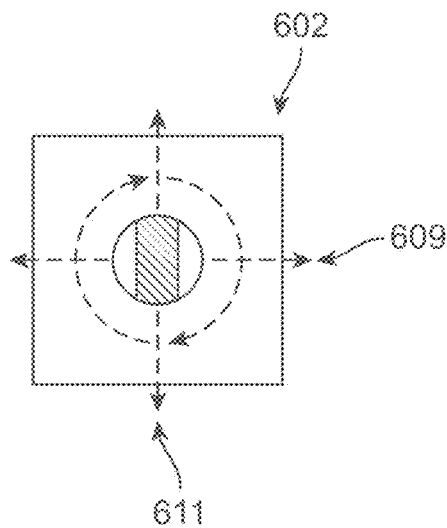

FIG. 6E depicts an exemplary embodiment of the Exemplary Device Coronal-Medial Angle positioning in the subject, along a front view of the Coronal Plane, and a top view along a transverse plane, according to some embodiments. In some embodiments, the insertable portions 107 are designed to interlock with the nasal cavity 11. In some embodiments, the insertable portions 107 are configured to key medial to the lateral aspects of septal cartilage, and bilaterally to the greater alar and lateral nasal cartilage, including the connective tissues of these structures. In some embodiments, the insertable portions 107 are locked in the y-axis rotation along the device 616, and locked in medially/laterally 604.

Figure 6F:
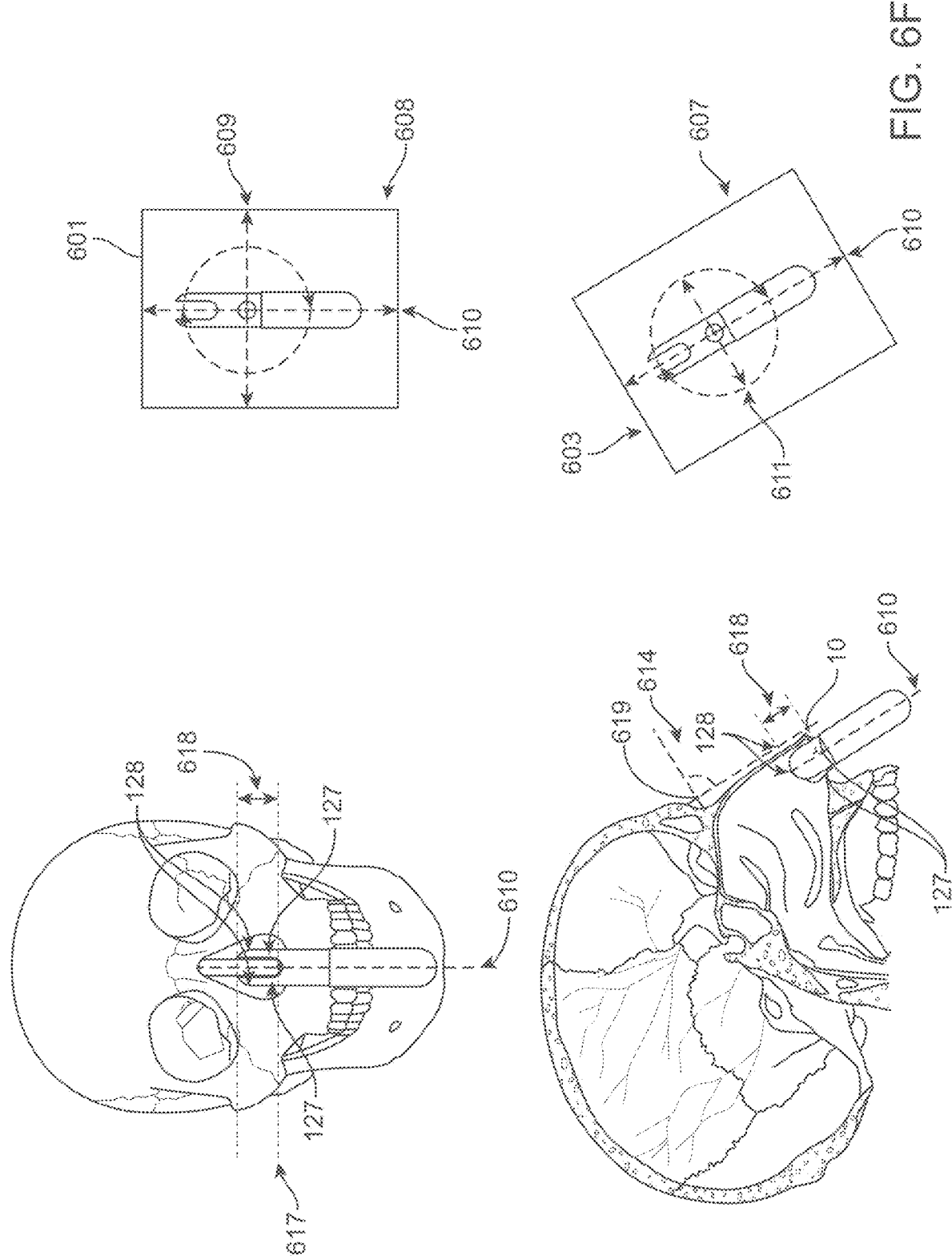
FIG. 6F depicts an exemplary embodiment of an Exemplary Device Depth positioning along a front view of the Coronal Plane, and along a side view of the Sagittal Plane in the subject, according to some embodiments.

FIG. 6F depicts an exemplary embodiment of the Exemplary Device Depth positioning along a front view of the Coronal Plane, and along a side view of the Sagittal Plane in the subject. In some embodiments, the insertable portions 107 are designed to position and interlock within the nasal cavity 11, creating a predictable/repeatable depth 618. In some embodiments, the insertable portions 107 are designed to key and hard stop on the columella 10 its supporting structures, e.g., the nasal spine and septal cartilage. In some embodiments, as the columella 10 comprises a depth datum 617 along the device y-axis, the ejection ports 126, e.g., along the cannulas, of the insertable portions 107 may be placed at desired and known distance from a target anatomy.

Figure 6G:
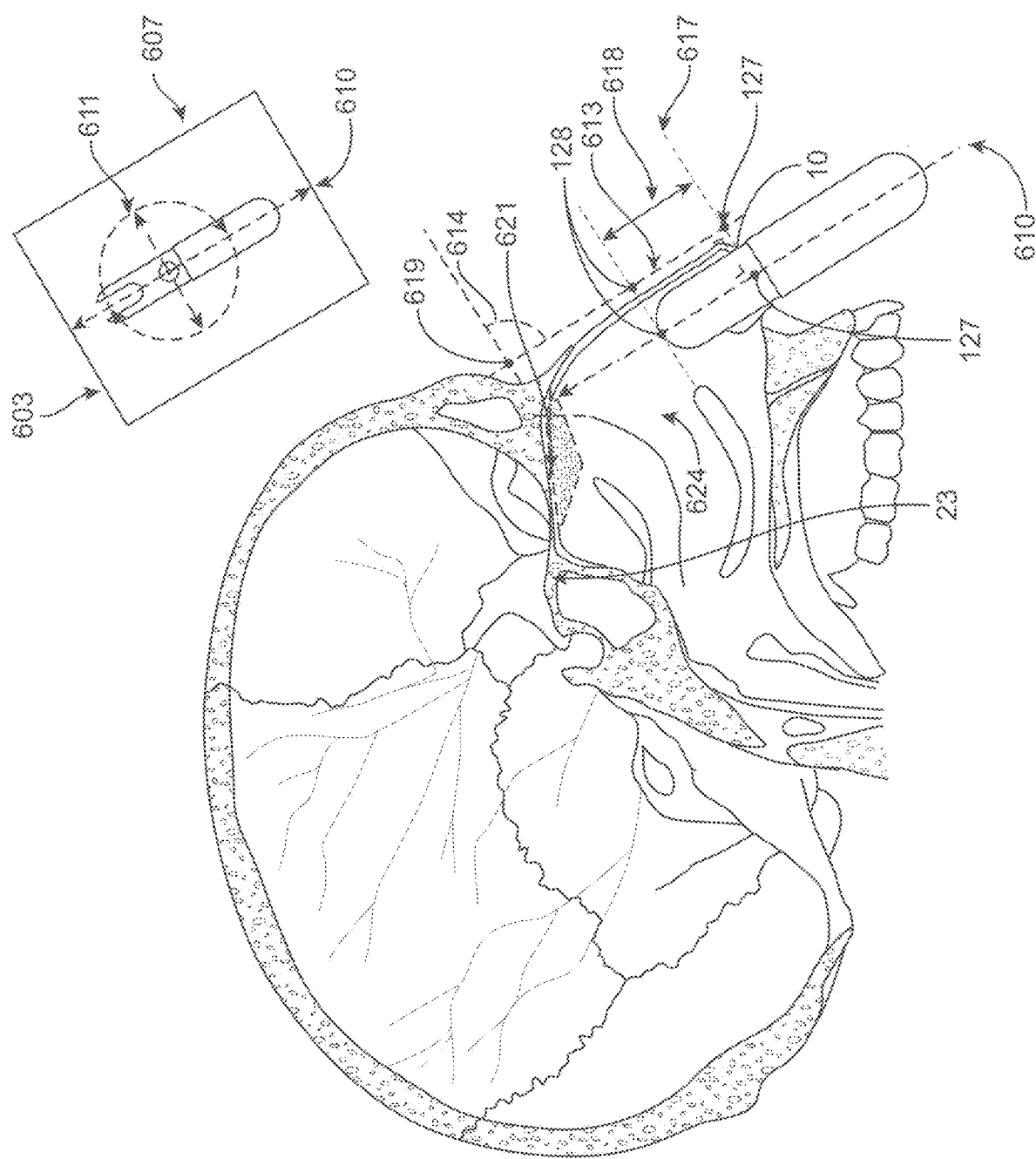
FIG. 6G depicts an exemplary embodiment of an Exemplary Device along a side view of the sagittal plane of delivery to the target region in the subject, according to some embodiments.

FIG. 6G depicts an exemplary embodiment of the Exemplary Device along a side view of the sagittal plane of delivery to the target region 19 in the subject. In some embodiments, with a known depth 618, Cartesian and angular reference of the insertable portions 107 relative to subject anatomies in the subject anatomy, exit ports, e.g., dispensing ports 126 along one or more dispensing elements 110, may be placed in a desired location to create a desired trajectory of the dose and a relative fluid profile and velocity may be chosen to deliver the composition 111 to a desired location, e.g., target region 19, repeatable and accurately. In some embodiments, a coherent jet may be chosen along the y-axis 610 of the device, creating a substantially unimpeded flow to the target region 19, e.g., the olfactory cleft 23, the middle meatus 30, or other nasal anatomy, or any combination thereof. In some embodiments, a coherent jet may be chosen along the z-axis of the device, creating a substantially unimpeded flow to the turbinates, e.g., superior turbinate 14, middle turbinate 15, or inferior turbinate 16, or a combination thereof.

In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end 128 of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition 111 is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition 111 is dispensed to all regions simultaneously.

FIG. 6H depicts an exemplary embodiment of the Exemplary Device along a side view of the sagittal plane aiming from the respiratory region in the subject. In some embodiments, with a known depth 618, Cartesian and angular reference of the insertable portions 107 relative to subject anatomies in the subject anatomy, exit ports, e.g., dispensing ports 126 along one or more dispensing elements 110, may be placed in a desired location to create a desired trajectory of the dose and a relative fluid profile and velocity may be chosen to deliver the composition 111 to a desired location, e.g., a target region 19, repeatable and accurately. In some embodiments, a coherent jet may be chosen along the y-axis 610 of the device, creating a substantially unimpeded flow to the target region 19, e.g., olfactory cleft 23, middle meatus 30, turbinate delivery, etc. In some embodiments, a coherent jet may be chosen along the z-axis of the device, creating a substantially unimpeded flow to the turbinates, e.g., superior turbinate 14, middle turbinate 15, or inferior turbinate 16, or a combination thereof.

In one aspect, the disclosure provides a device for intranasal delivery to a subject, the device comprising: a housing 101 comprising an insertable portion 107 comprising a distal end 128, and a proximal end 127; a subject engaging portion 106 which engages a columella region 10 of the subject to seat the distal end 128 of the insertable portion 107 within an ejection zone 29 of a nasal channel 20 of the subject. In some embodiments, the ejection zone 29 is: 0 mm to 30 mm superior to a horizontal line 627 that intersects the anterior aspect of the internal nasal valve 13, and 0 mm to 20 mm anterior to an inclined line 610 that intersects the anterior aspect of the middle turbinate 15 and the posterior aspect of the vestibule 21.

In some embodiments, the ejection zone 29 is further 0 mm to 40 mm inferior to a horizontal line 621 that is parallel to the inferior aspect of the olfactory cleft 23, 0 mm to 20 mm posterior to the internal nasal dorsum 622, 10 mm and 50 mm superior to a horizontal line 617 that intersects the inferior aspect of the columella 10, 0 mm to 30 mm superior to a horizontal line 624 that intersects the superior aspect of the inferior turbinate 16, 0 mm to 3 mm from the septum 24, or any combination thereof.

In some embodiments, the ejection zone 29 is a trapezium or irregular quadrilateral comprising (i) an inferior side 29A being a 10-25 mm line extending posteriorly and horizontally from the anterior aspect of the internal nasal valve 13, (ii) an anterior side 29B being a 10-35 mm line extending superiorly and parallel to the internal nasal dorsum 622 from the anterior aspect of the internal nasal valve 13, (iii) a superior side 29C being a 10-25 mm line extending posteriorly and horizontally from a point on the internal nasal dorsum 622 that is 0-10 mm inferior to the inferior aspect of the olfactory cleft 23, and (iv) a posterior line 29D being a 10-35 mm line extending vertically along a plane that intersects the anterior aspect of the middle turbinate 15. In some embodiments, the target region 19 is one or both olfactory clefts 23, or a sub-area thereof, and wherein dispensing the composition 111 from an anterior end of the dispensing element 110 increases on target delivery of the composition 111 to the target region. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition 111 is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition 111 is dispensed to all regions simultaneously.

In some embodiments, the device further comprises an actuator which delivers a composition 111 from the either one or both insertable portions 107 when the device is actuated. In some embodiments, wherein the housing 101 defines two dispensing elements 110, each for delivery of a composition into a nasal channel 20 of the subject, the device further comprises an actuator which delivers the composition 111 from the either or both insertable portions 107 when the device is actuated. In some embodiments, the dispensing element 110 is configured to dispense the composition 111 into a single nasal channel 20 of a subject. In some embodiments, the at least one insertable portion 107 fits proximal to a septal-lateral cartilage junction 27 of the subject. In some embodiments, the dispensing element 110 fits proximal to a septum 24 of the subject. In some embodiments, the dispensing element 110 comprises one or more cannulas. In some embodiments, the dispensing element 110 comprises one or more cannulas which are fixed relative to the insertable portion 107. In some embodiments, the dispensing element 110 comprises one or more cannulas which reveal from the insertable portion 107 when the device is transitioned from the first configuration 100 to the second configuration 200. In some embodiments, the insertable portion 107 comprises the dispensing element 110. In some embodiments, the insertable portion 107 is the dispensing element 110. In some embodiments, the one or more dispensing elements 110 comprises one or more cannulas, wherein the one or more cannulas comprise one or more dispensing ports 126. In some embodiments, the dispensing port 126 comprises one ejection port at its distal end. In some embodiments, the dispensing port 126 comprises one or more ejection ports 126 along its length. In some embodiments, the dispensing port 126 comprises one ejection port at its distal end, one or more ejection ports along its length, or a combination of both.

In some embodiments, the dispensing port 126 is directed at different target areas within the nasal channel 20. In some embodiments, the device ejects fluid from above the internal nasal valve 13. In some embodiments, the device ejects fluid from at least approximately 15-20 mm above the columella 10. In some embodiments, the device ejects fluid from above the area of primary high velocity/low pressure airflow. In some embodiments, the device ejects fluid from at least 25-30 mm from the columella region 10. In some embodiments, the dispensing port 126 comprises an atomizer. In some embodiments, the one or more dispensing elements are about 5-40 mm in length. In some embodiments, the one or more dispensing elements 110 reveal about _5-40 mm from the housing. In some embodiments, at least one dispensing element 110 is at least partially contained within the housing 101. In some embodiments, at least one dispensing element 110 reveals outwards from the housing 101 when in the second position 200. In some embodiments, the one or more dispensing elements 110 comprise multiple ejection ports 126. In some embodiments, the one or more dispensing elements 110 comprise multiple fluid channels 125. In some embodiments, one of the multiple fluid channels 125 are configured to dispense a gas 111. In some embodiments, one of the multiple fluid channels 125 is configured to dispense a gas 111 following dispensing a composition 111 by another fluid channel 125.

In some embodiments, the first and/or second insertable portion 107 limits a sagittal angle or an anterior-posterior 611 angle of the device. In some embodiments, the first and/or second insertable portion 107 limits a coronal angle or a medial-lateral angle 604 of the device. In some embodiments, the first and/or second insertable portion 107 limits a coronal angle or a medial-lateral angle 604 of the device. In some embodiments, the insertable portion 107 is flexible. In some embodiments, the one or more dispensing elements 110 are flexible. In some embodiments, the first and/or second insertable portion 107 is tortional flexible. In some embodiments, the first and/or second insertable portion 107 is tortional flexible so as to adjust to the angle of the anterior aspect of the internal nasal valve 13. In some embodiments, the first and/or second insertable portion 107 runs proximal to a septum 24 of the user. In some embodiments, the at least one insertable portion 107 comprises the following flexibility characteristics: a medial-lateral flexibility along a width 1103 orthogonal to a length 1100 of the insertable portion; a low anterior-posterior flexibility 1109 about a length 1100 of the insertable portion 107; an inferior-superior flexibility 1110 about a rotational axis orthogonal to a length 1100 of the insertable portion 107, or a combination thereof. In some embodiments, the at least one dispensing element 110 comprises the following flexibility characteristics: a medial-lateral flexibility 1108 along a width 1103 orthogonal to a length 1100 of the insertable portion 107; a low anterior-posterior flexibility 1109 about a length 1100 of the insertable portion 107; or an inferior-superior flexibility 1110 about a rotational axis orthogonal to a length 1100 of the insertable portion 107.

In some embodiments, the middle turbinate 15 poses a risk of misdirection down the meatus. In some embodiments, the device dispenses the composition 111 anteriorly to the middle turbinates 15, wherein the pathway to the olfactory cleft anterior 18 to the middle turbinates 15 is clear and more direct. In some embodiments, the device further comprises an actuation mechanism which moves the housing 101 from the second position to the first position and retracts the at least one dispensing element 110 following actuation of the device. In some embodiments, the one or more dispensing elements 110 comprise a first tubular section which surrounds the dispensing element. In some embodiments, the first tubular section remains within a first insertable portion 107 when the device is actuated to the second position 200.

Figure 8A:
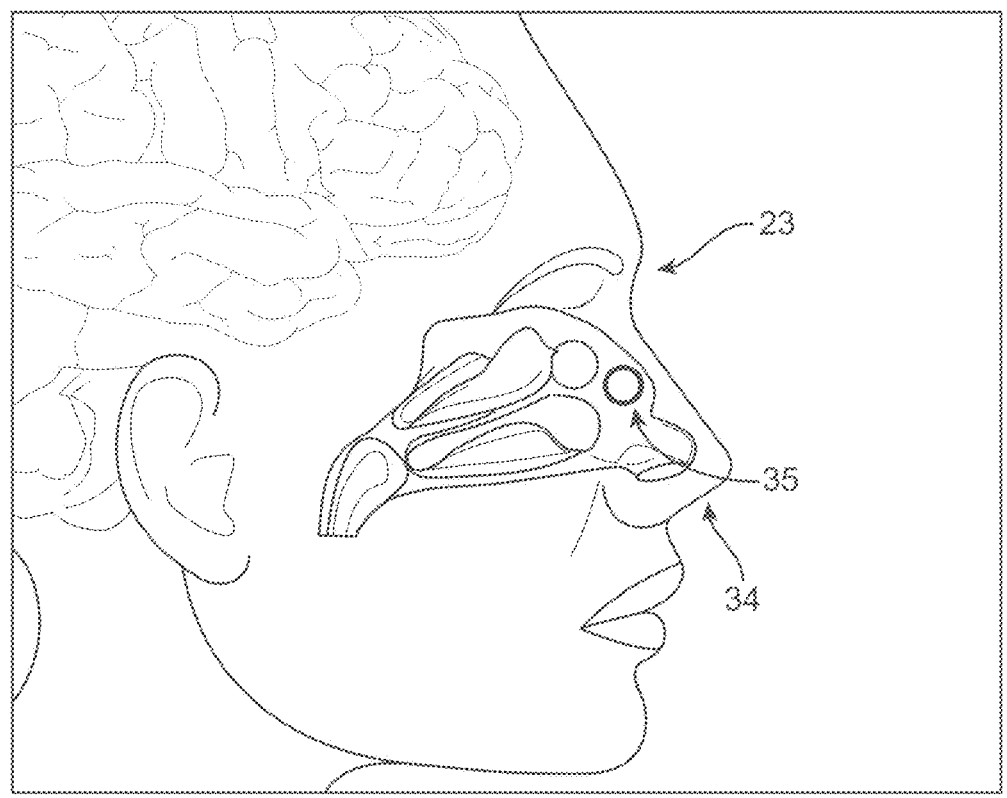
FIG. 8A depicts the anatomy of the nasal cavity in a subject, according to some embodiments.
Figure 8B:
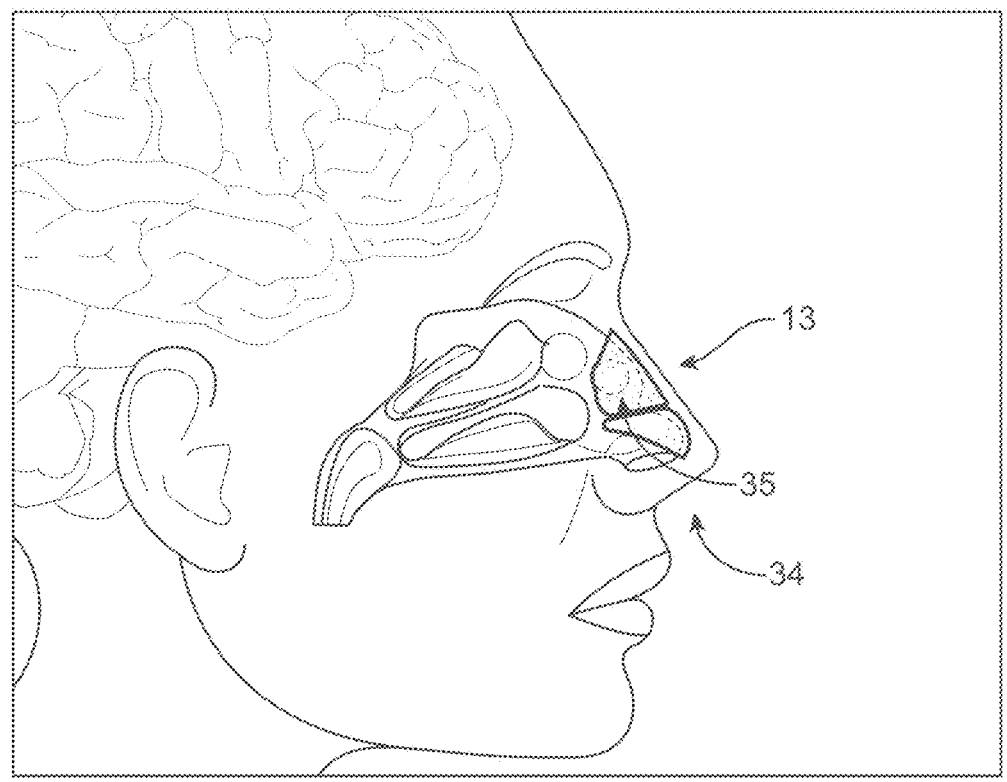
FIG. 8B depicts the anatomy of the nasal cavity in a subject, according to some embodiments.

FIG. 8A-8B depicts an exemplary embodiment of the anatomy of the subject's nasal cavity 11. In some embodiments, the anatomy of the subject's nasal cavity 11 comprises the olfactory cleft 23. In some embodiments, the anatomy of the subject's nasal cavity 11 comprises the lower nasal region 35. In some embodiments, the anatomy of the subject's nasal cavity 11 comprises the internal nasal valve 13. In some embodiments, the anatomy of the subject's nasal cavity 11 comprises a vantage point 34.

Figure 8C:
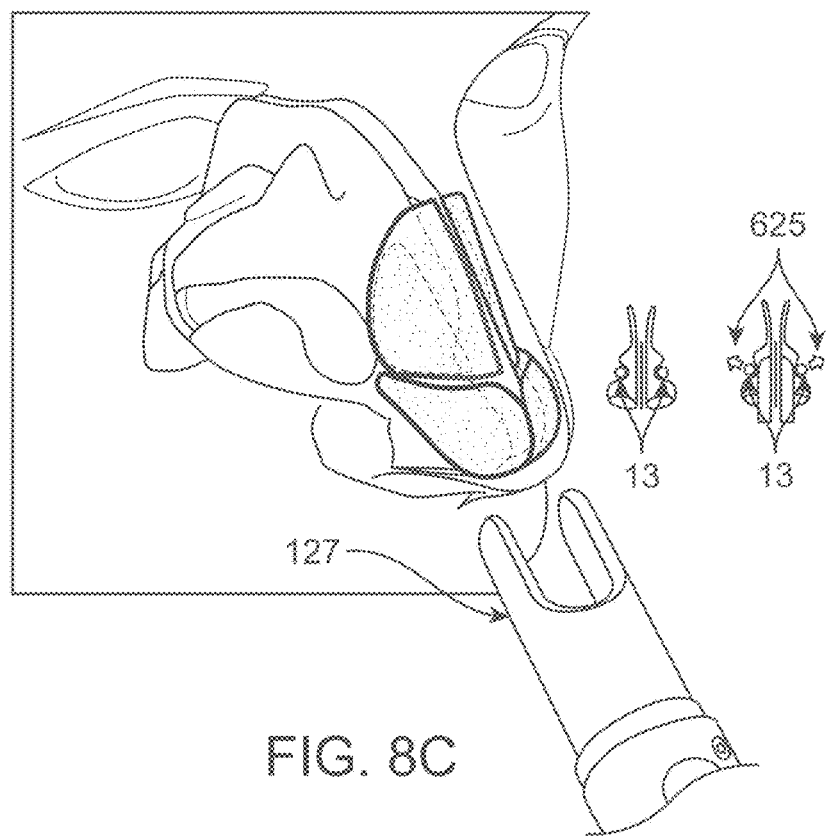
FIG. 8C depicts the anatomy of the nasal cavity in a subject and an exemplary device configuration, according to some embodiments.
Figure 8D:
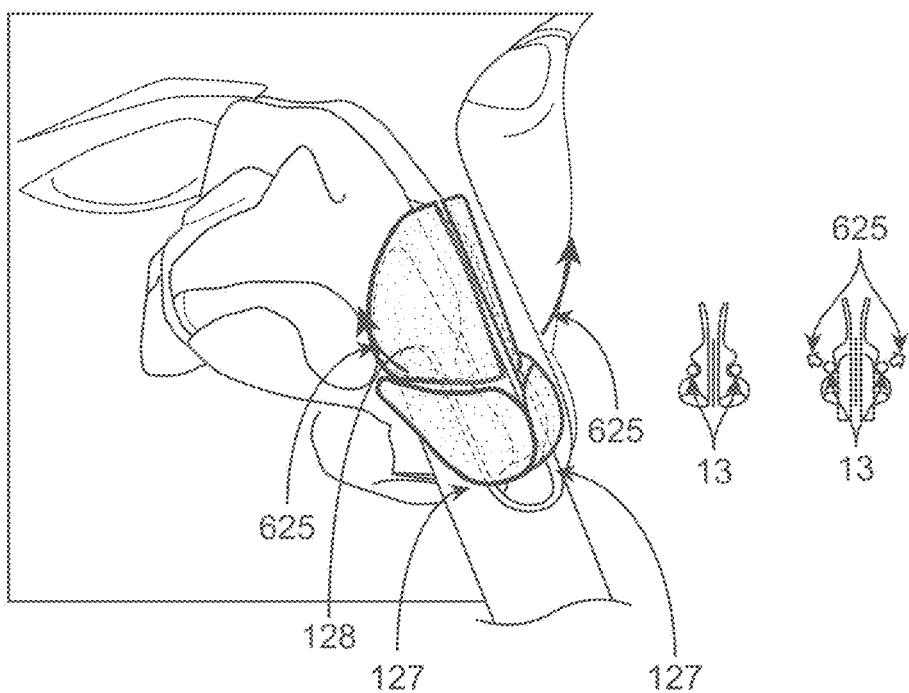
FIG. 8D depicts the anatomy of the nasal cavity in a subject and an exemplary device configuration opening or expanding an exemplary internal nasal valve, according to some embodiments.

FIG. 8C depicts the anatomy of the nasal cavity 11 and an exemplary device configuration. FIG. 8D depicts the anatomy of the nasal cavity and an exemplary device configuration opening or expanding an exemplary internal nasal valve. In some embodiments, the device positions the drug dispensing tip in the more discreet channel formed by the nasal bone 33 where odorants and pheromones safely travel to reach the olfactory 23. In some embodiments, the dispensing tipavoids the less predictable and sensitive thicker, softer tissue. In some embodiments, wherein the insertable portion 107, upon insertion into a nasal channel 20 of the subject, opens or expands the internal nasal valve 13 by pushing the upper lateral cartilage and surrounding tissue up and away 625 from the septum 24. In some embodiments, the insertable portion 107, upon insertion into a nasal channel 20 of the subject, is proximal to the septum 24. In some embodiments, the subject engaging portion 106 prevents movement of the distal aspect 131 within or away from the ejection zone 29 when the subject engaging portion 106 is seated on the columella region 10. In some embodiments, the ejection zone 29 is in line with the olfactory cleft 23 as defined by a linear vector between an olfactory cleft 23 and the distal end 128 of the insertable portion 107.

In some embodiments, dispensing a composition 111 from the ejection zone 29 increases on target deposition of the composition 111 to an olfactory cleft 23. In some embodiments, dispensing a composition 111 from the ejection zone 29 increases on target deposition of the composition 111 to an aspect of a respiratory region such as a middle turbinate 15.

In some embodiments, dispensing a composition 111 from the ejection zone 29 increases on target deposition of the composition to two or more regions or sub-regions of a nasal channel 20. In some embodiments, the subject engaging portion 106 is seated on the columella region 10 when the subject engaging portion 106 simultaneously contacts a downward facing lateral face of the columella 10, a leftward facing lateral face of the columella 10, and a rightward facing lateral face of the columella 10.

Figure 10:
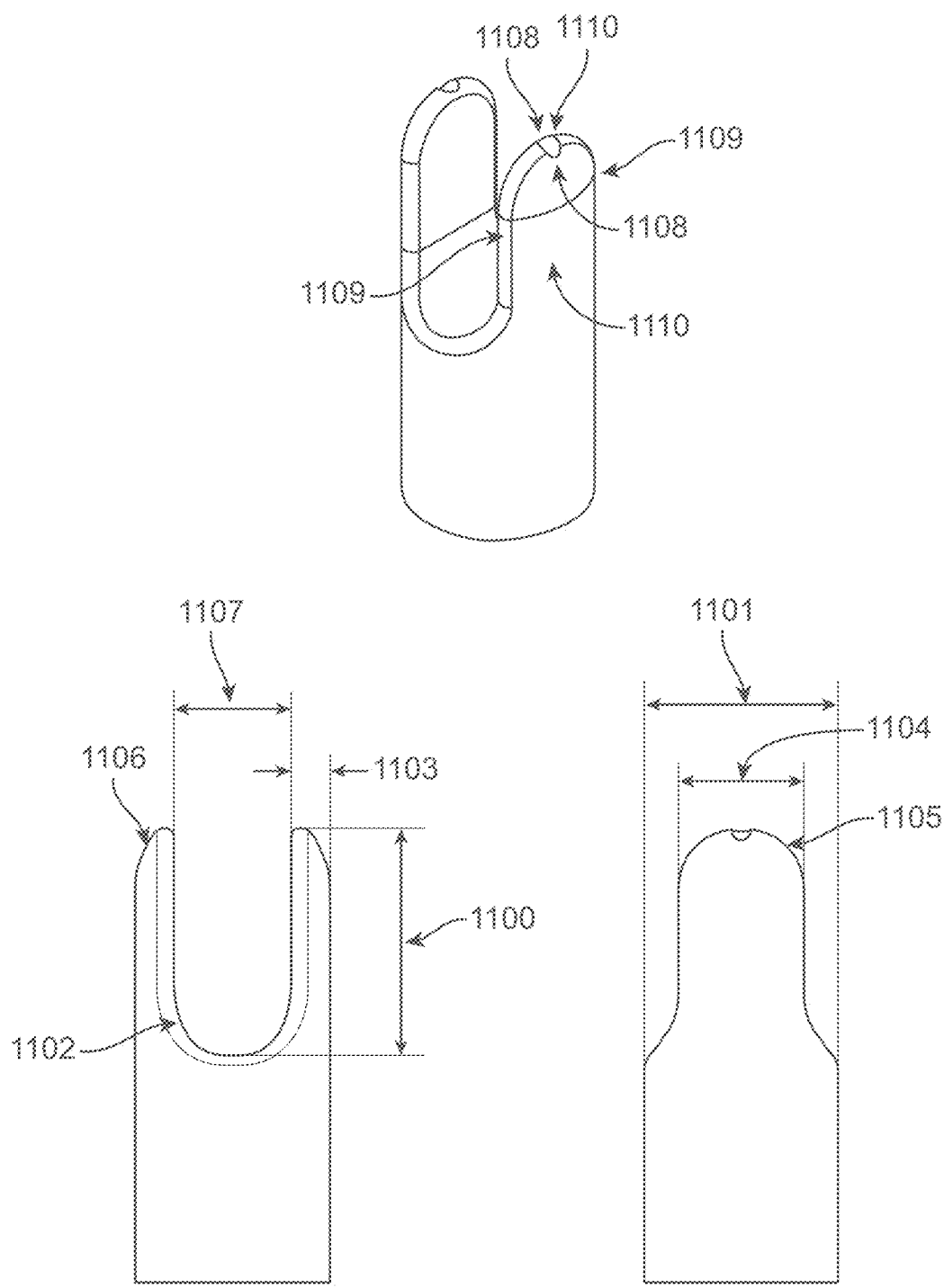
FIG. 10 depicts an exemplary embodiment perspective, front and side view of an Exemplary Columella Saddle in the first configuration, according to some embodiments.

FIG. 10 depicts an exemplary embodiment perspective, front and side view of an Exemplary Columella Saddle in the first configuration, according to some embodiments. In some embodiments, the device comprises a length 1100 of the insertable portions 107 from the base of the "U" shaped columella saddle 121 to the distal end 128 of the insertable portions 107. In some embodiments, the length 1100 of the insertable portions 107 from the base of the "U" shaped columella saddle 121 to the distal end 128 of the insertable portions 107 is about 20 mm. In some embodiments, the length 1100 of the insertable portions 107 from the base of the "U" shaped columella saddle 121 to the distal end 128 of the insertable portions 107 is between about 1 mm to about 20 mm. In some embodiments, the length 1100 of the insertable portions 107 from the base of the "U" shaped columella saddle 121 to the distal end 128 of the insertable portions 107 is between about 1 mm to about 25 mm. In some embodiments, the device comprises the depth 1101 of the distal end 128 of the insertable portions 107 from the base of the "U" shaped columella saddle 121. In some embodiments, the device comprises the depth 1101 of the base of the "U" shaped columella saddle 121 is about 17 mm. In some embodiments, the device comprises the depth 1101 of the base of the "U" shaped columella saddle 121 between about 1 to about 17 mm. In some embodiments, the device comprises the depth 1101 of the base of the "U" shaped columella saddle 121 between about 1 to about 22 mm. In some embodiments, the device comprises the radius 1102 of the "U" shaped s columella addle 121. In some embodiments, the radius 1102 of the "U" shaped saddle 121 is about 5 mm. In some embodiments, the radius 1102 of the "U" shaped columella saddle 121 is between about 1 mm to about 5 mm. In some embodiments, the radius 1102 of the "U" shaped columella saddle 121 is between about 1 mm to about 10 mm. In some embodiments, the device comprises the width 1103 of the insertable portions 107 at the vertical mid-point. In some embodiments, the width 1103 of the insertable portions 107 at the vertical mid-point is about 3.5 mm. In some embodiments, the width 1103 of the insertable portions 107 at the vertical mid-point is between about 1 mm to about 3.5 mm. In some embodiments, the width 1103 of the insertable portions 107 at the vertical mid-point is between about 1 mm to about 7 mm. In some embodiments, the device comprises the length 1100 of the insertable portions 107 at the vertical mid-point. In some embodiments, the length 1100 of the insertable portions 107 at the vertical mid-point is about 11 mm. In some embodiments, the length 1100 of the insertable portions 107 at the vertical mid-point is between about 1 mm to about 11 mm. In some embodiments, the length 1100 of the insertable portions 107 at the vertical mid-point is between about 1 mm to about 16 mm. In some embodiments, the device comprises the width 1104 of the insertable portions 107 at the vertical mid-point. In some embodiments, the width 1104 of the insertable portions 107 at the vertical mid-point is about 11 mm. In some embodiments, the width 1104 of the insertable portions 107 at the vertical mid-point is between about 1 mm to about 11 mm. In some embodiments, the width 1104 of the insertable portions 107 at the vertical mid-point is between about 1 mm to about 16 mm. In some embodiments, the device comprises the radius 1105 of the distal end 128 of the insertable portions 107 (along the depth). In some embodiments, the radius 1105 of the distal aspect of the insertable portions 107 (along the depth) is about 5.5 mm. In some embodiments, the radius 1105 of the distal aspect of the insertable portions 107 (along the depth) is between about 1 mm to about 5.5 mm. In some embodiments, the radius 1105 of the distal aspect of the insertable portions 107 (along the depth) is between about 1 mm to about 10 mm. In some embodiments, the device comprises the radius 1106 of the distal edge of the insertable portions 107 (along the width). In some embodiments, the device comprises the radius 1106 of the distal edge of the insertable portions 107 (along the width) is about 8.5 mm. In some embodiments, the device comprises the radius 1106 of the distal edge of the insertable portions 107 (along the width) is between about 1 mm to 8.5 mm. In some embodiments, the device comprises the radius 1106 of the distal edge of the insertable portions 107 (along the width) is between about 1 mm to 13.5 mm. In some embodiments, the device comprises the width 1107 between insertable portions 107 at the vertical mid-point. In some embodiments, the width 1107 between insertable portions 107 at the vertical mid-point is about 10 mm. In some embodiments, the width 1107 between insertable portions 107 at the vertical mid-point is between about 1 mm to about 10 mm. In some embodiments, the width 1107 between insertable portions 107 at the vertical mid-point is between about 1 mm to about 15 mm.

In some embodiments, the insertable portion 107 is configured to fit into a wedge shape of a nasal valve 13 where a septum 24 contacts a superior lateral cartilage 25. In some embodiments, the anterior aspect of the insertable portion 107 is configured to fit into the narrow anterior aspect of the internal nasal valve 13. In some embodiments, the anterior aspect of the insertable portion 107 is configured to fit into an opening comprising a 9 to 15 degree angle. In some embodiments, the angle of the insertable portion may be determined with reference to the axis of the nasal dorsum, with the midpoint of where the subject engaging portion touches the columella acting as a fulcrum point. Rotation of the device about this fulcrum point such that the tips of the insertable portions move away from the axis of the nasal dorsum would increase this angle, and may be necessary for precision targeting of an intranasal region or subregion such as the olfactory cleft. In some embodiments, this angle between the device axis and the axis of the nasal dorsum is between about 9 and 15 degrees. In some embodiments, the angle between the device axis and the axis of the nasal dorsum is between about 7 and 17 degrees. In some embodiments, the angle between the device axis and the axis of the nasal dorsum is between about 0 and 45 degrees. In some embodiments, the insertable portion 107 is configured to fit into the narrow anterior aspect of the internal nasal valve 13 when seated about the columella region 10. In some embodiments, the insertable portion 107 is configured to fit into an opening comprising a 9 to 15 degree angle when seated about the columella region 10. In some embodiments, the insertable portion 107 is configured to be inserted into a wedge shaped internal nasal valve 13 of a subject. In some embodiments, the insertable portion 107 is tapered about a distal end 128 of the insertable portion 107 and is configured to be inserted into a wedge shaped internal nasal valve 13 of a subject. In some embodiments, the insertable portion 107 is tapered about a distal end 128 of the insertable portion 107 with rounded edges 130 and is configured to be inserted into a wedge shaped internal nasal valve 13 of a subject. In some embodiments, the insertable portion 107 comprises a tip portion having a width 1104 which corresponds to an average diameter of an internal nasal valve 13. In some embodiments, the insertable portion 107 comprises a flat surface on a lateral face of the insertable portion 107 which contacts the septum 24. In some embodiments, the insertable portion 107 comprises a rounded surface on a lateral face of the insertable portion which is opposite the septum 24. In some embodiments, the insertable portion 107 comprises a width 1103 up to 3 mm. In some embodiments, the insertable portion 107 comprises a width 1103 up to 3.5 mm. In some embodiments, the insertable portion 107 comprises a width 1103 up to 5 mm. In some embodiments, one or both insertable portions 107 comprises a distal end 128, wherein a dispensing element 110 reveals from the distal end 128 of the insertable portion 107. In some embodiments, the distal end 128 of an insertable portion 107 is configured for insertion into the nasal channel 20 of the subject. In some embodiments, the revealing of the dispensing element 110 from the first insertable portion 107 upon transition of the device from the first configuration 100 to the second configuration 200 comprises extending of the dispensing element 110 from the first insertable portion 107. In some embodiments, the subject engaging portion 106 engages both a right side and a left side of the columella region 10. In some embodiments, the subject engaging portion 106 comprises a concave shape. In some embodiments, the subject engaging portion 106 comprises a U shape. In some embodiments, the subject engaging portion 106 comprises a saddle shape. In some embodiments, the subject engaging portion 106 comprises a concave ellipsoidal shape. In some embodiments, the subject engaging portion 106 comprises a trench with a rounded bottom or rounded edges. In some embodiments, the subject engaging portion 106 centers the two insertable portions 107 about the subject's columella 10. In some embodiments, the subject engaging portion 106 is a positioning element which aligns at least one of the insertable portion 107, the dispensing element 110, or the housing 101 relative to the user's nasal channel 20. In some embodiments, the device targets an olfactory cleft 23 or a portion thereof, wherein the subject engaging portion 106 aligns a dispensing element 110 with an olfactory cleft 23 of the subject. In some embodiments, an insertable portion 107 comprises a single dispensing channel 125 leading to a dispensing port 126 positioned at the distal end 128 of the insertable portion 107. In some embodiments, an insertable portion 107 comprises a single dispensing channel 125 leading to a dispensing port 126 positioned along the length 1100 of the insertable portion 107.

In some embodiments, an insertable portion 107 comprises two or more dispensing channels 125 leading to two or more dispensing ports 126 positioned at various aspects of the insertable portion 107. In some embodiments, an insertable portion 107 comprises a single dispensing channel 125 leading to a dispensing port 126 positioned to deliver a composition 111 to an olfactory cleft 23. In some embodiments, an insertable portion 107 comprises a single dispensing channel 125 leading to a dispensing port 126 positioned to deliver a composition 111 to an aspect of the respiratory region, such as a middle turbinate 15. In some embodiments, an insertable portion 107 comprises two or more dispensing channels 125 leading to two or more dispensing ports 126 positioned to deliver a composition 111 to one or more regions or sub-regions of a nasal channel 20 such as an olfactory cleft 23 and/or a middle turbinate 15. In some embodiments, a first insertable portion 107 comprises a single dispensing channel 125 leading to a dispensing port 126 positioned at the distal end 128 of the insertable portion 107 and a second insertable portion 107 comprises a single dispensing channel 125 leading to a dispensing port 126 positioned along the length 1100 of the insertable portion 107. In some embodiments, a first insertable portion 107 comprises a single dispensing channel 125 leading to a dispensing port 126 positioned at the distal end 128 of the insertable portion 107 and a second insertable portion 107 comprises two or more dispensing channels 125 leading to two or more dispensing ports 126 positioned at various aspects of the insertable portion 107. In some embodiments, a composition 111 is dispensed from two insertable portions 107 simultaneously.

In some embodiments, a composition 111 is dispensed from two insertable portions 107 sequentially. In some embodiments, a composition 111 is dispensed from two dispensing elements 110 simultaneously. In some embodiments, a composition 111 is dispensed from two dispensing elements 110 sequentially. In some embodiments, the trigger and/or the subject engaging portion 106 actuates the device and dispenses the composition 111 from one dispensing element 110 when pressed against the subject's columella 110. In some embodiments, the trigger and/or the subject engaging portion 106 comprises an actuator which dispenses the composition 111 from the reservoir when the housing 101 is moved from the first position to the second position. In some embodiments, the subject engaging portion 106 engages the columella 10 of the subject to limit depth of insertion of the first insertable portion 107 and the second insertable portion 107 into the subject's nasal channel 20. In some embodiments, the subject engaging portion 106 engages the columella 10 of the subject to limit depth of insertion of the first dispensing element 110 and the second dispensing element 110 into the subject's nasal channel 20. In some embodiments, the subject engaging portion 106 engages the columella 10 of the subject about multiple sides of the columella 10 in a concave shape.

In some embodiments, the trigger comprises a columella saddle 121 for receiving the columella 10 of the subject. In some embodiments, the columella saddle 121 positions the first insertable portion 107 and the second insertable portion 107 as to align the one or more dispensing elements 110 with the target region, e.g., the olfactory cleft 23, middle meatus 30, or other nasal anatomy, when the device is actuated. In some embodiments, the saddle portion 121, subject engaging portion 106, or positioning trigger comprises a shape which matches the anatomy of the subject's columella 10 and aligns the one or more dispensing elements 110 with the subject's olfactory cleft 23. In some embodiments, the one or more dispensing elements 110 are positioned in line with an unobstructed path to the olfactory cleft 23 of the subject when the subject engaging portion 106 is engaging the columella 10 of the subject. In some embodiments, the one or more dispensing elements 110 are positioned in line with an unobstructed path to the middle meatus 30 of the subject when the subject engaging portion 106 is engaging the columella 10 of the subject. In some embodiments, the one or more dispensing elements 110 are positioned in line with an unobstructed path to the middle turbinate 15 of the subject when the subject engaging portion 106 is engaging the columella 10 of the subject.

In some embodiments, the dispensing element 110 is positioned 0 mm to about 40 mm from the inferior aspect of an olfactory cleft 23 of the subject when the subject engaging portion 106 is engaging the columella 10 of the subject. In some embodiments, the dispensing element 110 is positioned 0 mm to about 40 mm from the middle meatus 30 of the subject when the subject engaging portion 106 is engaging the columella 10 of the subject. In some embodiments, the dispensing element 110 is positioned 0 mm to about 40 mm from the middle turbinate 15 of the subject when the subject engaging portion 106 is engaging the columella 10 of the subject. In some embodiments, the saddle 121 comprises an impression of the subject's columella 10.

In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end 128 of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, wherein the composition 111 is dispensed to both regions sequentially. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition 111 is dispensed to all regions sequentially.

In some embodiments, the subject engaging portion 106 comprises dimension of about 20 mm by about 17 mm.

In some embodiments, the columella saddle 121 engages the columella 10 of the subject about multiple sides of the columella 10. In some embodiments, the subject engaging portion 106 depresses a trigger release 104 coupled to the subject engaging portion 106 to actuate the device. In some embodiments, the first and/or second insertable portion 107 limits a sagittal angle 607 or an anterior-posterior 611 angle of the device. In some embodiments, the first and/or second insertable portion 107 limits a coronal angle 608 or a medial-lateral angle 604 of the device. In some embodiments, the first and/or second insertable portion 107 limits a sagittal angle 607 or an anterior-posterior 611 angle of the device. In some embodiments, the first and/or second insertable portion 107 and subject engaging portion 106 limits a sagittal angle 607, an anterior-posterior 611 angle of the device, a coronal angle 608 or a medial-lateral angle 604 of the device, a sagittal angle 607 or an anterior-posterior 611 angle of the device, or any combination thereof.

In some embodiments, an internal nasal valve 13 of the subject is bounded medially by the septum 24, laterally by the caudal portion of the upper lateral cartilage 25 and inferiorly by the head of the inferior turbinate 16. In some embodiments, the first and/or second insertable portion 107 displaces the upper lateral cartilage 25 thereby opening or enlarging at least a portion of internal nasal valve 13 of the subject.

In some embodiments, the first and/or second insertable portion 107 is torsionally flexible. In some embodiments, the first and/or second insertable portion 107 is tortional flexible so as to adjust to the angle of an anterior aspect or wedge of the internal nasal valve 13. In some embodiments, the first and/or second insertable portion(s) 107 runs proximal to a septum 24 of the user. In some embodiments, one or more dispensing elements 110 extend outwards or are revealed from the insertable portion 107 when the device is actuated. In some embodiments, two dispensing elements 110 reveal outwards from the insertable portion 107 when the device is actuated. In some embodiments, the device dispenses a composition 111 from one or more dispensing elements 110 when the device is actuated. In some embodiments, the housing 101 further comprises a second insertable portion 107 for insertion into a second nasal channel 20 of the user. In some embodiments, the first and/or second insertable portion 107 moves tissue within the nasal channel 20 to define a path between the one or more dispensing elements 110 and a delivery site. In some embodiments, the first and/or second insertable portion 107 moves tissue within the nasal channel 20 to open or enlarge an internal nasal valve 13 of a subject. In some embodiments, the dispensing element 110 is contained within the insertable portion 107. In some embodiments, the device further comprises a second dispensing element 110, wherein the first dispensing elements 110 is contained within the first insertable portion 107, wherein the second dispensing element 110 is contained within the second insertable portion 107. In some embodiments, an end of the dispensing element is coextensive with the end of the insertable portion. In some embodiments, a dispensing element is entirely contained within the insertable portion when the device is actuated, or when the housing is moved from the first position to the second position (see FIGS. 2G-2J). In some embodiments, an end of the dispensing element is coextensive with an end of the insertable portion when the device is actuated, or when the housing is moved from the first position to the second position (see FIGS. 2G-2J). In some embodiments, the dispensing element does not extend or reveal from the insertable portion when the device is actuated, or when the housing is moved from the first position to the second position (see FIGS. 2G-2J). In some embodiments, the device may further include a trigger or trigger release 104 coupled to the subject engaging portion 106 on the columella saddle, and may actuate the device when pressure is applied to the trigger release 104 by a subject's columella (see FIGS. 2G-2H). In some embodiments, dispensing element comprises a cannula.

In some embodiments, the at least one insertable portion 107 limits a sagittal angle 607 or an anterior-posterior angle of the device. In some embodiments, the at least one insertable portion 107 limits a coronal angle or a medial-lateral angle 604 of the device. In some embodiments, the at least one insertable portion 107 limits a coronal angle or a medial-lateral angle 604 of the device. In some embodiments, the at least one insertable portion 107 is flexible. In some embodiments, the at least one insertable portion 107 is tortional flexible. In some embodiments, the at least one insertable portion 107 is tortional flexible so as to adjust to the angle of the anterior aspect of the internal nasal valve 13. In some embodiments, the at least one insertable portion 107 runs proximal to a septum 24 of the user. In some embodiments, the at least one insertable portion 107 comprises the following flexibility characteristics: a medial-lateral flexibility 1108 along a width 1103 orthogonal to a length 1100 of the insertable portion; a lack of anterior-posterior flexibility 1109 about a length 1100 of the insertable portion 107; an inferior-superior flexibility 1110 about a rotational axis orthogonal to a length 1100 of the insertable portion, or a combination thereof.

In some embodiments, the first and/or second insertable portion 107 comprises dimension of about 20 mm by about 3.5 mm.

In some embodiments, the first and/or second insertable portion 107 are shaped 130, wherein the shape comprises a wedge-shaped, paddle-shaped, cylindrical, bulbous, cone-shaped, spherical, hemispherical, or any combination thereof. In some embodiments, the transition of the device from the first configuration 100 to the second configuration 200 is actuated by the subject engaging portion 106 which reveals the dispensing element 110 from the first insertable portion 107. In some embodiments, the transition of the device from the first configuration 100 to the second configuration 200 is actuated by an actuator which reveals the dispensing element 110 from the first insertable portion 107. In some embodiments, the first or second insertable portion 107 displaces cartilage and/or tissue within the nasal channel 20 when the device is inserted in the first configuration 100. In some embodiments, the first or second insertable portion 107 fits proximal to a septal-lateral cartilage junction 27 of the subject when the device is in the second configuration 200.

In some embodiments, the housing 101 is movable from a first position to the second position. In some embodiments, the housing 101 comprises a first portion 1020 and a second portion 105, wherein the second portion 105 is pushed relative to the first portion 1020 to actuate the device when the housing 101 is transitioned from the first configuration 100 to the second configuration 200. In some embodiments, the first portion 1020 is inserted into the second portion 105 when the housing 101 is transitioned from the first configuration 100 to the second configuration 200. In some embodiments, upon transition from the first configuration 100 to the second configuration 200, the second portion 105 moves relative to the subject, while the first portion 1020 remains stationary relative to the subject, wherein the first portion 1020 is coupled to the dispensing element 110. In some embodiments, upon transition from the first configuration 100 to the second configuration 200, the dispensing element 110 reveals outward from the first portion 1020.

In some embodiments, the columella region 10 comprises: the subnasale, the subnasion, the anterior nasal spine 32, or any combination thereof. In some embodiments, the insertable portion 107 has the following flexibility characteristics: a medial-lateral flexibility 1108 along a width 1103 orthogonal to a length 1100 of the insertable portion 107; a lack anterior-posterior flexibility 1109 about a length 1100 of the insertable portion; or an inferior-superior flexibility 1110 about a rotational axis orthogonal to a length 1100 of the insertable portion 107. In some embodiments, the dispensing element 110 is configured to dispense the composition 111 into a single nasal channel 20 of a subject. In some embodiments, the dispensing element 110 fits proximal to a septal-lateral cartilage junction 27 of the subject. In some embodiments, the dispensing element 110 fits proximal to a septum 24 of the subject. In some embodiments, the dispensing element 110 comprises a dispensing port 126. In some embodiments, a dispensing element 110 comprises a cannula or a catheter.

In some embodiments, the one or more insertable portions 107 comprise a plurality of dispensing ports 126. In some embodiments, the one or more dispensing elements 110 comprise a dispensing port 126. In some embodiments, the dispensing port 126 has one dispensing port 126 at its distal aspect 131, one or more dispensing ports 126 along its length, or a combination of both. In some embodiments, the dispensing port 126 is directed at different target areas within the nasal channel 20. In some embodiments, the dispensing port 126 comprises an atomizer. In some embodiments, the dispensing element 110 comprises an atomizer. In some embodiments, the one or more dispensing elements 110 are 20 mm to 50 mm in length. In some embodiments, the one or more dispensing elements 110 reveal 0 mm to 40 mm from the insertable portion 107. In some embodiments, the one or more dispensing elements 110 comprise multiple dispensing ports 126. In some embodiments, the one or more dispensing elements 110 comprise multiple fluid channels 125. In some embodiments, the one or more dispensing elements 110 comprise a dispensing port 126. In some embodiments, one of the multiple fluid channels 125 is configured to dispense a gas. In some embodiments, one of the multiple fluid channels 125 is configured to dispense a gas following dispensing a composition 111 by another fluid channel 125. In some embodiments, the device is configured to target the target region 19, e.g., the olfactory cleft 23 or a portion thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously. In some embodiments, the target region 19 is the olfactory region 23 and the middle meatus 30, and other regions of the nasal anatomy, wherein the composition is dispensed to all regions sequentially.

In some embodiments, the one or more dispensing elements 110 comprise a first tubular section which surrounds the dispensing element 110. In some embodiments, the first tubular section remains within a first insertable portion 107 when the device is actuated to the second position 200. In some embodiments, the insertable portion 107 is flexible. In some embodiments, the one or more dispensing elements 110 are flexible. In some embodiments, the device further comprises a reservoir fluidically connected to the one or more insertable portions 107. In some embodiments, the device further comprises a reservoir fluidically connected to the one or more dispensing elements 110.

In some embodiments, the compound 111 comprises a therapeutic agent. In some embodiments, the compound 111 comprises a sampling agent. In some embodiments, the compound comprises 111 a liquid, powder or gas, or a combination thereof. In some embodiments, the target region 19 is one or both olfactory clefts 23, or a sub-area thereof. In some embodiments, the target area 19 is one or both respiratory areas, or a sub-area thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end 128 of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition 111 is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

In some embodiments, the actuator is spring loaded. In some embodiments, the actuator dispenses approximately equal amounts of fluid 111 form each insertable portion 107. In some embodiments, the actuator dispenses approximately equal amounts of fluid from each dispensing element 110. In some embodiments, the actuator dispenses fluid from only one insertable portion 107. In some embodiments, the actuator dispenses fluid from only one dispensing element 110. In some embodiments, the one or more dispensing elements 110 are contained with a secondary tubular member 324. In some embodiments, the reservoir is removable. In some embodiments, the reservoir is comprised within a removable cartridge. In some embodiments, the positioned trigger depresses a switch 104 underneath the positioning trigger to actuate the device.

In some embodiments, the device comprises a central tube fluidically connected to the one or more insertable portions 107, wherein the central tube is inserted into the reservoir when the device is actuated. In some embodiments, further comprising a central tube fluidically connected to the one or more dispensing elements 110, wherein the central tube is inserted into the reservoir when the device is actuated. In some embodiments, the device comprises a central tube fluidically connected to two insertable portions 107, wherein the central tube is inserted into the reservoir when the device is actuated. In some embodiments, the device comprising a central tube fluidically connected to two dispensing elements 110, wherein the central tube is inserted into the reservoir when the device is actuated. In some embodiments, the device further comprises a one or more bases connected to the bottom of the one or more dispensing elements 110 which move the one or more dispensing elements 110 upon actuation of the device. In some embodiments, the dispensing channels 125 comprise a diameter of about 0.3 mm to about 3 mm. In some embodiments, the dispensing element 110 comprises an inner diameter 129 of about 0.3 mm to about 3 mm. In some embodiments, the dispensing element 110 is configured to prevent the introduction of bacteria or microbes from the lower nasal cavity 11 or external environment into different another region of the nasal cavity 11.

In one aspect, the disclosure provides a device for intranasal delivery to a subject, the device transitionable from a first configuration 100 to a second configuration 200, the device comprising: a housing 101 defining two insertable portions 107 comprising at least one dispensing element 110, each insertable portion for insertion into a nasal channel 20 of the subject, wherein, upon insertion of the first insertable portion 107 into a nasal channel 20 of the subject, the first insertable portion 107 engages tissue within the nasal channel 20 to open or expand an internal nasal valve 13 of the subject thereby positioning at least one of the dispensing elements 110 for delivery of a composition 111 to the subject; a subject engaging portion 106 coupled to the housing 101 comprising a trigger, the trigger comprising a subject engaging portion 106 which engages a columella region 10, wherein upon application of pressure to the subject engaging portion 106, the trigger permits actuation of the device to deliver a composition 111 to the subject from the dispensing element 110; and the dispensing element 110 revealing from the first insertable portion 107 upon transition of the device from the first configuration 100 to the second configuration 200.

In one aspect, the disclosure provides a device for intranasal delivery to a subject, the device transitionable from a first configuration 100 to a second configuration 200, the device comprising: a housing 101 defining two insertable portions 107, each insertable portion 107 for insertion into a nasal channel 20 of the subject for delivery of a composition 111 into a nasal channel 20 of the subject, wherein, upon insertion of the first insertable portion 107 into a nasal channel 20 of the subject, the first insertable portion 107 engages tissue within the nasal channel 20 to open or expand an internal nasal valve 13 of the subject thereby positioning at least one of the insertable portions 107 for delivery of a composition 111 to the subject; and a subject engaging portion 106 coupled to the housing comprising a trigger, the trigger comprising a subject engaging portion 106 which engages a columella region 10, wherein upon application of pressure to the subject engaging portion 106, the trigger permits actuation of the device to deliver a composition 111 to the subject from at least one of the insertable portions 107.

FIG. 6A depicts an exemplary embodiment of a cartesian reference plane of (left to right) a front, a top, and a side view of the Exemplary Device. FIG. 6B depicts an exemplary embodiment of the subject plane. FIG. 6C depicts an exemplary embodiment of (left to right) a front Coronal Plane, a top Transverse Plane, and a side Sagittal Plane view of angular reference plane of the Exemplary Device. In some embodiments, the device is configured for a subject having a coronal or frontal plane 601, horizontal or axial or transverse plane 602, sagittal or longitudinal plane 603, median plane 604, or parasagittal plane 605, or combination thereof. In some embodiments, the device comprises a relative angular coordinate system of roll on the Y-axis of the device 606, pitch on the subject sagittal plane 607, and yaw on the subject coronal plane 608. In some embodiments the device is configured for a subject having a subject linear coordinate system x relative to subject medial/lateral 609, y relative to subject superior/inferior 610, and z relative to subject anterior/posterior 611. FIG. 6D depicts an exemplary embodiment of the Exemplary Device Sagittal Angle positioning in the subject.

Method

In one aspect, the disclosure provides a method for intranasal delivery to a subject with a device, the method comprising: positioning an insertable portion 107 of the device within an ejection zone 29 of a nasal cavity 11 of the subject by engaging a columella region 10 of the subject with a subject engaging portion 106 of the device, seating the insertable portion 107 within the ejection zone 29 of the subject's nasal cavity 11, wherein the ejection zone 29 is: 0 mm to 30 mm superior to a horizontal line 627 that intersects the anterior aspect of the internal nasal valve 13, and 0 mm to 20 mm anterior to an inclined line 610 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 23, 0 mm to 20 mm posterior to the internal nasal dorsum 622, 10 mm and 50 mm superior to a horizontal line 623 that intersects the inferior aspect of the columella 10, 0 mm to 30 mm superior to a horizontal line 624 that intersects the superior aspect of the inferior turbinate 16, 0 mm to 3 mm from the septum 24 or any combination thereof.

In some embodiments, the method further comprises actuating the device by applying pressure to the columella region 10 of the subject with the subject engaging portion 106 of the device. In some embodiments, the positioning the insertable portion 107 of the device comprises positioning two insertable portions 107 into two nasal channels 20 of the subject, thereby opening or expanding an opening of an internal nasal valve 13 of the subject. In some embodiments, the positioning the dispensing element 110 of the device comprises positioning two dispensing elements 110 of the device into a nasal channel 20 of the subject, wherein the two dispensing elements 110 reveal from the insertable portion 107. In some embodiments, the method further comprising transitioning the device from a first configuration 100 to a second configuration 200, wherein the dispensing element 110 reveals from the insertable portion 107 upon transition of the device from the first configuration 100 to the second configuration 200.

In one aspect, the disclosure provides a method for intranasal delivery to a subject with a device, the method comprising: inserting two insertable portions 107 into nasal channels 20 of the subject, wherein upon the inserting at least one of the insertable portion 107 engages tissue within the nasal channel 20 thereby opening or expanding an opening of an internal nasal valve 13 of the subject, thereby positioning at least one of the insertable portions 107 for delivery of a composition 111 to the subject. In some embodiments, the method further comprising positioning the insertable portions 107 into nasal channels 20 of the subject by engaging a columella region 10 of the subject with a subject engaging portion 106 of the device, thereby limiting a depth of insertion of the device into the subject's nasal channel 20 and aligning the insertable portions 107 within the nasal channel 20 of the subject. In some embodiments, the method further comprising actuating the device by applying pressure to the subject engaging portion 106 of the device with the columella region 10 of the subject. In some embodiments, the two insertable portions 107 comprise at least one dispensing element 110. In some embodiments, the at least one dispensing element 110 reveals outwards from at least one of the two insertable portions 107. In some embodiments, the method further comprises transitioning the device from a first configuration 100 to a second configuration 200, wherein the dispensing element 110 reveals from the insertable portion 107 upon transition of the device from the first configuration 100 to the second configuration 200. In some embodiments, the inserting two insertable portions 107 of a. advances the two insertable portions 107 along the inner dorsum 622 and/or on along either side of the septum 24 until a columella 10 engaging region of the device contacts a columella 10 of the subject, preventing further insertion, and establishing a depth datum 617. In some embodiments, a dispensing port 126 is positioned at a targeted region or subregion in the nasal cavity 11. In some embodiments, the targeted region is the olfactory cleft, middle turbinate, inferior turbinate, superior turbinate, superior middle inferior meatuses, or combinations thereof.

In some embodiments, the inserting two insertable portions 107 of a. uses the nasofrontal angle 614 as an angular reference to position the insertable portions 107 within the nasal channels 20. In some embodiments, a dispensing port 126 is positioned at a targeted region or subregion in the nasal cavity 20. In some embodiments, the inserting two insertable portions 107 of a. advances the two insertable portions 107 along the inner dorsum 622 until a columella engaging region 106 of the device contacts a columella 10 of the subject, preventing further insertion, and establishing a depth datum 617, and wherein the inserting two insertable portions 107 of a. uses the nasofrontal angle 614 as an angular reference to position the insertable portions 107 within the nasal channels 20, thereby positioning the two insertable portions 107 within the nasal cavity 20 at known position.

In some embodiments, the inserting two insertable portions 107 of a. comprises inserting the two insertable portions 107 past a nasal vestibule 21. In some embodiments, the inserting two insertable portions 107 of a. comprises inserting the two insertable portions 107 along soft tissues of a superior cleft in an orientation parallel to the soft tissues. In some embodiments, the inserting two insertable portions 107 of a. prevents rotation of the device about an axis parallel to the subject's height 601. In some embodiments, the inserting two insertable portions 107 of a. creates a reference yaw angle 608 a coronal plane 601 relative to a y-axis of the device. In some embodiments, the inserting two insertable portions 107 of a. creates a substantially unimpeded flow channel to the target region 19, e.g., an olfactory cleft 23. In some embodiments, the inserting two insertable portions 107 of a. creates a substantially unimpeded flow to a nasal turbinate. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

In one aspect, the disclosure provides a method for intranasal delivery to a subject with a device, the method comprising: positioning an insertable portion 107 of the device within a nasal channel 20 of the subject; and transitioning the device from a first configuration 100 to a second configuration 200 by applying pressure about a longitudinal axis 610 of the device, thereby revealing a dispensing element 110 from the first insertable portion 107 and simultaneously actuating the device to deliver the composition 111 to the subject. In some embodiments, the simultaneous actuation refers to transition for the first configuration 100 to the second configuration 200 and actuation occurring in a single motion upon application of pressure about a longitudinal axis 610 of the device. In some embodiments, the positioning the insertable portion 107 of the device within the nasal channel 20 of the subject occurs by engaging a columella region 10 of the subject with a subject engaging portion 106 of the device. In some embodiments, the method further comprising actuating the device by applying pressure to the subject engaging portion 106 of the device with the columella region 10 of the subject. In some embodiments, the positioning the insertable portion 107 of the device within the nasal channel 20 of the subject engages tissue within the nasal channel 20 to open or expand an internal nasal valve 13 of the subject, thereby positioning the insertable portion 107 for delivery of a composition 111 to the subject. In some embodiments, the insertable portion 107 of the device comprises two insertable portions 107, each for insertion into a nasal channel 20 of the subject, wherein a. comprises inserting two insertable portions 107 into nasal channels 20 of the subject. In some embodiments, the inserting two insertable portions 107 of a. advances the two insertable portions 107 along the inner dorsum 622 and/or on along either side of the septum 24 until a columella engaging region 106 of the device contacts a columella 10 of the subject, preventing further insertion, and establishing a depth datum 617. In some embodiments, the inserting two insertable portions 107 of a. uses the nasofrontal angle 614 as an angular reference to position the insertable portions 107 within the nasal channels 20. In some embodiments, a dispensing port 126 is positioned at a targeted region or subregion in the nasal cavity 11. In some embodiments, the inserting two insertable portions 107 of a. advances the two insertable portions 107 along the inner dorsum 622 and/or on along either side of the septum 24 until a columella engaging region 106 of the device contacts a columella 10 of the subject, preventing further insertion, and establishing a depth datum 617, and wherein the inserting two insertable portions 107 of a. uses the nasofrontal angle 614 as an angular reference to position the insertable portions 107 within the nasal channels 20, thereby positioning the two insertable portions 107 within the nasal cavity 20 at known position. In some embodiments, the inserting two insertable portions 107 of a. comprises inserting the two insertable portions 107 past a nasal vestibule 2121. In some embodiments, the inserting two insertable portions 107 of a. comprises inserting the two insertable portions 107 along soft tissues of a superior cleft in an orientation parallel to the soft tissues. In some embodiments, the inserting two insertable portions 107 of a. prevents rotation of the device about an axis parallel to the subject's height 601. In some embodiments, the inserting two insertable portions 107 of a. creates a reference yaw angle 608 a coronal plane 601 relative to a y-axis of the device. In some embodiments, the inserting two insertable portions 107 of a. creates a substantially unimpeded flow channel to the target region 19, e.g., the olfactory cleft 23. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

Figure 9A:
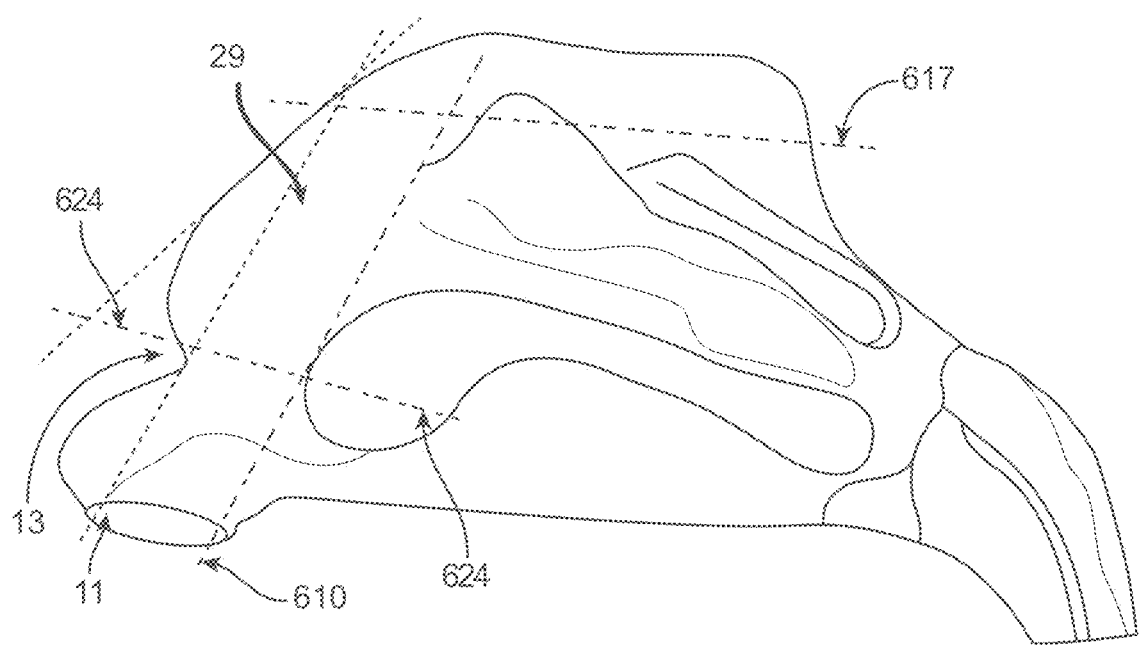
FIG. 9A depicts a side view of a ejection zone, according to some embodiments.

FIG. 9A depicts a side view of an exemplary embodiment of a representation subject's target ejection point.

The devices, systems and methods disclosed herein are advantageous over currently available intranasal delivery devices, in that the disclosed devices are well-matched for placement with respect to the internal nasal valve.

In some embodiments, the exemplary devices disclosed herein are located intra-internal nasal valve (within), or supra-internal nasal valve (above the level of the internal nasal valve).

In some embodiments, the internal nasal valve is located approximately 10 mm-15 mm from the nostril opening, depending on individual variations. In some embodiments, the inferior (lower) aspect of the nasal valve, which is closer to the nostril, is towards the lower end of this range. In some embodiments, the superior (upper) aspect of the internal nasal valve is on average 2 cm-2.5 cm from the nostril opening.

The devices, systems and methods disclosed herein are advantageous over currently available intranasal delivery devices, in that the disclosed devices are well-matched for placement with respect to the nostril opening.

In some embodiments, the exemplary devices disclosed herein are located more than 10 mm-15 mm from the nostril opening.

In some embodiments, the exemplary devices disclosed herein comprise an area of 10 mm-15 mm located intra-internal nasal valve (within).

In some embodiments, the exemplary devices disclosed herein are designed to be within or above the nasal valve.

The devices, systems and methods disclosed herein are advantageous over currently available intranasal delivery devices, in that the disclosed devices comprise a vantage point well-matched for ejection in the patient nasal anatomy. In some embodiments, the device comprises an increased composition to target delivery due to the vantage point being within or above the internal nasal valve.

The devices, systems and methods disclosed herein are advantageous over currently available intranasal delivery devices, in that the disclosed devices comprise an ejection trajectory well-matched for patient nasal anatomy, wherein the device bypasses anatomical obstructions. In some embodiments, exemplary devices disclosed herein are located intra-internal nasal valve (within), or supra-internal nasal valve (above the level of the internal nasal valve). In some embodiments, the device positioning allows for an increased ejection trajectory. In some embodiments, the device positioning allows for a superior/anterior tendency. In some embodiments, the device positioning also allows for a direct anterior to an inferior/anterior formulation delivery—over stepping anatomical obstructions experienced by other devices.

In one aspect, the disclosure provides a method for intranasal delivery of a composition 111 to a target region 19 of the nasal cavity 11 of a subject, the method comprising: inserting a dispensing element 110 into an ejection zone 29 of a nasal cavity 11, wherein the ejection zone 29 is: 0 mm to 30 mm superior to a horizontal line 627 that intersects the anterior aspect of the internal nasal valve 13, and 0 mm to 20 mm anterior to an inclined line 610 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 23, 0 mm to 20 mm posterior to the internal nasal dorsum 622, 10 mm and 50 mm superior to a horizontal line 623 that intersects the inferior aspect of the columella 10, 0 mm to 30 mm superior to a horizontal line 624 that intersects the superior aspect of the inferior turbinate 16, 0 mm to 3 mm from the septum 24 or any combination thereof, and dispensing the composition 111 from the dispensing element 110 to contact the target region 19 with the composition 111, wherein dispensing the composition 111 from the ejection zone 29: a) increases on target delivery of the composition 111 to the target region 19, b) decreases off target delivery of the composition 111 to the nasal cavity 11, or c) both.

In some embodiments, the ejection zone 29 is: 0 mm to 30 mm superior to a horizontal line 627 that intersects the anterior aspect of the internal nasal valve 13, and 0 mm to 20 mm anterior to an inclined line 610 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 23, 0 mm to 20 mm posterior to the internal nasal dorsum 622, 10 mm and 50 mm superior to a horizontal line that intersects the inferior aspect of the columella 623, 0 mm to 30 mm superior to a horizontal line 624 that intersects the superior aspect of the inferior turbinate 16, 0 mm to 3 mm from the septum 24, or any combination thereof. In some embodiments, the subject engaging portion 106 prevents movement of the distal end 128 within or away from the ejection zone 29 when the subject engaging portion 106 is seated on the columella region 10. In some embodiments, the ejection zone 29 is in line with the olfactory cleft 23 as defined by a linear vector between the olfactory cleft 23 and the distal end 128 of the insertable portion 107.

In some embodiments, dispensing a composition 111 from the ejection zone 29 increases on target deposition of the composition 111 to the olfactory cleft 23. In some embodiments, the subject engaging portion 106 is seated on the columella region 10 when the subject engaging portion 106 simultaneously contacts a downward facing lateral face of the columella 10, a leftward facing lateral face of the columella 10, and a rightward facing lateral face of the columella 10. In some embodiments, dispensing a composition 111 from the ejection zone 29 increases on target deposition of the composition 111 to an aspect of a respiratory region such as a the middle turbinate 15. In some embodiments, the ejection zone 29 is a trapezium or irregular quadrilateral comprising (i) an inferior side 29A being a 10-25 mm line 627 extending posteriorly and horizontally from the anterior aspect of the internal nasal valve 13, (ii) an anterior side 29B being a 10-35 mm line extending superiorly and parallel to the internal nasal dorsum 622 from the anterior aspect of the internal nasal valve 13, (iii) a superior side 29C being a 10-25 mm line extending posteriorly and horizontally from a point on the internal nasal dorsum 622 that is 0-10 mm inferior to the inferior aspect of the olfactory cleft 23, and (iv) a posterior line 29D being a 10-35 mm line extending vertically along a plane that intersects the anterior aspect of the middle turbinate 15. In some embodiments, the target region 19 is one or both olfactory clefts 23, or a sub-area thereof, and wherein dispensing the composition 111 from an anterior end of the dispensing element 110 increases on target delivery of the composition 111 to the target region 19. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition 111 is dispensed to all regions simultaneously.

In one aspect, the disclosure provides a method for intranasal delivery to a subject with a device, the method comprising: positioning an insertable portion 107 of the device within a nasal channel 20 of the subject by engaging a columella region 10 of the subject with a subject engaging portion 106 of the device, thereby limiting a depth of insertion of the insertable portion 107 into the subject's nasal channel 20 and aligning the insertable portion 107 within the nasal channel 20 of the subject. In some embodiments, the method further comprises actuating the device by applying pressure to the columella region 10 of the subject with the subject engaging portion 106 of the device. In some embodiments, the positioning the insertable portion 107 of the device comprises positioning two insertable portions 107 into two nasal channels 20 of the subject, thereby opening or expanding the internal nasal valve 13 by pushing the upper lateral cartilage 25 and surrounding tissue up and away from the septum 24 of the subject thereby positioning the two insertable portions 107 for delivery of the compound 111, e.g., drugs, small and large molecules, medicaments in liquid, powder, or gas form, or a combination thereof to the subject. In some embodiments, the positioning the dispensing element 110 of the device comprises positioning at least one dispensing element 110 of the device into a nasal channel 20 of the subject, wherein the at least one dispensing element 110 reveal from the insertable portion 107. In some embodiments, the method further comprises transitioning the device from a first configuration 100 to a second configuration 200, wherein the dispensing element 110 reveals from the insertable portion 107 upon transition of the device from the first configuration 100 to the second configuration 200.

In one aspect, this disclosure provides for a method for intranasal delivery to a subject with a device, the method comprising: inserting two insertable portions 107 into nasal channels 20 of the subject, wherein upon the inserting at least one of the insertable portion 107 opens or expands the internal nasal valve 13 by pushing the upper lateral cartilage 25 and surrounding tissue up and away 625 from the septum 24 of the subject thereby positioning at least one of the insertable portions 107 for delivery of the compound 111, e.g., drugs, small and large molecules, medicaments in liquid, powder, or gas form, or a combination thereof to the subject. In some embodiments, the method further comprises positioning the insertable portions 107 into nasal channels 20 of the subject by engaging a columella region 10 of the subject with a subject engaging portion 106 of the device, thereby limiting a depth of insertion of the device into the subject's nasal channel 20 and aligning the insertable portions 107 within the nasal channel 20 of the subject. In some embodiments, the method further comprises actuating the device by applying pressure to the subject engaging portion 106 of the device with the columella region 10 of the subject. In some embodiments, the method comprises the two insertable portions 107, wherein the two insertable portions 107 comprise at least one dispensing element 110. In some embodiments, the method comprises the at least one dispensing element 110, wherein the at least one dispensing element 110 is configured to reveal outwards from the at least one of the two insertable portions 107. In some embodiments, the method further comprises transitioning the device from a first configuration 100 to a second configuration 200, wherein the dispensing element 110 reveals from the insertable portion 107 upon transition of the device from the first configuration 100 to the second configuration 200.

In one aspect this disclosure provides, a method for intranasal delivery to a subject with a device, the method comprising: positioning an insertable portion 107 of the device within a nasal channel 20 of the subject; and transitioning the device from a first configuration 100 to a second configuration 200, thereby extending from or revealing from a dispensing element 110 from the first insertable portion 107. In some embodiments, the method comprises the positioning the insertable portion 107 of the device within the nasal channel 20 of the subject occurs by engaging a columella region 10 of the subject with a subject engaging portion 106 of the device. In some embodiments, the method further comprises actuating the device by applying pressure to the subject engaging portion 106 of the device with the columella region 10 of the subject. In some embodiments, the method comprises positioning the insertable portion 107 of the device within the nasal channel 20 of the subject, wherein the insertable portion 107 opens or expands the internal nasal valve 13 by pushing the upper lateral cartilage 25 and surrounding tissue up and away 625 from the septum 24 of the subject thereby positioning at least one of the insertable portions 107 for delivery of the compound 111, e.g., drugs, small and large molecules, medicaments in liquid, powder, or gas form, or a combination thereof to the subject. In some embodiments, the method comprises two insertable portions 107, each for insertion into a nasal channel 20 of the subject.

In one aspect this disclosure provides, a method of using the columella 10 as an anchor to control insertion depth and angle, and to trigger the device.

In one aspect this disclosure provides, a method of using the columella 10 as a (fixed) reference 617 as part of anthropometric calculation(s) to establish proper cannula length.

FIG. 6A depicts an exemplary embodiment of a cartesian reference plane of (left to right) a front, a top, and a side view of the Exemplary Device. FIG. 6B depicts an exemplary embodiment of the subject plane. FIG. 6C depicts an exemplary embodiment of (left to right) a front Coronal Plane, a top Transverse Plane, and a side Sagittal Plane view. In some embodiments, the method further comprises creating a predictable/repeatable relationship of an inserter to subject anatomy. In some embodiments, the method further comprises the subject having a coronal or frontal plane 601, horizontal or axial or transverse plane 602, sagittal or longitudinal plane 603, medial plane 604, or parasagittal plane 605, or combination thereof. In some embodiments, the method further comprises creating a relative angular coordinate system of roll on the Y-axis of the device 606, pitch on the subject sagittal plane 607, and yaw on the subject coronal plane 608. In some embodiments, the method further comprises creating a subject linear coordinate system x 609 relative to subject medial/lateral, y relative to subject superior/inferior 610, and z relative to subject anterior/posterior 611.

FIG. 6D depicts an exemplary embodiment of the Exemplary Device Sagittal Angle positioning in the subject. In some embodiments, the method further comprises positioning the insertable portions 107 along its y-axis in relation to other anatomy, creating a predictable/repeatable relationship with regards to the devices pitch angle on the subject's sagittal plane. In some embodiments, the method further comprises, from the devices predictable/repeatable relationship to other anatomy, the pitch angle can be related to known anthropometric data. In some embodiments, the method further comprises the insertable portions 107 configured to follow the shape of the interior dorsum cleft 612, and lateral aspects of the septum 24 in the nasal cavity 11, allowing it to maintain a consistent and repeatable angle on the sagittal plane 603, wherein this positioning is achieved when the insertable portions 107 are inserted past the nasal vestibule 21 and into the nasal cavity 11. In some embodiments, the method further comprises the insertable portions 107 configured to hold it to, and guide it along the soft tissues of the superior cleft, ensuring that it remains parallel to these tissues. In some embodiments, the method further comprises, as the tissues of the superior cleft are parallel to known anthropometric axis 613 drawn from nasion 619 to tip 128, used in both the nasofacial and nasofrontal angle 614, a known angler anthropometric range can be determined for the position of the inserter Y axis 610 on the sagittal plane 603 relative to subject anatomy.

FIG. 6E depicts an exemplary embodiment of the Exemplary Device Coronal-Medial Angle positioning in the subject, along a front view of the Coronal Plane, and a top view along a transverse plane, according to some embodiments. In some embodiments, the method further comprises the insertable portions 107 are designed to interlock with the nasal cavity 11. In some embodiments, the method further comprises the insertable portions 107 are designed to key medial to the lateral aspects of septal cartilage, and bilaterally to the greater alar and lateral nasal cartilage, including the connective tissues of these structures. In some embodiments, the method further comprises the insertable portions 107 locked in the y-axis rotation along the device 616, and locked in medially/laterally 604. FIG. 6F depicts an exemplary embodiment of the Exemplary Device Depth positioning along a front view of the Coronal Plane, and along a side view of the Sagittal Plane in the subject. In some embodiments, the method further comprises the insertable portions 107 configured to position and interlock within the nasal cavity 11, creating a predictable/repeatable depth 618. In some embodiments, the method further comprises the insertable portions 107 configured to key and hard stop on the columella 10 its supporting structures, e.g., the nasal spine and septal cartilage. In some embodiments, the method further comprises, as the columella 10 comprises a depth datum 617 along the device y-axis, the ejection ports, e.g., the dispensing elements 110, of the insertable portions 107 may be placed at desired and known distance from a target anatomy 617.

FIG. 6G depicts an exemplary embodiment of the Exemplary Device along a side view of the sagittal plane of delivery to the target region 19 in the subject. In some embodiments, the method further comprises, with a known depth, Cartesian and angular reference of the insertable portions 107 relative to subject anatomies in the subject anatomy, exit ports, e.g., dispensing port(s) 126 along one or more dispensing elements 110, that may be placed in a desired location to create a desired trajectory of the dose and a relative fluid profile and velocity that may be chosen to deliver the composition to a desired location, e.g., a target region 19, repeatable and accurately. In some embodiments, the method further comprises a coherent jet may be chosen along the y-axis of the device, creating a substantially unimpeded flow to the target region 19, e.g., the olfactory cleft. In some embodiments, the method further comprises a coherent jet may be chosen along the z-axis of the device, creating a substantially unimpeded flow to the turbinates, e.g., superior turbinate 14, middle turbinate 15, or inferior turbinate 16, or a combination thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

FIG. 6H depicts an exemplary embodiment of the Exemplary Device along a side view of the sagittal plane aiming from the respiratory region in the subject. In some embodiments, the method further comprises, with a known depth, Cartesian and angular reference of the insertable portions 107 relative to subject anatomies in the subject anatomy, exit ports, e.g., dispensing port(s) 126 along one or more dispensing elements 110, may be placed in a desired location to create a desired trajectory of the dose and a relative fluid profile and velocity may be chosen to deliver the composition to a desired location, e.g., a target region 19, repeatable and accurately. In some embodiments, the method further comprises creating a coherent jet may be chosen along the y-axis of the device, creating a substantially unimpeded flow to the target region 19, e.g., turbinate delivery. In some embodiments, the method further comprises, a coherent jet may be chosen along the z-axis of the device, creating a substantially unimpeded flow to the turbinates, e.g., superior turbinate 14, middle turbinate 15, or inferior turbinate 16, or a combination thereof.

In some embodiments, the ejection zone 29 is a trapezium or irregular quadrilateral comprising (i) an inferior side 29A being a 10-25 mm line 627 extending posteriorly and horizontally from the anterior aspect of the internal nasal valve 13, (ii) an anterior side 29B being a 10-35 mm line extending superiorly and parallel to the internal nasal dorsum 622 from the anterior aspect of the internal nasal valve 13, (iii) a superior side 29C being a 10-25 mm line extending posteriorly and horizontally from a point on the internal nasal dorsum 622 that is 0-10 mm inferior to the inferior aspect of the olfactory cleft 23, and (iv) a posterior line 29D being a 10-35 mm line extending vertically along a plane that intersects the anterior aspect of the middle turbinate 15. In some embodiments, the target region 19 is one or both olfactory clefts 23, or a sub-area thereof, and wherein dispensing the composition 111 from an anterior end of the dispensing element 110 increases on target delivery of the composition 111 to the target region. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end 128 of the insertable portion 107. In some embodiments, the target region 19 is one or both olfactory clefts 23, or a sub-area thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end 128 of the insertable portion 107. In some embodiments, the target region 19 is one or both olfactory clefts 23, or a sub-area thereof. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the ejection zone 29 is in line with the olfactory cleft 23 as defined by a linear vector between the olfactory cleft 23 and the distal end of the insertable portion 107. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

In some embodiments, the ejection zone is superior to a horizontal line that intersects the anterior aspect of the internal nasal valve by about 1 mm to about 30 mm. In some embodiments, the ejection zone is superior to a horizontal line that intersects the anterior aspect of the internal nasal valve by about 1 mm to about 2 mm, about 1 mm to about 4 mm, about 1 mm to about 6 mm, about 1 mm to about 8 mm, about 1 mm to about 10 mm, about 1 mm to about 14 mm, about 1 mm to about 18 mm, about 1 mm to about 22 mm, about 1 mm to about 26 mm, about 1 mm to about 30 mm, about 2 mm to about 4 mm, about 2 mm to about 6 mm, about 2 mm to about 8 mm, about 2 mm to about 10 mm, about 2 mm to about 14 mm, about 2 mm to about 18 mm, about 2 mm to about 22 mm, about 2 mm to about 26 mm, about 2 mm to about 30 mm, about 4 mm to about 6 mm, about 4 mm to about 8 mm, about 4 mm to about 10 mm, about 4 mm to about 14 mm, about 4 mm to about 18 mm, about 4 mm to about 22 mm, about 4 mm to about 26 mm, about 4 mm to about 30 mm, about 6 mm to about 8 mm, about 6 mm to about 10 mm, about 6 mm to about 14 mm, about 6 mm to about 18 mm, about 6 mm to about 22 mm, about 6 mm to about 26 mm, about 6 mm to about 30 mm, about 8 mm to about 10 mm, about 8 mm to about 14 mm, about 8 mm to about 18 mm, about 8 mm to about 22 mm, about 8 mm to about 26 mm, about 8 mm to about 30 mm, about 10 mm to about 14 mm, about 10 mm to about 18 mm, about 10 mm to about 22 mm, about 10 mm to about 26 mm, about 10 mm to about 30 mm, about 14 mm to about 18 mm, about 14 mm to about 22 mm, about 14 mm to about 26 mm, about 14 mm to about 30 mm, about 18 mm to about 22 mm, about 18 mm to about 26 mm, about 18 mm to about 30 mm, about 22 mm to about 26 mm, about 22 mm to about 30 mm, or about 26 mm to about 30 mm, including increments therein. In some embodiments, the ejection zone is superior to a horizontal line that intersects the anterior aspect of the internal nasal valve by about 1 mm, about 2 mm, about 4 mm, about 6 mm, about 8 mm, about 10 mm, about 14 mm, about 18 mm, about 22 mm, about 26 mm, or about 30 mm. In some embodiments, the ejection zone is superior to a horizontal line that intersects the anterior aspect of the internal nasal valve by at least about 1 mm, about 2 mm, about 4 mm, about 6 mm, about 8 mm, about 10 mm, about 14 mm, about 18 mm, about 22 mm, or about 26 mm. In some embodiments, the ejection zone is superior to a horizontal line that intersects the anterior aspect of the internal nasal valve by at most about 2 mm, about 4 mm, about 6 mm, about 8 mm, about 10 mm, about 14 mm, about 18 mm, about 22 mm, about 26 mm, or about 30 mm. In some embodiments, the ejection zone is anterior to an inclined line that intersects the anterior aspect of the middle turbinate and the posterior aspect of the vestibule by about 1 mm to about 20 mm. In some embodiments, the ejection zone is anterior to an inclined line that intersects the anterior aspect of the middle turbinate and the posterior aspect of the vestibule by about 1 mm to about 2 mm, about 1 mm to about 4 mm, about 1 mm to about 6 mm, about 1 mm to about 8 mm, about 1 mm to about 10 mm, about 1 mm to about 12 mm, about 1 mm to about 14 mm, about 1 mm to about 16 mm, about 1 mm to about 18 mm, about 1 mm to about 20 mm, about 2 mm to about 4 mm, about 2 mm to about 6 mm, about 2 mm to about 8 mm, about 2 mm to about 10 mm, about 2 mm to about 12 mm, about 2 mm to about 14 mm, about 2 mm to about 16 mm, about 2 mm to about 18 mm, about 2 mm to about 20 mm, about 4 mm to about 6 mm, about 4 mm to about 8 mm, about 4 mm to about 10 mm, about 4 mm to about 12 mm, about 4 mm to about 14 mm, about 4 mm to about 16 mm, about 4 mm to about 18 mm, about 4 mm to about 20 mm, about 6 mm to about 8 mm, about 6 mm to about 10 mm, about 6 mm to about 12 mm, about 6 mm to about 14 mm, about 6 mm to about 16 mm, about 6 mm to about 18 mm, about 6 mm to about 20 mm, about 8 mm to about 10 mm, about 8 mm to about 12 mm, about 8 mm to about 14 mm, about 8 mm to about 16 mm, about 8 mm to about 18 mm, about 8 mm to about 20 mm, about 10 mm to about 12 mm, about 10 mm to about 14 mm, about 10 mm to about 16 mm, about 10 mm to about 18 mm, about 10 mm to about 20 mm, about 12 mm to about 14 mm, about 12 mm to about 16 mm, about 12 mm to about 18 mm, about 12 mm to about 20 mm, about 14 mm to about 16 mm, about 14 mm to about 18 mm, about 14 mm to about 20 mm, about 16 mm to about 18 mm, about 16 mm to about 20 mm, or about 18 mm to about 20 mm, including increments therein. In some embodiments, the ejection zone is anterior to an inclined line that intersects the anterior aspect of the middle turbinate and the posterior aspect of the vestibule by about 1 mm, about 2 mm, about 4 mm, about 6 mm, about 8 mm, about 10 mm, about 12 mm, about 14 mm, about 16 mm, about 18 mm, or about 20 mm. In some embodiments, the ejection zone is anterior to an inclined line that intersects the anterior aspect of the middle turbinate and the posterior aspect of the vestibule by at least about 1 mm, about 2 mm, about 4 mm, about 6 mm, about 8 mm, about 10 mm, about 12 mm, about 14 mm, about 16 mm, or about 18 mm. In some embodiments, the ejection zone is anterior to an inclined line that intersects the anterior aspect of the middle turbinate and the posterior aspect of the vestibule by at most about 2 mm, about 4 mm, about 6 mm, about 8 mm, about 10 mm, about 12 mm, about 14 mm, about 16 mm, about 18 mm, or about 20 mm. In some embodiments, the ejection zone is inferior to a horizontal line that is parallel to the inferior aspect of the olfactory cleft by about 1 mm to about 35 mm. In some embodiments, the ejection zone is inferior to a horizontal line that is parallel to the inferior aspect of the olfactory cleft by about 1 mm to about 2 mm, about 1 mm to about 3 mm, about 1 mm to about 4 mm, about 1 mm to about 5 mm, about 1 mm to about 12 mm, about 1 mm to about 15 mm, about 1 mm to about 18 mm, about 1 mm to about 21 mm, about 1 mm to about 25 mm, about 1 mm to about 30 mm, about 1 mm to about 35 mm, about 2 mm to about 3 mm, about 2 mm to about 4 mm, about 2 mm to about 5 mm, about 2 mm to about 12 mm, about 2 mm to about 15 mm, about 2 mm to about 18 mm, about 2 mm to about 21 mm, about 2 mm to about 25 mm, about 2 mm to about 30 mm, about 2 mm to about 35 mm, about 3 mm to about 4 mm, about 3 mm to about 5 mm, about 3 mm to about 12 mm, about 3 mm to about 15 mm, about 3 mm to about 18 mm, about 3 mm to about 21 mm, about 3 mm to about 25 mm, about 3 mm to about 30 mm, about 3 mm to about 35 mm, about 4 mm to about 5 mm, about 4 mm to about 12 mm, about 4 mm to about 15 mm, about 4 mm to about 18 mm, about 4 mm to about 21 mm, about 4 mm to about 25 mm, about 4 mm to about 30 mm, about 4 mm to about 35 mm, about 5 mm to about 12 mm, about 5 mm to about 15 mm, about 5 mm to about 18 mm, about 5 mm to about 21 mm, about 5 mm to about 25 mm, about 5 mm to about 30 mm, about 5 mm to about 35 mm, about 12 mm to about 15 mm, about 12 mm to about 18 mm, about 12 mm to about 21 mm, about 12 mm to about 25 mm, about 12 mm to about 30 mm, about 12 mm to about 35 mm, about 15 mm to about 18 mm, about 15 mm to about 21 mm, about 15 mm to about 25 mm, about 15 mm to about 30 mm, about 15 mm to about 35 mm, about 18 mm to about 21 mm, about 18 mm to about 25 mm, about 18 mm to about 30 mm, about 18 mm to about 35 mm, about 21 mm to about 25 mm, about 21 mm to about 30 mm, about 21 mm to about 35 mm, about 25 mm to about 30 mm, about 25 mm to about 35 mm, or about 30 mm to about 35 mm, including increments therein. In some embodiments, the ejection zone is inferior to a horizontal line that is parallel to the inferior aspect of the olfactory cleft by about 1 mm, about 2 mm, about 3 mm, about 4 mm, about 5 mm, about 12 mm, about 15 mm, about 18 mm, about 21 mm, about 25 mm, about 30 mm, or about 35 mm. In some embodiments, the ejection zone is inferior to a horizontal line that is parallel to the inferior aspect of the olfactory cleft by at least about 1 mm, about 2 mm, about 3 mm, about 4 mm, about 5 mm, about 12 mm, about 15 mm, about 18 mm, about 21 mm, about 25 mm, or about 30 mm. In some embodiments, the ejection zone is inferior to a horizontal line that is parallel to the inferior aspect of the olfactory cleft by at most about 2 mm, about 3 mm, about 4 mm, about 5 mm, about 12 mm, about 15 mm, about 18 mm, about 21 mm, about 25 mm, about 30 mm, or about 35 mm. In some embodiments, the ejection zone is posterior to the internal nasal dorsum by about 1 mm to about 20 mm. In some embodiments, the ejection zone is posterior to the internal nasal dorsum by about 1 mm to about 2 mm, about 1 mm to about 3 mm, about 1 mm to about 4 mm, about 1 mm to about 6 mm, about 1 mm to about 8 mm, about 1 mm to about 10 mm, about 1 mm to about 12 mm, about 1 mm to about 14 mm, about 1 mm to about 16 mm, about 1 mm to about 18 mm, about 1 mm to about 20 mm, about 2 mm to about 3 mm, about 2 mm to about 4 mm, about 2 mm to about 6 mm, about 2 mm to about 8 mm, about 2 mm to about 10 mm, about 2 mm to about 12 mm, about 2 mm to about 14 mm, about 2 mm to about 16 mm, about 2 mm to about 18 mm, about 2 mm to about 20 mm, about 3 mm to about 4 mm, about 3 mm to about 6 mm, about 3 mm to about 8 mm, about 3 mm to about 10 mm, about 3 mm to about 12 mm, about 3 mm to about 14 mm, about 3 mm to about 16 mm, about 3 mm to about 18 mm, about 3 mm to about 20 mm, about 4 mm to about 6 mm, about 4 mm to about 8 mm, about 4 mm to about 10 mm, about 4 mm to about 12 mm, about 4 mm to about 14 mm, about 4 mm to about 16 mm, about 4 mm to about 18 mm, about 4 mm to about 20 mm, about 6 mm to about 8 mm, about 6 mm to about 10 mm, about 6 mm to about 12 mm, about 6 mm to about 14 mm, about 6 mm to about 16 mm, about 6 mm to about 18 mm, about 6 mm to about 20 mm, about 8 mm to about 10 mm, about 8 mm to about 12 mm, about 8 mm to about 14 mm, about 8 mm to about 16 mm, about 8 mm to about 18 mm, about 8 mm to about 20 mm, about 10 mm to about 12 mm, about 10 mm to about 14 mm, about 10 mm to about 16 mm, about 10 mm to about 18 mm, about 10 mm to about 20 mm, about 12 mm to about 14 mm, about 12 mm to about 16 mm, about 12 mm to about 18 mm, about 12 mm to about 20 mm, about 14 mm to about 16 mm, about 14 mm to about 18 mm, about 14 mm to about 20 mm, about 16 mm to about 18 mm, about 16 mm to about 20 mm, or about 18 mm to about 20 mm, including increments therein. In some embodiments, the ejection zone is posterior to the internal nasal dorsum by about 1 mm, about 2 mm, about 3 mm, about 4 mm, about 6 mm, about 8 mm, about 10 mm, about 12 mm, about 14 mm, about 16 mm, about 18 mm, or about 20 mm. In some embodiments, the ejection zone is posterior to the internal nasal dorsum by at least about 1 mm, about 2 mm, about 3 mm, about 4 mm, about 6 mm, about 8 mm, about 10 mm, about 12 mm, about 14 mm, about 16 mm, or about 18 mm. In some embodiments, the ejection zone is posterior to the internal nasal dorsum by at most about 2 mm, about 3 mm, about 4 mm, about 6 mm, about 8 mm, about 10 mm, about 12 mm, about 14 mm, about 16 mm, about 18 mm, or about 20 mm. In some embodiments, the ejection zone is superior to a horizontal line that intersects the inferior aspect of the columella by about 10 mm to about 50 mm. In some embodiments, the ejection zone is superior to a horizontal line that intersects the inferior aspect of the columella by about 10 mm to about 12 mm, about 10 mm to about 16 mm, about 10 mm to about 20 mm, about 10 mm to about 24 mm, about 10 mm to about 28 mm, about 10 mm to about 32 mm, about 10 mm to about 36 mm, about 10 mm to about 40 mm, about 10 mm to about 45 mm, about 10 mm to about 50 mm, about 12 mm to about 16 mm, about 12 mm to about 20 mm, about 12 mm to about 24 mm, about 12 mm to about 28 mm, about 12 mm to about 32 mm, about 12 mm to about 36 mm, about 12 mm to about 40 mm, about 12 mm to about 45 mm, about 12 mm to about 50 mm, about 16 mm to about 20 mm, about 16 mm to about 24 mm, about 16 mm to about 28 mm, about 16 mm to about 32 mm, about 16 mm to about 36 mm, about 16 mm to about 40 mm, about 16 mm to about 45 mm, about 16 mm to about 50 mm, about 20 mm to about 24 mm, about 20 mm to about 28 mm, about 20 mm to about 32 mm, about 20 mm to about 36 mm, about 20 mm to about 40 mm, about 20 mm to about 45 mm, about 20 mm to about 50 mm, about 24 mm to about 28 mm, about 24 mm to about 32 mm, about 24 mm to about 36 mm, about 24 mm to about 40 mm, about 24 mm to about 45 mm, about 24 mm to about 50 mm, about 28 mm to about 32 mm, about 28 mm to about 36 mm, about 28 mm to about 40 mm, about 28 mm to about 45 mm, about 28 mm to about 50 mm, about 32 mm to about 36 mm, about 32 mm to about 40 mm, about 32 mm to about 45 mm, about 32 mm to about 50 mm, about 36 mm to about 40 mm, about 36 mm to about 45 mm, about 36 mm to about 50 mm, about 40 mm to about 45 mm, about 40 mm to about 50 mm, or about 45 mm to about 50 mm, including increments therein. In some embodiments, the ejection zone is superior to a horizontal line that intersects the inferior aspect of the columella by about 10 mm, about 12 mm, about 16 mm, about 20 mm, about 24 mm, about 28 mm, about 32 mm, about 36 mm, about 40 mm, about 45 mm, or about 50 mm. In some embodiments, the ejection zone is superior to a horizontal line that intersects the inferior aspect of the columella by at least about 10 mm, about 12 mm, about 16 mm, about 20 mm, about 24 mm, about 28 mm, about 32 mm, about 36 mm, about 40 mm, or about 45 mm. In some embodiments, the ejection zone is superior to a horizontal line that intersects the inferior aspect of the columella by at most about 12 mm, about 16 mm, about 20 mm, about 24 mm, about 28 mm, about 32 mm, about 36 mm, about 40 mm, about 45 mm, or about 50 mm. In some embodiments, the ejection zone is superior to a horizontal line that intersects the superior aspect of the inferior turbinate by about 1 mm to about 30 mm. In some embodiments, the ejection zone is superior to a horizontal line that intersects the superior aspect of the inferior turbinate by about 1 mm to about 2 mm, about 1 mm to about 4 mm, about 1 mm to about 6 mm, about 1 mm to about 8 mm, about 1 mm to about 10 mm, about 1 mm to about 12 mm, about 1 mm to about 15 mm, about 1 mm to about 18 mm, about 1 mm to about 21 mm, about 1 mm to about 25 mm, about 1 mm to about 30 mm, about 2 mm to about 4 mm, about 2 mm to about 6 mm, about 2 mm to about 8 mm, about 2 mm to about 10 mm, about 2 mm to about 12 mm, about 2 mm to about 15 mm, about 2 mm to about 18 mm, about 2 mm to about 21 mm, about 2 mm to about 25 mm, about 2 mm to about 30 mm, about 4 mm to about 6 mm, about 4 mm to about 8 mm, about 4 mm to about 10 mm, about 4 mm to about 12 mm, about 4 mm to about 15 mm, about 4 mm to about 18 mm, about 4 mm to about 21 mm, about 4 mm to about 25 mm, about 4 mm to about 30 mm, about 6 mm to about 8 mm, about 6 mm to about 10 mm, about 6 mm to about 12 mm, about 6 mm to about 15 mm, about 6 mm to about 18 mm, about 6 mm to about 21 mm, about 6 mm to about 25 mm, about 6 mm to about 30 mm, about 8 mm to about 10 mm, about 8 mm to about 12 mm, about 8 mm to about 15 mm, about 8 mm to about 18 mm, about 8 mm to about 21 mm, about 8 mm to about 25 mm, about 8 mm to about 30 mm, about 10 mm to about 12 mm, about 10 mm to about 15 mm, about 10 mm to about 18 mm, about 10 mm to about 21 mm, about 10 mm to about 25 mm, about 10 mm to about 30 mm, about 12 mm to about 15 mm, about 12 mm to about 18 mm, about 12 mm to about 21 mm, about 12 mm to about 25 mm, about 12 mm to about 30 mm, about 15 mm to about 18 mm, about 15 mm to about 21 mm, about 15 mm to about 25 mm, about 15 mm to about 30 mm, about 18 mm to about 21 mm, about 18 mm to about 25 mm, about 18 mm to about 30 mm, about 21 mm to about 25 mm, about 21 mm to about 30 mm, or about 25 mm to about 30 mm, including increments therein. In some embodiments, the ejection zone is superior to a horizontal line that intersects the superior aspect of the inferior turbinate by about 1 mm, about 2 mm, about 4 mm, about 6 mm, about 8 mm, about 10 mm, about 12 mm, about 15 mm, about 18 mm, about 21 mm, about 25 mm, or about 30 mm. In some embodiments, the ejection zone is superior to a horizontal line that intersects the superior aspect of the inferior turbinate by at least about 1 mm, about 2 mm, about 4 mm, about 6 mm, about 8 mm, about 10 mm, about 12 mm, about 15 mm, about 18 mm, about 21 mm, or about 25 mm. In some embodiments, the ejection zone is superior to a horizontal line that intersects the superior aspect of the inferior turbinate by at most about 2 mm, about 4 mm, about 6 mm, about 8 mm, about 10 mm, about 12 mm, about 15 mm, about 18 mm, about 21 mm, about 25 mm, or about 30 mm. In some embodiments, the ejection zone is away from the septum by about 0.1 mm to about 3 mm. In some embodiments, the ejection zone is away from the septum by about 0.1 mm to about 0.2 mm, about 0.1 mm to about 0.4 mm, about 0.1 mm to about 0.6 mm, about 0.1 mm to about 0.8 mm, about 0.1 mm to about 1 mm, about 0.1 mm to about 1.25 mm, about 0.1 mm to about 1.5 mm, about 0.1 mm to about 1.75 mm, about 0.1 mm to about 2 mm, about 0.1 mm to about 2.5 mm, about 0.1 mm to about 3 mm, about 0.2 mm to about 0.4 mm, about 0.2 mm to about 0.6 mm, about 0.2 mm to about 0.8 mm, about 0.2 mm to about 1 mm, about 0.2 mm to about 1.25 mm, about 0.2 mm to about 1.5 mm, about 0.2 mm to about 1.75 mm, about 0.2 mm to about 2 mm, about 0.2 mm to about 2.5 mm, about 0.2 mm to about 3 mm, about 0.4 mm to about 0.6 mm, about 0.4 mm to about 0.8 mm, about 0.4 mm to about 1 mm, about 0.4 mm to about 1.25 mm, about 0.4 mm to about 1.5 mm, about 0.4 mm to about 1.75 mm, about 0.4 mm to about 2 mm, about 0.4 mm to about 2.5 mm, about 0.4 mm to about 3 mm, about 0.6 mm to about 0.8 mm, about 0.6 mm to about 1 mm, about 0.6 mm to about 1.25 mm, about 0.6 mm to about 1.5 mm, about 0.6 mm to about 1.75 mm, about 0.6 mm to about 2 mm, about 0.6 mm to about 2.5 mm, about 0.6 mm to about 3 mm, about 0.8 mm to about 1 mm, about 0.8 mm to about 1.25 mm, about 0.8 mm to about 1.5 mm, about 0.8 mm to about 1.75 mm, about 0.8 mm to about 2 mm, about 0.8 mm to about 2.5 mm, about 0.8 mm to about 3 mm, about 1 mm to about 1.25 mm, about 1 mm to about 1.5 mm, about 1 mm to about 1.75 mm, about 1 mm to about 2 mm, about 1 mm to about 2.5 mm, about 1 mm to about 3 mm, about 1.25 mm to about 1.5 mm, about 1.25 mm to about 1.75 mm, about 1.25 mm to about 2 mm, about 1.25 mm to about 2.5 mm, about 1.25 mm to about 3 mm, about 1.5 mm to about 1.75 mm, about 1.5 mm to about 2 mm, about 1.5 mm to about 2.5 mm, about 1.5 mm to about 3 mm, about 1.75 mm to about 2 mm, about 1.75 mm to about 2.5 mm, about 1.75 mm to about 3 mm, about 2 mm to about 2.5 mm, about 2 mm to about 3 mm, or about 2.5 mm to about 3 mm, including increments therein. In some embodiments, the ejection zone is away from the septum by about 0.1 mm, about 0.2 mm, about 0.4 mm, about 0.6 mm, about 0.8 mm, about 1 mm, about 1.25 mm, about 1.5 mm, about 1.75 mm, about 2 mm, about 2.5 mm, or about 3 mm. In some embodiments, the ejection zone is away from the septum by at least about 0.1 mm, about 0.2 mm, about 0.4 mm, about 0.6 mm, about 0.8 mm, about 1 mm, about 1.25 mm, 1.5 mm, about 1.75 mm, about 2 mm, or about 2.5 mm. In some embodiments, the ejection zone is away from the septum by at most about 0.2 mm, about 0.4 mm, about 0.6 mm, about 0.8 mm, about 1 mm, about 1.25 mm, about 1.5 mm, about 1.75 mm, about 2 mm, about 2.5 mm, or about 3 mm.

Definitions

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Reference in the specification to "some embodiments," "an embodiment," "one embodiment" or "other embodiments" means that a feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" as used herein when referring to a measurable value such as a parameter, an amount, a temporal duration, and the like, is meant to encompass variations of +/−10% or less from the specified value, insofar such variations are appropriate to perform in the present disclosure. It is to be understood that the value to which the modifier "about" or "approximately" refers is itself also specifically disclosed.

The "columella" is the firm tissue bridge that separates the nostrils at the base of the nose. The "columella" is the most anteroinferior portion of the nasal septum. The term "columella" or "columella region" is the subnasale, or an anterior nasale spine, or a combination thereof. The columella region may comprise a subnasale, or a combination thereof. The columella shape may be defined by an anterior nasal spine located posteriorly to the columella e.g., 1 cm.

The term "composition" or "compound" or "therapeutic" or "sampling compound" or "sampling fluid" is therapeutics, medicaments, drugs, small and large molecules, medicaments in liquid, powder, or gas form, or a combination thereof having a low, intermediate, or high viscosity.

The "introduction pathway" is, in sequence, the vestibule, the anterior aspect of the internal nasal valve, and the anterior aspect of the respiratory region—anterior of the turbinates.

The "internal nasal valve" (INV) is a space bounded medially by the dorsal septum 24 (or just septum), laterally by the caudal portion of the upper lateral cartilage, and inferiorly by the head of the inferior turbinate.

The term "nasal cavity" includes two nasal channels, each comprises each comprised of a vestibule, respiratory region and olfactory cleft, and a nasopharynx.

The term "trigger" refers to the part of the device that actuates the ejection mechanism, which in turn (through a variety of possible mechanism designs), delivers a compound from the device.

The term "turbinates" refers to superior turbinate, middle turbinate, or inferior turbinate, or a combination thereof.

Nasal Cavity: This is the large, air-filled space behind the nose, where air passes on its way to the throat during inhalation.

Internal Nasal Valve: This is the narrowest part of the nasal airway, located just beyond the nostril. It's formed by the edge of the nasal septum, the upper lateral cartilage, and the floor of the nose. The internal nasal valve plays a critical role in regulating airflow through the nose. The area of interest is superior (above) to this structure.

Nasal Septum: This is the thin wall of bone and cartilage that separates the right and left nostrils. It forms the medial (towards the middle) boundary of the region of interest.

Lateral Nasal Wall: This is the side wall of the nasal cavity, which is opposite to the nasal septum. It's a complex structure that includes the turbinates (long, curled bones that protrude into the nasal cavity) and the meatuses (grooves or channels between the turbinates). The lateral nasal wall forms the lateral (towards the side) boundary of the region of interest.

Middle and Superior Meatuses: These are the spaces within the nasal cavity located between the turbinates. The middle meatus is located beneath the middle turbinate and above the inferior turbinate, and the superior meatus is located beneath the superior turbinate. The region of interest encompasses parts of these spaces.

Nostrils (External Nares): These are the two openings of the nose where air enters.

Nasal Vestibule: The nasal vestibule is the most anterior part of the nasal cavity, just inside the nostrils. It's the area of the nose that protrudes outside the face predominantly. This area is lined with skin and contains hair follicles, and it acts as the initial filtering and warming area for inhaled air before it moves deeper into the nasal cavity. The nasal vestibule extends posteriorly to the nasal valve, which is the narrowest part of the nasal airway and located just beyond the nostril.

Nasal Septum: This is a thin wall made of bone and cartilage that separates the left and right sides of the nasal cavity.

Turbinates (Nasal Conchae): These are three pairs of bony projections (inferior, middle, and superior) covered in mucous membrane that protrude into the nasal cavity from the lateral walls. They increase the surface area of the nasal cavity, aiding in the warming, humidification, and filtration of inhaled air.

Meatuses: These are the spaces located between the turbinates. Each turbinate has a corresponding meatus underneath it (i.e., inferior, middle, and superior meatus).

Olfactory Region: This is a small area located at the top of the nasal cavity, where the sense of smell is located.

EXAMPLES

The following illustrative examples are representative of embodiments, of the compositions and methods described herein and are not meant to be limiting in any way.

Example 1: Ejection from the Nasal Vestibule or from Below the Internal Nasal Valve (INV)

FIGS. 12A-12I depicts the exemplary nasal cavity of a subject during pre-ejection, ejection and post-ejection of a composition with the exemplary device from various positions and angles at the nasal vestibule or below the internal nasal valve.

The tests performed utilized a tunable jug with low-speed device, 3D printed nasal cavity model, syringe with 200 µL and 1 cP viscosity, dispensing element (cannula), magnetic support structure for nasal cavity model, magnetic base for support structure, high-speed camera and flashlight.

Two different sets of experiments were performed for the internal nasal valve including vestibule ejections with varying front angles (meaning sagittal-lateral or side-to-side looking at the nose head on) and Vestibule ejections with varying side angles (meaning anterior-posterior or front-to-back looking at the nose from the side).

The fluid was ejected from the dispensing element at two different velocities of 1.5 m/s and 2 m/s with a 1 cP fluid. The tunable rig was set up to eject fluid at 1.5 m/s. The syringe (with 200 ul) and cannula were mounted on the tunable rig. A reference line was drawn to define as a center positioning point for the cannula in the middle of the Vestibule.

For Vestibule ejections with varying front angles, the tip of the cannula was positioned in the middle of the Vestibule (aiming past the notch/nasal valve) so that fluid doesn't get deflected by it. All the angles were approximated using a protractor vertically from the side face (side to side) of the model. Different ejections were done at sagittal-lateral angles (−10, 0, 10, 15 degrees) and all the ejections were recorded using a high speed camera.

For Vestibule ejections with anterior-posterior angles, different ejections were done with varying side angles (anterior-posterior) (0, 10, 20 angles) and all the ejections were recorded using a high speed camera. All the angles were approximated using a protractor with respect to the reference line. The same procedures were repeated with the fluid ejected at 2 m/s (1 cP) using a tunable jig low speed device from above and the results were recorded.

Figure 12A:
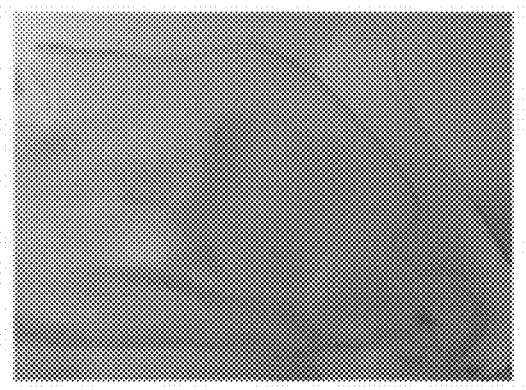
FIGS. 12A-12C, show images of an exemplary nasal cavity of a subject during pre-ejection (top), during ejection (middle) and post-ejection (bottom) of a composition with the exemplary device from a position where the dispensing element is straight in position with a front side of the nasal cavity, and illustrates that dispensing a composition from outside the ejection zone in this position prevents deposition of the composition to a target region.
Figure 12B:
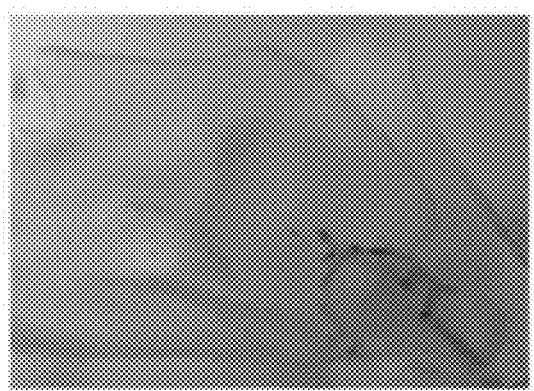
Figure 12C:
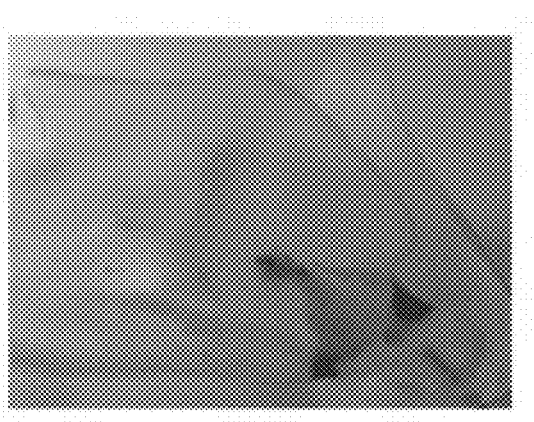

FIGS. 12A-12C, show images of an exemplary nasal cavity of a subject during pre-ejection (top), during ejection (middle) and post-ejection (bottom) of a composition with the exemplary device from a position where the dispensing element is straight in position with a front side of the nasal cavity. The dispensing element comprises a composition volume of 200 µL and 1 cP viscosity. The composition is ejected from the dispensing element at a velocity of 2 m/s (1 cP). This test shows the failure of a device to administer the composition to the olfactory cleft due to blockage by the internal nasal valve.

Figure 12D:
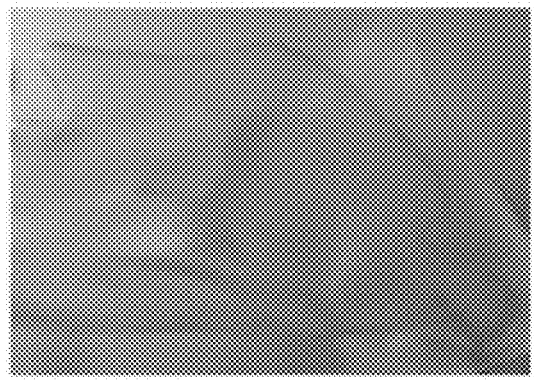
FIGS. 12D-12F, show images of an exemplary nasal cavity of a subject during pre-ejection (top), during ejection (middle) and post-ejection (bottom) of a composition with the exemplary device from a position where the dispensing element approximately at a 20 degree angle with respect to the front side of the nasal cavity, and illustrates that dispensing a composition from outside the ejection zone in this position prevents deposition of the composition to a target region.
Figure 12E:
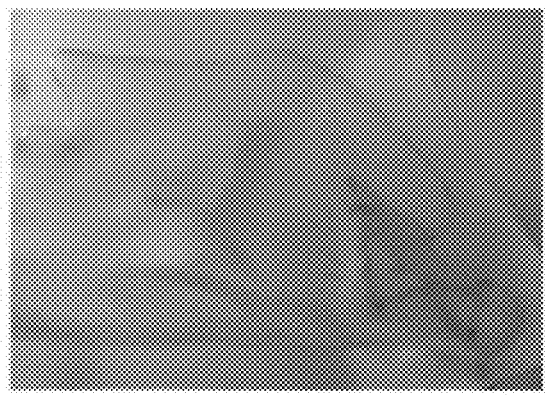
Figure 12F:
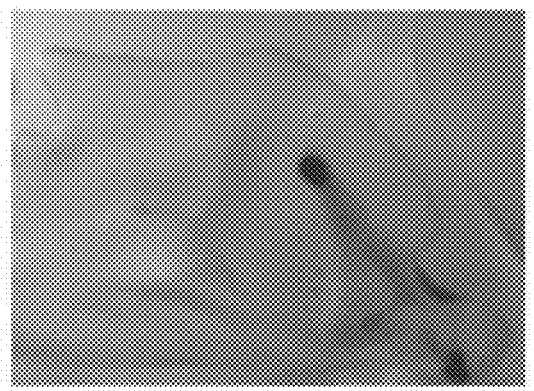

FIGS. 12D-12F, show images of an exemplary nasal cavity of a subject during pre-ejection (top), during ejection (middle) and post-ejection (bottom) of a composition with the exemplary device from a position where the dispensing element approximately at a 20 degree angle with respect to the front side of the nasal cavity. The dispensing element comprises a composition volume of 200 µL and 1 cP viscosity. The composition is ejected from the dispensing element at a velocity of 2 m/s (1 cP). This test shows the failure of a device to administer the composition to the olfactory cleft due to blockage by the internal nasal valve.

FIGS. 14A-14C, show images of an exemplary nasal cavity of a subject during pre-ejection (left), during ejection (middle) and post-ejection (right) of a composition with the exemplary device from varying front angles from a position of a −10 degree angle towards the center of the nasal cavity, and illustrates that dispensing a composition from this position prevents deposition of the composition to a target region. The dispensing element comprises a composition volume of 200 μL and 1 cP viscosity. The composition is ejected from the dispensing element at a velocity of 2 m/s (1 cP). This test shows the failure of a device to administer the composition to the olfactory cleft due to blockage by the internal nasal valve.

FIGS. 14D-14F, show images of an exemplary nasal cavity of a subject during pre-ejection (left), during ejection (middle) and post-ejection (right) of a composition with the exemplary device from varying front angles from a position where the angle is 0 degrees from the center of the nasal cavity, and illustrates that dispensing a composition from this position prevents deposition of the composition to a target region. The dispensing element comprises a composition volume of 200 μL and 1 cP viscosity. The composition is ejected from the dispensing element at a velocity of 2 m/s (1 cP). This test shows the failure of a device to administer the composition to the olfactory cleft due to blockage by the internal nasal valve.

FIGS. 14G-14I, show images of an exemplary nasal cavity of a subject during pre-ejection (left), during ejection (middle) and post-ejection (right) of a composition with the exemplary device from varying front angles from a position where the angle is increased 15 degrees from the center of the nasal cavity, and illustrates that dispensing a composition from this position prevents deposition of the composition to a target region. The dispensing element comprises a composition volume of 200 μL and 1 cP viscosity. The composition is ejected from the dispensing element at a velocity of 2 m/s (1 cP). This test shows the failure of a device to administer the composition to the olfactory cleft due to partial blockage by the internal nasal valve, and overshot of the remaining composition.

FIGS. 14J-14L, show images of an exemplary nasal cavity of a subject during pre-ejection (left), during ejection (middle) and post-ejection (right) of a composition with the exemplary device from varying front angles from a position where the angle is increased 30 degrees from the center of the nasal cavity, and illustrates that dispensing a composition from this position permits for deposition of the composition to a target region. The dispensing element comprises a composition volume of 200 μL and 1 cP viscosity. The composition is ejected from the dispensing element at a velocity of 2 m/s (1 cP). This test shows the failure of a device to administer the composition to the olfactory cleft due to almost complete blockage by the internal nasal valve, and only partial disposition of the remaining composition.

Figure 15:
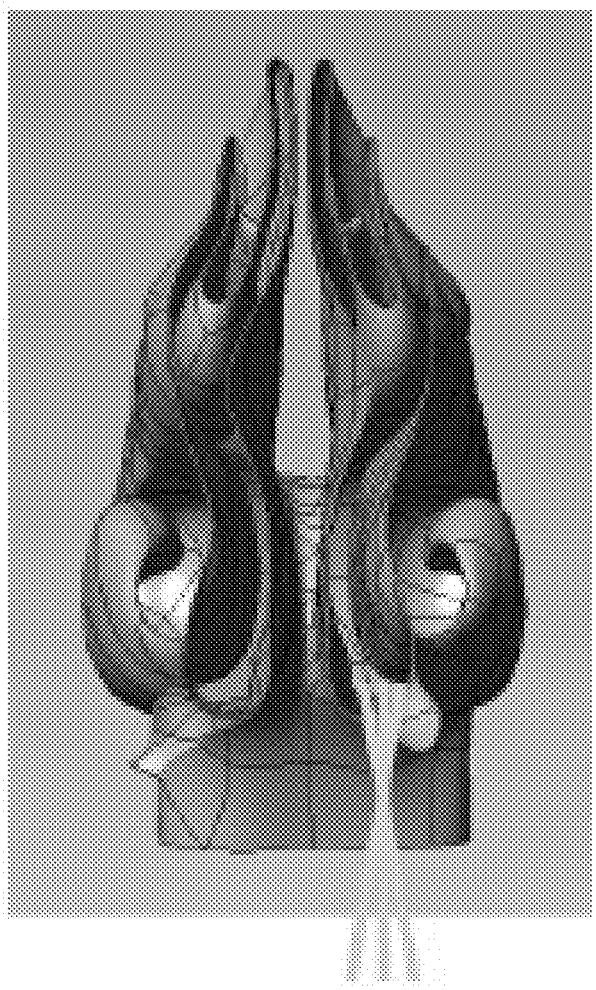
FIG. 15 illustrates the anatomy of the nasal vestibules from a front view, with the varying ejection angles show in FIGS. 16A-16I.

FIG. 15 illustrates the anatomy of the nasal vestibules from a front view, with the varying ejection angles shown in FIGS. 16A-16I.

Figure 16A:
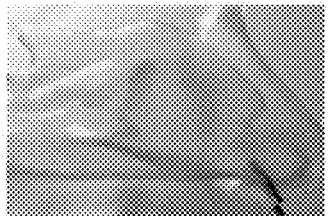
FIGS. 16A-16C, show images of an exemplary nasal cavity of a subject during pre-ejection (left), during ejection (middle) and post-ejection (right) of a composition with the exemplary device from varying side angles from a position where the angle is at 0 degree relative to the reference line, and illustrates that dispensing a composition from this position prevents deposition of the composition to a target region.
Figure 16B:
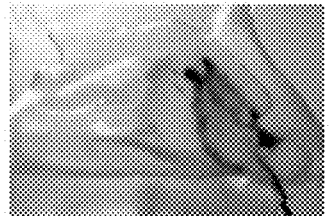
Figure 16C:
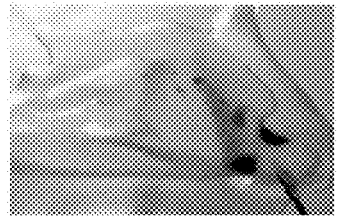

FIGS. 16A-16C, show images of an exemplary nasal cavity of a subject during pre-ejection (left), during ejection (middle) and post-ejection (right) of a composition with the exemplary device from varying side angles from a position where the angle is at 0 degree relative to the reference line, and illustrates that dispensing a composition from this position prevents deposition of the composition to a target region. The dispensing element comprises a composition volume of 200 μL and 1 cP viscosity. The composition is ejected from the dispensing element at a velocity of 2 m/s (1 cP). This test shows the failure of a device to administer the composition to the olfactory cleft due to blockage by the internal nasal valve, and deposition of the remaining composition in the middle turbinate.

Figure 16D:
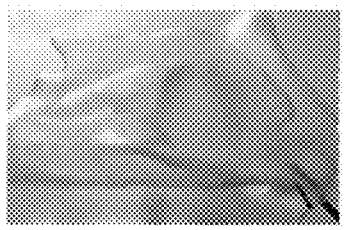
FIGS. 16D-16F, show images of an exemplary nasal cavity of a subject during pre-ejection (left), during ejection (middle) and post-ejection (right) of a composition with the exemplary device from varying side angles from a position where the angle is at 10 degree relative to the reference line, and illustrates that dispensing a composition from this position permits for partial deposition of the composition to a target region.
Figure 16E:
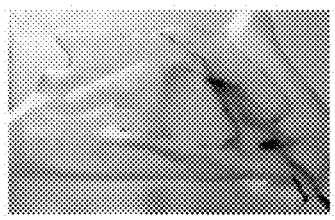
Figure 16F:
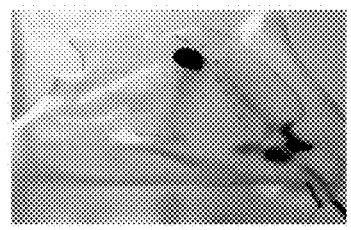

FIGS. 16D-16F, show images of an exemplary nasal cavity of a subject during pre-ejection (left), during ejection (middle) and post-ejection (right) of a composition with the exemplary device from varying side angles from a position where the angle is at 10 degree relative to the reference line, and illustrates that dispensing a composition from this position permits deposition of the composition to a target region. The dispensing element comprises a composition volume of 200 μL and 1 cP viscosity. The composition is ejected from the dispensing element at a velocity of 2 m/s (1 cP). This test shows the failure of a device to administer the composition to the olfactory cleft due to almost complete blockage by the internal nasal valve, and only partial deposition of the remaining composition.

Figure 16G:
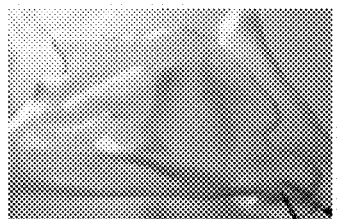
FIGS. 16G-16I, show images of an exemplary nasal cavity of a subject during pre-ejection (left), during ejection (middle) and post-ejection (right) of a composition with the exemplary device from varying side angles from a position where the angle is at 20 degree relative to the reference line, and illustrates that dispensing a composition from this position prevents deposition of the composition to a target region.
Figure 16H:
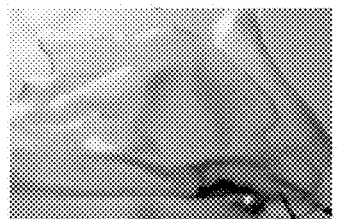
Figure 16I:
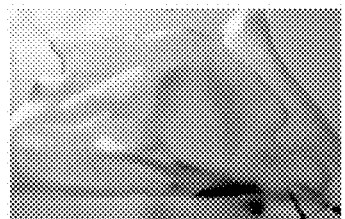

FIGS. 16G-16I, show images of an exemplary nasal cavity of a subject during pre-ejection (left), during ejection (middle) and post-ejection (right) of a composition with the exemplary device from varying side angles from a position where the angle is at 20 degree relative to the reference line, and illustrates that dispensing a composition from this position prevents deposition of the composition to a target region. The dispensing element comprises a composition volume of 200 μL and 1 cP viscosity. The composition is ejected from the dispensing element at a velocity of 2 m/s (1 cP). This test shows the failure of a device to administer the composition to the olfactory cleft due to blockage by the internal nasal valve, and deposition of the remaining composition in the middle turbinate.

Vestibule ejections with varying front angles (meaning sagittal-lateral or side-to-side looking at the nose head on) results in of the three, two are outright olfactory cleft deposition failures and one is a partial olfactory cleft deposition failure. The described data shows failure of hitting the olfactory cleft (or hitting any specific sub region of the nasal cavity) because of the presence of these two regions in the nasal anatomy.

Vestibule ejections with varying side angles (meaning anterior-posterior or front-to-back looking at the nose from the side). Of the three, two are outright OC deposition failures and one is a partial OC deposition failure.

Example 2: Ejection from the Middle Turbinate

FIGS. 13A-13I show images of an exemplary nasal cavity of a subject during pre-ejection, ejection and post-ejection of a composition with the exemplary device from various positions and angles at the middle turbinate.

The tests performed utilized a tunable jug with low-speed device, 3D printed nasal cavity model, syringe with 200 μL and 1 cP viscosity, dispensing element (cannula), magnetic support structure for nasal cavity model, magnetic base for support structure, high-speed camera and flashlight.

The fluid was ejected from the dispensing element at a velocity of 1.5 m/s (1 cP). The tunable jig was set up to eject and deliver fluid at 1.5 m/s into the middle turbinate of the nasal cavity model. The 3D printed nasal cavity model was mounted on the magnetic support structure and attached to the magnetic base. The syringe was loaded with 200 ul of the 1 cP fluid. The cannula and syringe were mounted to the tunable jig to achieve desired velocity. Each ejection was recorded using the high-speed camera. The cannula was inserted into the nasal cavity model at a depth of 37.5 mm from the columella point and positioned to aim at the front side of the middle turbinate in the nasal cavity model. It was observed that the ejected fluid enters the middle turbinate region and flows down. The angle of the cannula was changed to roughly 5 degrees posterior to the back side of the middle turbinate, then the fluid was eject again using the same parameters. It was observed that the ejected fluid splits when it hits the center bottom of the middle turbinate, where half of it goes up to the olfactory region and the other half goes inside the middle turbinate. The ejection test was repeated with the cannula angle changed roughly 5 degrees again. It was observed that the fluid lands at the back of the olfactory region.

Figure 13A:
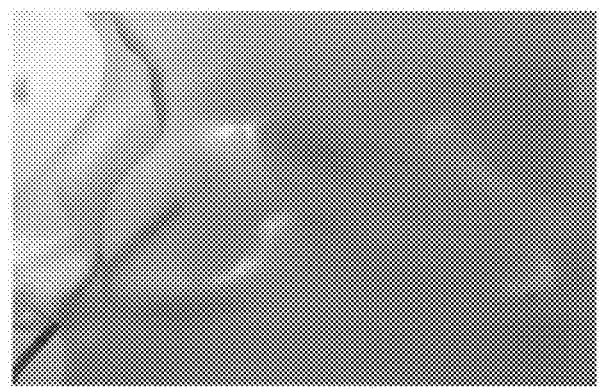
FIGS. 13A-13C, show images of an exemplary nasal cavity of a subject during pre-ejection (top), during ejection (middle) and post-ejection (bottom) of a composition with the exemplary device from a position where the ejected fluid is aimed at the front part of the middle turbinate, and illustrates that dispensing a composition from outside the ejection zone in this position prevents deposition of the composition to a target region.
Figure 13B:
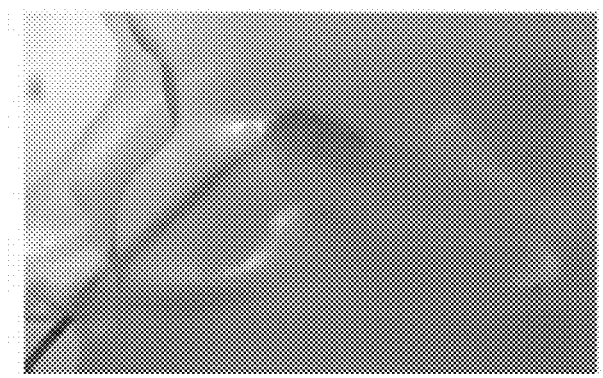
Figure 13C:
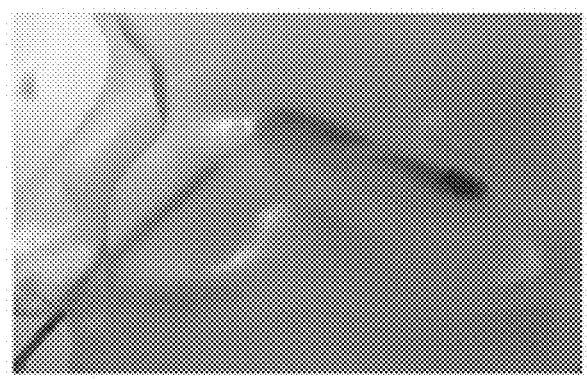

FIGS. 13A-13C, show images of an exemplary nasal cavity of a subject during pre-ejection (top), during ejection (middle) and post-ejection (bottom) of a composition with the exemplary device from a position where the ejected fluid is aimed at the front part of the middle turbinate. The images show that no deposit of the composition was made in the olfactory cleft.

Figure 13D:
FIGS. 13D-13F, show images of an exemplary nasal cavity of a subject during pre-ejection (top), during ejection (middle) and post-ejection (bottom) of a composition with the exemplary device from a position where the angle is increased 10 degrees towards the posterior side, and illustrates that dispensing a composition from this position prevents deposition of the composition to a target region.
Figure 13E:
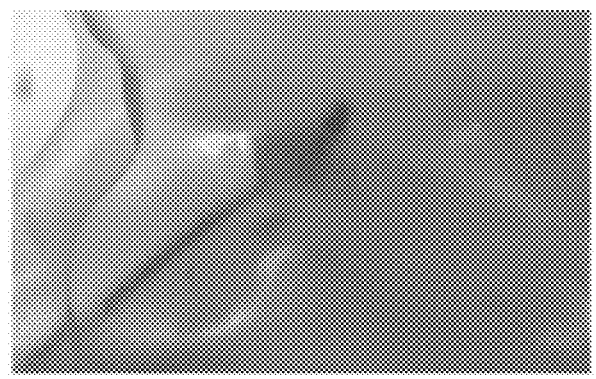
Figure 13F:
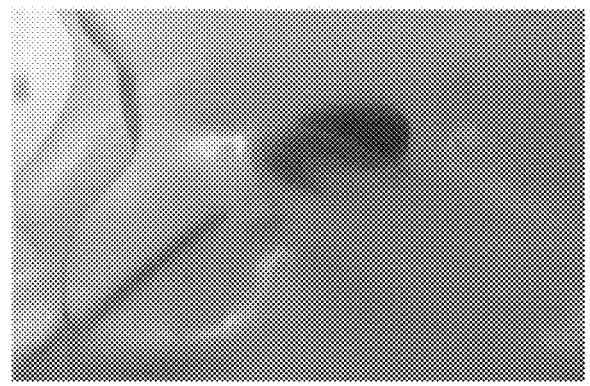

FIGS. 13D-13F, show images of an exemplary nasal cavity of a subject during pre-ejection (top), during ejection (middle) and post-ejection (bottom) of a composition with the exemplary device from a position where the angle is increased 10 degrees towards the posterior side. The dispensing element comprises a composition volume of 200 µL and 1 cP viscosity. The composition is ejected from the dispensing element at a velocity of 2 m/s (1 cP). The images show that about one half of the composition was deposited in the olfactory cleft, however, in the olfactory cleft's lower aspect (not against the cribriform plate).

Figure 13G:
FIGS. 13G-13I, show images of an exemplary nasal cavity of a subject during pre-ejection (top), during ejection (middle) and post-ejection (bottom) of a composition with the exemplary device from a position where the angle is increased 20 degrees towards the posterior side, and illustrates that dispensing a composition from outside the ejection zone in this position prevents deposition of the composition to a target region.
Figure 13H:
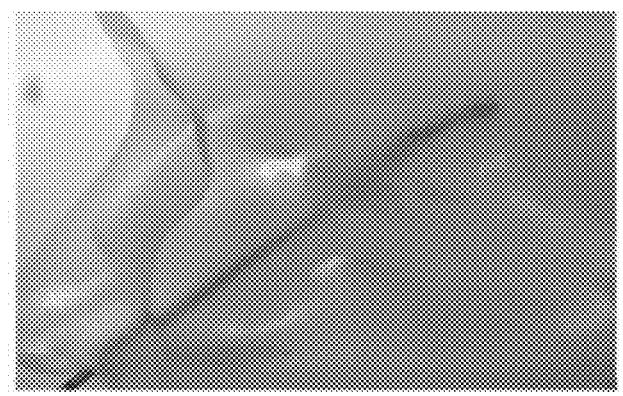
Figure 13I:
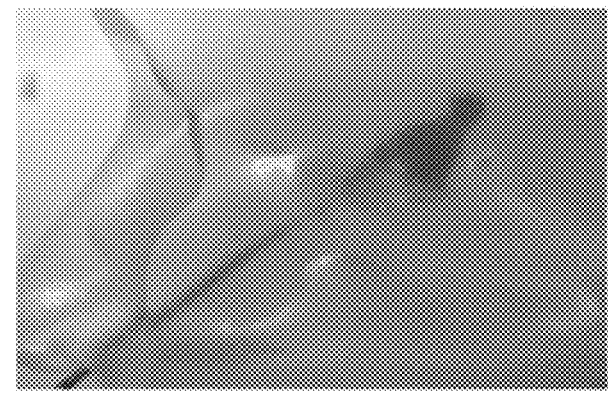

FIGS. 13G-13I, show images of an exemplary nasal cavity of a subject during pre-ejection (top), during ejection (middle) and post-ejection (bottom) of a composition with the exemplary device from a position where the angle is increased 20 degrees towards the posterior side. The dispensing element comprises a composition volume of 200 µL and 1 cP viscosity. The composition is ejected from the dispensing element at a velocity of 2 m/s (1 cP). The images show that most of the composition was deposited in the olfactory cleft, however, mostly in the back of the olfactory cleft and only a small portion against the cribriform plate.

By going from anterior to posterior angles, FIGS. 13A-13C illustrate that the fluid did not deposit in the olfactory cleft, FIGS. 13D-13F illustrate that about half the fluid deposited in the olfactory cleft, but in its lower aspect (not against the cribriform plate), and FIGS. 13G-13I illustrate that most of the fluid deposited in the in the olfactory cleft, but only in the back of the olfactory cleft and only a small portion against the cribriform plate.

Example 3: Device Position with Respect to Target Patient Anatomy

Figure 9B:
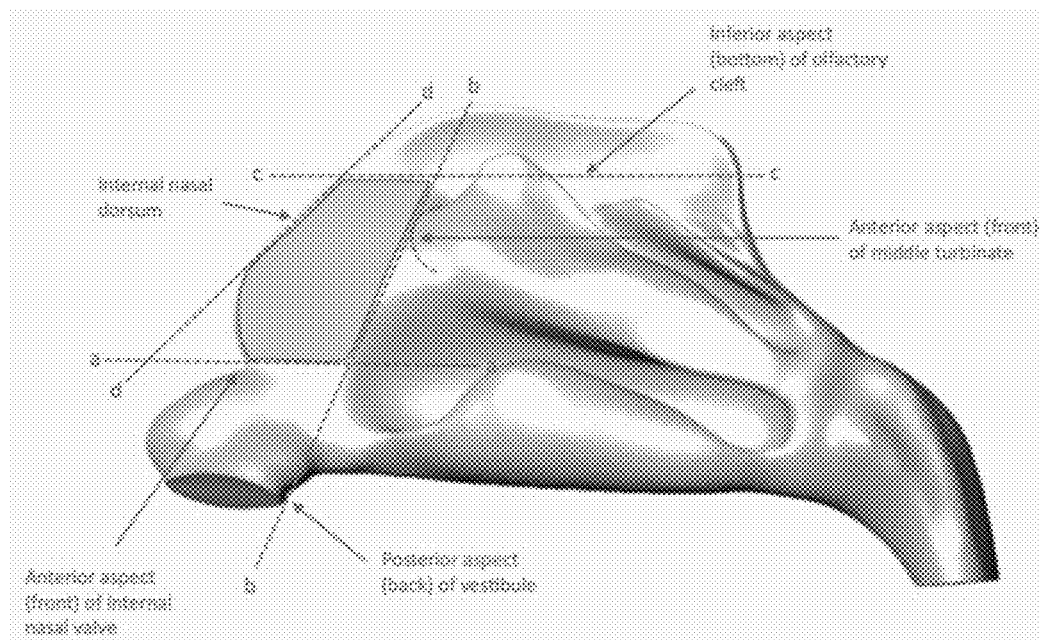
FIG. 9B depicts a side view of a ejection zone with respect to other nasal cavity anatomy, according to some embodiments.

In some embodiments, the position where the distal tip of exemplary devices disclosed herein is designed to be within the nasal vestibule, and any placement of ejection port on the device including extendable ports such as a cannula, is described below relative to patient anatomy, FIG. 9B depicts a side view of a target ejection zone with respect to other nasal cavity anatomy, In some embodiments, the nasal anatomy outlined herein creates a boundary region plane for the target ejection zone. In some embodiments, the device tips may be present in all or a portion of the boundary regions.

In some embodiments, the superior boundary of exemplary devices disclosed herein is designed to be within the nasal vestibule and is bounded by the inferior aspect of the olfactory cleft, as depicted in plane c-c. In some embodiments, the superior boundary and depth guide is achieved by utilizing the structures of the columella as a datum or hard stop coming in contact with the columella saddle and choosing a specific length of the device tip relative to anthropometric variables.

In some embodiments, the inferior boundary of exemplary devices disclosed herein is designed to be positioned within the nasal vestibule, either intra-internal nasal valve (within), or supra-internal nasal valve (above the level of the internal nasal valve), as depicted in plane a-a. In some embodiments, the inferior boundary and depth guide is achieved by utilizing the structures of the columella as a datum or hard stop, and choosing specific lengths of the device tip relative to anthropometric variables.

In some embodiments, the anterior boundary of exemplary devices disclosed herein is designed to be positioned within the nasal vestibule, and is bounded by the internal dorsum of the nasal cavity, as depicted in place d-d. In some embodiments, the anterior boundary is achieved by utilizing the ridge/trough-like structures of the internal dorsum as a hard stop and trajectory guide and having a corresponding edge design on the device tips that follow and is bounded by this anatomy. In some embodiments, the edge design on the device tips that follows and is bounded by the internal dorsum may be used as a known offset for positioning ejection ports.

In some embodiments, the medial boundary of exemplary devices disclosed herein is designed to be positioned within the nasal vestibule, lateral of the nasal septum, and is bounded by the thin wall of bone, cartilage, and mucosa that separates the right and left nostrils. In some embodiments, the medial boundary forms the medial (towards the middle) boundary of the region of interest. In some embodiments, the medial boundary is achieved by utilizing the structures of the septum as a hard stop and trajectory guide and has a corresponding internal face design on the device tips that follows and is bounded by this anatomy.

In some embodiments, the lateral boundary of exemplary devices disclosed herein is designed to be positioned within the nasal vestibule, medial of the soft tissue of the lateral internal nasal wall. In some embodiments, the lateral boundary is achieved by utilizing the structures of the lateral internal nasal wall as a hard stop and trajectory guide and has a corresponding external face design on the device tips that follows and is bounded by this anatomy.

In some embodiments, the angular position of exemplary devices disclosed herein is achieved by utilizing the corresponding edge design on the device tips as a trajectory guide that follows and is bounded by the internal nasal dorsum, as described in the anterior boundary, In some embodiments, the angular position may also be aided by the inferior, posterior, medial, and lateral boundaries and the corresponding design features of the device tips as described above.

Example 4: Device Position with Respect to Patient Nasal Anatomy

The devices, systems and methods disclosed herein are advantageous over currently available intranasal delivery devices, in that the disclosed devices are well-matched for placement with respect to the internal nasal valve.

In some embodiments, the exemplary devices disclosed herein are located intra-internal nasal valve (within), or supra-internal nasal valve (above the level of the internal nasal valve).

In some embodiments, the internal nasal valve is located approximately 10 mm-15 mm from the nostril opening, depending on individual variations. In some embodiments, the inferior (lower) aspect of the nasal valve, which is closer to the nostril, is towards the lower end of this range. In some embodiments, the superior (upper) aspect of the internal nasal valve is on average 2 cm-2.5 cm from the nostril opening.

The devices, systems and methods disclosed herein are advantageous over currently available intranasal delivery devices, in that the disclosed devices are well-matched for placement with respect to the nostril opening.

In some embodiments, the exemplary devices disclosed herein are located more than 10 mm-15 mm from the nostril opening.

In some embodiments, the exemplary devices disclosed herein comprise an area of 10-15 mm located intra-internal nasal valve (within).

In some embodiments, the exemplary devices disclosed herein are designed to be within or above the nasal valve. This is a key anthropometric and use-case delta.

The devices, systems and methods disclosed herein are advantageous over currently available intranasal delivery devices, in that the disclosed devices comprise a vantage point well-matched for ejection in the patient nasal anatomy. In some embodiments, the device comprises an increased composition to target delivery due to the vantage point being within or above the internal nasal valve.

The devices, systems and methods disclosed herein are advantageous over currently available intranasal delivery devices, in that the disclosed devices comprise an ejection trajectory well-matched for patient nasal anatomy, wherein the device bypasses anatomical obstructions some embodiments, exemplary devices disclosed herein are located intra-internal nasal valve (within), or supra-internal nasal valve (above the level of the internal nasal valve). In some embodiments, the device positioning allows for an increased ejection trajectory. In some embodiments, the device positioning allows for a superior/anterior tendency. In some embodiments, the device positioning also allows for a direct anterior to an inferior/anterior formulation delivery—over stepping anatomical obstructions experienced by other devices.

Example 5: Ejection from the Described Ejection Zone

Figure 17A:
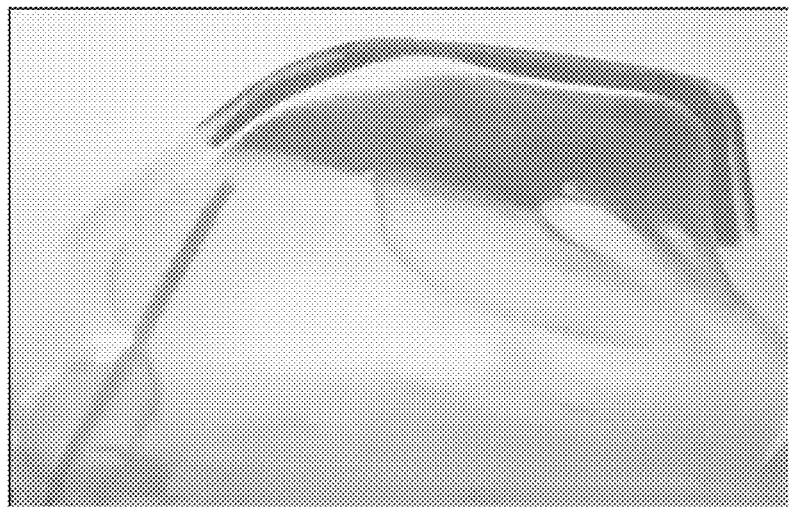
FIGS. 17A-17C, show images of a transparent model nasal cavity with a colored solution demonstrating delivery to an olfactory region of the model.
Figure 17B:
Figure 17C:
Figure 18A:
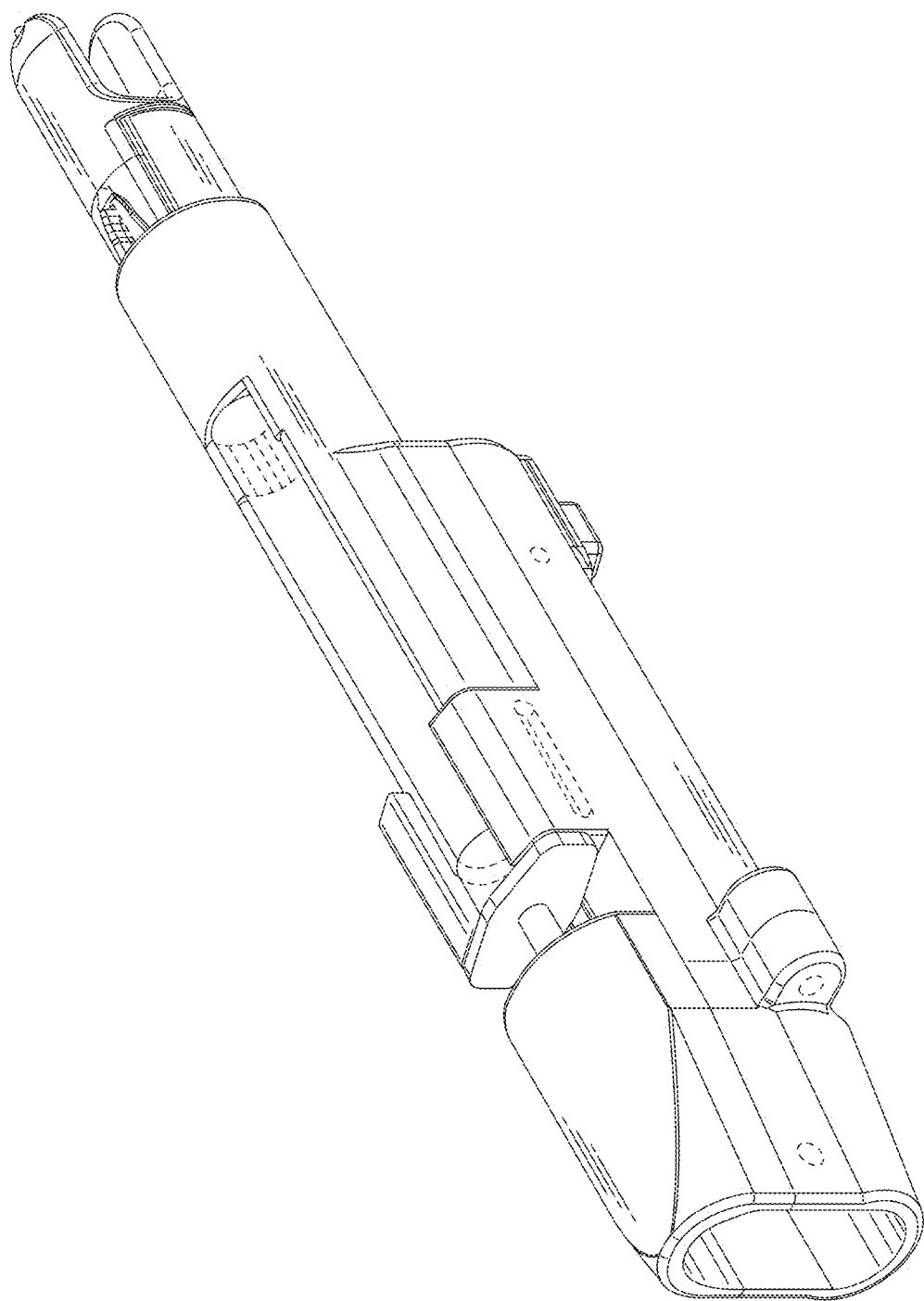
FIG. 18A shows a front, right perspective view of an intranasal delivery device.
Figure 18B:
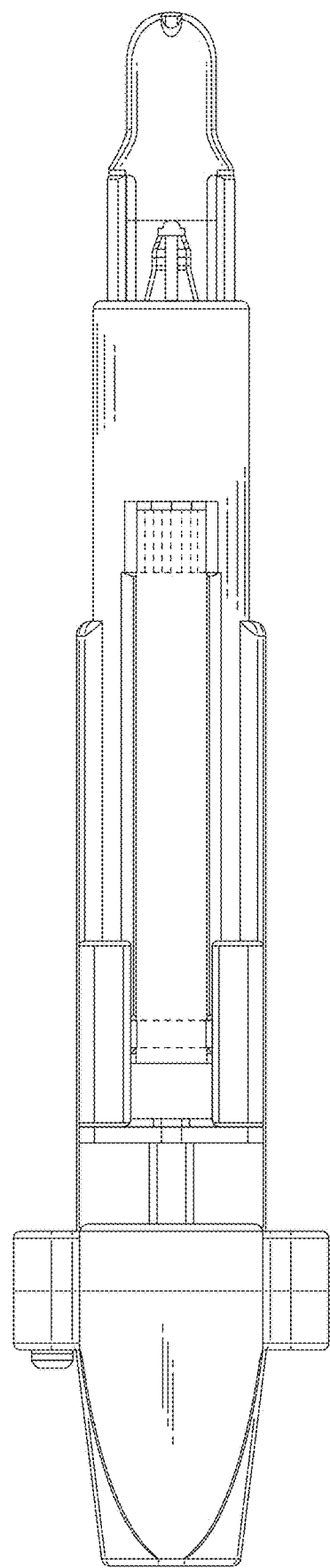
FIG. 18B shows a top plan view of an intranasal delivery device.
Figure 18C:
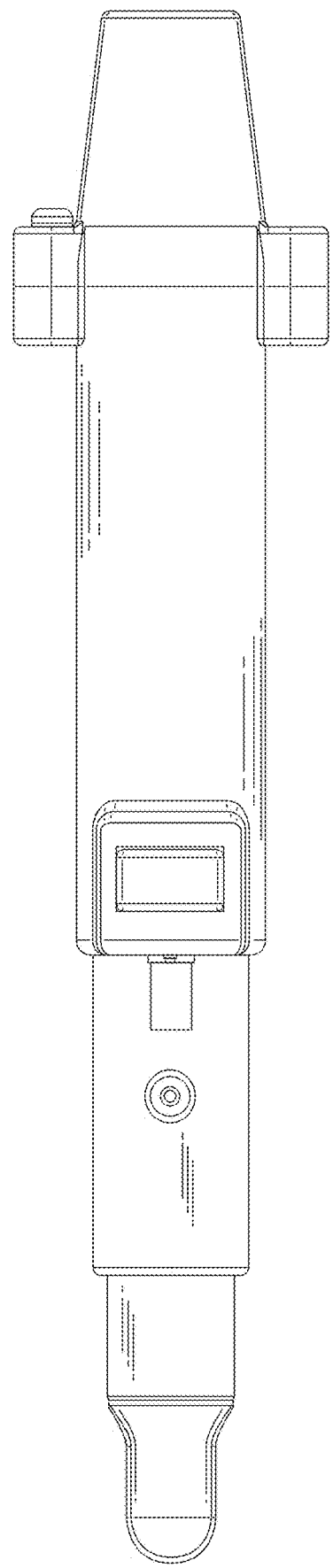
FIG. 18C shows a bottom plan view of an intranasal delivery device.
Figure 18D:
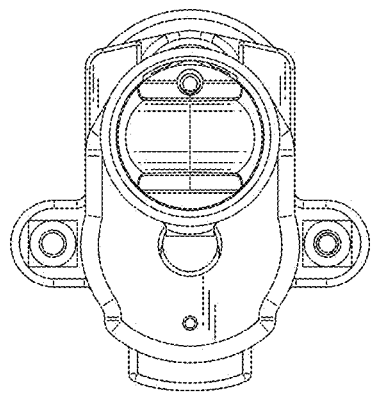
FIG. 18D shows a front elevational view of an intranasal delivery device.
Figure 18E:
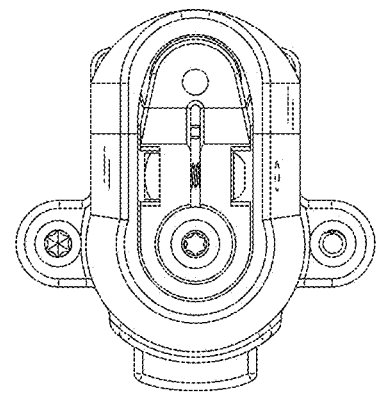
FIG. 18E shows a back elevational view of an intranasal delivery device.
Figure 18F:
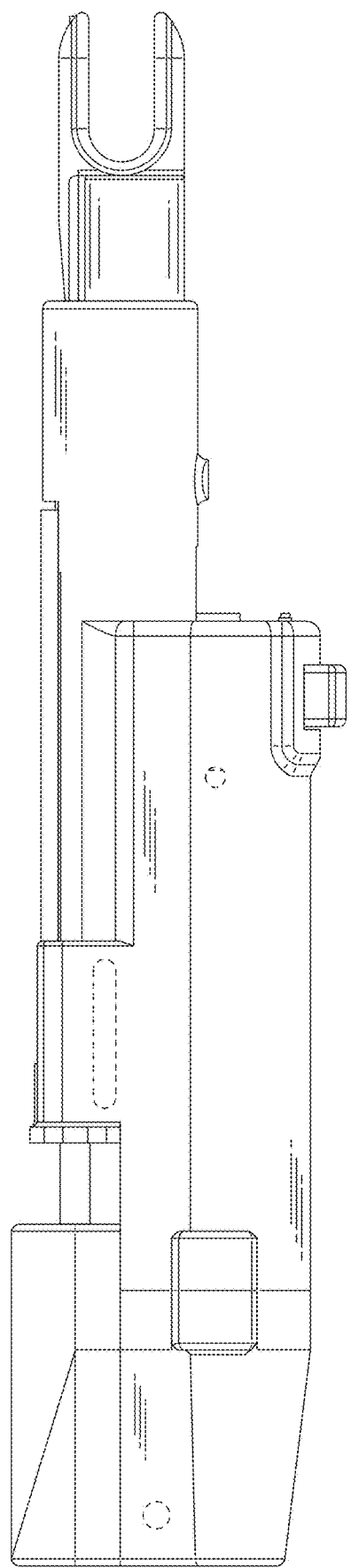
FIG. 18F shows a right side elevational view of an intranasal delivery device.
Figure 18G:
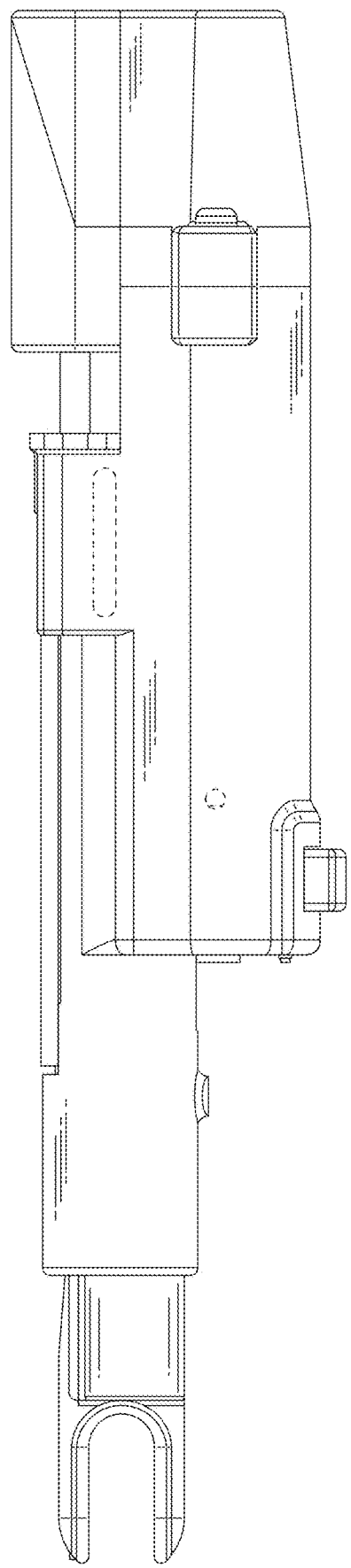
FIG. 18G shows a left side elevational view of an intranasal delivery device.

FIGS. 17A-17C show images of an exemplary nasal cavity of a subject during pre-ejection (top), ejection (middle), and post-ejection (bottom) of a composition with the exemplary device from within the described ejection zone, and illustrates that when administering a composition from the described ejection zone, that reliable and accurate delivery of a composition to the olfactory cleft can be achieved.

The tests performed utilized a tunable jug with low-speed device, 3D printed nasal cavity model, syringe with 200 µL and 1 cP viscosity, dispensing element (cannula), magnetic support structure for nasal cavity model, magnetic base for support structure, high-speed camera and flashlight.

The fluid was ejected from the dispensing element at a velocity of 1.5 m/s (1 cP). The tunable jig was set up to eject and deliver fluid at 1.5 m/s into the middle turbinate of the nasal cavity model. The 3D printed nasal cavity model was mounted on the magnetic support structure and attached to the magnetic base. The syringe was loaded with 200 ul of the 1 cP fluid. The cannula and syringe were mounted to the tunable jig to achieve desired velocity. Each ejection was recorded using the high-speed camera. The cannula was inserted into the nasal cavity model at a depth of 37.5 mm from the columella point and positioned to aim at the front side of the middle turbinate in the nasal cavity model.

As compared to FIGS. 13A-13I, 14A-14L, and 16A-16I, it is observed that when ejected from the described ejection zone (e.g., above the nasal valve, and more than 10-15 mm from the nostril opening, in front of an anterior aspect of the middle turbinate, underneath an inferior aspect of the olfactory cleft), that fluid bypasses the internal nasal valve, lower turbinate, and the middle turbinate; and is deposited in an accurate matter about the olfactory cleft and the cribriform plate. The ejected fluid exits the cannula above the nasal valve and middle turbinate, at a trajectory that is biased towards the nasal ridge, and is observed to travel along the interior upper surface of the internal nasal dorsum, and onto an upper surface of the olfactory cleft and the cribriform plate.

Example 6: Lateralized Olfactory Drug Delivery

Background: Intranasal drug delivery provides an alternative means for drug administration to a subject as compared to other forms such as intravenous or oral administration. The nasal cavity of a subject comprises anatomical features that intranasal drug delivery must overcome for effective drug administration. Of particular interest is the potential for lateralized drug delivery to different hemispheres and regions of the brain. For example, a fitted dual-cannula delivery device designed for precise orientation in the human nasal anatomy may be used to selectively deliver into either nostril, thereby facilitating selective delivery into either brain hemisphere. Additionally, utilizing a delivery device that is able to provide targeted delivery to a range of regions or subregions within the nasal cavity (i.e. lower nase to olfactory region) enables simultaneous delivery of two formulations into two subregions of the nasal anatomy. For example, in an intranasal opioid reversal rescue use case, delivery to the olfactory cleft may target the central nervous system and simultaneous delivery to the lower nase may target systemic absorption. The delivery device capable of delivery of a range of formulation viscosities (e.g. ranging from 1 cP to 1,000 cP) enables extended and/or delayed release of active pharmaceutical ingredients (APIs).

The inventors have determined a need for improved intranasal delivery devices and formulations to exploit the unique features of the olfactory anatomy.

Given the complex nature of the brain, the ability to specifically target distinct regions of the brain with wildly different functions would have tremendous benefit to providing current and novel therapies to a whole host of central nervous system diseases (i.e. ischemic stroke, traumatic brain injury, glioblastoma, neurodegenerative diseases etc). The ability to target and deliver therapies non-invasively to specific regions of the brain has, as of yet, been elusive requiring surgical and external manipulations (such as ultrasound) to provide functionality. Targeted regional brain delivery may also be beneficial in the following applications: mood or behaviour disorders, addictions treatments, neurodegenerative diseases, brain hemodynamics, major depressive disorder, GLP-1 signaling, and brain tumors.

Figure 22:
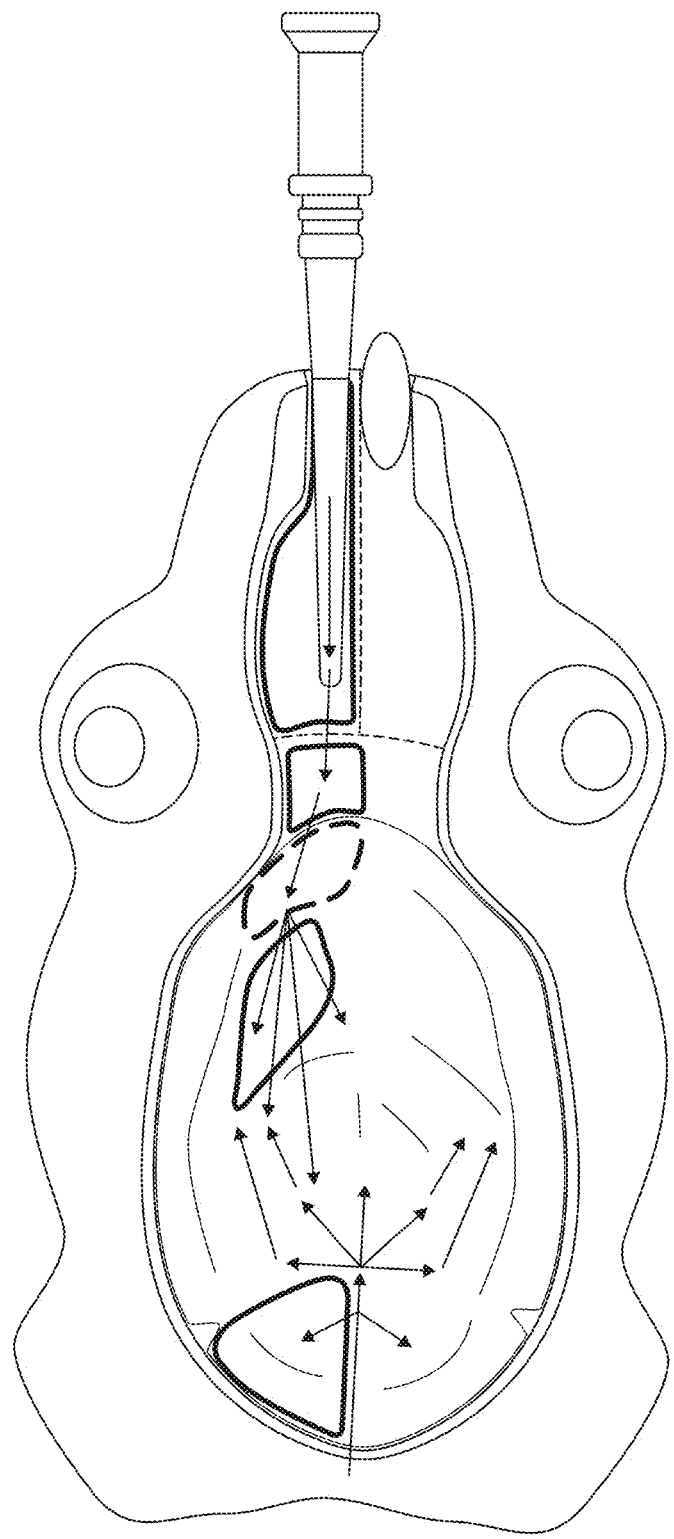
FIG. 22 shows an illustration demonstrating in vivo model targeted cannula lateralized delivery, including: a custom cannula design [2], that the animal has a physically occluded right nostril preventing right hemisphere access [3], active pharmaceutical ingredient (API) delivery via the cribiform plate [4], and uptake of the API via the olfactory delivery route, demonstrating lateralized delivery from the left nostril [5]. Note that in this example, the right brain hemisphere is targeted by delivery via the right nostril.
Figure 23A:
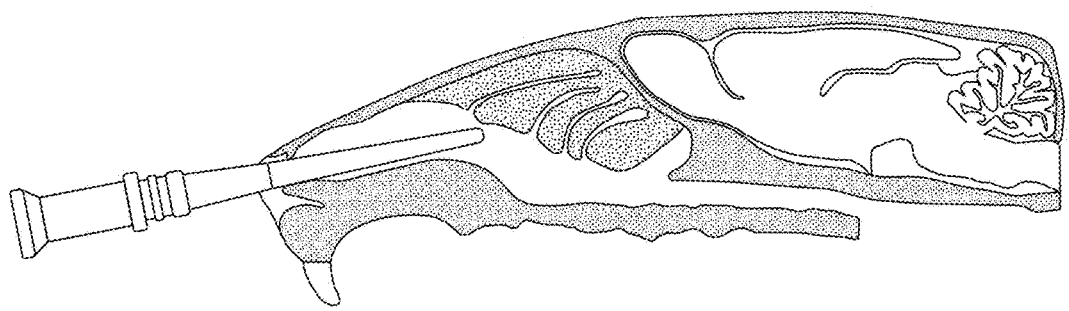
FIG. 23A shows a diagram illustrating cannula placement for successful olfactory delivery for group A using a 24 GA×0.75 in (0.6×19 mm) BD Insyte IV Catheter. Scale bar is 4 mm.
Figure 23B:
FIG. 23B shows an image of an in vivo model according to the diagram shown in FIG. 23A.

Experimental Details: The following experiment demonstrates that targeted (lateralized hemisphere) brain delivery can be achieved by olfactory delivery to a single nostril (FIG. 22). Sprague-Dawley male rats (150~250 g) n=3 per time point ×2 time points were used in this study. Animals were fasted per facility protocols (free access to water). Sedation by 50 mg/kg pentobarbital or equivalent procedure and maintenance with isoflurane. Test article administration: The animal is kept supine with the head kept at an angle to minimize movement of the olfactory plane above zero degrees (to prevent gravity drainage into the olfactory cleft). In this study Oxytocin (30 mg/kg) was delivered via the canulated olfactory delivery model which is: a 0.699 mm diameter cannula with lipophilic ointment spread on the catheter which is carefully inserted into the right nostril with a minimal angle of 20° to the target of the correct meatus. The left nostril is occluded with a non-toxic quick setting compound to prevent cross contamination. During insertion the catheter is rotated gently to advance it through the tight nasal cavity. Once the catheter reaches the ethmoid turbinate it cannot be advance gently anymore (~15 mm). 25 μL of oxytocin is slowly instilled in the olfactory region (FIGS. 23A-B). The animals were kept sedated for 2 hours. After 2 hours, the animals were humanely euthanized by cervical dislocation. Sample collection: Olfactory bulb and brain: Rats olfactory bulb and brain were collected and snap-freeze in liquid nitrogen. The tissue was stored at −80 C until analysis. Sample Preparation: Olfactory bulb and brain samples was homogenized with ice-cold phosphate buffer saline (pH 7.4) at a ratio of 4 (buffer):1(tissue) (v/w). An aliquot of 20 μL homogenate was spiked into 1.5 mL tube, and 100 μL of acetonitrile containing internal standard were added for protein precipitation. The mixture was vortexed, centrifuged at 14000 rpm for 5 min. 80 μL supernatant was transferred into a 96 well plate, and 240 μL of sterile deionized water was added, the mixture was vortexed and injected for LC-MS/MS analysis.

Figure 24:
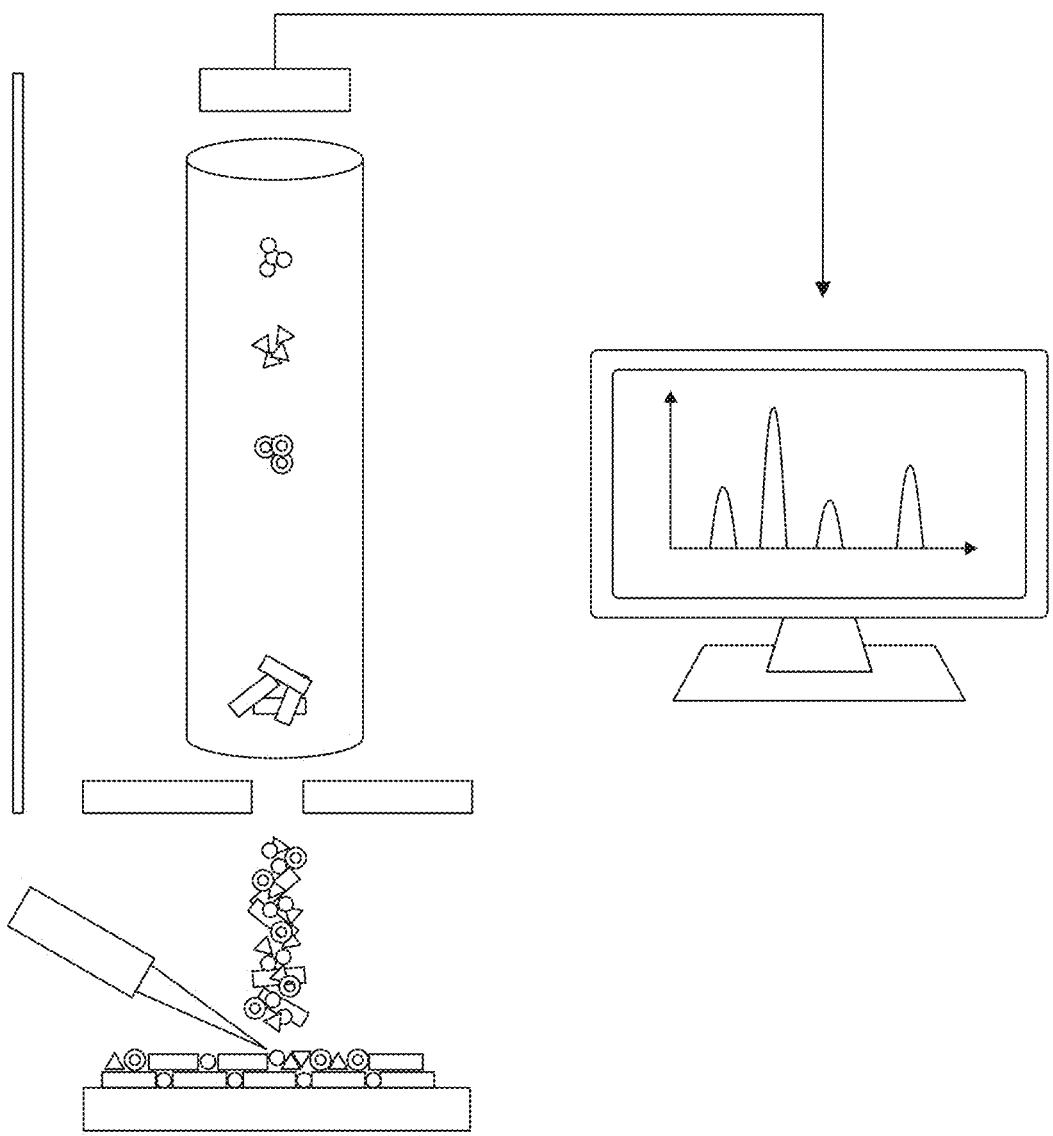
FIG. 24 shows an illustration demonstrating the imaging and detection of the molecules of interest via a time-of-flight mass analyzer.
Figure 25A:
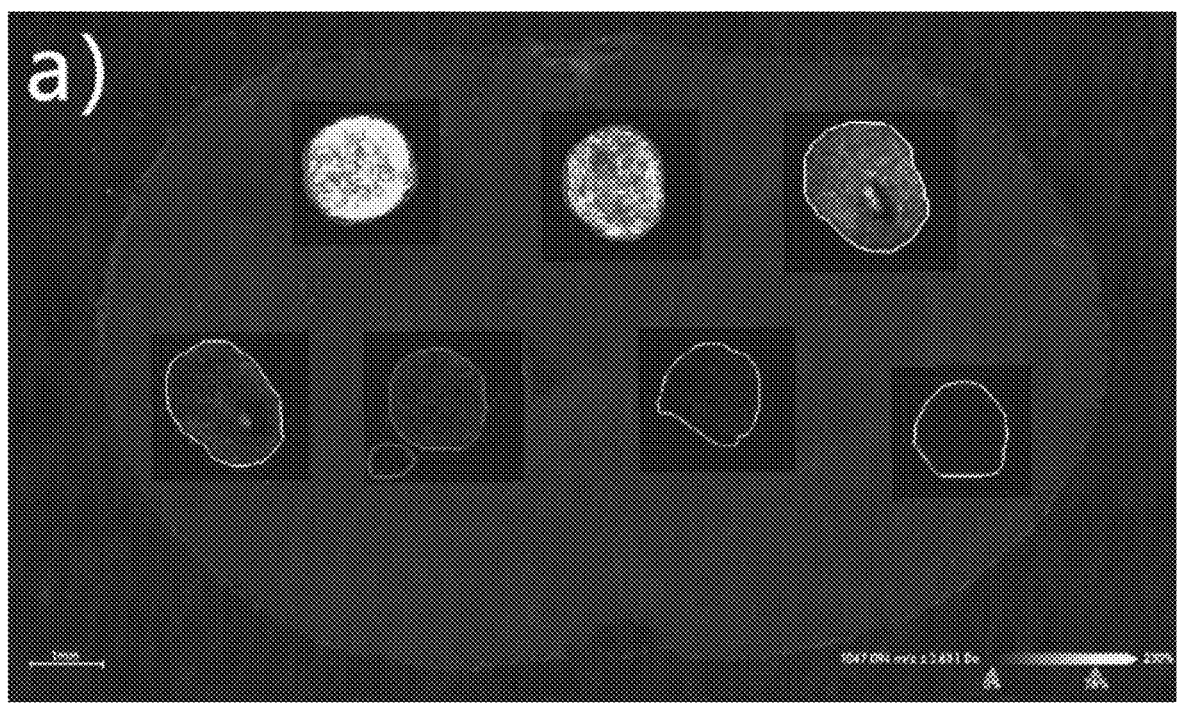
FIGS. 25A-D illustrate a standard curve for analysis and imaging of the oxytocin, with the intensity detected in FIG. 25A and FIG. 25C respectively used to generate the calibration curves in FIG. 25B and FIG. 25D.
Figure 25B:
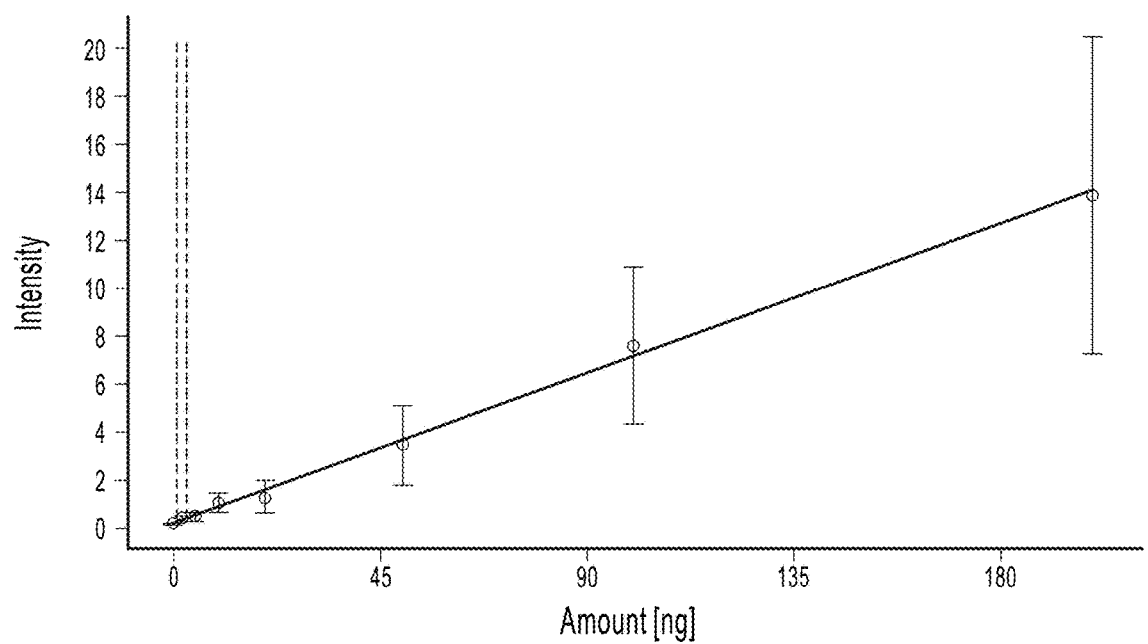
Figure 25C:
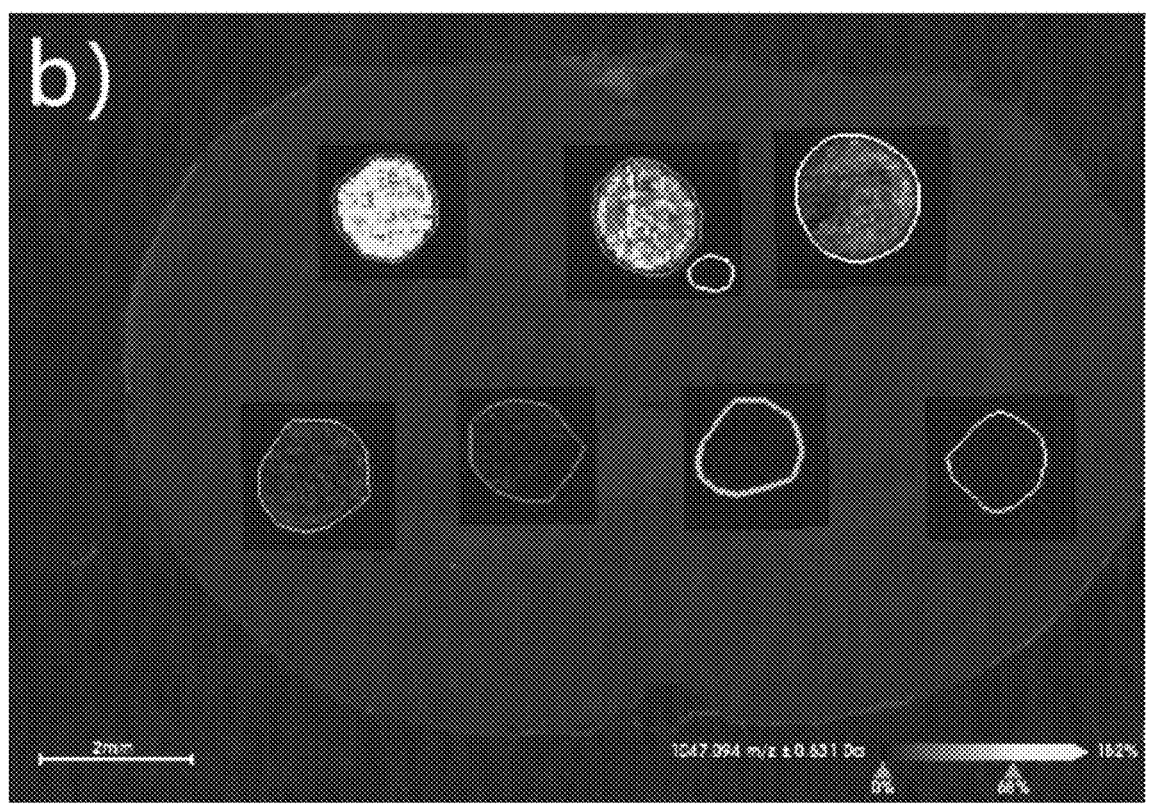
Figure 25D:
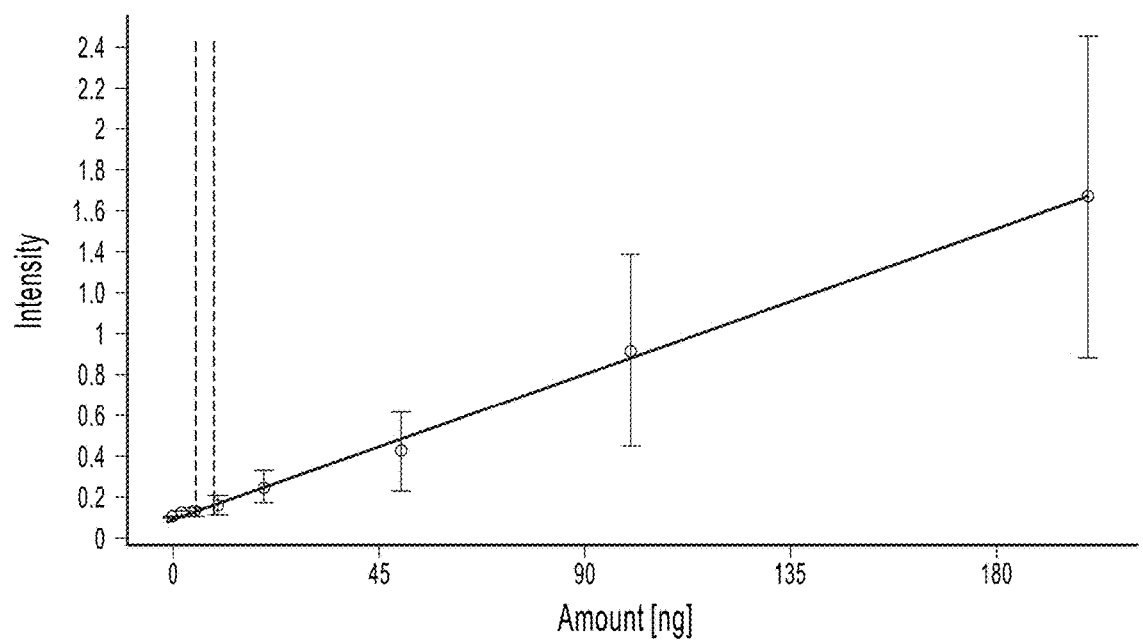
Figure 26:
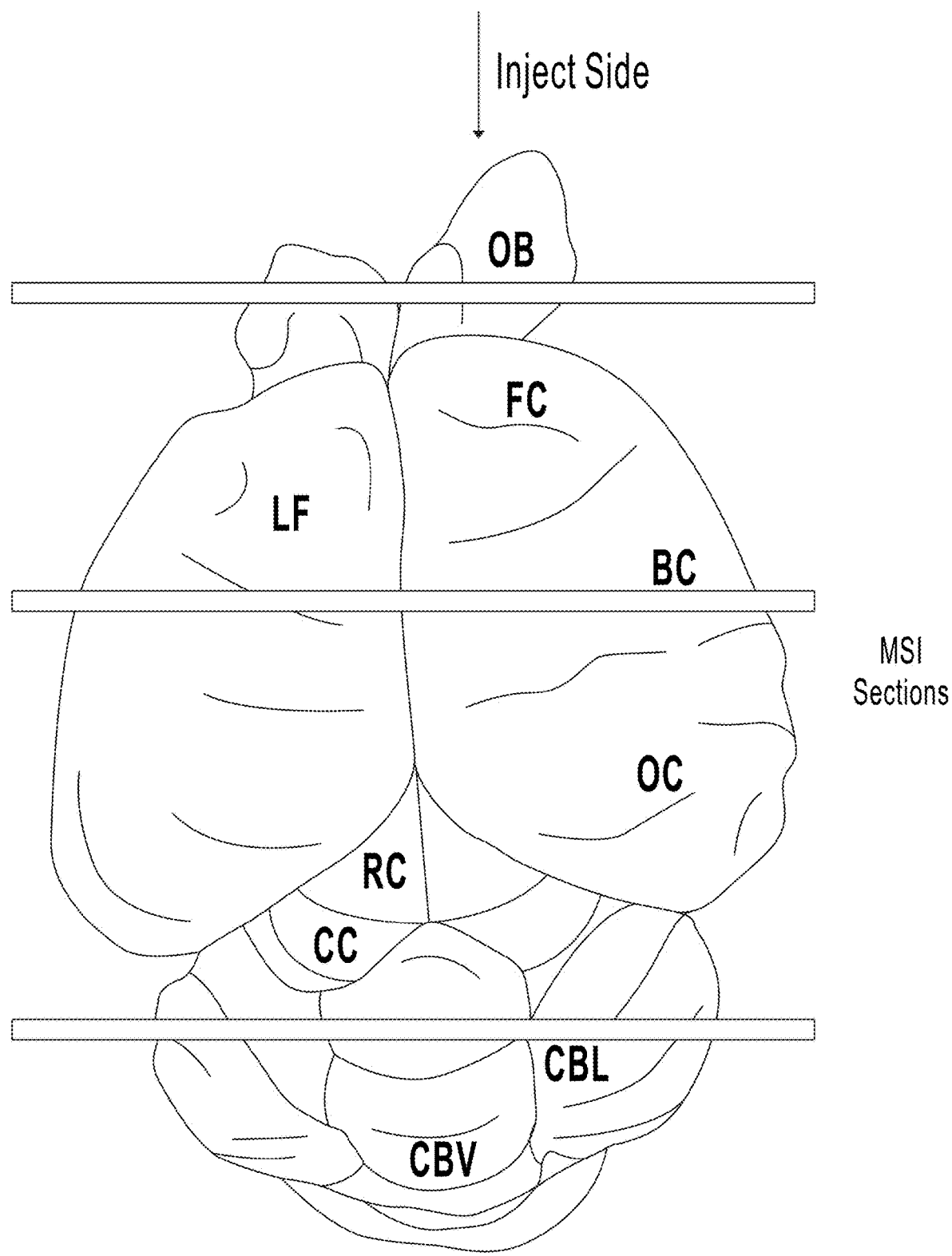
FIG. 26 shows an in vivo model animal brain, annotated to show dissection planes for the preparation of slices for mass spectrometry imaging (MSI). The slice closest to the injection side represents the olfactory bulb (OB). The middle slice represents the striatum. The slice furthest from the injection side represents the cerebrum. The inject side corresponds to the right brain hemisphere.
Figure 27A:
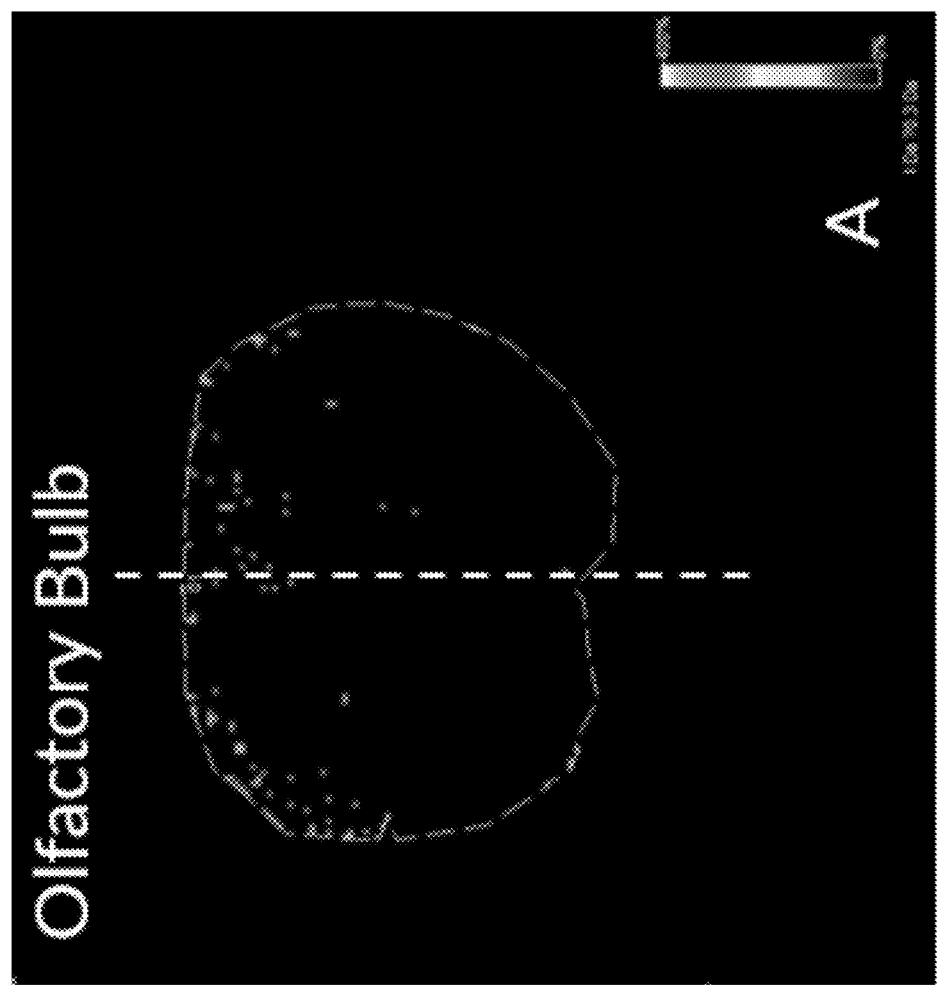
FIG. 27A shows mass spectrometry imaging (MSI) data from the olfactory bulb slice, showing a distribution of detected oxytocin demonstrating lateralization coinciding with the targeted (right) hemisphere. The dashed line delineates the hemispheres of the brain. Note that due to the orientation of the brain slice, the left side of the dashed line corresponds to the right hemisphere of the brain.
Figure 27B:
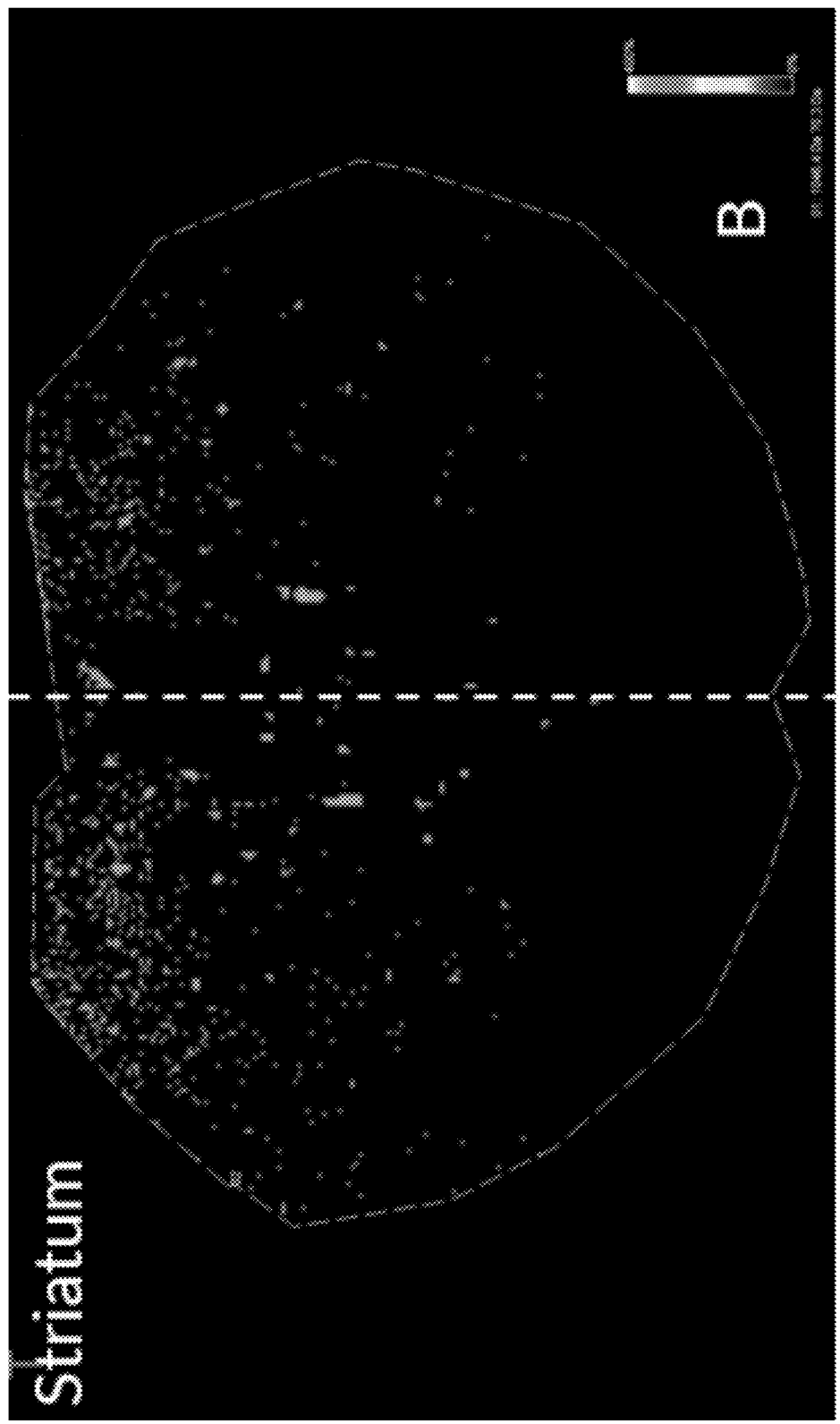
FIG. 27B shows mass spectrometry imaging (MSI) data from the striatum slice, showing a distribution of detected oxytocin demonstrating lateralization coinciding with the targeted (right) hemisphere. The dashed line delineates the hemispheres of the brain. Note that due to the orientation of the brain slice, the left side of the dashed line corresponds to the right hemisphere of the brain.
Figure 27C:
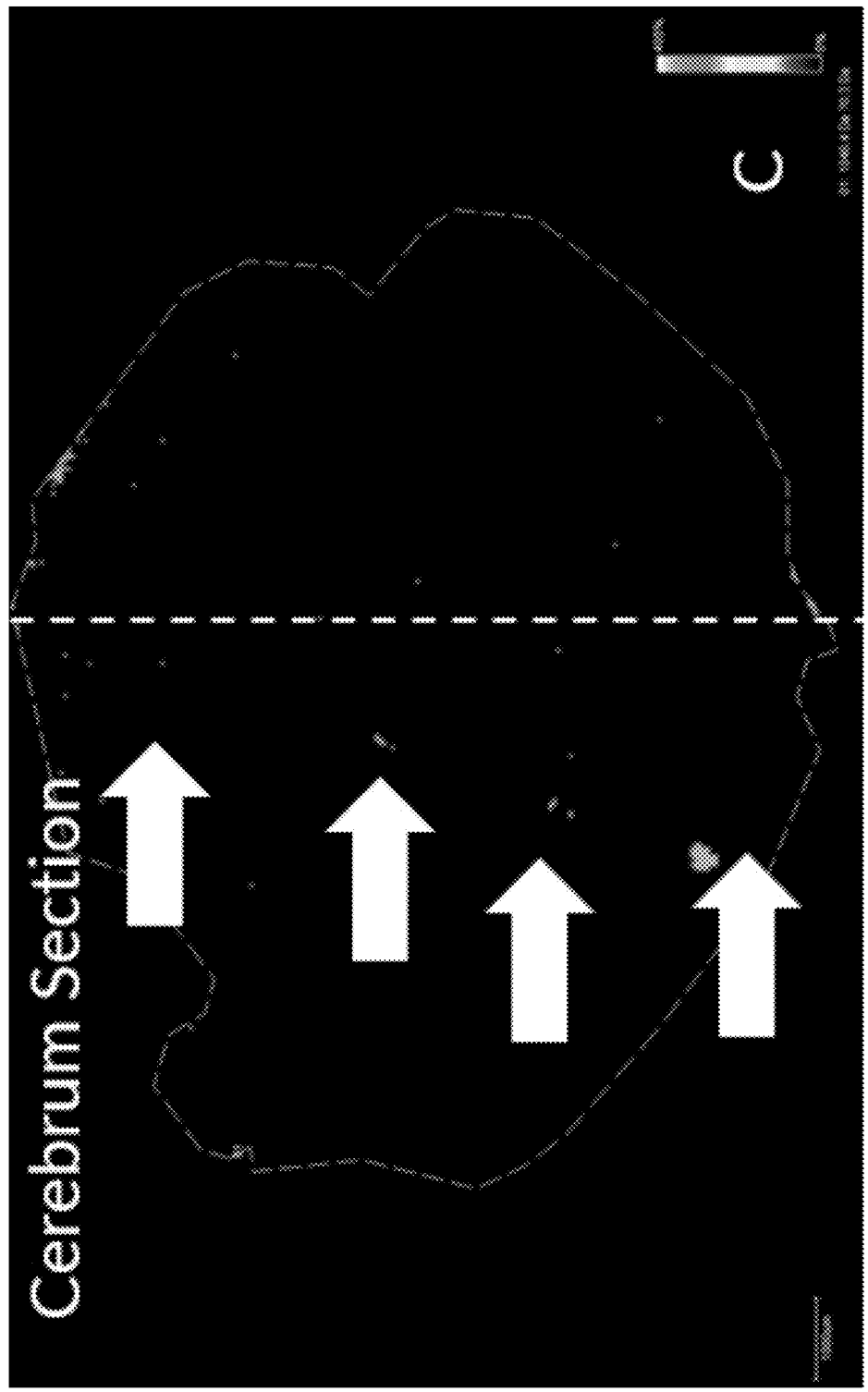
FIG. 27C shows mass spectrometry imaging (MSI) data from the cerebrum slice, showing a distribution of detected oxytocin demonstrating lateralization coinciding with the targeted (right) hemisphere. The dashed line delineates the hemispheres of the brain. Arrows indicate regions where lateralization is especially apparent. Note that due to the orientation of the brain slice, the left side of the dashed line corresponds to the right hemisphere of the brain.

Sample analysis: Test compound in olfactory bulb, brain, and plasma samples will be analyzed by LC/MS/MS. Calibration curve was constructed in blank olfactory bulb homogenate. Using a High-throughput RapifleX MALDI-TOF/TOF mass spectrometer the samples were analyzed utilizing non-labeled detection technologies. This is important as this technique explores the regional distribution patterns of target molecule (FIG. 24). The frozen section of brain tissue was cut into 12 μm sections. Oxytocin at 200, 10, 50, 20, 10, 5, 2 ng were used as standard in blank brain slide. And substrate were sprayed on the slides. The sample of the tissue section was ionized and desorbed with the substrate under the excitation of the laser beam. The released ions were identified with mass spectrometer. The detection levels were 2.68 ng/mm2 (FIGS. 25A-D). To visualize the lateralized drug transfer through the brain the brain was sectioned into olfactory bulb, striatum and cerebrum sections (FIG. 26) and imaged with the Mass Spectrometry Imaging (MSI) system. FIGS. 27A-C demonstrate the progress of the oxytocin through the brain. FIG. 27A demonstrates preferential right side distribution of oxytocin in the olfactory bulb, Figure FIG. 27B demonstrates continued preferential right side distribution and FIG. 27C demonstrates lateralization coinciding with the targeted (right) hemisphere.

The utility of using a canulated olfactory delivery to specifically target a specific hemisphere of the brain is the inventive step. The data demonstrating that distribution is preferential throughout the olfactory bulb and lateralizes at the cerebrum is non-obvious and novel.

Data Analysis:

The images shown in FIGS. 27A-C were analyzed to estimate the relative concentration of oxytocin on each side of the brain. Image data was converted into a standard RGB color-map, with each of the red (R), green (G), and blue (B) values taking a value between 0 and 255. Pixels with B-values exceeding 180 were counted on each side of the brain, yielding the results in Table 1.

TABLE 1

Intensity cooresponding to oxytocin in various brain regions

| Region | Cerebrum | | Olfactory | | Striatum | |
|---|---|---|---|---|---|---|
| Hemisphere | Right | Left | Right | Left | Right | Left |
| Blue Pixel Count | 921 | 638 | 962 | 475 | 7055 | 4085 |

Discussion: Table 1 demonstrates a consistently higher concentration of oxytocin (blue pixels) in the targeted over the untargeted halves of the brain, for each of the three studied regions. For the Cerebrum, the ratio was 921/638=1.44, for the Olfactory the ratio was 962/475=2.03, and for the Striatum the ratio was 7055/4085=1.73. All cases confirm the desired result of preferential drug delivery to the targeted side of the brain, with excess drug concentrations ranging from 44-103%. These comparisons indicate that the targeted delivery of this example provided lateralized dosing of the formulation to the brain, preferentially concentrating the therapeutic in the brain hemisphere corresponding to the selected nostril.

Devices of the present invention enable targeted delivery to distinct organ systems as illustrated by this example, which shows significant difference in the amount of a therapeutic agent to left and right hemispheres of the brain.

ENUMERATED EMBODIMENTS

Enumerated embodiment 1. A device for intranasal delivery to a subject, the device transitionable from a first configuration to a second configuration, the device comprising:
  a. two insertable portions each configured for insertion into a nasal channel of the subject, each of the two insertable portions comprising a distal end, and a proximal end;
  b. one or more dispensing elements, each of the one or two dispensing elements revealing from the corresponding insertable portion upon transition of the device from the first configuration to the second configuration;
  c. a subject engaging portion which engages a columella region of the subject to seat the distal end of each insertable portion within an ejection zone of a nasal channel of the subject, wherein the ejection zone is:
    i. 0 mm to 30 mm superior to a horizontal line that intersects the anterior aspect of the internal nasal valve, and
    ii. 0 mm to 20 mm anterior to an inclined line that intersects the anterior aspect of the middle turbinate and the posterior aspect of the vestibule; and
  d. a trigger release coupled to the subject engaging portion;
  wherein application of pressure by the subject engaging portion to the columella region of the subject is configured to:
    i. transition the device from the first configuration to the second configuration; and
    ii. release the trigger release, permitting actuation of the device to deliver a composition to the subject from either or both of the insertable portions.

Enumerated embodiment 2. A device for intranasal delivery to a subject, the device transitionable from a first configuration to a second configuration, the device comprising:
- a. two insertable portions each configured for insertion into a nasal channel of the subject, each of the two insertable portions comprising a distal end, and a proximal end;
- b. one or more dispensing elements, each of the one or two dispensing elements revealing from the corresponding insertable portion upon transition of the device from the first configuration to the second configuration; and
- c. a subject engaging portion which engages a columella region of the subject to seat the distal end of each insertable portion within an ejection zone of a nasal channel of the subject, wherein the ejection zone is:
  - i. 0 mm to 30 mm superior to a horizontal line that intersects the anterior aspect of the internal nasal valve, and
  - ii. 0 mm to 20 mm anterior to an inclined line that intersects the anterior aspect of the middle turbinate and the posterior aspect of the vestibule; and wherein application of pressure by the subject engaging portion to the columella region of the subject is configured to:
- iii. transition the device from the first configuration to the second configuration; and
- iv. enable or cause delivery of a composition to the subject from either or both of the insertable portions.

Enumerated embodiment 3. A device for intranasal delivery to a subject, the device comprising:
- a. a housing comprising an insertable portion comprising a distal end, and a proximal end;
- b. a subject engaging portion which engages a columella region of the subject to seat the distal end of the insertable portion within an ejection zone of a nasal channel of the subject, wherein the ejection zone is:
  - i. 0 mm to 30 mm superior to a horizontal line that intersects the anterior aspect of the internal nasal valve, and
  - ii. 0 mm to 20 mm anterior to an inclined line that intersects the anterior aspect of the middle turbinate and the posterior aspect of the vestibule.

Enumerated embodiment 4. The device of any one of the enumerated embodiments, wherein the ejection zone is further:
- i. 0 mm to 40 mm inferior to a horizontal line that is parallel to the inferior aspect of the olfactory cleft,
- ii. 0 mm to 20 mm posterior to the internal nasal dorsum,
- iii. 10 mm to 50 mm superior to a horizontal line that intersects the inferior aspect of the columella,
- iv. 0 mm to 30 mm superior to a horizontal line that intersects the superior aspect of the inferior turbinate,
- v. 0 mm to 5 mm from the septum, or
- vi. any combination thereof.

Enumerated embodiment 5. The device of any one of the enumerated embodiments, wherein the device is configured for dispensing the fluid therefrom as a laminar flow.

Enumerated embodiment 6. The device of any one of the enumerated embodiments, wherein the insertable portion, upon insertion into a nasal channel of the subject, opens or expands the internal nasal valve by pushing the upper lateral cartilage and surrounding tissue up and away from the septum.

Enumerated embodiment 7. The device of any one of the enumerated embodiments, wherein the insertable portion, upon insertion into a nasal channel of the subject, is proximal to the septum.

Enumerated embodiment 8. The device of any one of the enumerated embodiments, wherein the subject engaging portion prevents movement of the distal end within or away from the ejection zone when the subject engaging portion is seated on the columella region.

Enumerated embodiment 9. The device of any one of the enumerated embodiments, wherein the ejection zone is in line with the olfactory cleft as defined by a linear vector between an olfactory cleft and the distal end of the insertable portion.

Enumerated embodiment 10. The device of any one of the enumerated embodiments, wherein the device is configured to dispense a composition from the ejection zone such that at least 10%, at least 20%, at least 30%, at least 40%, at least 50%, at least 60%, at least 70%, at least 80%, at least 90%, or at least 99% of the dispensed composition is delivered to a target region or a target subregion.

Enumerated embodiment 11. The device of any one of the enumerated embodiments, wherein dispensing a composition from the ejection zone increases on target deposition of the composition to an olfactory cleft.

Enumerated embodiment 12. The device of any one of the enumerated embodiments, wherein dispensing a composition from the ejection zone increases on target deposition of the composition to an aspect of a respiratory region such as a middle turbinate.

Enumerated embodiment 13. The device of any one of the enumerated embodiments, wherein dispensing a composition from the ejection zone increases on target deposition of the composition to two or more regions or sub-regions of a nasal channel.

Enumerated embodiment 14. The device of any one of the enumerated embodiments, wherein the subject engaging portion is seated on the columella region when the subject engaging portion simultaneously contacts a downward facing lateral face of the columella, a leftward facing lateral face of the columella, and a rightward facing lateral face of the columella.

Enumerated embodiment 15. The device of any one of the enumerated embodiments, wherein the subject engaging portion limits a depth of insertion of the insertable portion into the nasal channel.

Enumerated embodiment 16. The device of any one of the enumerated embodiments, wherein the insertable portion incorporates one or more dispensing channels leading to one or more dispensing ports configured for delivery of a composition to one or more regions or sub-regions of the nasal channel of the subject.

Enumerated embodiment 17. The device of any one of the enumerated embodiments, wherein the insertable portion comprises a dispensing element for delivery of a composition to a region or sub-region of the nasal channel of the subject.

Enumerated embodiment 18. The device of any one of the enumerated embodiments, wherein the housing comprises a trigger, wherein upon application of pressure to the trigger, the trigger actuates the device to dispense a composition to the subject from the insertable portion or the dispensing element.

Enumerated embodiment 19. The device of any one of the enumerated embodiments, wherein the subject engaging portion comprises a trigger coupled to the housing and the subject engaging portion, wherein upon application of pressure of the subject engaging portion to the columella region, the trigger actuates the device to dispense a composition to the subject from the insertable portion or the dispensing element.

Enumerated embodiment 20. The device of any one of the enumerated embodiments, wherein the subject engaging portion comprises a trigger release coupled to the housing and the subject engaging portion, wherein upon application of pressure of the subject engaging portion to the columella region, the trigger release permits actuation of the device to deliver a composition to the subject from the insertable portion or the dispensing element.

Enumerated embodiment 21. The device of any one of the enumerated embodiments, further comprising a trigger which is actuatable upon engagement of the trigger release.

Enumerated embodiment 22. The device of any one of the enumerated embodiments, wherein the housing defines two insertable portions, each for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the insertable portions for delivery of a composition to the subject, the device further comprising an actuator which delivers a composition from the either or both of the insertable portions when the device is actuated.

Enumerated embodiment 23. The device of any one of the enumerated embodiments, wherein the housing defines two insertable portions, each for delivery of a composition into a nasal channel of the subject, the device further comprising an actuator which delivers the composition from either or both of the insertable portions when the device is actuated.

Enumerated embodiment 24. The device of any one of the enumerated embodiments, wherein the device is transitionable from a first configuration to a second configuration, the device further comprising one or two dispensing elements coupled to the insertable portion, the at least one dispensing element revealing from the at least one insertable portion upon transition of the device from the first configuration to the second configuration.

Enumerated embodiment 25. The device of any one of the enumerated embodiments, wherein the device is transitionable from the first configuration to the second configuration upon application of pressure about a longitudinal axis of the device, wherein the at least one dispensing element reveals in a linear vector relative to a longitudinal axis of the at least one insertable portion, or wherein the device is configured to be transitioned from the first configuration to the second configuration with only one hand.

Enumerated embodiment 26. The device of any one of the enumerated embodiments, wherein the device is simultaneously actuated upon being transitioned from the first configuration to the second configuration.

Enumerated embodiment 27. The device of any one of the enumerated embodiments, wherein the distal aspect of the at least one dispensing element is positioned in the ejection zone when the device is in the second configuration.

Enumerated embodiment 28. A device for intranasal delivery to a subject, the device comprising:
 a. a housing comprising an insertable portion configured for insertion into a nasal channel of the subject; and
 b. a subject engaging portion which engages a columella region of the subject coupled to the housing, wherein application of pressure by the subject engaging portion to the columella region of the subject enables and/or causes delivery of a composition to the subject from the insertable portion.

Enumerated embodiment 29. The device of any one of the enumerated embodiments, wherein the insertable portion incorporates one or more dispensing channels leading to one or more dispensing ports configured for intranasal delivery of a composition to one or more regions or sub-regions of the nasal channel of the subject.

Enumerated embodiment 30. The device of any one of the enumerated embodiments, wherein the insertable portion comprises a dispensing element for delivery of a composition to a region or sub-region of the nasal channel of the subject.

Enumerated embodiment 31. The device of any one of the enumerated embodiments, wherein the housing comprises a trigger, wherein the trigger actuates the device to deliver a composition to the subject from the insertable portion or the dispensing element.

Enumerated embodiment 32. The device of any one of the enumerated embodiments, wherein the subject engaging portion comprises a trigger coupled to the housing and the subject engaging portion, wherein upon application of pressure of the subject engaging portion to the columella region, the trigger actuates the device to dispense a composition to the subject from the insertable portion or the dispensing element.

Enumerated embodiment 33. The device of any one of the enumerated embodiments, wherein the subject engaging portion comprises a trigger release coupled to the housing and the subject engaging portion, wherein upon application of pressure of the subject engaging portion to the columella region, the trigger release permits actuation of the device to deliver a composition to the subject from the insertable portion or the dispensing element.

Enumerated embodiment 34. The device of any one of the enumerated embodiments, further comprising a trigger which is actuatable upon engagement of the trigger release.

Enumerated embodiment 35. The device of any one of the enumerated embodiments, wherein the subject engaging portion positions the insertable portion within a nasal channel of the subject and limits the depth of insertion of the insertable portion into the nasal channel.

Enumerated embodiment 36. The device of any one of the enumerated embodiments, wherein the housing defines two insertable portions, each for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the insertable portions for delivery of the composition to the subject, the device further comprising an actuator which delivers the composition from the either or both of the insertable portions when the device is actuated.

Enumerated embodiment 37. The device of any one of the enumerated embodiments, wherein the housing defines two insertable portions, each for delivery of the composition into a nasal channel of the subject, the device further comprising an actuator which delivers the composition from either or both of the insertable portions when the device is actuated.

Enumerated embodiment 38. The device of any one of the enumerated embodiments, wherein the device is transitionable from a first configuration to a second configuration, the device further comprising a dispensing element coupled to the housing, the dispensing element revealing from the first insertable portion upon transition of the device from the first configuration to the second configuration.

Enumerated embodiment 39. The device of any one of the enumerated embodiments, wherein the device is simultaneously actuated upon being transitioned from the first configuration to the second configuration.

Enumerated embodiment 40. The device of any one of the enumerated embodiments, wherein the device is transitionable from the first configuration to the second configuration upon application of pressure about a longitudinal axis of the device, wherein the dispensing element reveals in a linear vector relative to a longitudinal axis of the first insertable portion, or wherein the device is configured to be transitioned from the first configuration to the second configuration with only one hand.

Enumerated embodiment 41. The device of any one of the enumerated embodiments, wherein the subject engaging portion engages a columella region of the subject to seat a distal end of the insertable portion within an ejection zone of a nasal cavity of the subject.

Enumerated embodiment 42. The device of any one of the enumerated embodiments, wherein the ejection zone is:
  a. 0 mm to 30 mm superior to a horizontal line that intersects the anterior aspect of the internal nasal valve, and
  b. 0 mm to 20 mm anterior to an inclined line that intersects the anterior aspect of the middle turbinate and the posterior aspect of the vestibule, and one or more of the following:
    i. 0 mm to 40 mm inferior to a horizontal line that is parallel to the inferior aspect of the olfactory cleft, 0 mm to 20 mm posterior to the internal nasal dorsum,
    ii. 10 mm and 50 mm superior to a horizontal line that intersects the inferior aspect of the columella,
    iii. 0 mm to 30 mm superior to a horizontal line that intersects the superior aspect of the inferior turbinate,
    iv. 0 mm to 3 mm from the septum, or
    v. any combination thereof.

Enumerated embodiment 43. The device of any one of the enumerated embodiments, wherein the subject engaging portion prevents movement of the distal end within or away from the ejection zone when the subject engaging portion is seated on the columella region.

Enumerated embodiment 44. The device of any one of the enumerated embodiments, wherein the ejection zone is in line with the olfactory cleft as defined by a linear vector between the olfactory cleft and the distal end of the insertable portion.

Enumerated embodiment 45. The device of any one of the enumerated embodiments, wherein dispensing a composition from the ejection zone increases on target deposition of the composition to the olfactory cleft.

Enumerated embodiment 46. The device of any one of the enumerated embodiments, wherein the subject engaging portion is seated on the columella region when the subject engaging portion simultaneously contacts a downward facing lateral face of the columella, a leftward facing lateral face of the columella, and a rightward facing lateral face of the columella.

Enumerated embodiment 47. The device of any one of the enumerated embodiments, wherein dispensing a composition from the ejection zone increases on target deposition of the composition to an aspect of a respiratory region such as a middle turbinate.

Enumerated embodiment 48. A device for intranasal delivery to a subject, the device comprising:
  a. a housing defining first and second insertable portions, each for insertion into a nasal channel of the subject, wherein, upon insertion of the first insertable portion into the nasal channel of the subject, the at least one insertable portion engages tissue within the nasal channel to open or expand an internal nasal valve of the subject thereby positioning at least one of the insertable portions for delivery of a composition to the subject;
  b. an actuator which delivers the composition from the either or both of the insertable portions when the device is actuated.

Enumerated embodiment 49. The device of any one of the enumerated embodiments, wherein the at least one insertable portion to open or expand an internal nasal valve does so by moving a superior lateral cartilage defining the internal nasal valve away from a septum of the subject.

Enumerated embodiment 50. The device of any one of the enumerated embodiments, wherein the at least one insertable portion to open or expand an internal nasal valve does so by moving superior lateral cartilage defining the internal nasal valve towards an internal nasal dorsum of the subject.

Enumerated embodiment 51. The device of any one of the enumerated embodiments, wherein the insertable portion incorporates one or more dispensing channels leading to one or more dispensing ports configured for intranasal delivery of a composition to one or more regions or sub-regions of the nasal channel of the subject.

Enumerated embodiment 52. The device of any one of the enumerated embodiments, wherein the insertable portion comprises a dispensing element for delivery of a composition to a region or sub-region of the nasal channel of the subject.

Enumerated embodiment 53. The device of any one of the enumerated embodiments, further comprising a trigger coupled to the housing, wherein upon application of pressure to the trigger, the trigger actuates the device to dispense a composition to the subject from the insertable portion or the dispensing element.

Enumerated embodiment 54. The device of any one of the enumerated embodiments, further comprising a trigger coupled to the housing and the subject engaging portion, wherein upon application of pressure of the subject engaging portion to the columella region, the trigger actuates the device to dispense a composition to the subject from the insertable portion or the dispensing element.

Enumerated embodiment 55. The device of any one of the enumerated embodiments, further comprising a subject engaging portion, wherein the subject engaging portion comprises a trigger release coupled to the housing, wherein upon application of pressure of the subject engaging portion to the columella region, the trigger release permits actuation of the device to deliver a composition to the subject from the insertable portion or the dispensing element.

Enumerated embodiment 56. The device of any one of the enumerated embodiments, further comprising a trigger which is actuatable upon engagement of the trigger release.

Enumerated embodiment 57. The device of any one of the enumerated embodiments, further comprising a subject engaging portion coupled to the housing, which engages a columella region, wherein the subject engaging portion positions the insertable portion within the nasal channel of the subject and limits a depth of insertion of the delivery element into the nasal channel.

Enumerated embodiment 58. The device of any one of the enumerated embodiments, wherein the housing defines two insertable portions, each for delivery of a composition into a nasal channel of the subject, the device further comprising an actuator which delivers the composition from either or both of the dispensing elements when the device is actuated.

Enumerated embodiment 59. The device of any one of the enumerated embodiments, wherein the device is transitionable from a first configuration to a second configuration, the housing defining a first insertable portion, the device further comprising a dispensing element coupled to the housing, the dispensing element revealing from the first insertable portion upon transition of the device from the first configuration to the second configuration.

Enumerated embodiment 60. The device of any one of the enumerated embodiments, wherein the device is simultaneously actuated upon being transitioned from the first configuration to the second configuration.

Enumerated embodiment 61. The device of any one of the enumerated embodiments, wherein the device is transitionable from the first configuration to the second configuration upon application of pressure about a longitudinal axis of the device, wherein the dispensing element reveals in a linear vector relative to a longitudinal axis of the first insertable portion, or wherein the device is configured to be transitioned from the first configuration to the second configuration with only one hand.

Enumerated embodiment 62. The device of any one of the enumerated embodiments, wherein the subject engaging portion engages a columella region of the subject to seat a distal end of the insertable portion within an ejection zone of a nasal cavity of the subject, wherein the ejection zone is:
  a. 0 mm to 30 mm superior to a horizontal line that intersects the anterior aspect of the internal nasal valve, and
  b. 0 mm to 20 mm anterior to an inclined line that intersects the anterior aspect of the middle turbinate and the posterior aspect of the vestibule, and one or more of the following:
    i. 0 mm to 40 mm inferior to a horizontal line that is parallel to the inferior aspect of the olfactory cleft,
    ii. 0 mm to 20 mm posterior to the internal nasal dorsum,
    iii. 10 mm and 50 mm superior to a horizontal line that intersects the inferior aspect of the columella,
    iv. 0 mm to 30 mm superior to a horizontal line that intersects the superior aspect of the inferior turbinate,
    v. 0 mm to 3 mm from the septum. or
    vi. any combination thereof.

Enumerated embodiment 63. The device of any one of the enumerated embodiments, wherein the subject engaging portion prevents movement of the distal end within or away from the ejection zone when the subject engaging portion is seated on the columella region.

Enumerated embodiment 64. The device of any one of the enumerated embodiments, wherein the ejection zone is in line with the olfactory cleft as defined by a linear vector between the olfactory cleft and the distal end of the insertable portion.

Enumerated embodiment 65. The device of any one of the enumerated embodiments, wherein dispensing a composition from the ejection zone increases on target deposition of the composition to the olfactory cleft.

Enumerated embodiment 66. The device of any one of the enumerated embodiments, wherein the subject engaging portion is seated on the columella region when the subject engaging portion simultaneously contacts a downward facing lateral face of the columella, a leftward facing lateral face of the columella, and a rightward facing lateral face of the columella.

Enumerated embodiment 67. The device of any one of the enumerated embodiments, wherein dispensing a composition from the ejection zone increases on target deposition of the composition to an aspect of a respiratory region such as the middle turbinate.

Enumerated embodiment 68. A device for intranasal delivery to a subject, the device transitionable from a first configuration to a second configuration, the device comprising:
  a. a housing defining a first insertable portion configured to be inserted into a nasal channel of the subject; and
  b. a dispensing element coupled to the housing,
  c. wherein the device is transitioned from the first configuration to the second configuration by application of pressure about a longitudinal axis of the device, and wherein the device is simultaneously actuated upon being transitioned from the first configuration to the second configuration.

Enumerated embodiment 69. The device of any one of the enumerated embodiments, wherein the dispensing element the simultaneous actuation refers to transition for the first configuration to the second configuration and actuation occurring in a single motion upon application of pressure about a longitudinal axis of the device.

Enumerated embodiment 70. The device of any one of the enumerated embodiments, the dispensing element revealing from the first insertable portion upon transition of the device from the first configuration to the second configuration, wherein the dispensing element reveals in a linear vector parallel to the internal nasal dorsum from the first insertable portion at a location above an inferior turbinate of the subject.

Enumerated embodiment 71. The device any one of the enumerated embodiments, wherein the device avoids contaminating the dispensing element with bacteria from the lower nasal cavity by enclosing it in the insertable portion prior to revealing the dispensing element upon transition from the first configuration to the second configuration.

Enumerated embodiment 72. The device of any one of the enumerated embodiments, wherein the device avoids contaminating the dispensing element by concealing it within the insertable portion prior to actuation.

Enumerated embodiment 73. The device of any one of the enumerated embodiments, wherein the insertable portion incorporates one or more dispensing channels leading to one or more dispensing ports configured for intranasal delivery of a composition to one or more regions or sub-regions of the nasal channel of the subject.

Enumerated embodiment 74. The device of any one of the enumerated embodiments, wherein the dispensing element reveals in a linear vector relative to a longitudinal axis of the first insertable portion.

Enumerated embodiment 75. The device of any one of the enumerated embodiments, wherein the device is configured to be transitioned from the first configuration to the second configuration with only one hand.

Enumerated embodiment 76. The device of any one of the enumerated embodiments, wherein the dispensing element reveals from the insertable portion upon transition of the device from the first configuration to the second configuration.

Enumerated embodiment 77. The device of any one of the enumerated embodiments, wherein the dispensing element reveals from the insertable portion upon transition of the device from the first configuration to the second configuration, upon application of pressure of a portion of the housing to a columella region of a subject.

Enumerated embodiment 78. The device of any one of the enumerated embodiments, wherein the second configuration moves a first portion of the housing towards a second portion of the housing about a longitudinal axis of the device.

Enumerated embodiment 79. The device of any one of the enumerated embodiments, further comprising a subject engaging portion coupled to the housing which engages a columella region, wherein the subject engaging portion positions the insertable portion within a nasal channel of the subject and limits the depth of insertion of the dispensing element into the nasal channel.

Enumerated embodiment 80. The device of any one of the enumerated embodiments, wherein the subject engaging portion which engages a columella region of the subject seats the distal end of the dispensing element within an ejection zone of a nasal cavity of the subject, wherein the ejection zone is:

a. 0 mm to 30 mm superior to a horizontal line that intersects the anterior aspect of the internal nasal valve, and
b. 0 mm to 20 mm anterior to an inclined line that intersects the anterior aspect of the middle turbinate and the posterior aspect of the vestibule, and one or more of the following:
   i. 0 mm to 40 mm inferior to a horizontal line that is parallel to the inferior aspect of the olfactory cleft,
   ii. 0 mm to 20 mm posterior to the internal nasal dorsum,
   iii. 10 mm and 50 mm superior to a horizontal line that intersects the inferior aspect of the columella,
   iv. 0 mm to 30 mm superior to a horizontal line that intersects the superior aspect of the inferior turbinate,
   v. 0 mm to 3 mm from the septum. or
   vi. any combination thereof.

Enumerated embodiment 81. The device of any one of the enumerated embodiments, wherein the subject engaging portion prevents movement of the distal end of the dispensing element within or away from the ejection zone when the subject engaging portion is seated on the columella region.

Enumerated embodiment 82. The device of any one of the enumerated embodiments, wherein the ejection zone is in line with the olfactory cleft as defined by a linear vector between the olfactory cleft and the distal end of the insertable portion.

Enumerated embodiment 83. The device of any one of the enumerated embodiments, wherein dispensing a composition from the ejection zone increases on target deposition of the composition to the olfactory cleft.

Enumerated embodiment 84. The device of any one of the enumerated embodiments, wherein dispensing a composition from the ejection zone increases on target deposition of the composition to an aspect of a respiratory region such as a middle turbinate.

Enumerated embodiment 85. The device of any one of the enumerated embodiments, wherein the subject engaging portion is seated on the columella region when the subject engaging portion simultaneously contacts a downward facing lateral face of the columella, a leftward facing lateral face of the columella, and a rightward facing lateral face of the columella.

Enumerated embodiment 86. The device of any one of the enumerated embodiments, further comprising a trigger coupled to the housing and the subject engaging portion, the subject engaging portion engaging a columella region of the subject, wherein upon application of pressure of the subject engaging portion to the columella region, the trigger actuates the device to deliver a composition to the subject from the dispensing element.

Enumerated embodiment 87. The device of any one of the enumerated embodiments, wherein the housing defines two insertable portions, each for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the insertable portions for delivery of a composition to the subject, the device further comprising an actuator which delivers a composition from the either or both of the insertable portions when the device is actuated Enumerated embodiment 88. The device of any one of the enumerated embodiments, wherein the housing defines two dispensing elements, each for delivery of a composition into a nasal channel of the subject, the device further comprising an actuator which delivers the composition from either or both of the dispensing elements when the device is actuated.

Enumerated embodiment 89. The device of any one of the enumerated embodiments, further comprising a trigger release coupled to the housing and the subject engaging portion, wherein upon application of pressure of the subject engaging portion to the columella region, the trigger release permits actuation of the device to deliver a composition to the subject from the insertable portion.

Enumerated embodiment 90. The device of any one of the enumerated embodiments, further comprising a trigger which is actuatable upon engagement of the trigger release.

Enumerated embodiment 91. The device of any one of the enumerated embodiments, wherein the device avoids contaminating the dispensing element by concealing it within the insertable portion prior to actuation.

Enumerated embodiment 92. The device of any one of the enumerated embodiments, wherein the composition is dispensed from a distal end of the insertable portion.

Enumerated embodiment 93. The device of any one of the enumerated embodiments, wherein the dispensing element is in the ejection zone when the device is in the second configuration.

Enumerated embodiment 94. The device of any one of the enumerated embodiments, wherein the dispensing element is at a distal end of the ejection zone when the device is in the second configuration.

Enumerated embodiment 95. The device of any one of the enumerated embodiments, wherein the device is simultaneously actuated upon being transitioned from the first configuration to the second configuration.

Enumerated embodiment 96. The device of any one of the enumerated embodiments, wherein the dispensing element reveals in a linear vector parallel to the internal nasal dorsum from the first insertable portion at a location above an inferior turbinate of the subject.

Enumerated embodiment 97. The device of any one of the enumerated embodiments, wherein the device avoids contaminating the dispensing element with bacteria from the lower nasal cavity by enclosing it in the insertable portion prior to revealing the dispensing element upon transition from the first configuration to the second configuration.

Enumerated embodiment 98. The device of any one of the enumerated embodiments, wherein the at least one insertable portion to open or expand an internal nasal valve does so by moving upper lateral cartilage away from a septum of the subject.

Enumerated embodiment 99. The device of any one of the enumerated embodiments, wherein the at least one insertable portion to open or expand an internal nasal valve does so by moving upper lateral cartilage defining the internal nasal valve towards an internal nasal dorsum of the subject.

Enumerated embodiment 100. The device of any one of the enumerated embodiments, wherein the subject engaging portion prevents movement of the distal end of an insertable portion or a dispensing element within or away from the ejection zone when the subject engaging portion is seated on the columella region.

Enumerated embodiment 101. The device of any one of the enumerated embodiments, wherein the ejection zone is in line with the olfactory cleft as defined by a linear vector between the olfactory cleft and the distal end of the insertable portion.

Enumerated embodiment 102. The device of any one of the enumerated embodiments, wherein dispensing a composition from the ejection zone increases on target deposition of the composition to the olfactory cleft.

Enumerated embodiment 103. The device of any one of the enumerated embodiments, wherein dispensing a composition from the ejection zone increases on target deposition of the composition to an aspect of a respiratory region such as a middle turbinate.

Enumerated embodiment 104. The device of any one of the enumerated embodiments, wherein the subject engaging portion is seated on the columella region when the subject engaging portion simultaneously contacts a downward facing lateral face of the columella, a leftward facing lateral face of the columella, and a rightward facing lateral face of the columella.

Enumerated embodiment 105. The device of any one of the enumerated embodiments, wherein the subject engaging portion limits a depth of insertion of the insertable portion into the nasal channel.

Enumerated embodiment 106. The device of any one of the enumerated embodiments, wherein the subject engaging portion limits a depth of insertion of the dispensing element into the nasal channel.

Enumerated embodiment 107. The device of any one of the enumerated embodiments, wherein the first and second insertable portion are configured to dispense a composition from the first and second insertable portion simultaneously.

Enumerated embodiment 108. The device of any one of the enumerated embodiments, wherein the first and second insertable portion are configured to dispense a composition from the first and second insertable portion sequentially.

Enumerated embodiment 109. The device of any one of the enumerated embodiments, wherein the first and second dispensing elements are configured to dispense a composition from the first and second dispensing elements simultaneously.

Enumerated embodiment 110. The device of any one of the enumerated embodiments, wherein the first and second dispensing elements are configured to dispense a composition from the first and second dispensing elements sequentially.

Enumerated embodiment 111. The device of any one of the enumerated embodiments, wherein the first insertable portion moves along a septum and moves a superior lateral cartilage away from the septum.

Enumerated embodiment 112. The device of any one of the enumerated embodiments, wherein the first and second dispensing elements move along a septum.

Enumerated embodiment 113. The device of any one of the enumerated embodiments, wherein the two insertable portions each contact opposite sides of a septum.

Enumerated embodiment 114. The device of any one of the enumerated embodiments, wherein the two dispensing elements each contact opposite sides of a septum.

Enumerated embodiment 115. The device of any one of the enumerated embodiments, wherein the two insertable portions each contact opposite sides of a septum and apply force to a superior lateral cartilage in a direction away from the septum.

Enumerated embodiment 116. The device of any one of the enumerated embodiments, wherein the two insertable portions each contact opposite sides of a septum and apply force to a superior lateral cartilage in a direction orthogonal to a lateral axis of the septum.

Enumerated embodiment 117. The device of any one of the enumerated embodiments, wherein the at least one insertable portion to open or expand an internal nasal valve does so by moving a superior lateral cartilage defining the internal nasal valve away from a septum of the subject.

Enumerated embodiment 118. The device of any one of the enumerated embodiments, wherein the at least one insertable portion to open or expand an internal nasal valve does so by moving superior cartilage defining the internal nasal valve towards an internal nasal dorsum of the subject.

Enumerated embodiment 119. The device of any one of the enumerated embodiments, wherein the insertable portion is configured to fit into a wedge shape of a nasal valve where a septum contacts a superior lateral cartilage.

Enumerated embodiment 120. The device of any one of the enumerated embodiments, wherein the anterior aspect of the insertable portion is configured to fit into the narrow anterior aspect of the internal nasal valve.

Enumerated embodiment 121. The device of any one of the enumerated embodiments, wherein the anterior aspect of the insertable portion is configured to fit into an opening comprising a 9 to 15 degree angle.

Enumerated embodiment 122. The device of any one of the enumerated embodiments, wherein the insertable portion is configured to fit into the narrow anterior aspect of the internal nasal valve when seated about the columella region.

Enumerated embodiment 123. The device of any one of the enumerated embodiments, wherein the insertable portion is configured to fit into an opening comprising a 9 to 15 degree angle when seated about the columella region.

Enumerated embodiment 124. The device of any one of the enumerated embodiments, wherein the insertable portion is configured to be inserted into a wedge shaped internal nasal valve of a subject.

Enumerated embodiment 125. The device of any one of the enumerated embodiments, wherein the insertable portion is tapered about a distal end of the insertable portion and is configured to be inserted into a wedge shaped internal nasal valve of a subject.

Enumerated embodiment 126. The device of any one of the enumerated embodiments, wherein the insertable portion is tapered about a distal end of the insertable portion with rounded edges and is configured to be inserted into a wedge shaped internal nasal valve of a subject.

Enumerated embodiment 127. The device of any one of the enumerated embodiments, wherein the insertable portion comprises a tip portion having a width which corresponds to an average diameter of an internal nasal valve.

Enumerated embodiment 128. The device of any one of the enumerated embodiments, wherein the insertable portion comprises a flat surface on a lateral face of the insertable portion which contacts the septum.

Enumerated embodiment 129. The device of any one of the enumerated embodiments, wherein the insertable portion comprises a rounded surface on a lateral face of the insertable portion which is opposite the septum.

Enumerated embodiment 130. The device of any one of the enumerated embodiments, wherein the insertable portion comprises a width up to 3 mm.

Enumerated embodiment 131. The device of any one of the enumerated embodiments, wherein one or both insertable portions comprises a proximal end, wherein a dispensing element reveals from the proximal end of the insertable portion.

Enumerated embodiment 132. The device of any one of the enumerated embodiments, wherein the distal end of an insertable portion is configured for insertion into the nasal channel of the subject.

Enumerated embodiment 133. The device of any one of the enumerated embodiments, wherein the revealing of the dispensing element from the first insertable portion upon transition of the device from the first configuration to the second configuration comprises extending of the dispensing element from the first insertable portion.

Enumerated embodiment 134. The device of any one of the enumerated embodiments, wherein the subject engaging portion engages both a right side and a left side of the columella region.

Enumerated embodiment 135. The device of any one of the enumerated embodiments, wherein the subject engaging portion comprises a concave shape.

Enumerated embodiment 136. The device of any one of the enumerated embodiments, wherein the subject engaging portion comprises a U shape.

Enumerated embodiment 137. The device of any one of the enumerated embodiments, wherein the subject engaging portion comprises a saddle shape.

Enumerated embodiment 138. The device of any one of the enumerated embodiments, wherein the subject engaging portion comprises a concave ellipsoidal shape.

Enumerated embodiment 139. The device of any one of the enumerated embodiments, wherein the subject engaging portion comprises a trench with a rounded bottom or rounded edges.

Enumerated embodiment 140. The device of any one of the enumerated embodiments, wherein the subject engaging portion centers the two insertable portions about the subject's columella.

Enumerated embodiment 141. The device of any one of the enumerated embodiments, wherein the subject engaging portion is a positioning element which aligns at least one of the insertable portion, the dispensing element, or the housing relative to the user's nasal channel.

Enumerated embodiment 142. The device of any one of the enumerated embodiments, wherein the device targets an olfactory cleft or a portion thereof, wherein the subject engaging portion aligns a dispensing element with an olfactory cleft of the subject.

Enumerated embodiment 143. The device of any one of the enumerated embodiments, wherein an insertable portion comprises a single dispensing channel leading to a dispensing port positioned at the distal aspect of the insertable portion.

Enumerated embodiment 144. The device of any one of the enumerated embodiments, wherein an insertable portion comprises a single dispensing channel leading to a dispensing port positioned along the length of the insertable portion.

Enumerated embodiment 145. The device of any one of the enumerated embodiments, wherein an insertable portion comprises two or more dispensing channels leading to two or more dispensing ports positioned at various aspects of the insertable portion.

Enumerated embodiment 146. The device of any one of the enumerated embodiments, wherein an insertable portion comprises a single dispensing channel leading to a dispensing port positioned to deliver a composition to an olfactory cleft.

Enumerated embodiment 147. The device of any one of the enumerated embodiments, wherein an insertable portion comprises a single dispensing channel leading to a dispensing port positioned to deliver a composition to an aspect of the respiratory region, such as a middle turbinate.

Enumerated embodiment 148. The device of any one of the enumerated embodiments, wherein an insertable portion comprises two or more dispensing channels leading to two or more dispensing ports positioned to deliver a composition to one or more regions or sub-regions of a nasal channel such as an olfactory cleft and/or a middle turbinate.

Enumerated embodiment 149. The device of any one of the enumerated embodiments, wherein a first insertable portion comprises a single dispensing channel leading to a dispensing port positioned at the distal aspect of the insertable portion and a second insertable portion comprises a single dispensing channel leading to a dispensing port positioned along the length of the insertable portion.

Enumerated embodiment 150. The device of any one of the enumerated embodiments, wherein a first insertable portion comprises a single dispensing channel leading to a dispensing port positioned at the distal aspect of the insertable portion and a second insertable portion comprises two or more dispensing channels leading to two or more dispensing ports positioned at various aspects of the insertable portion.

Enumerated embodiment 151. The device of any one of the enumerated embodiments, wherein a composition is dispensed from two insertable portions simultaneously.

Enumerated embodiment 152. The device of any one of the enumerated embodiments, wherein a composition is dispensed from two insertable portions sequentially.

Enumerated embodiment 153. The device of any one of the enumerated embodiments, wherein a composition is dispensed from two dispensing elements simultaneously.

Enumerated embodiment 154. The device of any one of the enumerated embodiments, wherein a composition is dispensed from two dispensing elements sequentially.

Enumerated embodiment 155. The device of any one of the enumerated embodiments, wherein the trigger and/or the subject engaging portion actuates the device and dispenses the composition from one cannula when pressed against the subject's columella.

Enumerated embodiment 156. The device of any one of the enumerated embodiments, wherein the trigger and/or the subject engaging portion comprises an actuator which dispenses the composition from the reservoir when the housing is moved from the first position to the second position.

Enumerated embodiment 157. The device of any one of the enumerated embodiments, wherein the subject engaging portion engages the columella of the subject to limit depth of insertion of the first insertable portion and the second insertable portion into the subject's nasal channel.

Enumerated embodiment 158. The device of any one of the enumerated embodiments, wherein the subject engaging portion engages the columella of the subject to limit depth of insertion of the first dispensing element and the second dispensing element into the subject's nasal channel.

Enumerated embodiment 159. The device of any one of the enumerated embodiments, wherein the subject engaging portion engages the columella of the subject about multiple sides of the columella in a concave shape.

Enumerated embodiment 160. The device of any one of the enumerated embodiments, wherein the trigger comprises a saddle shaped portion for receiving the columella of the subject.

Enumerated embodiment 161. The device of any one of the enumerated embodiments ims, wherein the saddle shaped portion positions the first insertable portion and the second insertable portion as to align the one or more dispensing elements with the olfactory cleft when the device is actuated.

Enumerated embodiment 162. The device of any one of the enumerated embodiments, wherein the saddle portion, subject engaging portion, or positioning trigger comprises a shape which matches the anatomy of the subject's columella and aligns the one or more dispensing elements with the subject's olfactory cleft.

Enumerated embodiment 163. The device of any one of the enumerated embodiments, wherein the one or more dispensing elements are positioned in line with an unobstructed path to the olfactory cleft of the subject when the subject engaging portion is engaging the columella of the subject.

Enumerated embodiment 164. The device of any one of the enumerated embodiments, wherein the dispensing element is positioned 0 mm to about 40 mm from the inferior aspect of an olfactory cleft of the subject when the subject engaging portion is engaging the columella of the subject.

Enumerated embodiment 165. The device of any one of the enumerated embodiments, wherein the saddle comprises an impression of the subject's columella.

Enumerated embodiment 166. The device of any one of the enumerated embodiments, wherein the subject engaging portion comprises dimension of about 20 mm by about 17 mm.

Enumerated embodiment 167. The device of any one of the enumerated embodiments, wherein the saddle shaped portion engages the columella of the subject about multiple sides of the columella.

Enumerated embodiment 168. The device of any one of the enumerated embodiments, wherein the subject engaging portion depresses a trigger coupled to the subject engaging portion to actuate the device.

Enumerated embodiment 169. The device of any one of the enumerated embodiments, wherein the first and/or second insertable portion limits a sagittal angle or an anterior-posterior angle of the device.

Enumerated embodiment 170. The device of any one of the enumerated embodiments, wherein the first and/or second insertable portion limits a coronal angle or a medial-lateral angle of the device.

Enumerated embodiment 171. The device of any one of the enumerated embodiments, wherein the first and/or second insertable portion limits a sagittal angle or an anterior-posterior angle of the device.

Enumerated embodiment 172. The device of any one of the enumerated embodiments, wherein the first and/or second insertable portion and subject engaging portion limits a sagittal angle, an anterior-posterior angle of the device, a coronal angle or a medial-lateral angle of the device, a sagittal angle or an anterior-posterior angle of the device, or any combination thereof.

Enumerated embodiment 173. The device of any one of the enumerated embodiments, wherein an internal nasal valve of the subject is bounded medially by the septum, laterally by the caudal portion of the upper lateral cartilage and inferiorly by the head of the inferior turbinate.

Enumerated embodiment 174. The device of any one of the enumerated embodiments, wherein the first and/or second insertable portion displaces the upper lateral cartilage thereby opening or enlarging at least a portion of internal nasal valve of the subject.

Enumerated embodiment 175. The device of any one of the enumerated embodiments, wherein the first and/or second insertable portion is torsionally flexible.

Enumerated embodiment 176. The device of any one of the enumerated embodiments, wherein the first and/or second insertable portion is tortional flexible so as to adjust to the angle of an anterior aspect or wedge of the internal nasal valve.

Enumerated embodiment 177. The device of any one of the enumerated embodiments, wherein the first and/or second insertable portion(s) runs proximal to a septum of the user.

Enumerated embodiment 178. The device of any one of the enumerated embodiments, wherein one or more dispensing elements extend outwards or are revealed from the insertable portion when the device is actuated.

Enumerated embodiment 179. The device of any one of the enumerated embodiments, wherein two dispensing elements reveal outwards from the insertable portion when the device is actuated.

Enumerated embodiment 180. The device of any one of the enumerated embodiments, wherein the device dispenses a composition from one or more dispensing elements when the device is actuated.

Enumerated embodiment 181. The device of any one of the enumerated embodiments, wherein the housing further comprises a second insertable portion for insertion into a second nasal channel of the user.

Enumerated embodiment 182. The device of any one of the enumerated embodiments, wherein the first and/or second insertable portion moves tissue within the nasal channel to define a path between the one or more dispensing elements and a delivery site.

Enumerated embodiment 183. The device of any one of the enumerated embodiments, wherein the first and/or second insertable portion moves tissue within the nasal channel to open or enlarge an internal nasal valve of a subject.

Enumerated embodiment 184. The device of any one of the enumerated embodiments, wherein the dispensing element is contained within the insertable portion.

Enumerated embodiment 185. The device of any one of the enumerated embodiments, further comprising a second dispensing element, wherein the first dispensing elements is contained within the first insertable portion, wherein the second dispensing element is contained within the second insertable portion.

Enumerated embodiment 186. The device of any one of the enumerated embodiments, wherein the first and/or second insertable portion comprises dimension of about 20 mm by about 3.5 mm.

Enumerated embodiment 187. The device of any one of the enumerated embodiments, wherein the first and/or second insertable portion are wedge-shaped, paddle-shaped, cylindrical, bulbous, cone-shaped, spherical, hemispherical, or any combination thereof.

Enumerated embodiment 188. The device of any one of the enumerated embodiments, wherein the first and/or second insertable portion has a cross sectional shape comprising an elongated oval with consistent width and symmetrical rounded ends.

Enumerated embodiment 189. The device of any one of the enumerated embodiments, wherein the first and/or second insertable portion has a cross sectional shape comprising a long rounded rectangular shape with semi-circular ends.

Enumerated embodiment 190. The device of any one of the enumerated embodiments, wherein the transition of the device from the first configuration to the second configuration is actuated by the subject engaging portion which reveals the dispensing element from the first insertable portion.

Enumerated embodiment 191. The device of any one of the enumerated embodiments, wherein the transition of the device from the first configuration to the second configuration is actuated by an actuator which reveals the dispensing element from the first insertable portion.

Enumerated embodiment 192. The device of any one of the enumerated embodiments, wherein the first or second insertable portion displaces cartilage and/or tissue within the nasal channel when the device is inserted in the first configuration.

Enumerated embodiment 193. The device of any one of the enumerated embodiments, wherein the first or second insertable portion fits proximal to a septal-lateral cartilage junction of the subject when the device is in the second configuration.

Enumerated embodiment 194. The device of any one of the enumerated embodiments, wherein the housing is movable from a first position to the second position.

Enumerated embodiment 195. The device of any one of the enumerated embodiments, wherein the housing comprises a proximal portion and a distal portion, wherein the distal portion is pushed relative to the proximal portion to actuate the device when the housing is transitioned from the first configuration to the second configuration.

Enumerated embodiment 196. The device of any one of the enumerated embodiments, wherein the proximal portion is inserted into the distal portion when the housing is transitioned from the first configuration to the second configuration.

Enumerated embodiment 197. The device of any one of the enumerated embodiments, wherein the distal portion is inserted into the proximal portion when the housing is transitioned from the first configuration to the second configuration.

Enumerated embodiment 198. The device of any one of the enumerated embodiments, upon transition from the first configuration to the second configuration, the distal portion moves relative to the subject, while the proximal portion remains stationary relative to the subject, wherein the proximal portion is coupled to the dispensing element.

Enumerated embodiment 199. The device of any one of the enumerated embodiments, upon transition from the first configuration to the second configuration, the dispensing element reveals outward from the proximal portion.

Enumerated embodiment 200. The device of any one of the enumerated embodiments, wherein the columella region comprises: the subnasale, the subnasion, the anterior nasal spine, or any combination thereof.

Enumerated embodiment 201. The device of any one of the enumerated embodiments, wherein the insertable portion has the following flexibility characteristics:
  a. a medial-lateral flexibility along a width orthogonal to a length of the insertable portion;
  b. a lack anterior-posterior flexibility about a length of the insertable portion; or
  c. an inferior-superior flexibility about a rotational axis orthogonal to a length of the insertable portion.
Enumerated embodiment 202. The device of any one of the enumerated embodiments, wherein the dispensing element is configured to dispense the composition into a single nasal channel of a subject.
Enumerated embodiment 203. The device of any one of the enumerated embodiments, wherein the dispensing element fits proximal to a septal-lateral cartilage junction of the subject.
Enumerated embodiment 204. The device of any one of the enumerated embodiments, wherein the dispensing element fits proximal to a septum of the subject.
Enumerated embodiment 205. The device of any one of the enumerated embodiments, wherein the dispensing element comprises a dispensing port.
Enumerated embodiment 206. The device of any one of the enumerated embodiments, wherein a dispensing element comprises a cannula or a catheter.
Enumerated embodiment 207. The device of any one of the enumerated embodiments, wherein the one or more insertable portions comprise a plurality of dispensing ports.
Enumerated embodiment 208. The device of any one of the enumerated embodiments, wherein the one or more dispensing elements comprise a dispensing port.
Enumerated embodiment 209. The device of any one of the enumerated embodiments, wherein the dispensing port has one dispensing port at its distal end, one or more dispensing ports along its length, or a combination of both.
Enumerated embodiment 210. The device of any one of the enumerated embodiments, wherein the dispensing port is directed at different target areas within the nasal channel.
Enumerated embodiment 211. The device of any one of the enumerated embodiments, wherein the dispensing port comprises an atomizer.
Enumerated embodiment 212. The device of any one of the enumerated embodiments, wherein the dispensing element comprises an atomizer.
Enumerated embodiment 213. The device of any one of the enumerated embodiments, wherein the one or more dispensing elements are 20 mm to 50 mm in length.
Enumerated embodiment 214. The device of any one of the enumerated embodiments, wherein the one or more dispensing elements reveal 0 mm to 40 mm from the insertable portion.
Enumerated embodiment 215. The device of any one of the enumerated embodiments, wherein the one or more dispensing elements comprise multiple dispensing ports.
Enumerated embodiment 216. The device of any one of the enumerated embodiments, wherein the one or more dispensing elements comprise multiple fluid channels.
Enumerated embodiment 217. The device of any one of the enumerated embodiments, wherein the one or more dispensing elements comprise a dispensing port.
Enumerated embodiment 218. The device of any one of the enumerated embodiments, wherein one of the multiple fluid channels is configured to dispense a gas.
Enumerated embodiment 219. The device of any one of the enumerated embodiments, wherein one of the multiple fluid channels is configured to dispense a gas following dispensing a composition by another fluid channel.
Enumerated embodiment 220. The device of any one of the enumerated embodiments, wherein the device is configured to target the olfactory cleft or a portion thereof.
Enumerated embodiment 221. The device of any one of the enumerated embodiments, wherein the one or more dispensing elements comprise a first tubular section which surrounds the dispensing element.
Enumerated embodiment 222. The device of any one of the enumerated embodiments, wherein the first tubular section remains within a first insertable portion when the device is actuated to the second position.
Enumerated embodiment 223. The device of any one of the enumerated embodiments, wherein the insertable portion is flexible.
Enumerated embodiment 224. The device of any one of the enumerated embodiments, wherein the one or more dispensing elements are flexible.
Enumerated embodiment 225. The device of any one of the enumerated embodiments, further comprising a reservoir fluidically connected to the one or more insertable portions.
Enumerated embodiment 226. The device of any one of the enumerated embodiments, further comprising a reservoir fluidically connected to the one or more dispensing elements.
Enumerated embodiment 227. The device of any one of the enumerated embodiments, wherein the compound comprises a therapeutic agent.
Enumerated embodiment 228. The device of any one of the enumerated embodiments, wherein the compound comprises a sampling agent.
Enumerated embodiment 229. The device of any one of the enumerated embodiments, wherein the compound comprises a liquid, powder or gas, or a combination thereof.
Enumerated embodiment 230. The device of any one of the enumerated embodiments, wherein the target region is one or both olfactory clefts, or a sub-area thereof.
Enumerated embodiment 231. The device of any one of the enumerated embodiments, wherein the target area is one or both respiratory areas, or a sub-area thereof.
Enumerated embodiment 232. The device of any one of the enumerated embodiments, wherein the actuator is spring loaded.
Enumerated embodiment 233. The device of any one of the enumerated embodiments, wherein the actuator dispenses approximately equal amounts of fluid form each insertable portion.
Enumerated embodiment 234. The device of any one of the enumerated embodiments, wherein the actuator dispenses approximately equal amounts of fluid form each dispensing element.
Enumerated embodiment 235. The device of any one of the enumerated embodiments, wherein the actuator dispenses fluid from only one insertable portion.
Enumerated embodiment 236. The device of any one of the enumerated embodiments, wherein the actuator dispenses fluid from only one dispensing element.

Enumerated embodiment 237. The device of any one of the enumerated embodiments, wherein the one or more dispensing are contained with a secondary tubular member.

Enumerated embodiment 238. The device of any one of the enumerated embodiments, wherein the reservoir is removable.

Enumerated embodiment 239. The device of any one of the enumerated embodiments, wherein the reservoir is comprised within a removable cartridge.

Enumerated embodiment 240. The device of any one of the enumerated embodiments, wherein the positioned trigger depresses a switch underneath the positioning trigger to actuate the device.

Enumerated embodiment 241. The device of any one of the enumerated embodiments, further comprising a central tube fluidically connected to the one or more insertable portions, wherein the central tube is inserted into the reservoir when the device is actuated.

Enumerated embodiment 242. The device of any one of the enumerated embodiments, further comprising a central tube fluidically connected to the one or more dispensing elements, wherein the central tube is inserted into the reservoir when the device is actuated.

Enumerated embodiment 243. The device of any one of the enumerated embodiments, further comprising a central tube fluidically connected to two insertable portions, wherein the central tube is inserted into the reservoir when the device is actuated.

Enumerated embodiment 244. The device of any one of the enumerated embodiments, further comprising a central tube fluidically connected to two dispensing elements, wherein the central tube is inserted into the reservoir when the device is actuated.

Enumerated embodiment 245. The device of any one of the enumerated embodiments, further comprising a one or more bases connected to the bottom of the one or more dispensing elements which move the one or more dispensing elements upon actuation of the device.

Enumerated embodiment 246. The device of any one of the enumerated embodiments, wherein the dispensing channels comprise a diameter of about 0.3 mm to about 3 mm.

Enumerated embodiment 247. The device of any one of the enumerated embodiments, wherein the dispensing element comprises an inner diameter of about 0.3 mm to about 3 mm.

Enumerated embodiment 248. The device of any one of the enumerated embodiments, wherein the dispensing element is configured to prevent the introduction of bacteria or microbes from the lower nasal cavity or external environment into different another region of the nasal cavity.

Enumerated embodiment 249. The device of any one of the enumerated embodiments, wherein an end of the dispensing element is coextensive with the end of the insertable portion.

Enumerated embodiment 250. The device of any one of the enumerated embodiments, wherein the dispensing element is entirely contained within the insertable portion.

Enumerated embodiment 251. The device of any one of the enumerated embodiments, wherein the end of the dispensing element is coextensive with the end of the insertable portion when the device is actuated.

Enumerated embodiment 252. The device of any one of the enumerated embodiments, wherein an end of the dispensing element is coextensive with the end of the insertable portion when the device is transitioned from the first position to the second position, or the first configuration to the second configuration.

Enumerated embodiment 253. The device of any one of the enumerated embodiments, wherein the dispensing element does not extend or reveal from the insertable portion when the device is actuated.

Enumerated embodiment 254. The device of any one of the enumerated embodiments, wherein the trigger is positioned on the subject engaging portion or the columella saddle, and is configured to actuate the device when pressure is applied to the trigger by a subject's columella.

Enumerated embodiment 255. A device for intranasal delivery to a subject, the device transitionable from a first configuration to a second configuration, the device comprising:
  a. a housing defining two insertable portions comprising at least one dispensing element, each insertable portion for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the dispensing elements for delivery of a composition to the subject;
  b. a subject engaging portion coupled to the housing comprising a trigger, the trigger comprising a subject engaging portion which engages a columella region, wherein upon application of pressure to the subject engaging portion, the trigger permits actuation of the device to deliver a composition to the subject from the dispensing element; and
  c. the dispensing element revealing from the first insertable portion upon transition of the device from the first configuration to the second configuration.

Enumerated embodiment 256. A device for intranasal delivery to a subject, the device transitionable from a first configuration to a second configuration, the device comprising:
  a. a housing defining two insertable portions, each insertable portion for insertion into a nasal channel of the subject for delivery of a composition into a nasal channel of the subject, wherein, upon insertion of the first insertable portion into a nasal channel of the subject, the first insertable portion engages tissue within the nasal channel to open or expand an internal nasal valve of the subject thereby positioning at least one of the insertable portions for delivery of a composition to the subject;
  b. a subject engaging portion coupled to the housing comprising a trigger, the trigger comprising a subject engaging portion which engages a columella region, wherein upon application of pressure to the subject engaging portion, the trigger permits actuation of the device to deliver a composition to the subject from at least one of the insertable portions.

Enumerated embodiment 257. A method for intranasal delivery to a subject with a device, the method comprising:
  a. positioning an insertable portion of the device within an ejection zone of a nasal cavity of the subject by engaging a columella region of the subject with a subject engaging portion of the device, seating the insertable portion within the ejection zone of the subject's nasal cavity, wherein the ejection zone is:
b. 0 mm to 30 mm superior to a horizontal line that intersects the anterior aspect of the internal nasal valve, and
c. 0 mm to 20 mm anterior to an inclined line that intersects the anterior aspect of the middle turbinate and the posterior aspect of the vestibule, and one or more of the following:
 i. 0 mm to 40 mm inferior to a horizontal line that is parallel to the inferior aspect of the olfactory cleft,
 ii. 0 mm to 20 mm posterior to the internal nasal dorsum,
 iii. 10 mm and 50 mm superior to a horizontal line that intersects the inferior aspect of the columella,
 iv. 0 mm to 30 mm superior to a horizontal line that intersects the superior aspect of the inferior turbinate,
 v. 0 mm to 3 mm from the septum. or
 vi. any combination thereof.

Enumerated embodiment 258. The method of any one of the enumerated embodiments, further comprising actuating the device by applying pressure to the columella region of the subject with the subject engaging portion of the device.

Enumerated embodiment 259. The method of any one of the enumerated embodiments, wherein the positioning the insertable portion of the device comprises positioning two insertable portions into two nasal channels of the subject, thereby opening or expanding an opening of an internal nasal valve of the subject.

Enumerated embodiment 260. The method of any one of the enumerated embodiments, wherein the positioning the dispensing element of the device comprises positioning two dispensing elements of the device into a nasal channel of the subject, wherein the two dispensing elements reveal from the insertable portion.

Enumerated embodiment 261. The method of any one of the enumerated embodiments, further comprising transitioning the device from a first configuration to a second configuration, wherein the dispensing element reveals from the insertable portion upon transition of the device from the first configuration to the second configuration.

Enumerated embodiment 262. A method for intranasal delivery of a composition to a subject with a device, the method comprising:
a. inserting two insertable portions into nasal channels of the subject, wherein upon the inserting at least one of the insertable portion engages tissue within the nasal channel thereby opening or expanding an opening of an internal nasal valve of the subject, thereby positioning at least one of the insertable portions for delivery of a composition to the subject.

Enumerated embodiment 263. The method of any one of the enumerated embodiments, further comprising positioning the insertable portions into nasal channels of the subject by engaging a columella region of the subject with a subject engaging portion of the device, thereby limiting a depth of insertion of the device into the subject's nasal channel and aligning the insertable portions within the nasal channel of the subject.

Enumerated embodiment 264. The method of any one of the enumerated embodiments, further comprising actuating the device by applying pressure to the subject engaging portion of the device with the columella region of the subject.

Enumerated embodiment 265. The method of any one of the enumerated embodiments, wherein the two insertable portions comprise at least one dispensing element.

Enumerated embodiment 266. The method of any one of the enumerated embodiments, wherein the at least one dispensing element reveals outwards from at least one of the two insertable portions.

Enumerated embodiment 267. The method of any one of the enumerated embodiments, further comprising transitioning the device from a first configuration to a second configuration, wherein the dispensing element reveals from the insertable portion upon transition of the device from the first configuration to the second configuration.

Enumerated embodiment 268. The method of any one of the enumerated embodiments, wherein the inserting two insertable portions of a. advances the two insertable portions along the inner dorsum and/or on along either side of the septum until a columella engaging region of the device contacts a columella of the subject, preventing further insertion, and establishing a depth datum.

Enumerated embodiment 269. The method of any one of the enumerated embodiments, wherein a dispensing port is positioned at a targeted region or subregion in the nasal cavity.

Enumerated embodiment 270. The method of any one of the enumerated embodiments, wherein the inserting two insertable portions of a. uses the nasofrontal angle as an angular reference to position the insertable portions within the nasal channels.

Enumerated embodiment 271. The method of any one of the enumerated embodiments, wherein a dispensing port is positioned at a targeted region or subregion in the nasal cavity.

Enumerated embodiment 272. The method of any one of the enumerated embodiments, wherein the inserting two insertable portions of a. advances the two insertable portions along the inner dorsum until a columella engaging region of the device contacts a columella of the subject, preventing further insertion, and establishing a depth datum, and wherein the inserting two insertable portions of a. uses the nasofrontal angle as an angular reference to position the insertable portions within the nasal channels, thereby positioning the two insertable portions within the nasal cavity at known position.

Enumerated embodiment 273. The method of any one of the enumerated embodiments, wherein the inserting two insertable portions of a. comprises inserting the two insertable portions past a nasal vestibule.

Enumerated embodiment 274. The method of any one of the enumerated embodiments, wherein the inserting two insertable portions of a. comprises inserting the two insertable portions along soft tissues of a superior cleft in an orientation parallel to the soft tissues.

Enumerated embodiment 275. The method of any one of the enumerated embodiments, wherein the inserting two insertable portions of a. prevents rotation of the device about an axis parallel to the subject's height.

Enumerated embodiment 276. The method of any one of the enumerated embodiments, wherein the inserting two insertable portions of a. creates a reference yaw angle a coronal plane relative to a y-axis of the device.

Enumerated embodiment 277. The method of any one of the enumerated embodiments, wherein the inserting two insertable portions of a. creates a substantially unimpeded flow channel to an olfactory cleft.

Enumerated embodiment 278. The method of any one of the enumerated embodiments, wherein the inserting two insertable portions of a. creates a substantially unimpeded flow to a nasal turbinate.

Enumerated embodiment 279. A method for intranasal delivery of a composition to a subject with a device, the method comprising:
 a. positioning an insertable portion of the device within a nasal channel of the subject; and
 b. transitioning the device from a first configuration to a second configuration by applying pressure about a longitudinal axis of the device, thereby revealing a dispensing element from the first insertable portion and simultaneously actuating the device to deliver the composition to the subject.

Enumerated embodiment 280. The method of any one of the enumerated embodiments, wherein the simultaneous actuation refers to transition for the first configuration to the second configuration and actuation occurring in a single motion upon application of pressure about a longitudinal axis of the device Enumerated embodiment 281. The method of any one of the enumerated embodiments, wherein the positioning the insertable portion of the device within the nasal channel of the subject occurs by engaging a columella region of the subject with a subject engaging portion of the device.

Enumerated embodiment 282. The method of any one of the enumerated embodiments, further comprising actuating the device by applying pressure to the subject engaging portion of the device with the columella region of the subject.

Enumerated embodiment 283. The method of any one of the enumerated embodiments, wherein the positioning the insertable portion of the device within the nasal channel of the subject engages tissue within the nasal channel to open or expand an internal nasal valve of the subject, thereby positioning the insertable portion for delivery of a composition to the subject.

Enumerated embodiment 284. The method of any one of the enumerated embodiments, wherein the insertable portion of the device comprises two insertable portions, each for insertion into a nasal channel of the subject, wherein a. comprises inserting two insertable portions into nasal channels of the subject.

Enumerated embodiment 285. The method of any one of the enumerated embodiments, wherein the inserting two insertable portions of a. advances the two insertable portions along the inner dorsum and/or on along either side of the septum until a columella engaging region of the device contacts a columella of the subject, preventing further insertion, and establishing a depth datum.

Enumerated embodiment 286. The method of any one of the enumerated embodiments, wherein the inserting two insertable portions of a. uses the nasofrontal angle as an angular reference to position the insertable portions within the nasal channels.

Enumerated embodiment 287. The method of any one of the enumerated embodiments, wherein a dispensing port is positioned at a targeted region or subregion in the nasal cavity.

Enumerated embodiment 288. The method of any one of the enumerated embodiments, wherein the inserting two insertable portions of a. advances the two insertable portions along the inner dorsum and/or on along either side of the septum until a columella engaging region of the device contacts a columella of the subject, preventing further insertion, and establishing a depth datum, and wherein the inserting two insertable portions of a. uses the nasofrontal angle as an angular reference to position the insertable portions within the nasal channels, thereby positioning the two insertable portions within the nasal cavity at known position.

Enumerated embodiment 289. The method of any one of the enumerated embodiments, wherein the inserting two insertable portions of a. comprises inserting the two insertable portions past a nasal vestibule.

Enumerated embodiment 290. The method of any one of the enumerated embodiments, wherein the inserting two insertable portions of a. comprises inserting the two insertable portions along soft tissues of a superior cleft in an orientation parallel to the soft tissues.

Enumerated embodiment 291. The method of any one of the enumerated embodiments, wherein the inserting two insertable portions of a. prevents rotation of the device about an axis parallel to the subject's height.

Enumerated embodiment 292. The method of any one of the enumerated embodiments, wherein the inserting two insertable portions of a. creates a reference yaw angle a coronal plane relative to a y-axis of the device.

Enumerated embodiment 293. The method of any one of the enumerated embodiments, wherein the inserting two insertable portions of a. creates a substantially unimpeded flow channel to an olfactory cleft.

Enumerated embodiment 294. A method for intranasal delivery of a composition to a target region of the nasal cavity of a subject, the method comprising:
 a. inserting a dispensing element into an ejection zone of a nasal cavity, wherein the ejection zone is:
 b. 0 mm to 30 mm superior to a horizontal line that intersects the anterior aspect of the internal nasal valve, and
 c. 0 mm to 20 mm anterior to an inclined line that intersects the anterior aspect of the middle turbinate and the posterior aspect of the vestibule, and one or more of the following:
  i. 0 mm to 40 mm inferior to a horizontal line that is parallel to the inferior aspect of the olfactory cleft,
  ii. 0 mm to 20 mm posterior to the internal nasal dorsum,
  iii. 10 mm and 50 mm superior to a horizontal line that intersects the inferior aspect of the columella,
  iv. 0 mm to 30 mm superior to a horizontal line that intersects the superior aspect of the inferior turbinate,
  v. 0 mm to 3 mm from the septum. or
  vi. any combination thereof.
 d. dispensing the composition from the dispensing element to contact the target region with the composition, wherein dispensing the composition from the ejection zone: a) increases on target delivery of the composition to the target region, b) decreases off target delivery of the composition to the nasal cavity, or c) both.

Enumerated embodiment 295. The method of any one of the enumerated embodiments, wherein the ejection zone is a trapezium or irregular quadrilateral comprising (i) an inferior side being a 10-25 mm line extending posteriorly and horizontally from the anterior aspect of the internal nasal valve, (ii) an anterior side being a 10-35 mm line extending superiorly and parallel to the internal nasal dorsum from the anterior aspect of the internal nasal valve, (iii) a superior side being a 10-25 mm line extending posteriorly and horizontally from a point on the internal nasal dorsum that is 0-10 mm inferior to the inferior aspect of the olfactory cleft, and (iv) a posterior line being a 10-35 mm line extending vertically along a plane that intersects the anterior aspect of the middle turbinate Enumerated embodiment 296. The method of any one of the enumerated embodiments, wherein the target region is one or both olfactory clefts, or a sub-area thereof, and wherein dispensing the composition from an anterior end of the dispensing element increases on target delivery of the composition to the target region.

Enumerated embodiment 297. The method of any one of the enumerated embodiments, wherein the target region is the middle meatus, and wherein dispensing the composition from a posterior end of the dispensing element increases on target delivery of the composition to the target region.

Enumerated embodiment 298. The method of any one of the enumerated embodiments, wherein the ejection zone is further: parallel with a middle turbinate of the subject, and not within the middle meatus.

Enumerated embodiment 299. The method of any one of the enumerated embodiments, wherein the ejection zone is in line with the olfactory cleft as defined by a linear vector between the olfactory cleft and the distal end of the insertable portion.

Enumerated embodiment 300. The method of any one of the enumerated embodiments, wherein the target region is one or both olfactory clefts, or a sub-area thereof.

Enumerated embodiment 301. A method of treating a subject having a disease or disorder via lateralized delivery of a therapeutic composition, the method comprising:
a. diagnosing the subject with a disease or disorder suitable for treatment via lateralized delivery of a therapeutic composition;
b. providing a device for lateralized intranasal delivery of the therapeutic composition; and
c. actuating the device to selectively deliver the therapeutic composition to a targeted region of the subject's brain while delivering less of the therapeutic composition to a corresponding region in the opposite hemisphere of the subject's brain.

Enumerated embodiment 302. The method of any one of the enumerated embodiments, wherein at least 20 percent more of the therapeutic composition is delivered to a region of the subject's brain than to a corresponding region in the opposite hemisphere of the subject's brain.

Enumerated embodiment 303. The method of any one of the enumerated embodiments, wherein wherein the lateralized delivery results in a first amount of the therapeutic composition in a targeted brain region or subregion at a time post delivery, and a second amount of the therapeutic composition in a corresponding brain region or subregion in the opposite brain hemisphere at the same time post delivery.

Enumerated embodiment 304. The method of any one of the enumerated embodiments, wherein the amount of the therapeutic composition delivered to the targeted brain region or subregion at a time post delivery is at least about 10%, at least about 20%, at least about 30%, at least about 40%, at least about 50%, at least about 60%, at least about 70%, at least about 80%, at least about 90%, or at least about 100% more than the amount of the therapeutic composition in a corresponding brain region or subregion in the opposite brain hemisphere at the same time post delivery.

Enumerated embodiment 305. The method of any one of the enumerated embodiments, wherein the amount of the therapeutic composition delivered to the targeted brain hemisphere at a time post delivery is at least about 10%, at least about 20%, at least about 30%, at least about 40%, at least about 50%, at least about 60%, at least about 70%, at least about 80%, at least about 90%, or at least about 100% more than the amount of the therapeutic composition in the opposite brain hemisphere at the same time post delivery.

Enumerated embodiment 306. The method of any one of the enumerated embodiments, wherein the amount of the therapeutic composition delivered to the targeted brain region or subregion at a time post delivery is at least about 2, 3, 4, 5, 6, 7, 8, 9, 10, 12, 14, 16, 18, 20, 25, 30, 40, 50, 60, 70, 80, 90, or 100 times more than the amount of the therapeutic composition in a corresponding brain region or subregion in the opposite brain hemisphere at the same time post delivery.

Enumerated embodiment 307. The method of any one of the enumerated embodiments, wherein the time post delivery is about 5 minutes, about 10 minutes, about 15, minutes, about 20 minutes, about 25 minutes, about 30 minutes, about 35 minutes, about 40 minutes, about 45 minutes, about 50 minutes, about 55 minutes, about 60 minutes, about 70 minutes, about 80 minutes, about 90 minutes, about 100 minutes, about 110 minutes, about 120 minutes, or greater than 120 minutes.

Enumerated embodiment 308. The method of any one of the enumerated embodiments, wherein the device is configured to orient in the human nasal anatomy with a left dispensing element in a left nasal cavity and a right dispensing element in a right nasal cavity, and not with the dispensing elements in opposite nasal cavities.

Enumerated embodiment 309. The method of any one of the enumerated embodiments, wherein the device is configured to selectively deliver the therapeutic composition to either or both of the nasal channels independently.

Enumerated embodiment 310. The method of any one of the enumerated embodiments, wherein the device is configured to selectively deliver the therapeutic composition to a right olfactory cleft or a left olfactory cleft.

Enumerated embodiment 311. A method of targeted delivery to a brain hemisphere or lateralized brain region of a subject, the method comprising: selectively delivering a composition to an intranasal region or subregion of an ipsilateral nasal channel such that the therapeutic composition selectively targets the corresponding brain hemisphere.

Enumerated embodiment 312. The method of any one of the enumerated embodiments, wherein the therapeutic composition is delivered to an olfactory region or subregion.

Enumerated embodiment 313. The method of any one of the enumerated embodiments, additionally comprising providing a device configured for lateralized intranasal delivery Enumerated embodiment 314. The method of any one of the enumerated embodiments, wherein the composition is a therapeutic composition.

Enumerated embodiment 315. The method of any one of the enumerated embodiments, wherein the composition is configured to aid in the diagnostic testing of an implanted neurological electronic interface.

Enumerated embodiment 316. The method of any one of the enumerated embodiments, wherein the composition is configured to aid in enhancement of mood, memory, cognitive ability, movement coordination, or other brain function.

Enumerated embodiment 317. The method of any one of the enumerated embodiments, wherein the composition is configured to aid in enhancement of extra-cerebral function.

Enumerated embodiment 318. A method of preferential delivery of a formulation to the brain of a subject, the method comprising selectively delivering the formulation to one or more intranasal regions such that non-equal proportions of the formulation are delivered to the left and right hemisphere of the brain and a concentration of a composition of the formulation in a targeted hemisphere is at least 10%, 20%, 30%, 40%, 50%, 60%, 70%, 80%, 90%, or 100% greater than a concentration of the composition in an untargeted hemisphere.

Enumerated embodiment 319. A device for preferential delivery of a formulation to the brain of a subject such that non-equal proportions of the formulation are delivered to the left and right hemisphere of the brain and a concentration of a composition of the formulation in a targeted hemisphere is at least 10%, 20%, 30%, 40%, 50%, 60%, 70%, 80%, 90%, or 100% greater than a concentration of the composition in an untargeted hemisphere.

Enumerated embodiment 320. A device of any one of the enumerated embodiments, wherein an angle between an axis of the device and an axis of the nasal dorsum is between about 0 and about 45 degrees.

Enumerated embodiment 321. A device of any one of the enumerated embodiments, wherein an angle between an axis of the device and an axis of the nasal dorsum is between about 7 and about 17 degrees.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

The invention claimed is:

1. A method for intranasal delivery of a composition to a target region of a nasal cavity of a subject, the method comprising:
   a. inserting a dispensing element revealable from an insertable portion into an ejection zone of the nasal cavity, wherein the ejection zone is:
      i. 0 mm to 30 mm superior to a horizontal line that intersects an anterior aspect of an internal nasal valve, and
      ii. 0 mm to 20 mm anterior to an inclined line that intersects an anterior aspect of a middle turbinate and a posterior aspect of a vestibule, and one or more of the following:
         1. 0 mm to 40 mm inferior to a horizontal line that is parallel to an inferior aspect of an olfactory cleft,
         2. 0 mm to 20 mm posterior to an internal nasal dorsum,
         3. 10 mm and 50 mm superior to a horizontal line that intersects an inferior aspect of a columella,
         4. 0 mm to 30 mm superior to a horizontal line that intersects a superior aspect of an inferior turbinate, and
         5. 0 mm to 3 mm from the septum;
   b. dispensing the composition from the dispensing element to contact the target region with the composition, wherein dispensing the composition from the ejection zone: a) increases on target delivery of the composition to the target region, b) decreases off target delivery of the composition to the nasal cavity, or c) both.

2. The method of claim 1, wherein the target region is one or both olfactory clefts, or a sub-area thereof.

3. The method of claim 1, further comprising positioning the insertable portion in a nasal channel of the subject by engaging a columella region of the subject to limit a depth of insertion of the insertable portion.

* * * * *